US010927263B2

(12) United States Patent
Endo et al.

(10) Patent No.: US 10,927,263 B2
(45) Date of Patent: Feb. 23, 2021

(54) POLYMERIZABLE COMPOSITION AND OPTICALLY ANISOTROPIC BODY PRODUCED USING THE SAME

(71) Applicant: DIC Corporation, Tokyo (JP)

(72) Inventors: Kouichi Endo, Kita-adachi-gun (JP); Yasuhiro Kuwana, Kita-adachi-gun (JP); Mika Takasaki, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 51 days.

(21) Appl. No.: 16/317,963

(22) PCT Filed: Jul. 13, 2017

(86) PCT No.: PCT/JP2017/025517
§ 371 (c)(1),
(2) Date: Jan. 15, 2019

(87) PCT Pub. No.: WO2018/012579
PCT Pub. Date: Jan. 18, 2018

(65) Prior Publication Data
US 2019/0264034 A1 Aug. 29, 2019

(30) Foreign Application Priority Data

Jul. 15, 2016 (JP) .............................. JP2016-140424

(51) Int. Cl.
C09D 4/00 (2006.01)
C09D 7/41 (2018.01)
C07D 277/82 (2006.01)
C07D 417/04 (2006.01)
C08F 20/38 (2006.01)
C08F 22/24 (2006.01)
C08K 5/42 (2006.01)
C09D 133/14 (2006.01)
C09D 135/02 (2006.01)
G02B 3/00 (2006.01)
G02F 1/1335 (2006.01)
G02B 5/30 (2006.01)
C09D 5/33 (2006.01)
G02B 1/04 (2006.01)
H01L 51/50 (2006.01)
C09D 7/63 (2018.01)
F21V 9/14 (2006.01)
G02B 1/08 (2006.01)
(Continued)

(52) U.S. Cl.
CPC ............ C09D 4/00 (2013.01); C07D 277/82 (2013.01); C07D 417/04 (2013.01); C08F 20/38 (2013.01); C08F 22/24 (2013.01); C08K 5/42 (2013.01); C09D 5/004 (2013.01); C09D 7/41 (2018.01); C09D 7/63 (2018.01); C09D 133/14 (2013.01); C09D 135/02 (2013.01); G02B 1/04 (2013.01); G02B 3/00 (2013.01); G02B 5/30 (2013.01); G02F 1/1335 (2013.01); H01L 51/50 (2013.01); C08F 2/38 (2013.01); C08F 220/1818 (2020.02); C08F 220/301 (2020.02); C08F 220/302 (2020.02); C08F 220/303 (2020.02); C08F 220/36 (2013.01); C08F 220/40 (2013.01); C08F 220/54 (2013.01); C08F 222/102 (2020.02); C08F 222/1025 (2020.02); C08F 222/1035 (2020.02); C08F 222/205 (2020.02); C08F 222/225 (2020.02); C08F 222/245 (2020.02); C08F 222/30 (2013.01); F21V 9/14 (2013.01); G02B 1/041 (2013.01); G02B 1/08 (2013.01); G02B 5/08 (2013.01); G02B 5/3083 (2013.01); G02F 1/13363 (2013.01); H01L 51/5293 (2013.01)

(58) Field of Classification Search
CPC ...... C09D 4/00; C09D 135/02; C09D 133/14; C09D 7/41; C08F 22/24; C08F 20/38; C08K 5/42; G02B 5/3083; C07D 277/82; C07D 417/04
USPC .......................................................... 524/159
See application file for complete search history.

(56) References Cited

U.S. PATENT DOCUMENTS

2010/0072422 A1 3/2010 Parri et al.
2012/0224245 A1 9/2012 Adlem et al.
(Continued)

FOREIGN PATENT DOCUMENTS

JP 2008-107767 A 5/2008
JP 2010-096892 A 4/2010
(Continued)

OTHER PUBLICATIONS

Office Action dated Feb. 19, 2020, issued in counterpart KR Application No. 10-2019-7001366, with English translation.
(Continued)

Primary Examiner — Hui H Chin
(74) Attorney, Agent, or Firm — Westerman, Hattori, Daniels & Adrian, LLP

(57) ABSTRACT

An object of the present invention is to provide a polymerizable composition with which a polymer having a high degree of hardness can be produced. Another object is to provide, for example, an optically anisotropic body, a phase retardation film, an optical compensation film, an antireflection film, a lens, and a lens sheet that are composed of the polymerizable composition and a liquid crystal display element, an organic light-emitting display element, a lighting element, an optical component, a coloring agent, a security marker, a laser emission member, a polarizing film, a coloring material, and a printed item that are produced using the polymerizable composition. The present invention provides a polymerizable composition including a polymerizable compound represented by General Formula (IA) which has a specific structure including a plurality of polymerizable groups.

19 Claims, No Drawings

(51) Int. Cl.
*G02B 5/08* (2006.01)
*G02F 1/13363* (2006.01)
*H01L 51/52* (2006.01)
*C08F 220/36* (2006.01)
*C08F 220/40* (2006.01)
*C08F 222/30* (2006.01)
*C08F 2/38* (2006.01)
*C08F 220/54* (2006.01)
*C08F 220/30* (2006.01)
*C08F 220/18* (2006.01)
*C08F 222/10* (2006.01)
*C08F 222/20* (2006.01)
*C08F 222/22* (2006.01)
*C08F 222/24* (2006.01)

(56) References Cited

U.S. PATENT DOCUMENTS

2014/0142266 A1* 5/2014 Sakamoto ............... C07C 69/92
526/257

2015/0277010 A1* 10/2015 Aimatsu ................. G02B 1/04
359/489.07
2016/0257659 A1* 9/2016 Sakamoto ............... G02B 5/30
2017/0306233 A1 10/2017 Horiguchi et al.
2017/0369783 A1 12/2017 Horiguchi et al.

FOREIGN PATENT DOCUMENTS

| JP | 2010096892 A * | 4/2010 |
|----|----------------|--------|
| JP | 2010-522892 A | 7/2010 |
| JP | 2013-509458 A | 3/2013 |
| JP | 2016-98258 A | 5/2016 |
| WO | 2012/147904 A1 | 11/2012 |
| WO | 2014/065243 A1 | 5/2014 |
| WO | 2015/064698 A1 | 5/2015 |
| WO | 2016/056542 A1 | 4/2016 |
| WO | 2016/104317 A1 | 6/2016 |

OTHER PUBLICATIONS

International Search Report dated Sep. 12, 2017, issued in counterpart International Application No. PCT/JP2017/025517 (3 pages).

\* cited by examiner

POLYMERIZABLE COMPOSITION AND OPTICALLY ANISOTROPIC BODY PRODUCED USING THE SAME

TECHNICAL FIELD

The present invention relates to a polymerizable composition suitable as a component of an optically anisotropic polymer or film required to have various optical properties; an optically anisotropic body, a phase retardation film, an optical compensation film, an antireflection film, a lens, and a lens sheet that are composed of the polymerizable composition; and a liquid crystal display element, an organic light-emitting display element, a lighting element, an optical component, a polarizing film, a coloring agent, a security marker, a laser emission member, a printed item, and the like that are produced using the polymerizable composition.

BACKGROUND ART

Compounds that include a polymerizable group (polymerizable compounds) are used in the production of various optical materials. For example, a polymer having uniform alignment can be produced by aligning a polymerizable composition including a polymerizable compound while the polymerizable composition is in a liquid crystal state and subsequently polymerizing the polymerizable composition. Such a polymer can be used for producing a polarizing plate, a phase retardation plate, and the like, which are necessary for displays. In many cases, such polymerizable compositions include two or more polymerizable compounds in order to meet the demands for optical properties, polymerization rate, solubility, melting point, glass-transition temperature, and the transparency, mechanical strength, surface hardness, heat resistance, and lightfastness of the polymer. In such a case, it is necessary that the polymerizable compounds impart suitable physical properties to the polymerizable composition without degrading the other properties of the polymerizable composition.

There has been a demand for phase retardation films having a small or reverse wavelength dispersion of birefringence in order to increase the viewing angles of liquid crystal displays. Accordingly, various polymerizable liquid crystal compounds having a reverse- or small-wavelength dispersion have been developed as a material for such phase retardation films. However, when such polymerizable compounds are added to a polymerizable composition, the polymerizable compounds may cause crystals to precipitate, that is, the polymerizable compounds may degrade the preservation stability of the polymerizable composition (PTL 1). Furthermore, when such polymerizable compositions are applied to a substrate and subsequently polymerized, inconsistencies are likely to be formed in the resulting coating film (PTL 1 to PTL 3). If a film having inconsistencies is used in the production of, for example, a display, nonuniformity in the brightness of the display and unnatural colors may occur, which significantly degrade the quality of the display. Therefore, the development of a polymerizable liquid crystal compound having a reverse- or small-wavelength dispersion, with which the above issues may be addressed, has been anticipated.

While we have been engaged in the development of a polymerizable liquid crystal compound having a reverse-wavelength dispersion (PTL 4), there has been a demand for the development of a polymerizable compound with which a polymer having a degree of hardness high enough to maintain the durability of the film at a sufficient level can be produced when the polymerizable compound is added to such a polymerizable composition and polymerized.

CITATION LIST

Patent Literature

PTL 1: Japanese Unexamined Patent Application Publication No. 2008-107767
PTL 2: Japanese Unexamined Patent Application Publication (Translation of PCT Application) No. 2010-522892
PTL 3: Japanese Unexamined Patent Application Publication (Translation of PCT Application) No. 2013-509458
PTL 4: WO2016/056542A1

SUMMARY OF INVENTION

Technical Problem

An object of the present invention is to provide a polymerizable composition with which a polymer having a high degree of hardness can be produced. Another object is to provide, for example, an optically anisotropic body, a phase retardation film, an optical compensation film, an antireflection film, a lens, and a lens sheet that are composed of the polymerizable composition and a liquid crystal display element, an organic light-emitting display element, a lighting element, an optical component, a coloring agent, a security marker, a laser emission member, a polarizing film, a coloring material, and a printed item that are produced using the polymerizable composition.

Solution to Problem

In order to achieve the above objects, the present invention conducted extensive studies while focusing on a polymerizable composition including a liquid crystal compound having a specific structure including a plurality of polymerizable groups and, consequently, made the present invention.

Specifically, the present invention provides a polymerizable composition including a polymerizable compound represented by General Formula (IA) which has a specific structure including a plurality of polymerizable groups.

The present invention also provides, for example, an optically anisotropic body, a phase retardation film, an optical compensation film, an antireflection film, a lens, and a lens sheet that are composed of the polymerizable composition and a liquid crystal display element, an organic light-emitting display element, a lighting element, an optical component, a coloring agent, a security marker, a laser emission member, and a printed item that are produced using the polymerizable composition.

Advantageous Effects of Invention

Since the polymerizable composition according to the present invention includes a liquid crystal compound having a specific structure including a plurality of polymerizable groups, the liquid crystal compound having a reverse-wavelength dispersion, the polymerizable composition can be formed into a polymer having a degree of hardness high enough to maintain the durability of the film at a sufficient degree.

DESCRIPTION OF EMBODIMENTS

The best mode of the polymerizable composition according to the present invention is described below. The term "liquid crystalline compound" used herein refers to a compound having a mesogenic skeleton; a liquid crystalline compound does not always exhibit a liquid crystal property by itself. The polymerizable composition can be polymerized into a polymer (i.e., a film) by being irradiated with light, such as ultraviolet radiation, or heated.

(Trifunctional Polymerizable Compound)

The polymerizable composition according to the present invention includes, as an essential component, a compound represented by General Formula (IA) which includes three polymerizable groups (i.e., a trifunctional polymerizable compound).

[Chem. 1]

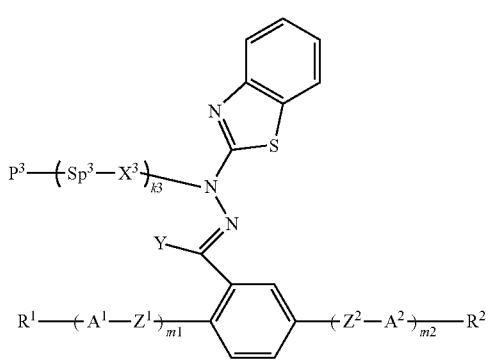

(IA)

In General Formula (IA), $P^3$ represents a polymerizable group; and $Sp^3$ represents a spacer group and, when a plurality of $Sp^3$ groups are present, they may be identical to or different from one another.

In General Formula (IA), $X^3$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^3$ groups are present, they may be identical to or different from one another ($P^3$-($Sp^3$-$X^3$)$_{k3}$— does not include an —O—O— linkage).

In General Formula (IA), k3 represents an integer of 1 to 10.

In General Formula (IA), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and the above groups may be optionally substituted with one or more L substituents; and L represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom, and, when a plurality of L substituents are present in the compound, they may be identical to or different from one another. In General Formula (IA), $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, when a plurality of $Z^1$ groups are present, they may be identical to or different from one another, and, when a plurality of $Z^2$ groups are present, they may be identical to or different from one another; and m1 and m2 each independently represent an integer of 0 to 6, and m1+m2 is an integer of 0 to 6.

In General Formula (IA), Y represents a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom.

In General Formula (IA), $R^1$ represents a group represented by $P^1$-($Sp^1$-$X^1$)$_{k1}$— (where, $P^1$ represents a polymerizable group; $Sp^1$ represents a spacer group and, when a plurality of $Sp^1$ groups are present, they may be identical to or different from one another; $X^1$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^1$ groups are present, they may be identical to or different from one another ($P^1$-($Sp^1$-$X^1$)$_{k1}$— does not include an —O—O— linkage); and k1 represents an integer of 0 to 10).

In General Formula (IA), $R^2$ represents a group represented by $P^2\text{-}(Sp^2\text{-}X^2)_{k2}$— (where, P represents a polymerizable group; $Sp^2$ represents a spacer group and, when a plurality of $Sp^2$ groups are present, they may be identical to or different from one another; $X^2$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of X groups are present, they may be identical to or different from one another ($P^2\text{-}(Sp^2\text{-}X^2)_{k2}$— does not include an —O—O— linkage); and k2 represents an integer of 0 to 10).

In General Formula (IA), $P^1$, $P^2$, and $P^3$ each independently represent a polymerizable group and preferably each independently represent a group selected from Formulae (P-1) to (P-19) below.

[Chem. 2]

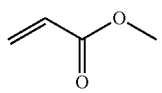
(P-1)

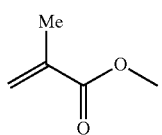
(P-2)

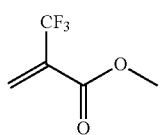
(P-3)

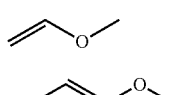
(P-4)

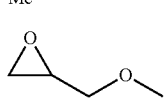
(P-5)

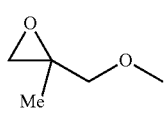
(P-6)

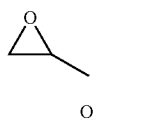
(P-7)

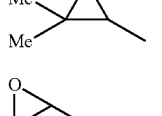
(P-8)

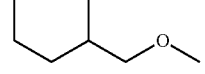
(P-9)

(P-10)

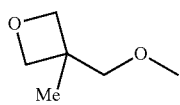
(P-11)

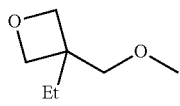
(P-12)

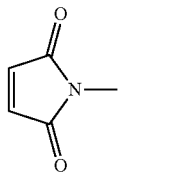
(P-13)

(P-14)

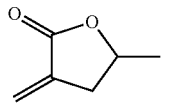
(P-15)

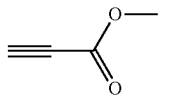
(P-16)

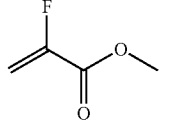
(P-17)

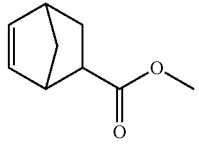
(P-18)

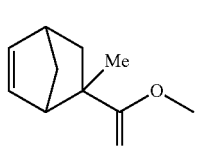
(P-19)

The above polymerizable groups undergo polymerization by radical polymerization, radical addition polymerization, cationic polymerization, or anionic polymerization. In particular, in the case where ultraviolet polymerization is performed, Formulae (P-1), (P-2), (P-3), (P-4), (P-6), (P-10), (P-12), (P-14), and (P-17) are preferable, Formulae (P-1), (P-2), (P-6), (P-10), and (P-12) are more preferable, Formulae (P-1), (P-2), and (P-3) are further preferable, and Formulae (P-1) and (P-2) are particularly preferable.

In General Formula (IA), $Sp^1$, $Sp^2$, and $Sp^3$ each independently represent a spacer group. When a plurality of $Sp^1$ groups, a plurality of $Sp^2$ groups, and/or a plurality of $Sp^3$ groups are present, they may be identical to or different from one another. In consideration of liquid crystal property, the availability of raw materials, and ease of synthesis, $Sp^1$, $Sp^2$, and $Sp^3$ preferably each independently represent an alkylene group having 1 to 20 carbon atoms in which one —CH$_2$— group or two or more —CH$_2$— groups that are not adjacent to one another may be each independently replaced with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C— and, when a plurality of Sp$^1$ groups, a plurality of Sp$^2$ groups, and/or a plurality of Sp$^3$ groups are present, they may be identical to or different from one another; more preferably each independently represent a linear alkylene group having 1 to 20 carbon atoms in which one —CH$_2$— group or two or more —CH$_2$— groups that are not adjacent to one another may be each independently replaced with —O—, —COO—, —OCO—, or —OCO—O— and, when a plurality of Sp$^1$ groups, a plurality of Sp$^2$ groups, and/or a plurality of Sp$^3$ groups are present, they may be identical to or different from one another; and further preferably each independently represent a linear alkylene group having 1 to 12 carbon atoms in which one —CH$_2$— group or two or more —CH$_2$— groups that are not adjacent to one another may be each independently replaced with —O— and, when a plurality of Sp$^1$ groups, a plurality of Sp$^2$ groups, and/or a plurality of Sp$^3$ groups are present, they may be identical to or different from one another. In consideration of liquid crystal property and solubility in solvents, it is particularly preferable that Sp$^1$ and Sp$^2$ each independently represent a linear alkylene group having 1 to 12 carbon atoms and Sp$^3$ represent a linear alkylene group having 1 to 12 carbon atoms in which one —CH$_2$— group or two or more —CH$_2$— groups that are not adjacent to one another may be each independently replaced with —O—.

In General Formula (IA), X$^1$, X$^2$, and X$^3$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond. When a plurality of X$^1$ groups, a plurality of X$^2$ groups, and/or a plurality of X$^3$ groups are present, they may be identical to or different from one another. In consideration of the availability of raw materials and ease of synthesis, X$^1$, X$^2$, and X$^3$ preferably each independently represent —O—, —S—, —OCH$_2$—, —CH$_2$O—, —COO—, —OCO—, —CO—S—, —S—CO—, —O—CO—O—, —COO—CH$_2$CH$_2$—, —OCO—CH$_2$CH$_2$—, —CH$_2$CH$_2$—COO—, —CH$_2$CH$_2$—OCO—, or a single bond and, when a plurality of X$^1$ groups, a plurality of X$^2$ groups, and/or a plurality of X$^3$ groups are present, they may be identical to or different from one another; and more preferably each independently represent —O—, —COO—, —OCO—, or a single bond. In consideration of ease of synthesis, it is particularly preferable that X$^1$ and X$^2$ represent —O— and X$^3$ represent a single bond.

In General Formula (IA), k1 and k2 each independently represent an integer of 0 to 10. In consideration of liquid crystal property and the availability of raw materials, k1 and k2 preferably each independently represent an integer of 0 to 3. In consideration of cure shrinkage that may occur when the composition is formed into a film, k1 and k2 more preferably each independently represent an integer of 1 to 3 and particularly preferably represent 1.

In General Formula (IA), k3 represents an integer of 1 to 10. In consideration of liquid crystal property and the availability of raw materials, k3 preferably represents an integer of 1 to 3. In consideration of cure shrinkage that may occur when the composition is formed into a film, k3 particularly preferably represents 1.

In General Formula (IA), the group included in the group represented by P$^3$-(Sp$^3$-X$^3$)$_{k3}$— which is directly bonded to the N atom is preferably —CH$_2$— in consideration of ease of synthesis.

In General Formula (IA), the group represented by P$^3$—(Sp$^1$-X$^3$)$_{k3}$— is preferably a group selected from Formulae (P3-1), (P3-2), and (P3-3) below in consideration of the temporal stability of phase retardation and reverse-wavelength dispersion and detachment that may be caused by a long period of ultraviolet radiation:

[Chem. 3]

   (P3-1)

   (P3-2)

   (P3-3)

(in Formulae (P3-1), (P3-2), and (P3-3), P$^3$ represents the same thing as in General Formula (IA); k3a represents an integer of 2 to 20; and k3b represents an integer of 1 to 6). In Formula (P3-1), k3a more preferably represents an integer of 2 to 12 and particularly preferably represents an integer of 2 to 8 in consideration of liquid crystal property. In Formulae (P3-2) and (P3-3), k3b more preferably represents an integer of 1 to 3 and particularly preferably represents an integer of 1 or 2 in consideration of liquid crystal property.

In General Formula (IA), A$^1$ and A$^z$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more L substituents. In consideration of ease of synthesis, the availability of raw materials, and liquid crystal property, A$^1$ and A$^2$ more preferably each independently represent a 1,4-phenylene group, a 1,4-cyclohexylene group, or a naphthalene-2,6-diyl group that may be optionally substituted with one or more L substituents; and further preferably each independently represent a group selected from Formulae (A-1) to (A-11) below.

[Chem. 4]

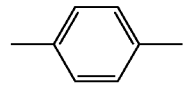   (A-1)

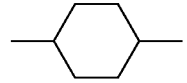   (A-2)

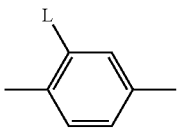
(A-3)

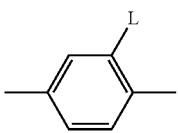
(A-4)

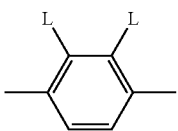
(A-5)

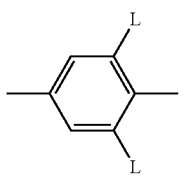
(A-6)

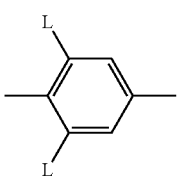
(A-7)

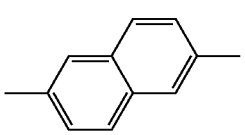
(A-8)

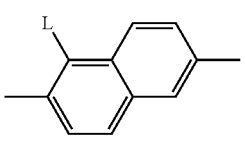
(A-9)

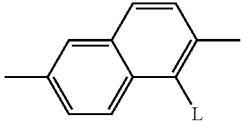
(A-10)

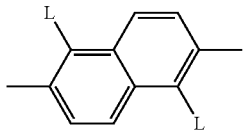
(A-11)

$A^1$ and $A^2$ much more preferably each independently represent a group selected from Formulae (A-1) to (A-8); and particularly preferably each independently represent a group selected from Formulae (A-1) to (A-4).

In General Formula (IA), L represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. In consideration of liquid crystal property and ease of synthesis, L preferably represents a fluorine atom, a chlorine atom, or a linear or branched alkyl group having 1 to 12 carbon atoms in which one —$CH_2$— group or two or more —$CH_2$— groups that are not adjacent to one another may be each independently replaced with a group selected from —O—, —COO—, and —OCO—, and a hydrogen atom may be replaced with a fluorine atom, and, when a plurality of L substituents are present, they may be identical to or different from one another; more preferably represents a fluorine atom, a chlorine atom, or a linear or branched alkyl or alkoxy group having 1 to 12 carbon atoms, in which a hydrogen atom may be replaced with a fluorine atom and, when a plurality of L substituents are present, they may be identical to or different from one another; further preferably represents a fluorine atom, a chlorine atom, or a linear alkyl or alkoxy group having 1 to 8 carbon atoms and, when a plurality of L substituents are present, they may be identical to or different from one another; and particularly preferably represents a fluorine atom, a chlorine atom, a methyl group, or a methoxy group and, when a plurality of L substituents are present, they may be identical to or different from one another. In General Formula (IA), $Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—, —N=CH—, —CH=N—N=CH—, —CF=CF—, —C≡C—, or a single bond. When a plurality of $Z^1$ groups are present, they may be identical to or different from one another. When a plurality of $Z^2$ groups are present, they may be identical to or different from one another. In consideration of liquid crystal property, the availability of raw materials, and ease of synthesis, $Z^1$ and $Z^2$ preferably each independently represent —$OCH_2$—, —$CH_2O$—, —COO—, —OCO—, —$CF_2O$—, —$OCF_2$—, —$CH_2CH_2$—, —$CF_2CF_2$—, —COO—$CH_2CH_2$—, —OCO—$CH_2CH_2$—, —$CH_2CH_2$—COO—, —$CH_2CH_2$—OCO—, or a single bond and, when a plurality of $Z^1$ groups and/or a plurality of $Z^2$ groups are present, they may be identical to or different from one another; more preferably each independently represent —$OCH_2$—, —$CH_2O$—, —COO—, —OCO—, —$CF_2O$—, —$OCF_2$—, or a single bond and, when a plurality of $Z^1$ groups and/or a plurality of $Z^2$ groups are present, they may be identical to or different from one another; and particularly preferably each independently represent —$OCH_2$—, —$CH_2O$—, —COO—, or —OCO— and, when a plurality of $Z^1$ groups and/or a plurality of $Z^2$ groups are present, they may be identical to or different from one another.

In General Formula (IA), m1 and m2 each independently represent an integer of 0 to 6, where m1+m2 is an integer of 0 to 6. In consideration of solubility in solvents, liquid crystal property, the temporal stability of phase retardation and reverse-wavelength dispersion, m1 and m2 preferably each independently represent an integer of 1 to 3, more preferably each independently represent 1 or 2, and particularly preferably represent 2.

In General Formula (IA), Y represents a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. In consideration of liquid crystal property and ease of synthesis, Y preferably represents a hydrogen atom, a fluorine atom, a chlorine atom, a nitro group, a cyano group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —S—, —CO—, —COO—, or —OCO—; more preferably represents a hydrogen atom or a linear or branched alkyl group having 1 to 12 carbon atoms in which a hydrogen atom may be replaced with a fluorine atom; further preferably represents a hydrogen atom or a linear alkyl group having 1 to 12 carbon atoms; and particularly preferably represents a hydrogen atom.

The compound represented by General Formula (IA) is preferably represented by General Formula (IA-i) below in consideration of the temporal stability of phase retardation and reverse-wavelength dispersion and resistance to detachment from a substrate which may be caused by ultraviolet radiation.

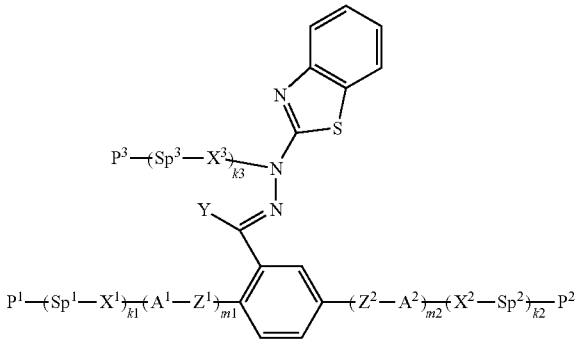

(in General Formula (IA-i), $P^1$, $P^2$, $P^3$, $Sp^1$, $Sp^2$, $Sp^3$, $X^1$, $X^2$, $X^3$, k1, k2, k3, $A^1$, $A^2$, $Z^1$, $Z^2$, m1, m2, and Y represent the same things as in General Formula (IA), and the preferable groups are the same as in General Formula (IA))

The compound represented by General Formula (IA) is more preferably represented by General Formula (IA-i-i) below:

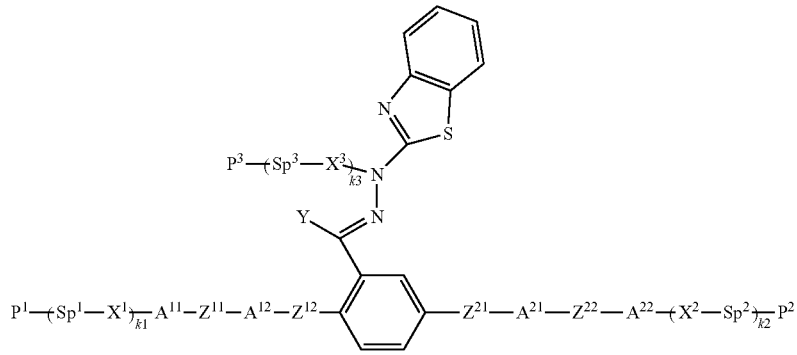

(in General Formula (IA-i-i), $P^1$, $P^2$, $P^3$, $Sp^1$, $Sp^2$, $Sp^3$, $X^1$, $X^2$, $X^3$, k1, k2, k3, and Y represent the same things as in General Formula (IA), and the preferable groups are the same as in General Formula (IA); $A^{11}$ and $A^{22}$ each independently represent a 1,4-phenylene group, a 1,4-cyclohexylene group, or a naphthalene-2,6-diyl group; $A^{12}$ and $A^{21}$ each independently represent a 1,4-phenylene group or a 1,4-cyclohexylene group; $Z^{11}$ and $Z^{22}$ each independently represent —$OCH_2$—, —$CH_2O$—, —$CH_2CH_2$—, —COO—, —OCO—, —$CF_2O$—, —$OCF_2$—, —CH=CH—COO—, —OCO—CH=CH—, or a single bond; and $Z^1$ and $Z^2$ each independently represent —$OCH_2$—, —$CH_2O$—, —$CH_2CH_2$—, —COO—, —OCO—, —$CF_2O$—, —$OCF_2$—, —COO—$CH_2CH_2$—, —OCO—$CH_2CH_2$—, —$CH_2CH_2$—COO—, —$CH_2CH_2$—OCO—, or a single bond).

The compound represented by General Formula (IA) is particularly preferably represented by General Formula (IA-i-i-i) below:

[Chem. 7]

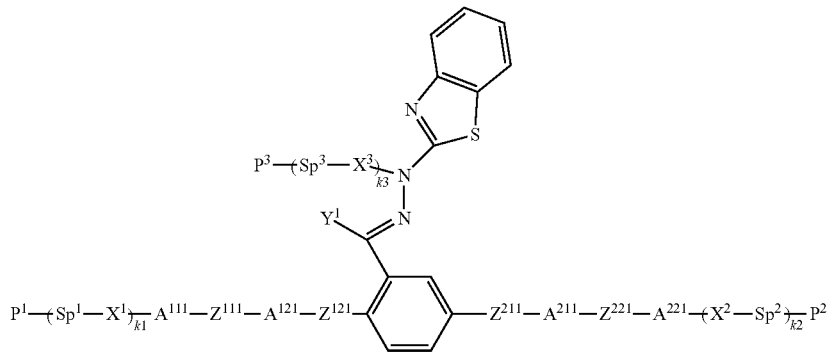

(IA-i-i-i)

(in General Formula (IA-i-i-i), $P^1$, $P^2$, $P^3$, $Sp^1$, $Sp^2$, $Sp^3$, $X^1$, $X^2$, $X^3$, k1, k2, and k3 represent the same things as in General Formula (IA), and the preferable groups are the same as in General Formula (IA); $A^{111}$ and $A^{221}$ represent a 1,4-phenylene group; $A^{121}$ and $A^{211}$ represent a 1,4-cyclohexylene group; $Z^{111}$ and $Z^{221}$ each independently represent —OCH$_2$—, —CH$_2$O—, —COO—, or —OCO—; $Z^1$1 and $Z^{21}$ each independently represent —OCH$_2$—, —CH$_2$O—, —COO—, or —OCO—; and $Y^1$ represents a hydrogen atom).

Specifically, the compound represented by General Formula (IA) is preferably selected from the compounds represented by Formulae (IA-1) to (IA-32) below.

[Chem. 8]

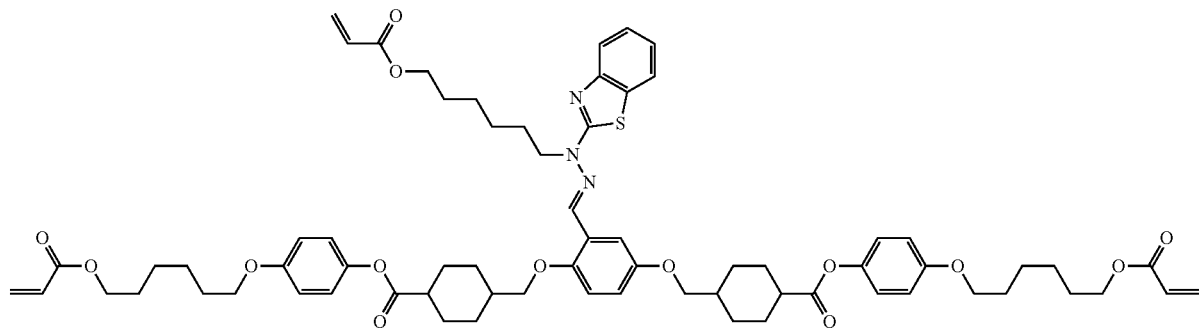

(IA-1)

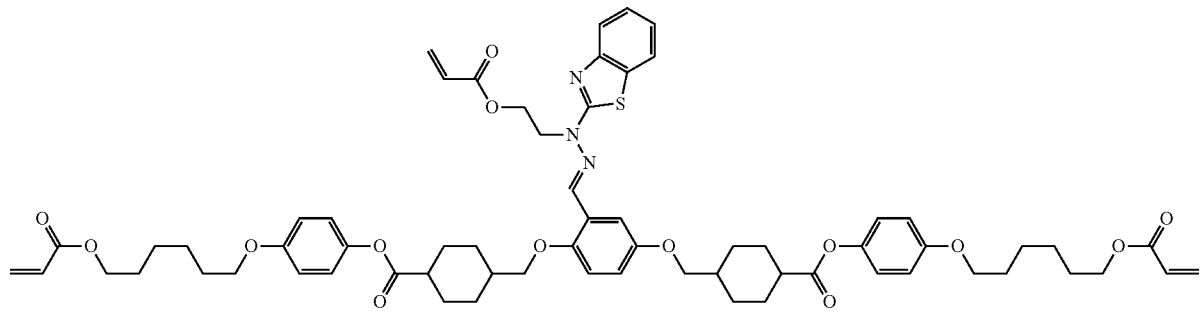

(IA-2)

-continued
(IA-3)
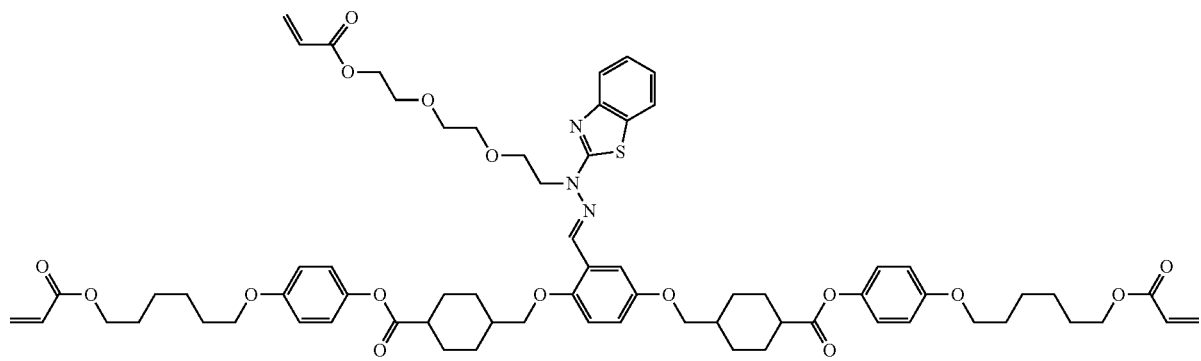
(IA-4)
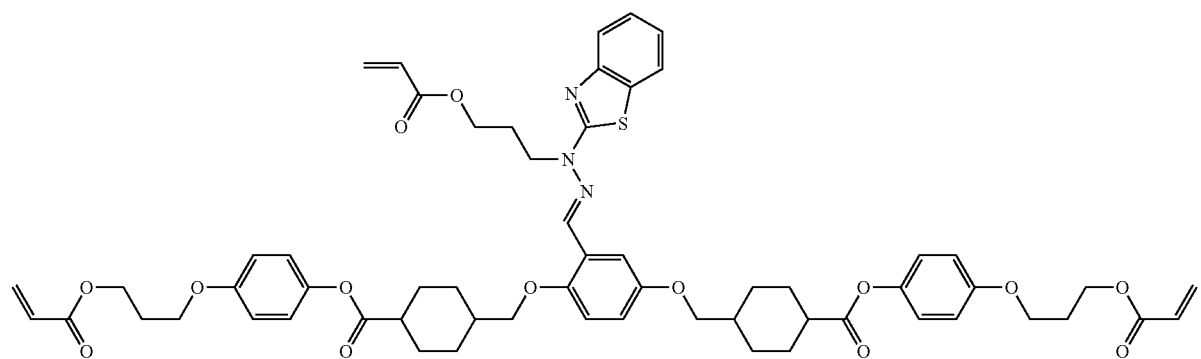
(IA-5)
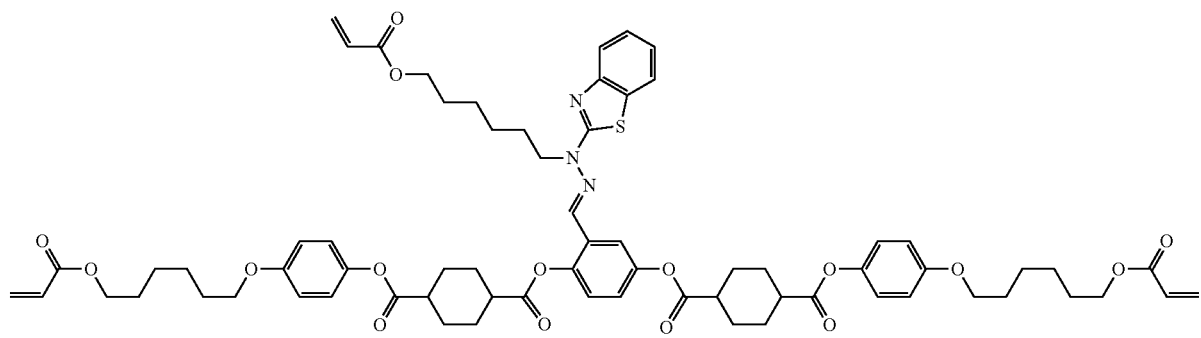

-continued
[Chem. 9]
(IA-6)
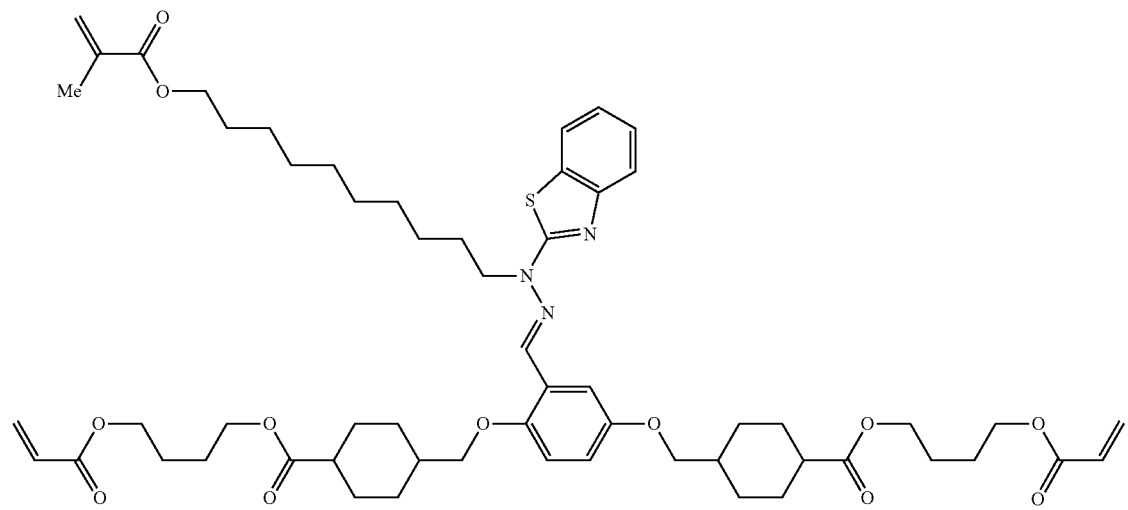
(IA-7)
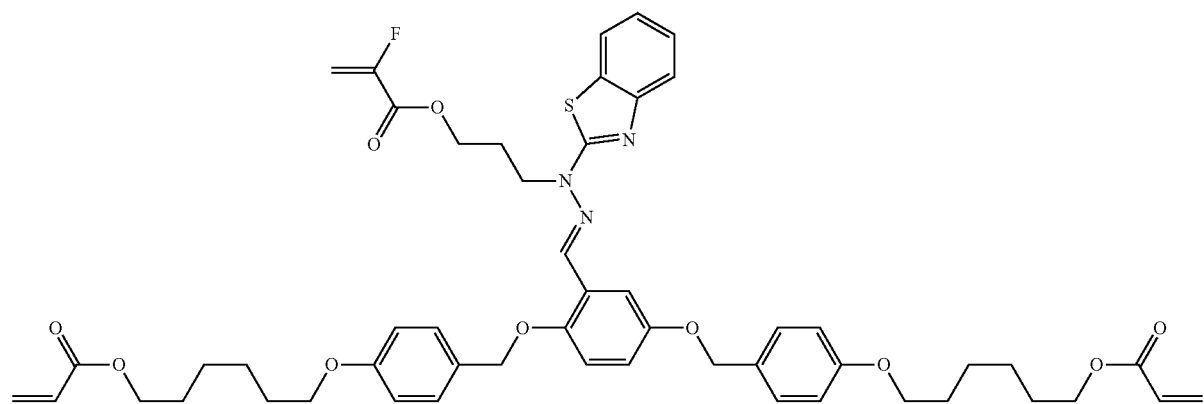
(IA-8)

-continued
(IA-9)
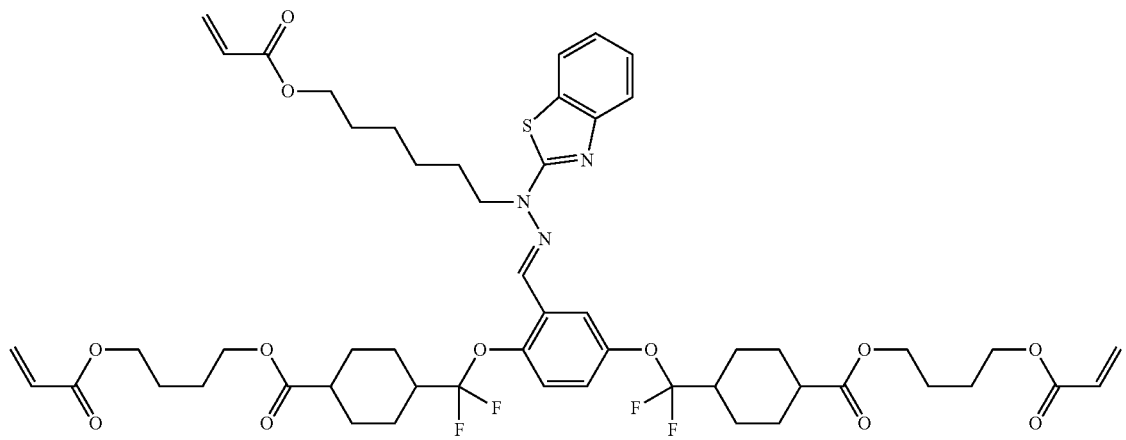
(IA-10)
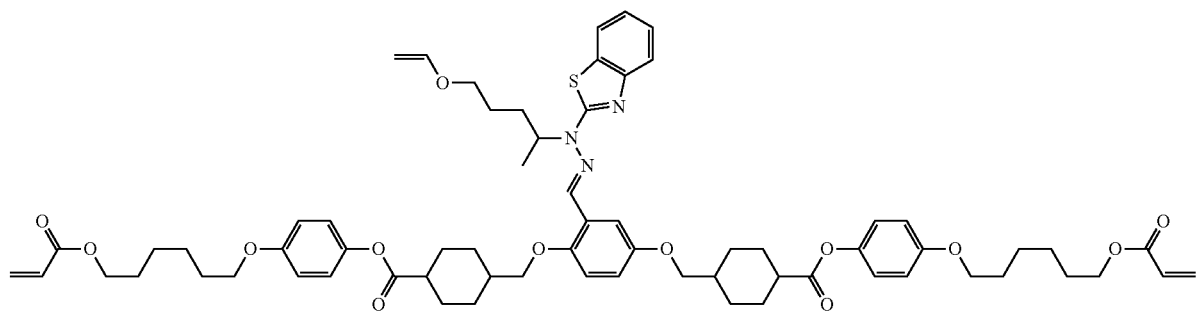
[Chem. 10]
(IA-11)
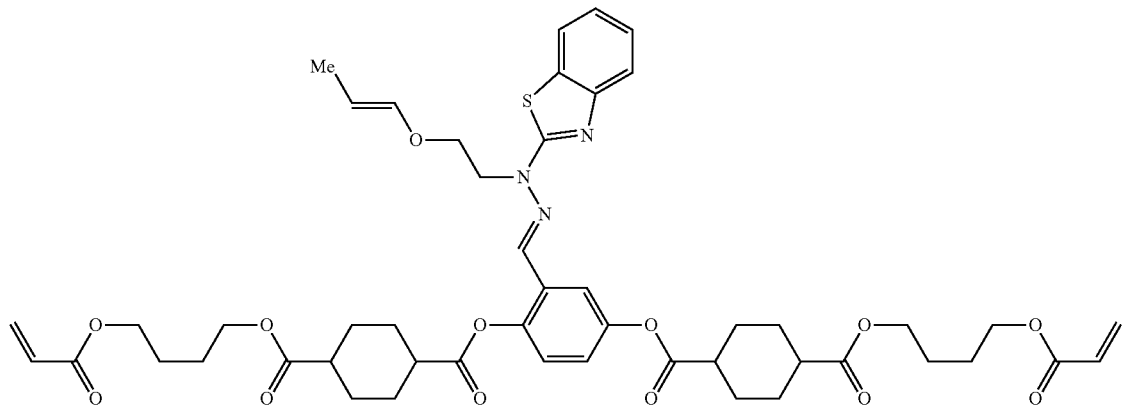

-continued
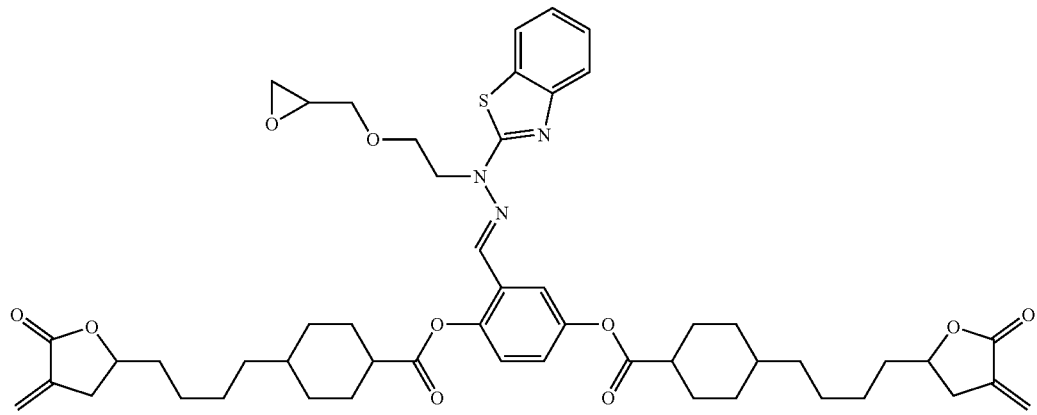
(IA-12)
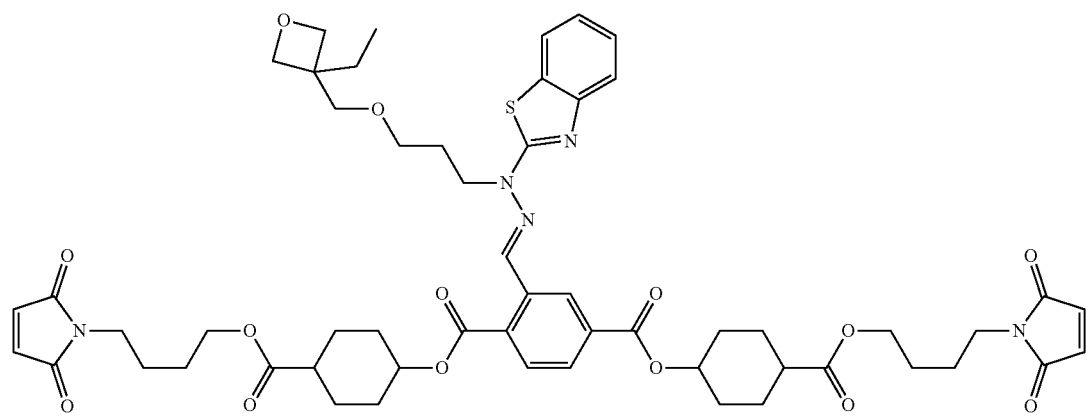
(IA-13)
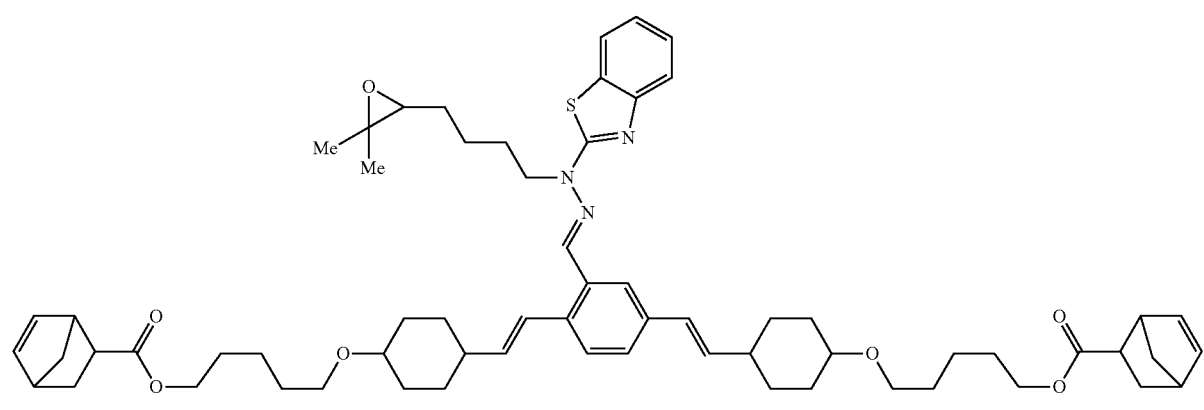
(IA-14)
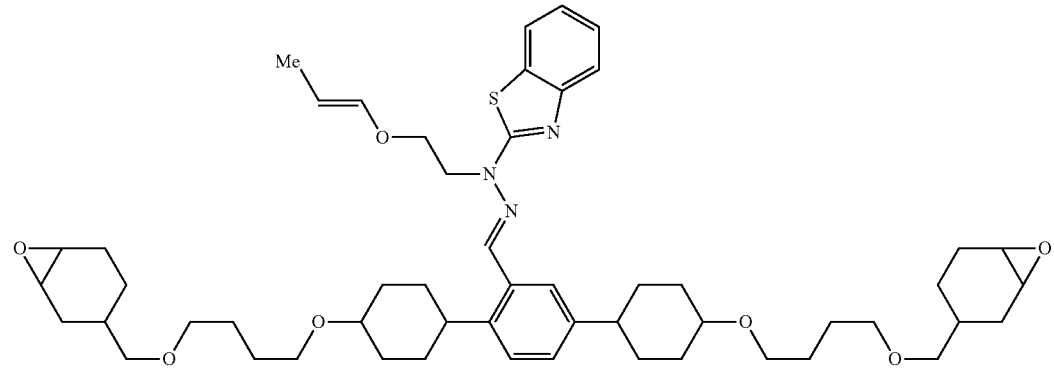
(IA-15)

-continued
[Chem. 11]
(IA-16)
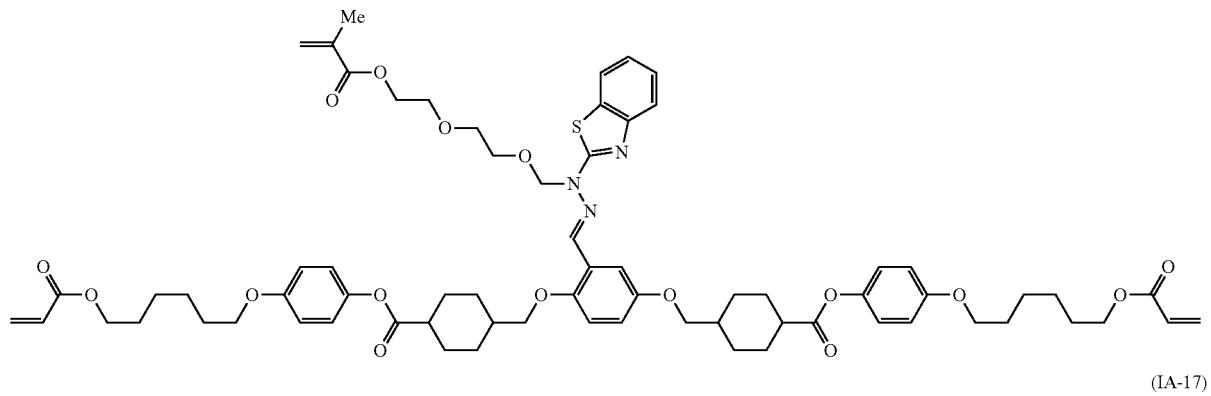
(IA-17)
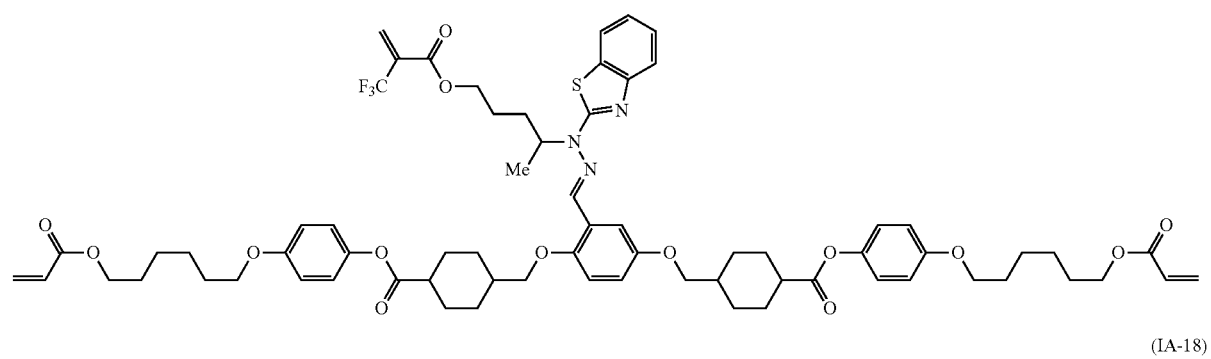
(IA-18)
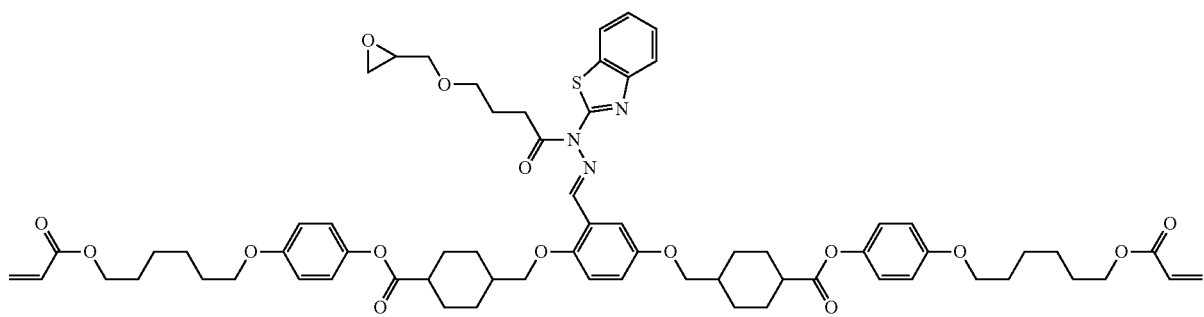
(IA-19)
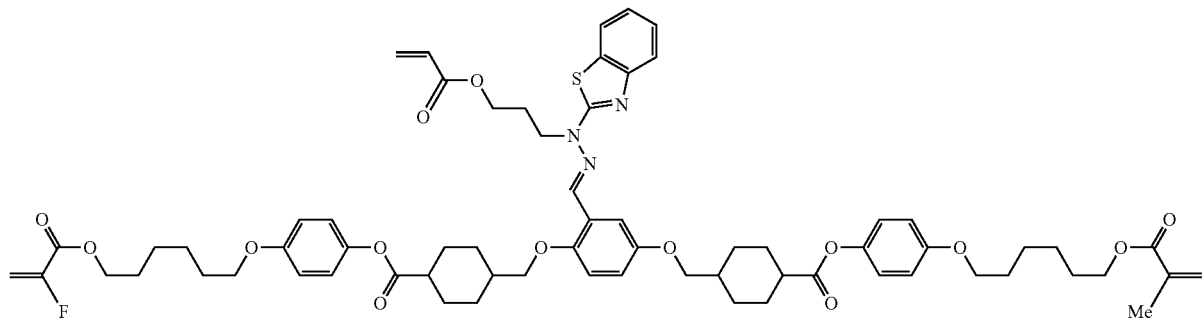

-continued
(IA-20)
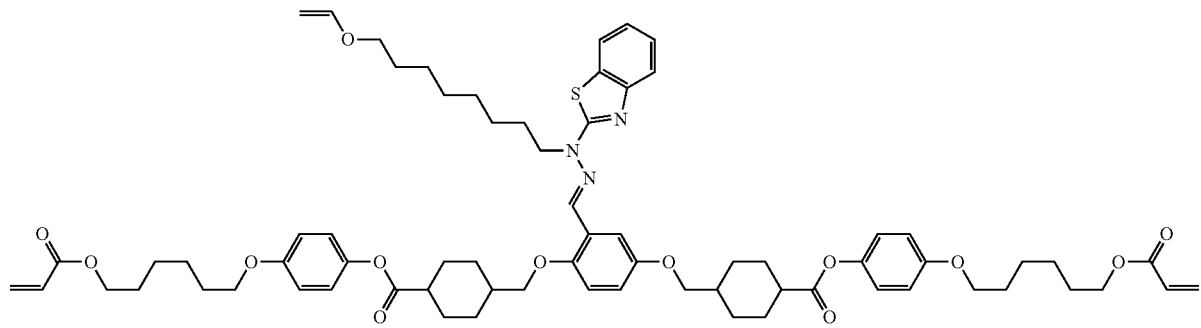
[Chem. 12]
(IA-21)
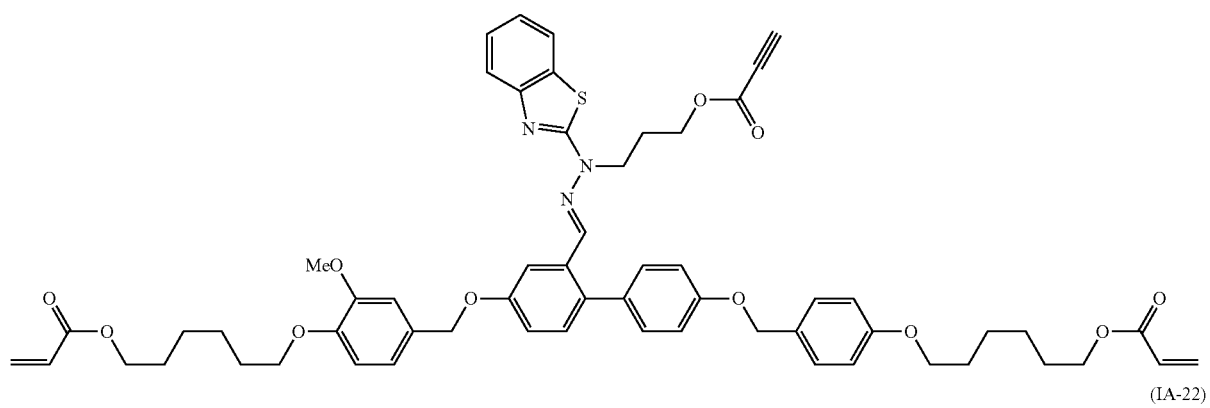
(IA-22)
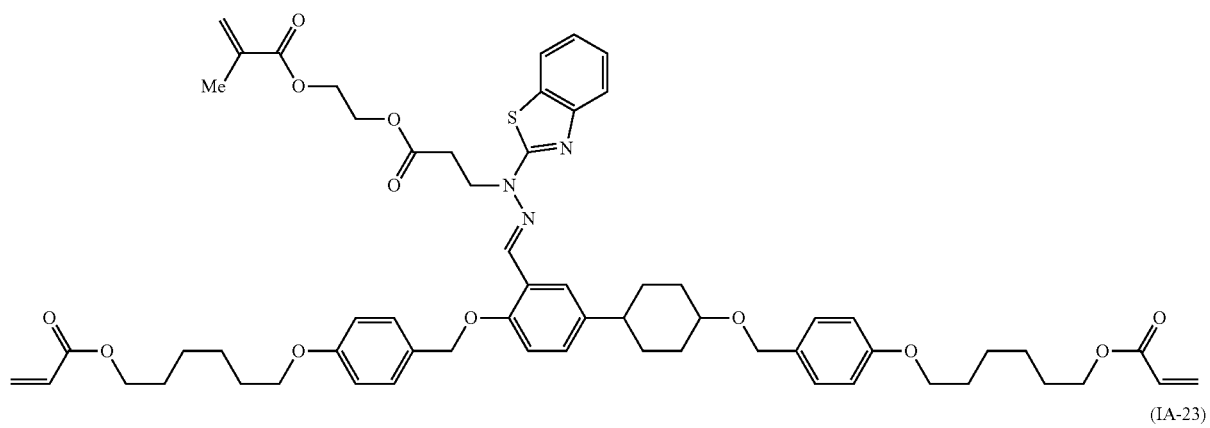
(IA-23)
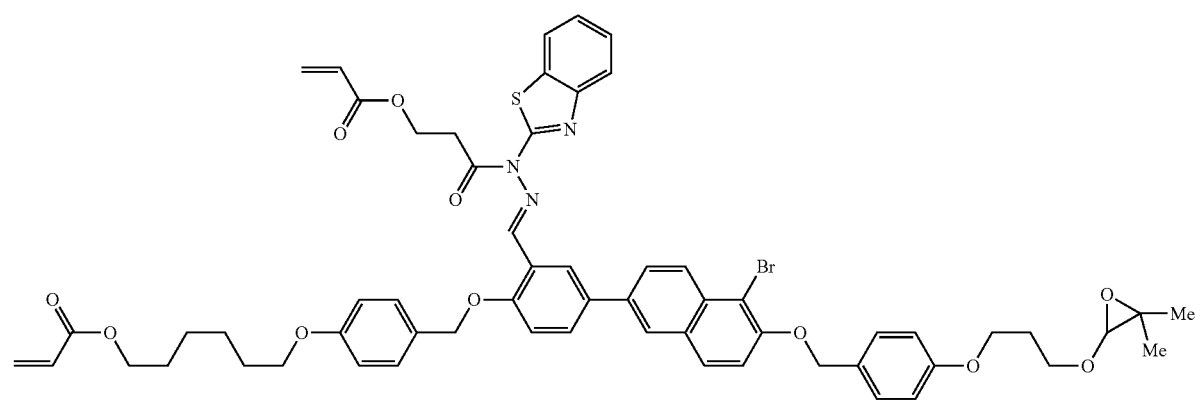

(IA-24)
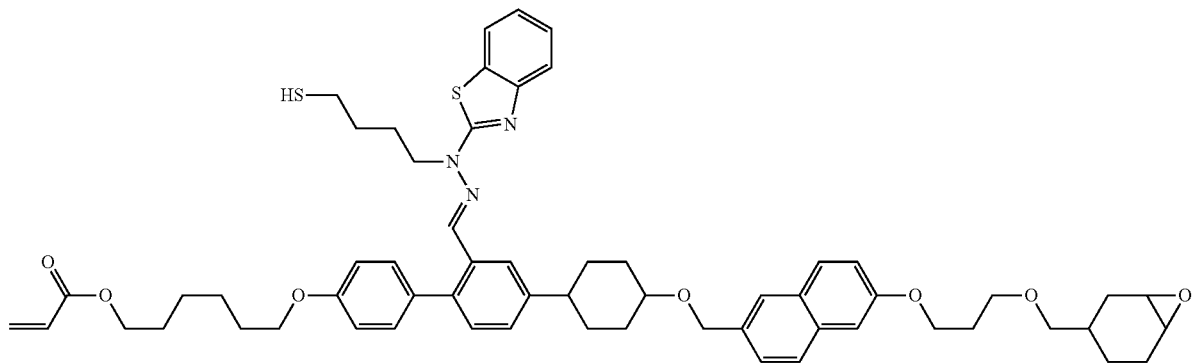
(IA-25)
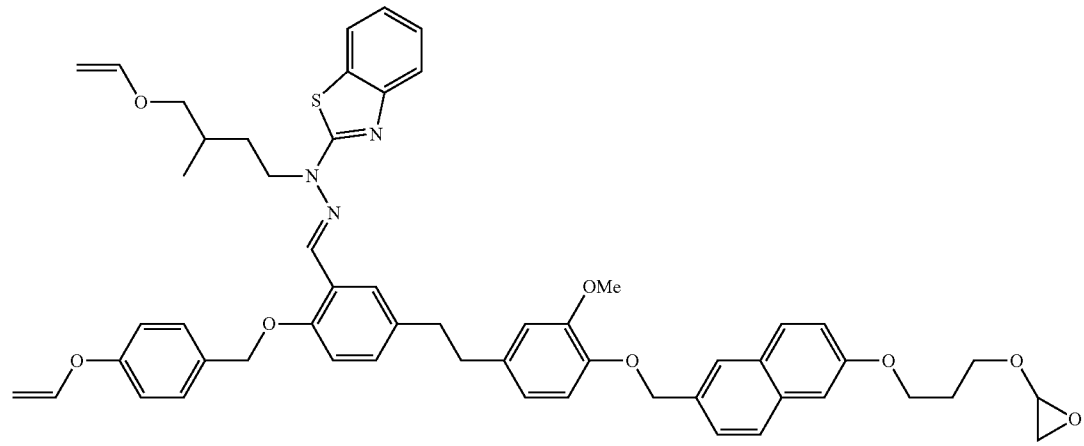
(IA-26)
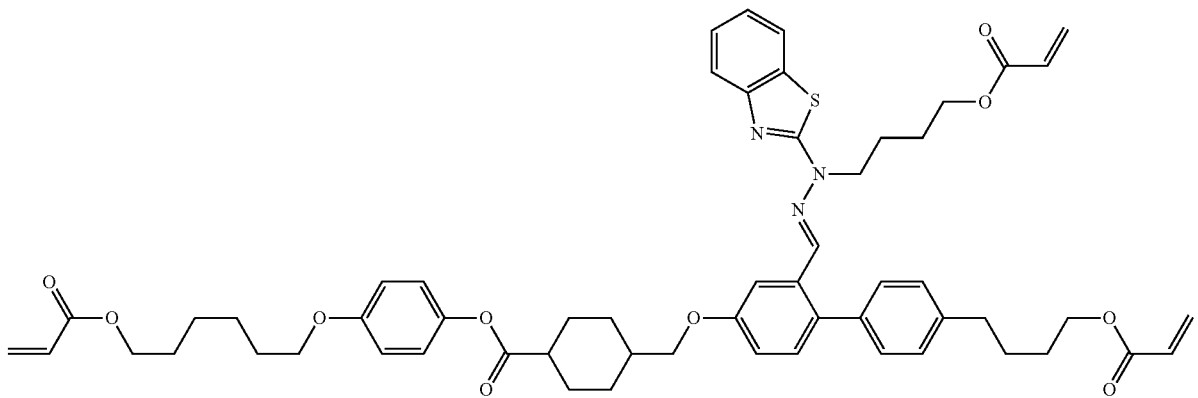

-continued
[Chem. 13]
(IA-27)
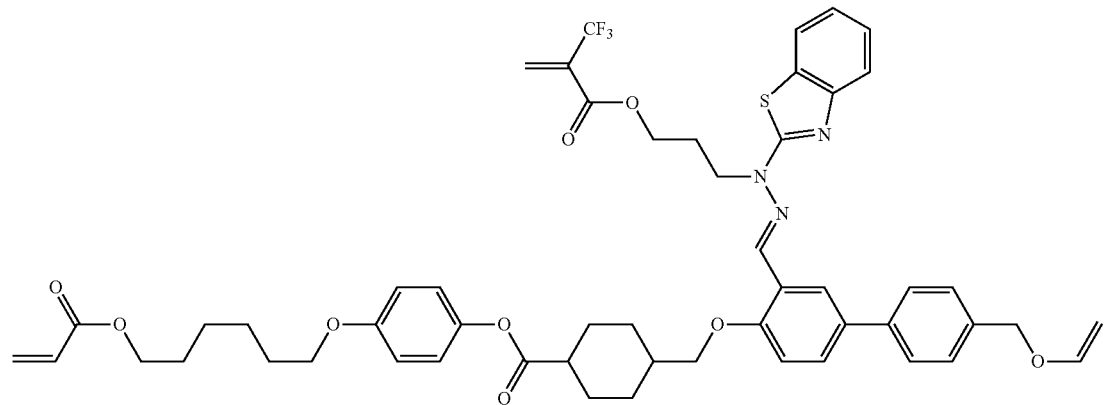
(IA-28)
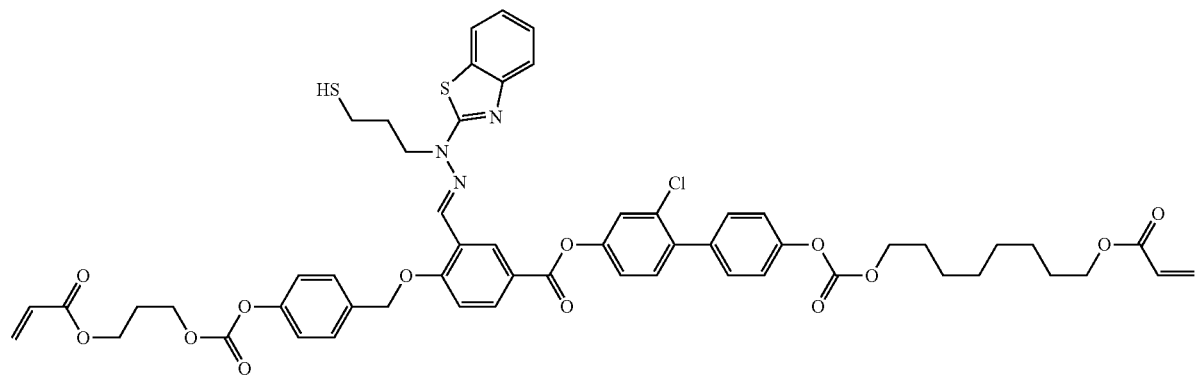
(IA-29)
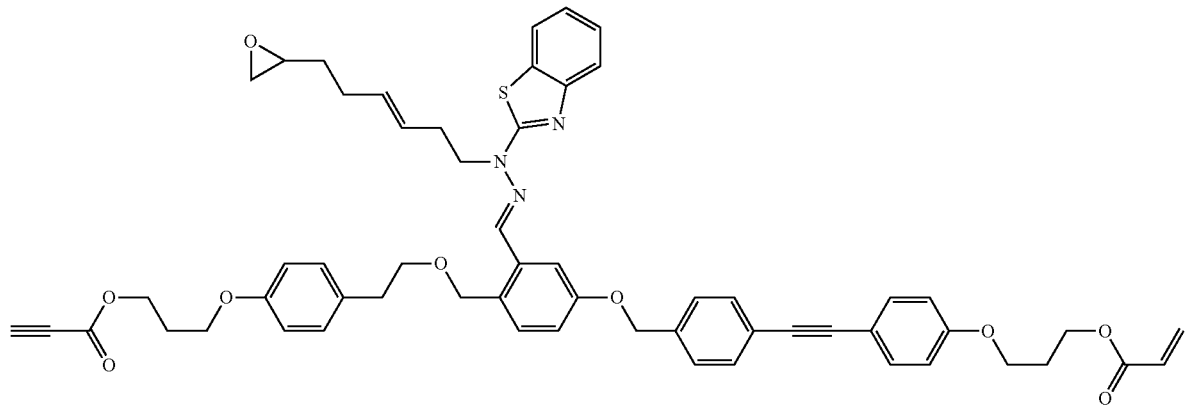

(IA-30)

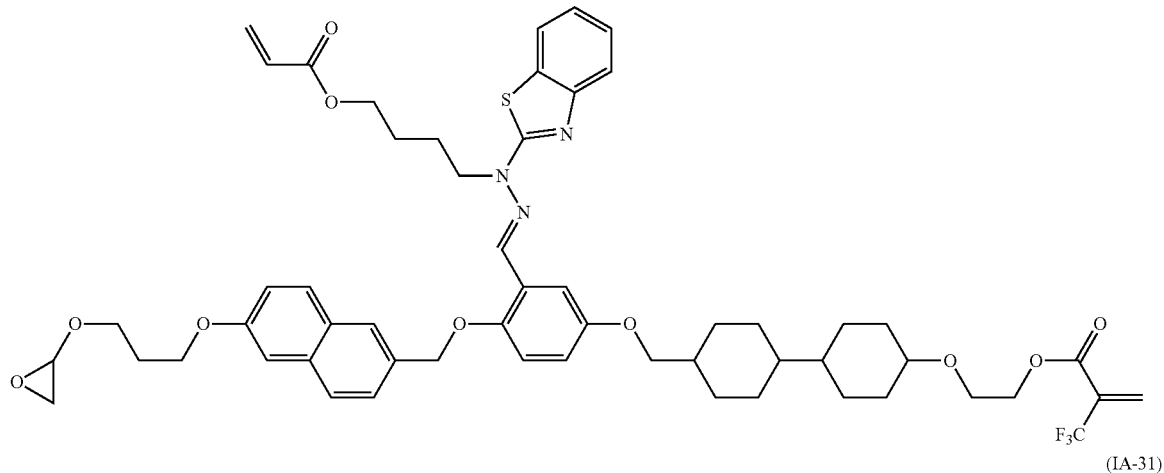

(IA-31)

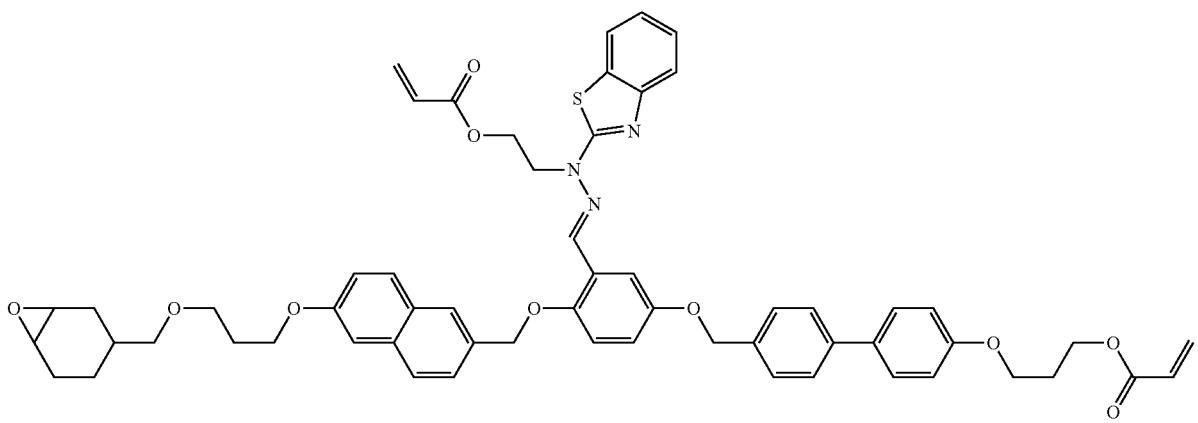

[Chem. 14]

(IA-32)

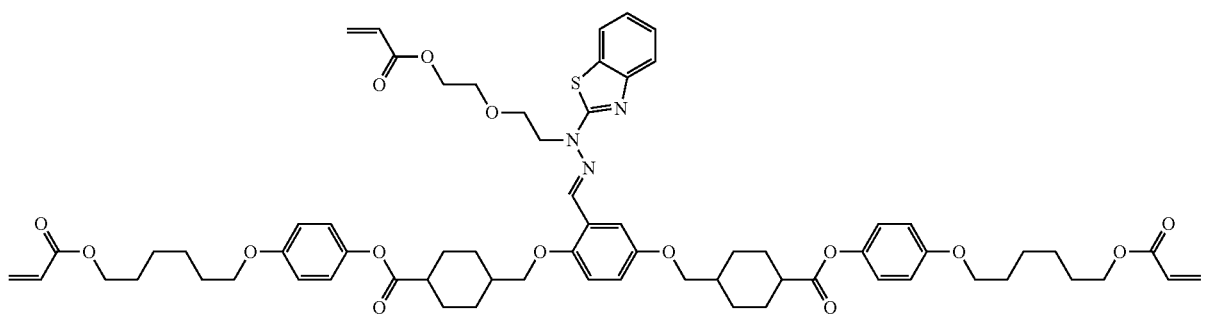

The total amount of the above trifunctional polymerizable compound is preferably 2% to 100% by mass, is more preferably 5% to 100% by mass, and is particularly preferably 5% to 100% by mass of the total amount of the polymerizable compounds included in the polymerizable composition.

In the case where primary importance is attached to the preservation stability of the polymerizable composition, the upper limit is preferably set to 95% by mass or less and is more preferably set to 90% by mass or less.

(Other Polymerizable Compounds)

The polymerizable composition according to the present invention preferably includes, in addition to the above-described trifunctional polymerizable compound, a polymerizable compound that includes one polymerizable group and has a reverse-wavelength dispersion (i.e., a reverse-wavelength dispersion monofunctional polymerizable compound) and/or a polymerizable compound that includes two polymerizable groups and has a reverse-wavelength dispersion (i.e., a reverse-wavelength dispersion difunctional polymerizable compound).

(Reverse-Wavelength Dispersion Monofunctional Polymerizable Compound)

The reverse-wavelength dispersion monofunctional polymerizable compound is preferably the polymerizable compound represented by General Formula (I-1):

[Chem. 15]

(1-1)

(in General Formula (I-1), $P^{11}$ represents a polymerizable group;
$S^{11}$ represents a spacer group or a single bond and, when a plurality of $S^{11}$ groups are present, they may be identical to or different from one another; $X^{11}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^{11}$ groups are present, they may be identical to or different from one another ($P^{11}$—($S^{11}$—$X^{11}$)$_{m11}$— does not include an —O—O— linkage);
$MG^{11}$ represents a mesogenic group; and
$R^{11}$ represents a hydrogen atom, a fluorine atom, a chlorine atom, a bromine atom, an iodine atom, a pentafluorosulfanyl group, a cyano group, a nitro group, an isocyano group, a thioisocyano group, or an alkyl group having 1 to 20 carbon atoms, the alkyl group may be linear or branched, a hydrogen atom included in the alkyl group may be replaced with a fluorine atom, and, in the alkyl group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—).

In General Formula (I-1), the mesogenic group $MG^{11}$ represents Formula (1-a):

[Chem. 16]

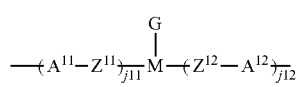

(1-a)

(in Formula (1-a), $A^{11}$ and $A^{12}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^1$ substituents, and, when a plurality of $A^{11}$ groups and/or a plurality of $A^{12}$ groups are present, they may be identical to or different from one another;
$Z^{11}$ and $Z^{12}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, and, when a plurality of $Z^{11}$ groups and/or a plurality of $Z^{12}$ groups are present, they may be identical to or different from one another;

M represents a group selected from Formulae (M-1) to (M-11) below:

[Chem. 17]

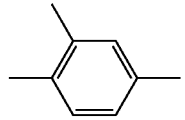

(M-1)

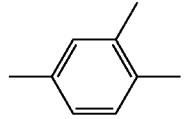

(M-2)

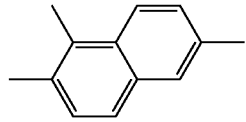

(M-3)

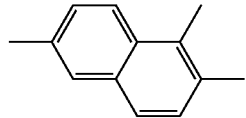

(M-4)

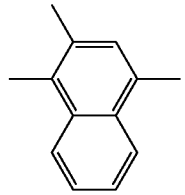

(M-5)

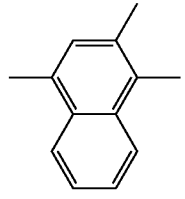

(M-6)

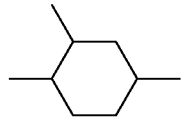

(M-7)

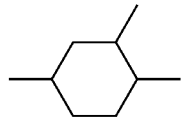

(M-8)

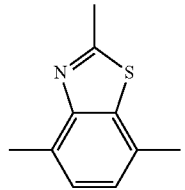

(M-9)

-continued

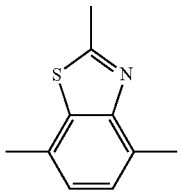
(M-10)

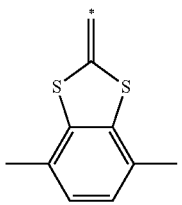
(M-11)

the above groups may be optionally substituted with one or more L¹ substituents; and
G is selected from Formulae (G-1) to (G-6) below:

[Chem. 18]

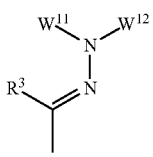
(G-1)

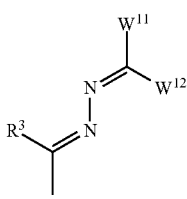
(G-2)

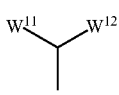
(G-3)

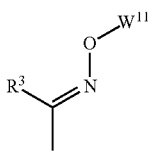
(G-4)

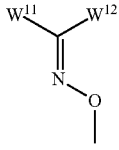
(G-5)

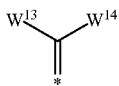
(G-6)

(in Formulae (G-1) to (G-6), $R^3$ represents a hydrogen atom or an alkyl group having 1 to 20 carbon atoms, the alkyl group may be linear or branched, a hydrogen atom included in the alkyl group may be replaced with a fluorine atom, and, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

$W^{11}$ represents a group having 5 to 30 carbon atoms, the group including at least one aromatic group, and the group may be optionally substituted with one or more $L^1$ substituents;

$W^{12}$ represents a hydrogen atom or an alkyl group having 1 to 20 carbon atoms, the alkyl group may be linear or branched, a hydrogen atom included in the alkyl group may be replaced with a fluorine atom and/or an —OH group, and, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, $W^{12}$ may represent the same thing as $W^{11}$, and $W^{11}$ and $W^{12}$ may be bonded to each other to form a ring structure;

$W^{13}$ and $W^{14}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms and, in the alkyl group, the cycloalkyl group, the alkenyl group, the cycloalkenyl group, the alkoxy group, the acyloxy group, and the alkylcarbonyloxy group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

when M is selected from Formulae (M-1) to (M-10), G is selected from Formulae (G-1) to (G-5) and, when M is Formula (M-11), G represents Formula (G-6);

$L^1$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms, the alkyl group may be linear or branched, a hydrogen atom may be replaced with a fluorine atom, and, in the alkyl group, one —$CH_2$— group or two or more —$CH_2$— groups that are not adjacent to one another may be each independently replaced with a group selected from —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—; and m11 represents an integer of 0 to 8, j11 represents an integer of 0 to 5, j12 represents an integer of 1 to 5, and j11+j12 is an integer of 1 to 5).

In General Formula (1-1), the polymerizable group $P^{11}$ preferably represents a group selected from Formulae (P-1) to (P-20) below.

[Chem. 19]

(P-1) 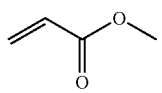
(P-2) 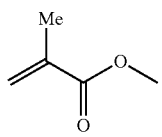
(P-3) 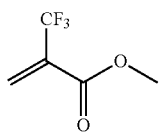
(P-4) 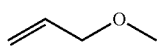
(P-5) 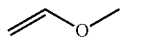
(P-6) 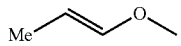
(P-7) 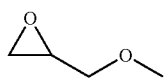
(P-8) 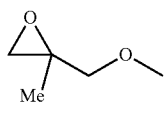
(P-9) 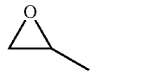
(P-10) 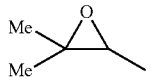
(P-11) 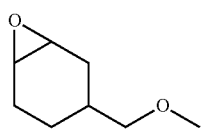
(P-12) 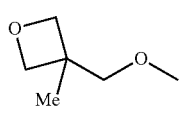
(P-13) 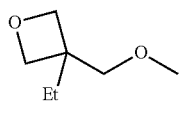
(P-14) 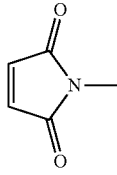
(P-15) HS—

-continued (P-16) 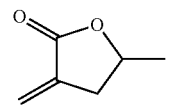
(P-17) 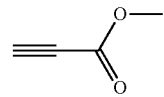
(P-18) 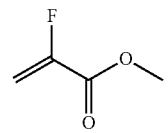
(P-19) 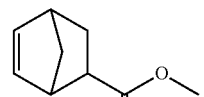
(P-20) 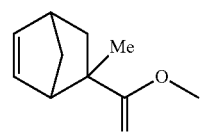

The above polymerizable groups undergo polymerization by radical polymerization, radical addition polymerization, cationic polymerization, or anionic polymerization. In particular, in the case where ultraviolet polymerization is performed, Formulae (P-1), (P-2), (P-3), (P-4), (P-5), (P-7), (P-11), (P-13), (P-15), and (P-18) are preferable; Formulae (P-1), (P-2), (P-7), (P-11), and (P-13) are more preferable; Formulae (P-1), (P-2), and (P-3) are further preferable; and Formulae (P-1) and (P-2) are particularly preferable.

In General Formula (1-1), $S^{11}$ represents a spacer group or a single bond. When a plurality of $S^{11}$ groups are present, they may be identical to or different from one another. The spacer group is preferably an alkylene group having 1 to 20 carbon atoms in which one —CH$_2$— group or two or more —CH$_2$— groups that are not adjacent to one another may be each independently replaced with —O—, —COO—, —OCO—, —OCO—O—, —CO—NH—, —NH—CO—, —CH=CH—, or —C≡C—. In consideration of the availability of raw materials and ease of synthesis, $S^{11}$ more preferably each independently represents an alkylene group having 1 to 10 carbon atoms in which one —CH$_2$— group or two or more —CH$_2$— groups that are not adjacent to one another may be each independently replaced with —O—, —COO—, or —OCO— or a single bond and, when a plurality of $S^{11}$ groups are present, they may be identical to or different from one another; further preferably each independently represents an alkylene group having 1 to 10 carbon atoms or a single bond; and particularly preferably represents an alkylene group having 1 to 8 carbon atoms and, when a plurality of $S^{11}$ groups are present, they may be identical to or different from one another.

In General Formula (1-1), $X^{11}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—

—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond. When a plurality of $X^{11}$ groups are present, they may be identical to or different from one another ($P^{11}$—($S^{11}$—$X^{11}$)$_{m11}$— does not include an —O—O— linkage). In consideration of the availability of raw materials and ease of synthesis, $X^{11}$ preferably each independently represents —O—, —S—, —OCH₂—, —CH₂O—, —COO—, —OCO—, —CO—S—, —S—CO—, —O—CO—O—, —CO—NH—, —NH—CO—, —COO—CH₂CH₂—, —OCO—CH₂CH₂—, —CH₂CH₂—COO—, —CH₂CH₂—OCO—, or a single bond and, when a plurality of $X^{11}$ groups are present, they may be identical to or different from one another; more preferably each independently represents —O—, —OCH₂—, —CH₂O—, —COO—, —OCO—, —COO—CH₂CH₂—, —OCO—CH₂CH₂—, —CH₂CH₂—COO—, —CH₂CH₂—OCO—, or a single bond; and particularly preferably each independently represents —O—, —COO—, —OCO—, or a single bond and, when a plurality of $X^{11}$ groups are present, they may be identical to or different from one another.

In General Formula (1-1), $A^{11}$ and $A^{12}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more L substituents. When a plurality of $A^{11}$ groups and/or a plurality of $A^{12}$ groups are present, they may be identical to or different from one another. In consideration of the availability of raw materials and ease of synthesis, $A^{11}$ and $A^{12}$ preferably each independently represent a 1,4-phenylene group, a 1,4-cyclohexylene group, or a naphthalene-2,6-diyl that may be optionally substituted with one or more $L^1$ substituents; and more preferably each independently represent a group selected from Formulae (A-1) to (A-11) below.

[Chem. 20]

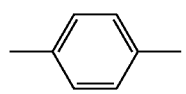
(A-1)

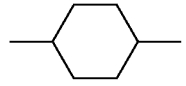
(A-2)

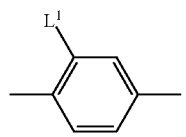
(A-3)

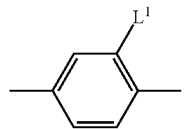
(A-4)

-continued

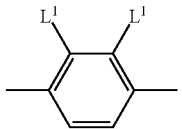
(A-5)

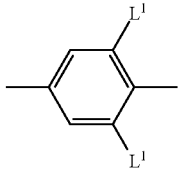
(A-6)

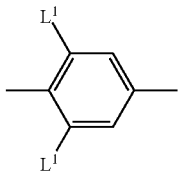
(A-7)

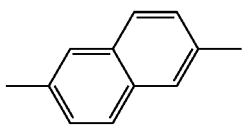
(A-8)

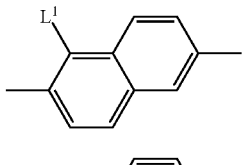
(A-9)

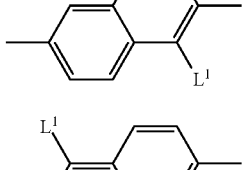
(A-10)

(A-11)

$A^{11}$ and $A^{12}$ further preferably each independently represent a group selected from Formulae (A-1) to (A-8) and particularly preferably each independently represent a group selected from Formulae (A-1) to (A-4).

In General Formula (1-1), $Z^{11}$ and $Z^{12}$ each independently represent —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—, —N=CH—, —CH=N—N=CH—, —CF=CF—, —C≡C—, or a single bond. When a plurality of $Z^{11}$ groups and/or a plurality of $Z^{12}$ groups are present, they may be identical to or different from one another. In consideration of the liquid crystal property of the compound, the availability of raw materials, and ease of synthesis, $Z^{11}$ and $Z^{12}$ preferably each independently represent, —OCH$_2$—, —CH$_2$O—, —COO—, —OCO—, —CF$_2$O—, —OCF$_2$—, —CH$_2$CH$_2$—, —CF$_2$CF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —CH═CH—, —CF═CF—, —C≡C—, or a single bond; more preferably each independently represent —OCH$_2$—, —CH$_2$O—, —CH$_2$CH$_2$—, —COO—, —OCO—, —COO—CH$_2$CH—, —OCO—CH$_2$CH$_2$—, —CH$_2$CH$_2$—COO—, —CH$_2$CH$_2$—OCO—, —CH═CH—, —C≡C—, or a single bond; further preferably each independently represent —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond; and particularly preferably each independently represent —CH$_2$CH$_2$—, —COO—, —OCO—, or a single bond.

In General Formula (1-1), M represents a group selected from Formulae (M-1) to (M-11) below.

[Chem. 21]

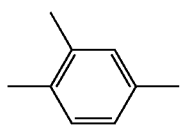
(M-1)

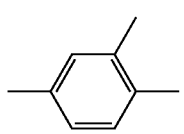
(M-2)

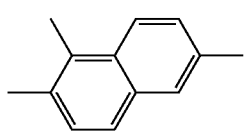
(M-3)

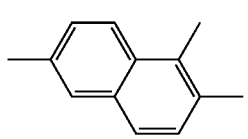
(M-4)

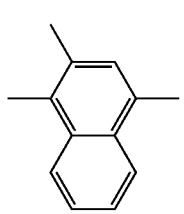
(M-5)

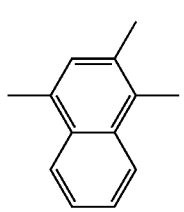
(M-6)

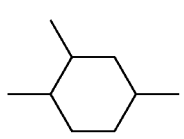
(M-7)

-continued

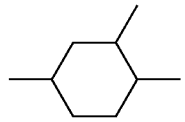
(M-8)

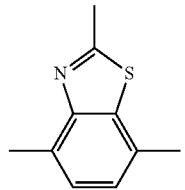
(M-9)

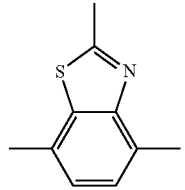
(M-10)

(M-11)

The above groups may be optionally substituted with one or more $L^1$ substituents. In consideration of the availability of raw materials and ease of synthesis, M preferably each independently represents Formula (M-1) or (M-2) that may be optionally substituted with one or more L substituents or a group selected from Formulae (M-3) to (M-6) which is not substituted; more preferably represents a group selected from Formulae (M-1) and (M-2) which may be optionally substituted with one or more $L^1$ substituents; and particularly preferably represents a group selected from Formulae (M-1) and (M-2) which is not substituted.

In General Formula (1-1), $R^{11}$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom. In consideration of liquid crystal property and ease of synthesis, $R^{11}$ preferably represents a hydrogen atom, a fluorine atom, a chlorine atom, a cyano group, or a linear or branched alkyl group having 1 to 12 carbon atoms in which one —CH$_2$— group or two or more —CH$_2$— groups that are not adjacent to one another may be each independently replaced with —O—, —COO—, —OCO—, or —O—CO—O—; more preferably represents a hydrogen atom, a fluorine atom, a chlorine atom, a cyano group, or a linear alkyl or alkoxy group having 1 to 12 carbon atoms; and particularly preferably represents a linear alkyl or alkoxy group having 1 to 12 carbon atoms.

In General Formula (1-1), G represents a group selected from Formulae (G-1) to (G-6) below.

[Chem. 22]

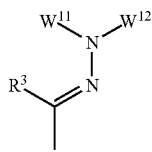
(G-1)

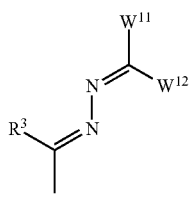
(G-2)

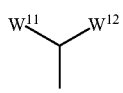
(G-3)

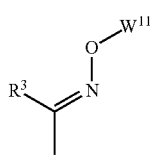
(G-4)

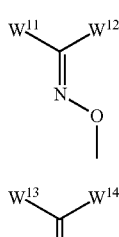
(G-5)

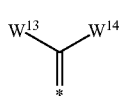
(G-6)

In Formulae (G-1) to (G-6), $R^3$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom.

$W^{11}$ represents a group having 5 to 30 carbon atoms, the group including at least one aromatic group, and the group may be optionally substituted with one or more $L^1$ substituents.

$W^{12}$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom and/or an —OH group. $W^{12}$ may represent the same thing as $W^{11}$. $W^{11}$ and $W^{12}$ may be bonded to each other to form a ring structure.

$W^{13}$ and $W^{14}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms. In the alkyl group, the cycloalkyl group, the alkenyl group, the cycloalkenyl group, the alkoxy group, the acyloxy group, and the alkylcarbonyloxy group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—.

$L^1$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms. The alkyl group may be linear or branched. A hydrogen atom may be replaced with a fluorine atom. In the alkyl group, one —$CH_2$— group or two or more —$CH_2$— groups that are not adjacent to one another may be each independently replaced with a group selected from —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—. When a plurality of $L^1$ substituents are present in the compound, they may be identical to or different from one another.

$R^3$ each independently represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom. In consideration of liquid crystal property and ease of synthesis, $R^3$ preferably represents a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with —O—, —COO—, or —OCO—; more preferably represents a linear or branched alkyl group having 1 to 12 carbon atoms in which a hydrogen atom may be replaced with a fluorine atom; and particularly preferably represents a linear alkyl group having 1 to 12 carbon atoms.

$W^{11}$ represents a group having 5 to 30 carbon atoms, the group including at least one aromatic group. The group may be optionally substituted with one or more $L^1$ substituents. The aromatic group included in $W^{11}$ may be an aromatic hydrocarbon group, an aromatic hetero group, or a group including an aromatic hydrocarbon group and an aromatic hetero group. The above aromatic groups may be bonded to one another with a single bond or a linking group or may form a condensed ring. $W^{11}$ may further include, in addition to an aromatic group, an acyclic structure and/or a cyclic structure other than an aromatic group. In consideration of the availability of raw materials and ease of synthesis, the aromatic group included in $W^{11}$ preferably represents a chemical structure selected from Formulae (W-1) to (W-19) below which may be optionally substituted with one or more $L^1$ substituents.

[Chem. 23]

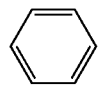 (W-1)

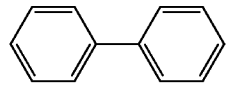 (W-2)

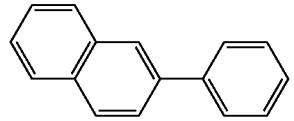 (W-3)

 (W-4)

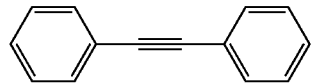 (W-5)

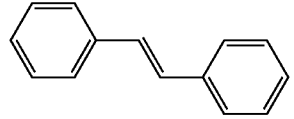 (W-6)

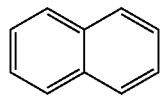 (W-7)

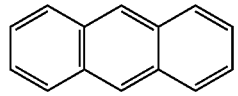 (W-8)

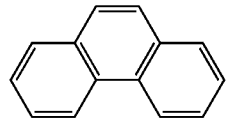 (W-9)

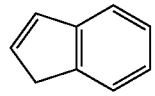 (W-10)

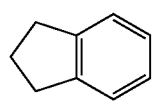 (W-11)

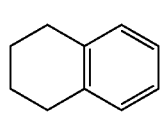 (W-12)

-continued

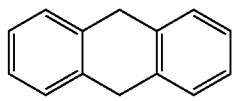 (W-13)

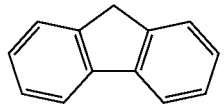 (W-14)

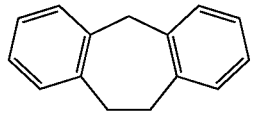 (W-15)

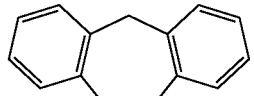 (W-16)

 (W-17)

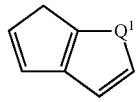 (W-18)

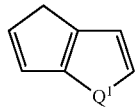 (W-19)

(in Formulae (W-1) to (W-19), the above groups may have a bond at any position; two or more aromatic groups selected from the above groups may be connected to one another with a single bond to form another group; and $Q^1$ represents —O—, —S—, —NR$^4$— (where R$^4$ represents a hydrogen atom or an alkyl group having 1 to 8 carbon atoms), or —CO—, in the above aromatic groups, —CH═ groups may be each independently replaced with —N═, and —CH$_2$— groups may be each independently replaced with —O—, —S—, —NR$^4$— (where R$^4$ represents a hydrogen atom or an alkyl group having 1 to 8 carbon atoms), or —CO— such that an —O—O— linkage is not included. The group represented by Formula (W-1) is preferably a group selected from Formulae (W-1-1) to (W-1-8) below which may be optionally substituted with one or more $L^1$ substituents:

[Chem. 24]

 (W-1-1)

 (W-1-2)

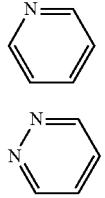 (W-1-3)

(in Formulae (W-1-1) to (W-1-8), the above groups may have a bond at any position). The group represented by Formula (W-7) is preferably a group selected from Formulae (W-7-1) to (W-7-7) below which may be optionally substituted with one or more $L^1$ substituents:

[Chem. 25]

(in Formulae (W-7-1) to (W-7-7), the above groups may have a bond at any position). The group represented by Formula (W-10) is preferably a group selected from Formulae (W-10-1) to (W-10-8) below which may be optionally substituted with one or more $L^1$ substituents:

[Chem. 26]

(in Formulae (W-10-1) to (W-10-8), the above groups may have a bond at any position; and $R^3$ represents a hydrogen atom or an alkyl group having 1 to 8 carbon atoms). The group represented by Formula (W-11) is preferably a group selected from Formulae (W-11-1) to (W-11-13) below which may be optionally substituted with one or more $L^1$ substituents:

[Chem. 27]

(W-11-3) 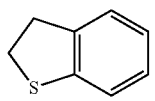
(W-11-4) 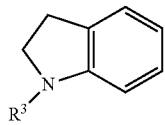
(W-11-5) 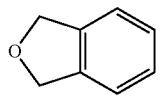
(W-11-6) 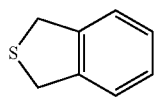
(W-11-7) 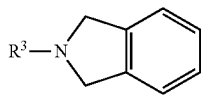
(W-11-8) 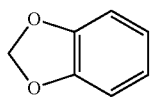
(W-11-9) 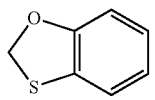
(W-11-10) 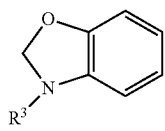
(W-11-11) 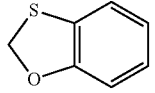
(W-11-12) 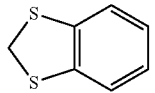
(W-11-13) 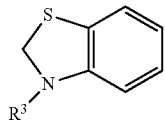
(in Formulae (W-11-1) to (W-11-13), the above groups may have a bond at any position; and $R^3$ represents a hydrogen atom or an alkyl group having 1 to 8 carbon atoms). The group represented by Formula (W-12) is preferably a group selected from Formulae (W-12-1) to (W-12-19) below which may be optionally substituted with one or more $L^1$ substituents:
[Chem. 28]
(W-12-1) 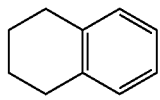
(W-12-2) 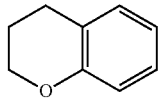
(W-12-3) 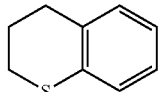
(W-12-4) 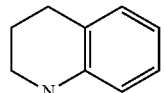
(W-12-5) 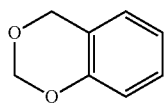
(W-12-6) 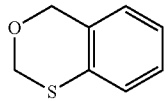
(W-12-7) 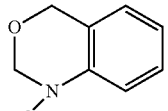
(W-12-8) 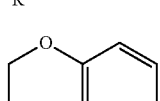
(W-12-9) 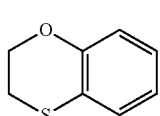
(W-12-10) 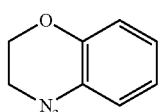
(W-12-11) 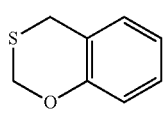
(W-12-12) 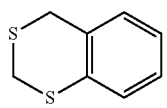
(W-12-13) 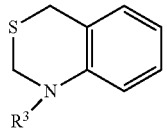

(W-12-14) 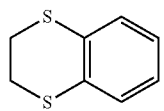

(W-12-15) 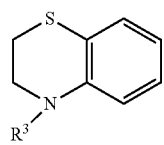

(W-12-16) 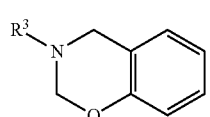

(W-12-17) 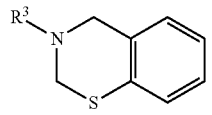

(W-12-18) 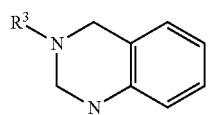

(W-12-19) 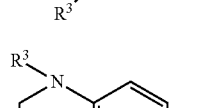

(in Formulae (W-12-1) to (W-12-19), the above groups may have a bond at any position; and $R^3$ represents a hydrogen atom or an alkyl group having 1 to 8 carbon atoms). The group represented by Formula (W-13) is preferably a group selected from Formulae (W-13-1) to (W-13-10) below which may be optionally substituted with one or more $L^1$ substituents:

[Chem. 29]

(W-13-1) 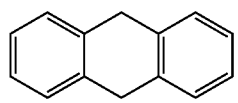

(W-13-2) 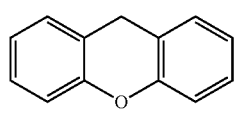

(W-13-3) 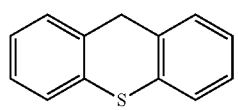

(W-13-4) 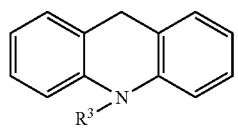

(W-13-5) 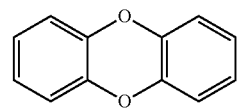

(W-13-6) 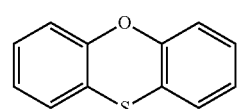

(W-13-7) 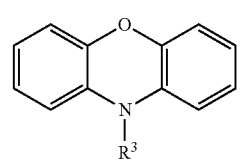

(W-13-8) 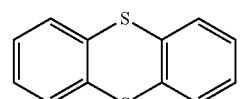

(W-13-9) 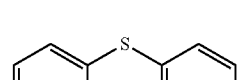

(W-13-10) 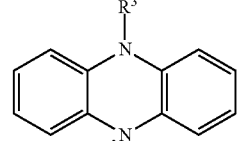

(in Formulae (W-13-1) to (W-13-10), the above groups may have a bond at any position; and $R^3$ represents a hydrogen atom or an alkyl group having 1 to 8 carbon atoms). The group represented by Formula (W-14) is preferably a group selected from Formulae (W-14-1) to (W-14-4) below which may be optionally substituted with one or more $L^1$ substituents:

[Chem. 30]

(W-14-1) 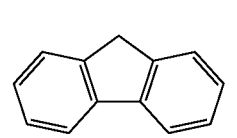

(W-14-2) 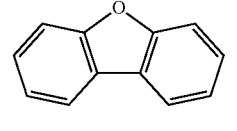

(W-14-3) 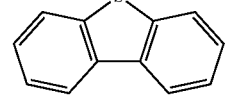

(W-14-4)

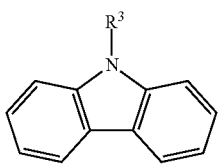

(in Formulae (W-14-1) to (W-14-4), the above groups may have a bond at any position; and R³ represents a hydrogen atom or an alkyl group having 1 to 8 carbon atoms). The group represented by Formula (W-15) is preferably a group selected from Formulae (W-15-1) to (W-15-18) below which may be optionally substituted with one or more L¹ substituents:

[Chem. 31]

(W-15-1)
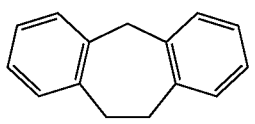

(W-15-2)
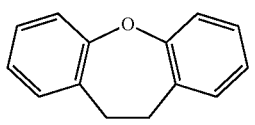

(W-15-3)
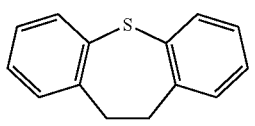

(W-15-4)
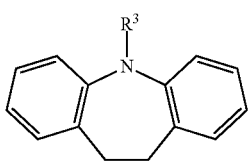

(W-15-5)
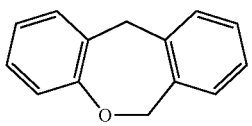

(W-15-6)
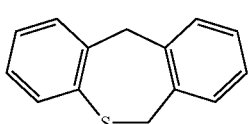

(W-15-7)
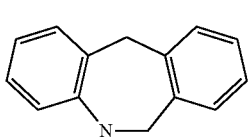

(W-15-8)
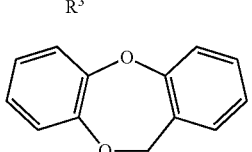

(W-15-11)
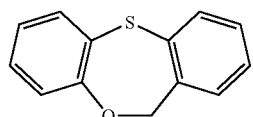

(W-15-12)
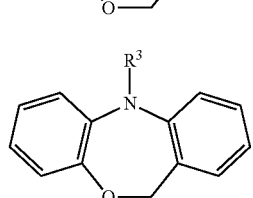

(W-15-13)
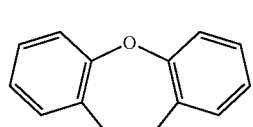

(W-15-14)
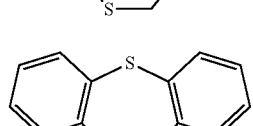

(W-15-15)
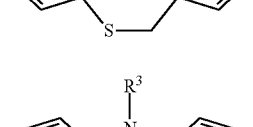

(W-15-16)
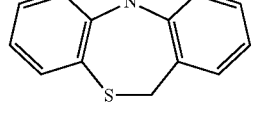

(W-15-17)
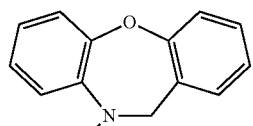

(W-15-18)
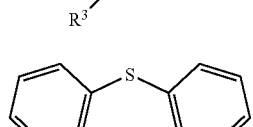

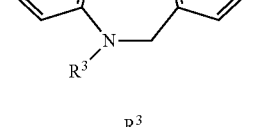

(in Formulae (W-15-1) to (W-15-18), the above groups may have a bond at any position; and R³ represents a hydrogen atom or an alkyl group having 1 to 8 carbon atoms). The group represented by Formula (W-16) is preferably a group selected from Formulae (W-16-1) to (W-16-4) below which may be optionally substituted with one or more L¹ substituents:

[Chem. 32]

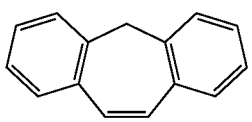
(W-16-1)

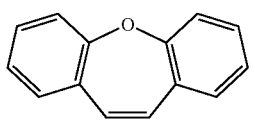
(W-16-2)

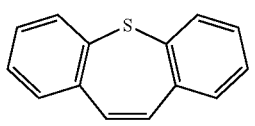
(W-16-3)

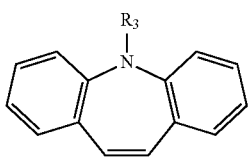
(W-16-4)

(in Formulae (W-16-1) to (W-16-4), the above groups may have a bond at any position; and $R^3$ represents a hydrogen atom or an alkyl group having 1 to 8 carbon atoms). The group represented by Formula (W-17) is preferably a group selected from Formulae (W-17-1) to (W-17-6) below which may be optionally substituted with one or more $L^1$ substituents:

[Chem. 33]

(W-17-1)

(W-17-2)

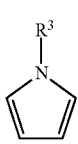
(W-17-3)

(W-17-4)

(W-17-5)

(W-17-6)

(in Formulae (W-17-1) to (W-17-6), the above groups may have a bond at any position; and $R^3$ represents a hydrogen atom or an alkyl group having 1 to 8 carbon atoms). The group represented by Formula (W-18) is preferably a group selected from Formulae (W-18-1) to (W-18-6) below which may be optionally substituted with one or more $L^1$ substituents:

[Chem. 34]

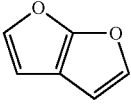
(W-18-1)

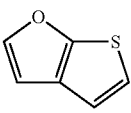
(W-18-2)

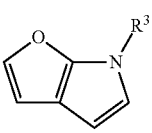
(W-18-3)

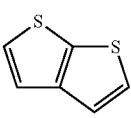
(W-18-4)

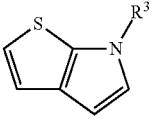
(W-18-5)

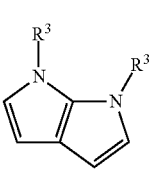
(W-18-6)

(in Formulae (W-18-1) to (W-18-6), the above groups may have a bond at any position; and $R^3$ represents a hydrogen atom or an alkyl group having 1 to 8 carbon atoms). The group represented by Formula (W-19) is preferably a group selected from Formulae (W-19-1) to (W-19-9) below which may be optionally substituted with one or more $L^1$ substituents:

[Chem. 35]

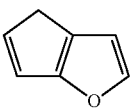
(W-19-1)

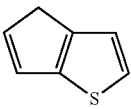
(W-19-2)

(W-19-3)
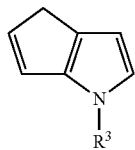

(W-19-4)
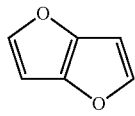

(W-19-5)
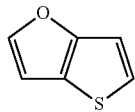

(W-19-6)
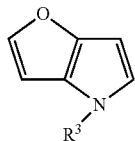

(W-19-7)
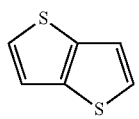

(W-19-8)
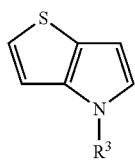

(W-19-9)
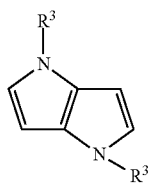

(in Formulae (W-19-1) to (W-19-9), the above groups may have a bond at any position; and $R^3$ represents a hydrogen atom or an alkyl group having 1 to 8 carbon atoms). The aromatic group included in $W^{11}$ is more preferably a group selected from Formulae (W-1-1), (W-7-1), (W-7-2), (W-7-7), (W-8), (W-10-6), (W-10-7), (W-10-8), (W-11-8), (W-11-9), (W-11-10), (W-11-11), (W-11-12), and (W-11-13) which may be optionally substituted with one or more $L^1$ substituents; and is particularly preferably a group selected from Formulae (W-1-1), (W-7-1), (W-7-2), (W-7-7), (W-10-6), (W-10-7), and (W-10-8) which may be optionally substituted with one or more $L^1$ substituents. $W^{11}$ particularly preferably represents a group selected from Formulae (W-a-1) to (W-a-6) below:

[Chem. 36]

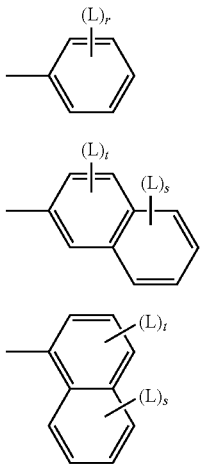

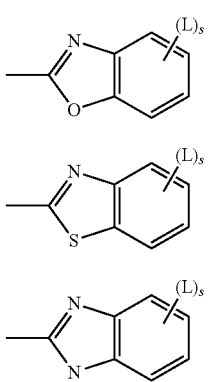

(in Formulae (W-a-1) to (W-a-6), r represents an integer of 0 to 5; s represents an integer of 0 to 4; and t represents an integer of 0 to 3).

$W^{12}$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. $W^{12}$ may represent the same thing as $W^{11}$. $W^{11}$ and $W^{12}$ may be bonded to each other to form a ring structure.

In consideration of the availability of raw materials and ease of synthesis, $W^{12}$ preferably represents a hydrogen atom or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —CO—, —COO—, —OCO—, —CH=CH—COO—, —OCO—CH=CH—, —CH=CH—, —CF=CF—, or —C≡C—; more preferably represents a hydrogen atom or a linear or branched alkyl group having 1 to 20 carbon atoms in which one —$CH_2$— group or two or more —$CH_2$— groups that are not adjacent to one another may be each independently replaced with —O—; and particularly preferably represents a hydrogen atom or a linear alkyl group having 1 to 12 carbon atoms in which one —CH$_2$— group or two or more —CH$_2$— groups that are not adjacent to one another may be each independently replaced with —O—. In the case where W$^{12}$ represents the same thing as W$^{11}$, W$^{12}$ may be identical to or different from W$^{11}$ and the preferable groups are the same as those of W$^{11}$. In the case where W$^{11}$ and W$^{12}$ are bonded to each other to form a ring structure, the cyclic group represented by —NW$^{11}$W$^{12}$ is preferably a group selected from Formulae (W-b-1) to (W-b-42) below which may be optionally substituted with one or more L$^1$ substituents:

[Chem. 37]

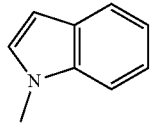
(W-b-1)

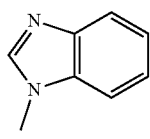
(W-b-2)

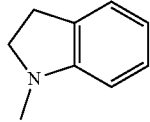
(W-b-3)

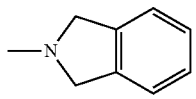
(W-b-4)

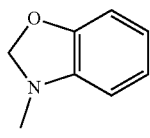
(W-b-5)

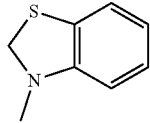
(W-b-6)

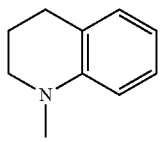
(W-b-7)

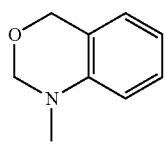
(W-b-8)

-continued

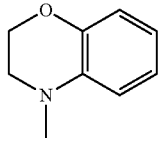
(W-b-9)

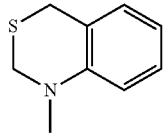
(W-b-9)

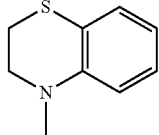
(W-b-10)

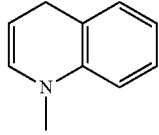
(W-b-11)

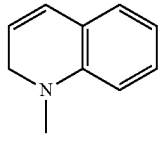
(W-b-11)

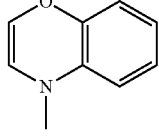
(W-b-12)

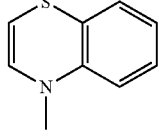
(W-b-13)

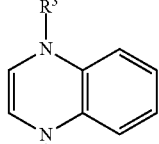
(W-b-14)

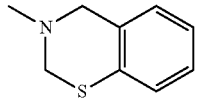
(W-b-15)

(W-b-16)

(W-b-17) 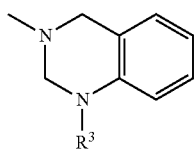
(W-b-18) 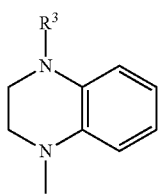
(W-b-19) 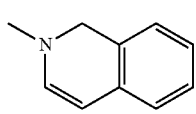
[Chem. 38]
(W-b-20) 
(W-b-21) 
(W-b-22) 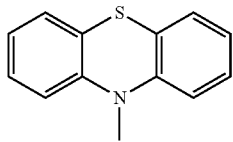
(W-b-23) 
(W-b-24) 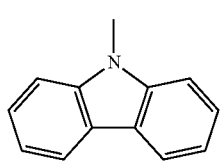
(W-b-25) 
(W-b-26) 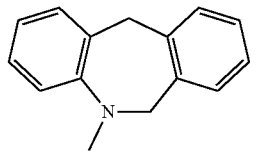
(W-b-27) 
(W-b-28) 
(W-b-29) 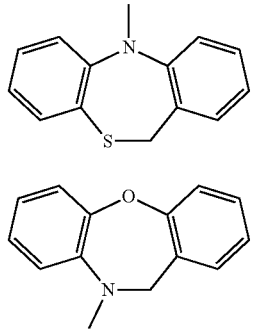
(W-b-30) 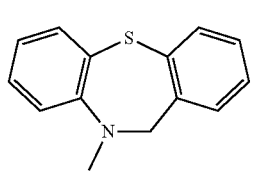
(W-b-31) 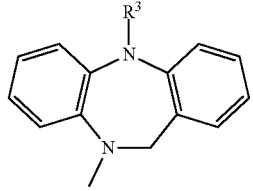
(W-b-32) 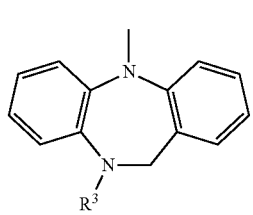
(W-b-33) 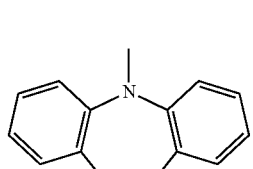
(W-b-34) 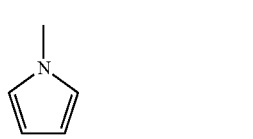

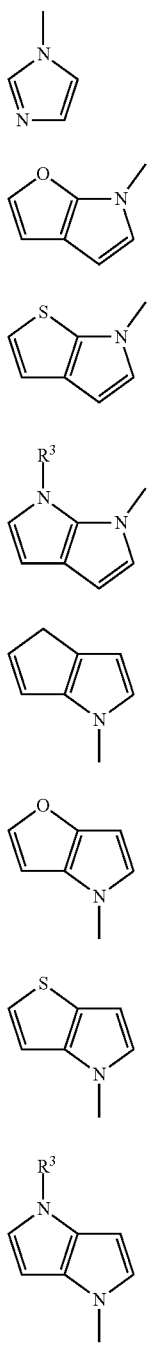
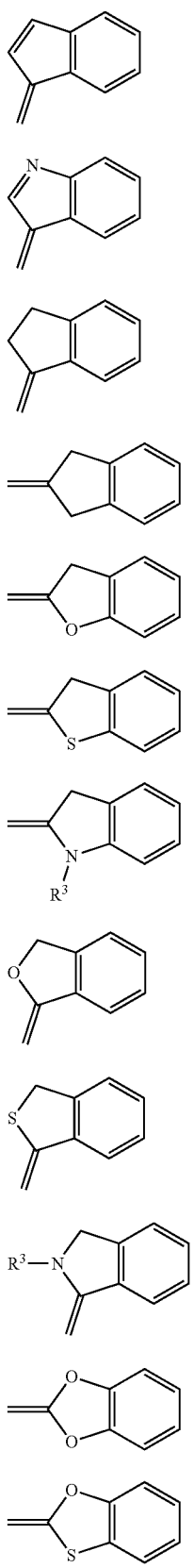

(in Formulae (W-b-1) to (W-b-42), $R^3$ represents a hydrogen atom or an alkyl group having 1 to 8 carbon atoms). In consideration of the availability of raw materials and ease of synthesis, the cyclic group represented by $-NW^{11}W^{12}$ is particularly preferably a group selected from Formulae (W-b-20), (W-b-21), (W-b-22), (W-b-23), (W-b-24), (W-b-25), and (W-b-33) which may be optionally substituted with one or more L substituents.

The cyclic group represented by $=CW^{11}W^{12}$ is preferably a group selected from Formulae (W-c-1) to (W-c-81) below which may be optionally substituted with one or more $L^1$ substituents:

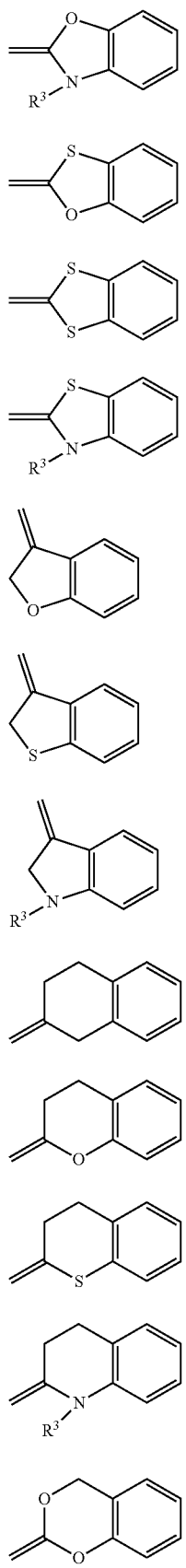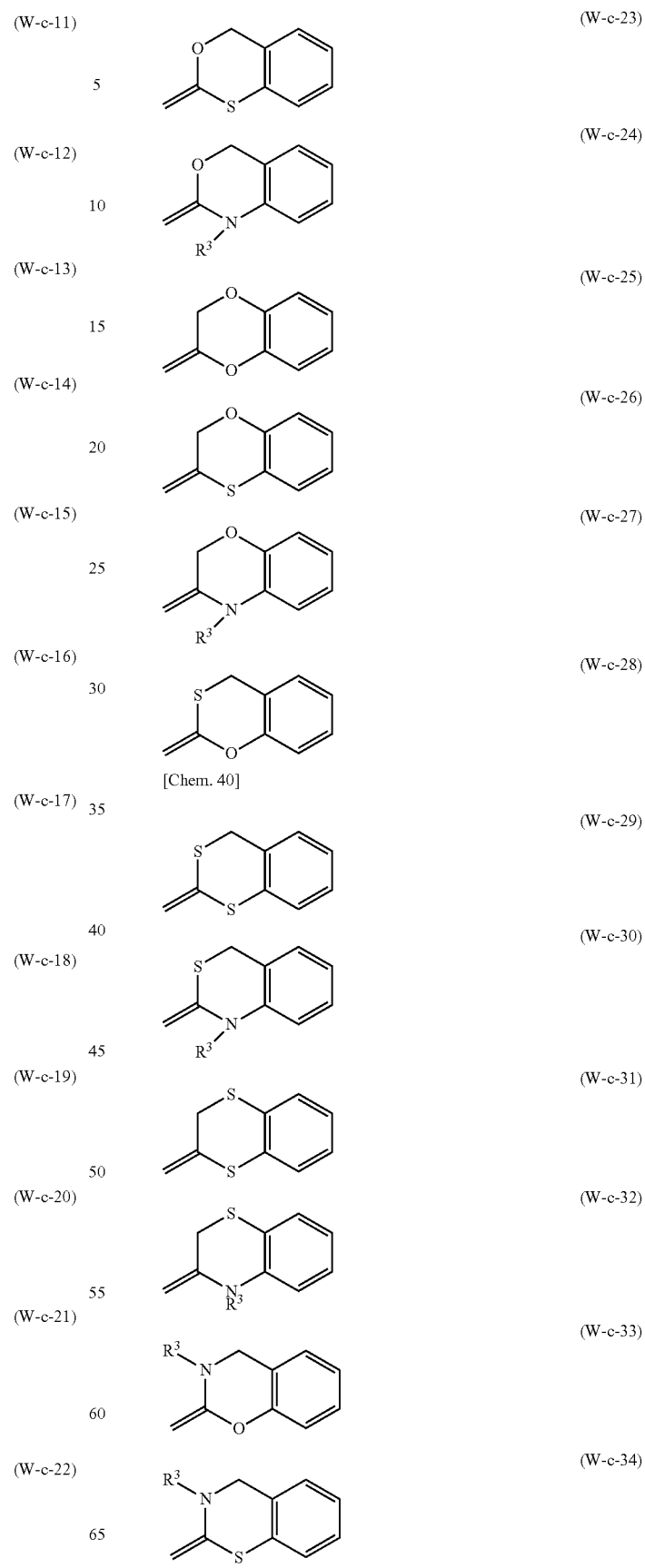

-continued
(W-c-35) 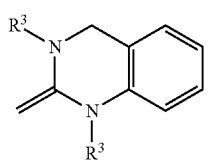
(W-c-36) 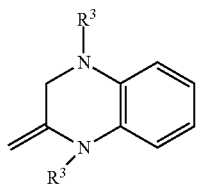
(W-c-37) 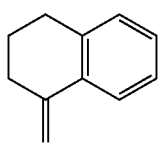
(W-c-38) 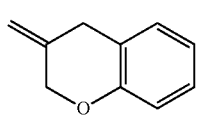
(W-c-39) 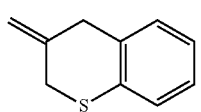
(W-c-40) 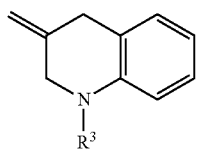
(W-c-41) 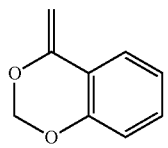
(W-c-42) 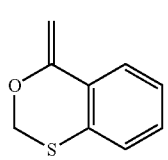
(W-c-43) 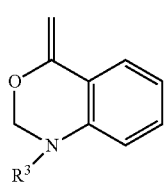
(W-c-44) 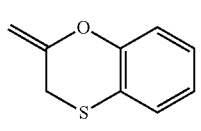
-continued
(W-c-45) 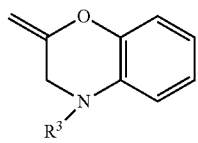
(W-c-46) 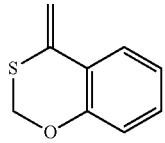
(W-c-47) 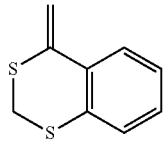
(W-c-48) 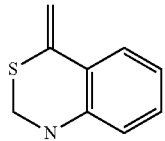
(W-c-49) 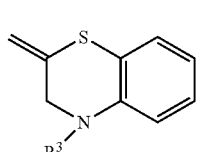
(W-c-50) 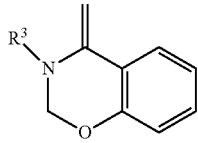
(W-c-51) 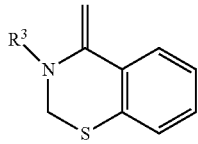
(W-c-52) 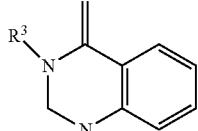
(W-c-53) 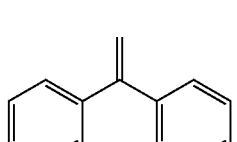
(W-c-54) 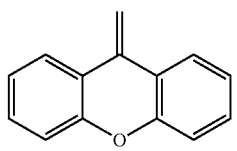

-continued
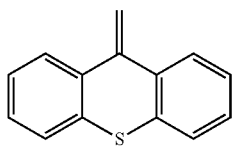
(W-c-55)
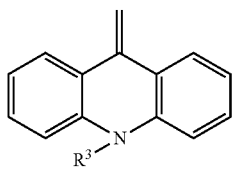
(W-c-56)
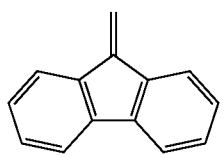
(W-c-57)
[Chem. 41]
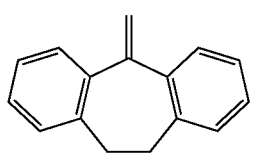
(W-c-58)
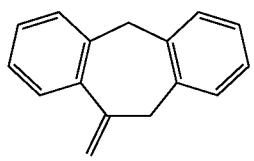
(W-c-59)
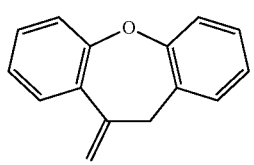
(W-c-60)
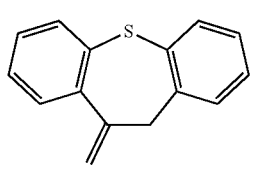
(W-c-61)
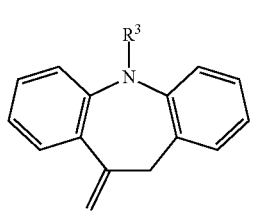
(W-c-62)
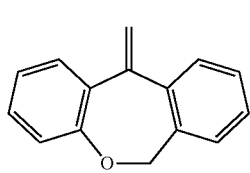
(W-c-63)
-continued
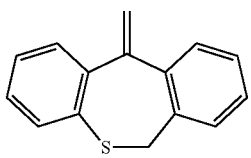
(W-c-64)
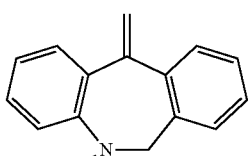
(W-c-65)
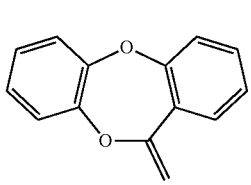
(W-c-66)
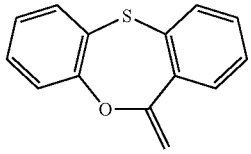
(W-c-67)
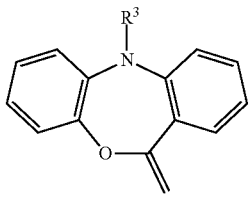
(W-c-68)
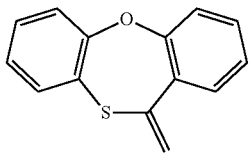
(W-c-69)
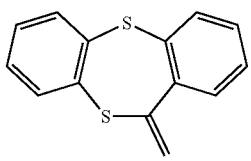
(W-c-70)
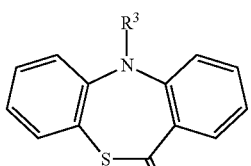
(W-c-71)
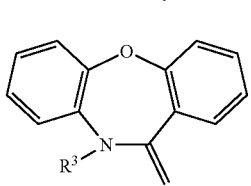
(W-c-72)

-continued

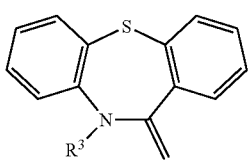
(W-c-73)

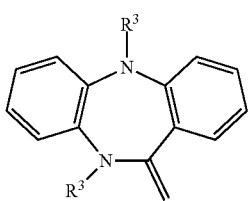
(W-c-74)

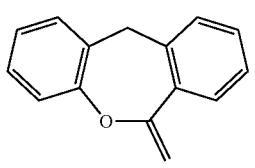
(W-c-75)

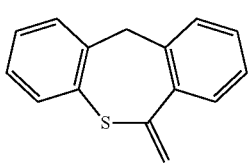
(W-c-76)

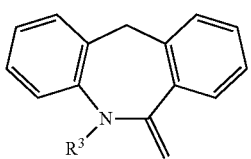
(W-c-77)

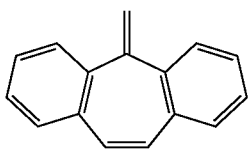
(W-c-78)

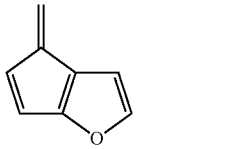
(W-c-79)

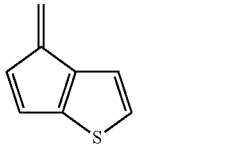
(W-c-80)

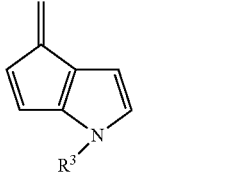
(W-c-81)

(in Formulae (W-c-1) to (W-c-81), $R^3$ represents a hydrogen atom or an alkyl group having 1 to 8 carbon atoms). In consideration of the availability of raw materials and ease of synthesis, the cyclic group represented by =$CW^{11}W^{12}$ is particularly preferably a group selected from Formulae (W-c-11), (W-c-12), (W-c-13), (W-c-14), (W-c-53), (W-c-54), (W-c-55), (W-c-56), (W-c-57), and (W-c-78) which may be optionally substituted with one or more $L^1$ substituents.

The total number of π electrons included in $W^{11}$ and $W^{12}$ is preferably 4 to 24 in consideration of wavelength dispersion property, preservation stability, liquid crystal property, and ease of synthesis.

$W^{13}$ is more preferably a group selected from a cyano group, a nitro group, a carboxyl group, and an alkyl, alkenyl, acyloxy, or alkylcarbonyloxy group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—; and is particularly preferably a group selected from a cyano group, a carboxyl group, and an alkyl, alkenyl, acyloxy, or alkylcarbonyloxy group having 1 to 20 carbon atoms in which one —$CH_2$— group or two or more —$CH_2$— groups that are not adjacent to one another may be each independently replaced with —CO—, —COO—, —OCO—, —O—CO—O—, —CO—NH—, —NH—CO—, or —C≡C—.

$W^{14}$ is more preferably a group selected from a cyano group, a nitro group, a carboxyl group, and an alkyl, alkenyl, acyloxy, or alkylcarbonyloxy group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—; and is particularly preferably a group selected from a group selected from a cyano group, a carboxyl group, and an alkyl, alkenyl, acyloxy, or alkylcarbonyloxy group having 1 to 20 carbon atoms in which one —$CH_2$— group or two or more —$CH_2$— groups that are not adjacent to one another may be each independently replaced with —CO—, —COO—, —OCO—, —O—CO—O—, —CO—NH—, —NH—CO—, or —C≡C—.

$L^1$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. In consideration of liquid crystal property and ease of synthesis, $L^1$ preferably represents a fluorine atom, a chlorine atom, a pentafluorosulfanyl group, a nitro group, a methylamino group, a dimethylamino group, a diethylamino group, a diisopropylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —S—, —CO—, —COO—, —OCO—, —O—CO—O—, —CH=CH—, —CF=CF—, or —C≡C—; more preferably represents a fluorine atom, a chlorine atom, or a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with —O—, —COO—, or —OCO—; further preferably represents a fluorine atom, a chlorine atom, or a linear or branched alkyl or alkoxy group having 1 to 12 carbon atoms in which a hydrogen atom may be replaced with a fluorine atom; and particularly preferably represents a fluorine atom, a chlorine atom, or a linear alkyl or alkoxy group having 1 to 8 carbon atoms.

m11 represents an integer of 0 to 8. In consideration of liquid crystal property, the availability of raw materials, and ease of synthesis, m11 preferably represents an integer of 0 to 4, more preferably represents an integer of 0 to 2, further preferably represents 0 or 1, and particularly preferably represents 1.

In General Formula (1-1), j11 represents an integer of 0 to 5; j12 represents an integer of 1 to 5; and j11+j12 is an integer of 1 to 5. In consideration of liquid crystal property, ease of synthesis, and preservation stability, j11 and j12 preferably each independently represent an integer of 1 to 4, more preferably each independently represent an integer of 1 to 3, and particularly preferably each independently represent 1 or 2; and j11+j12 is preferably an integer of 2 to 4.

Specifically, the compound represented by General Formula (1-1) is preferably selected from the compounds represented by Formulae (1-1-1) to (1-1-106) below.

[Chem. 42]

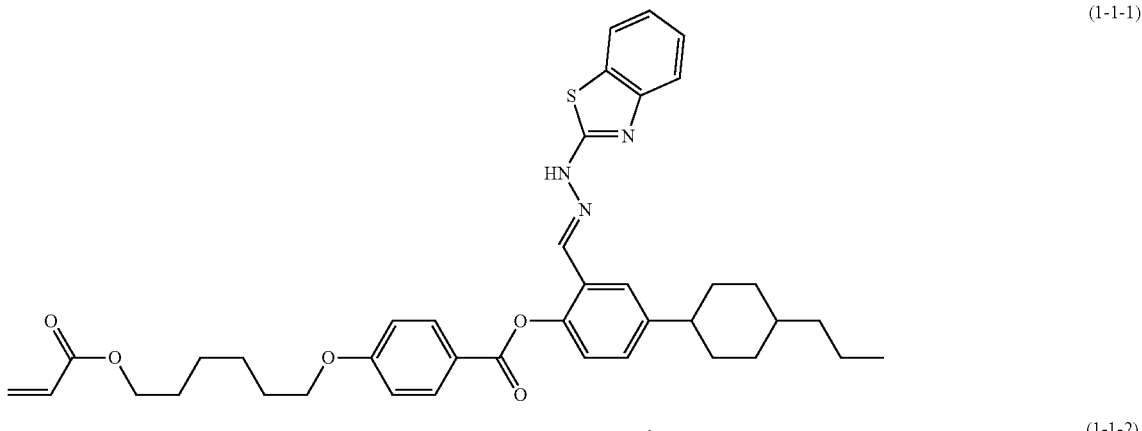

(1-1-1)

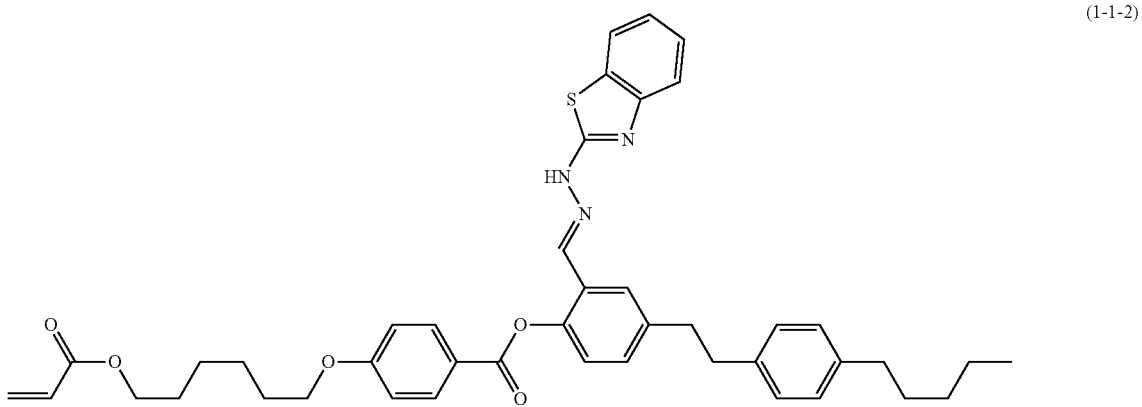

(1-1-2)

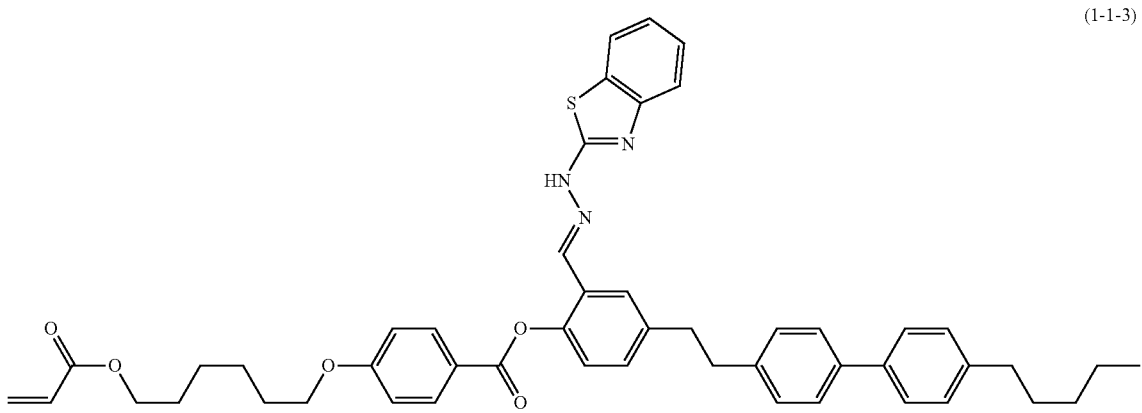

(1-1-3)

-continued
(1-1-4)
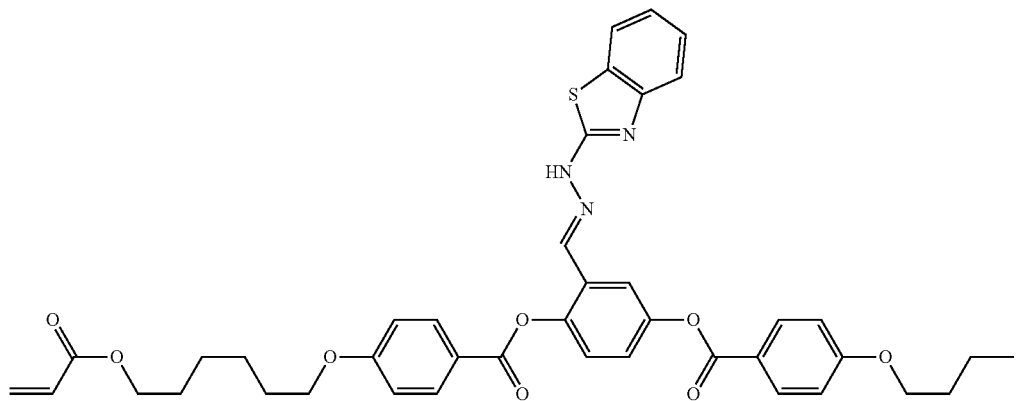
(1-1-5)
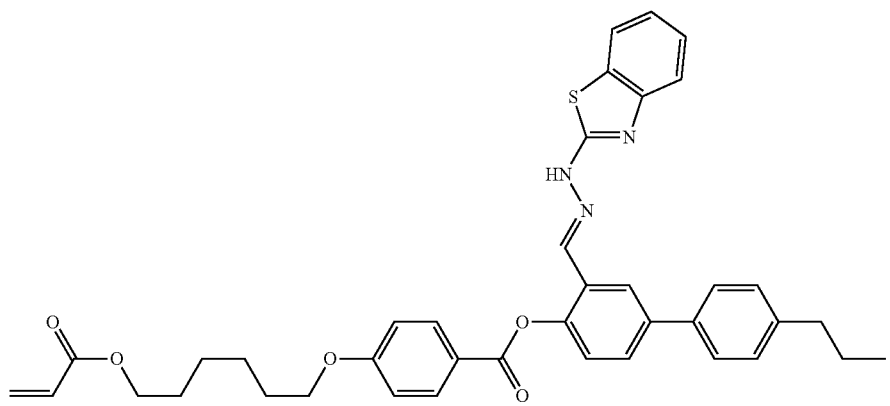
[Chem. 43]
(1-1-6)
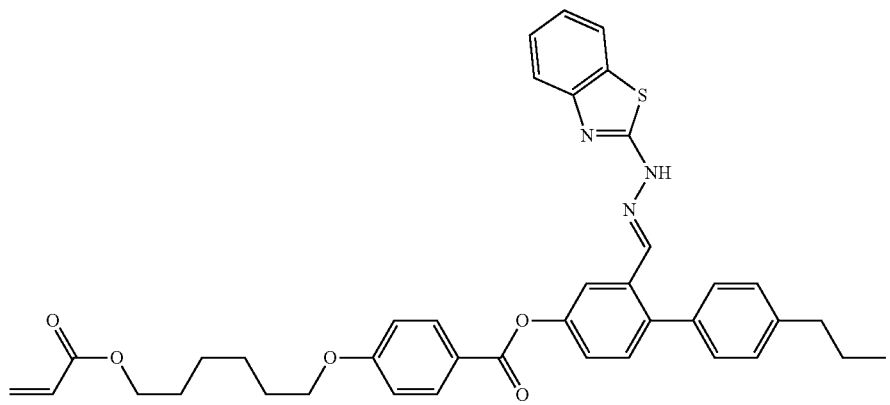
(1-1-7)
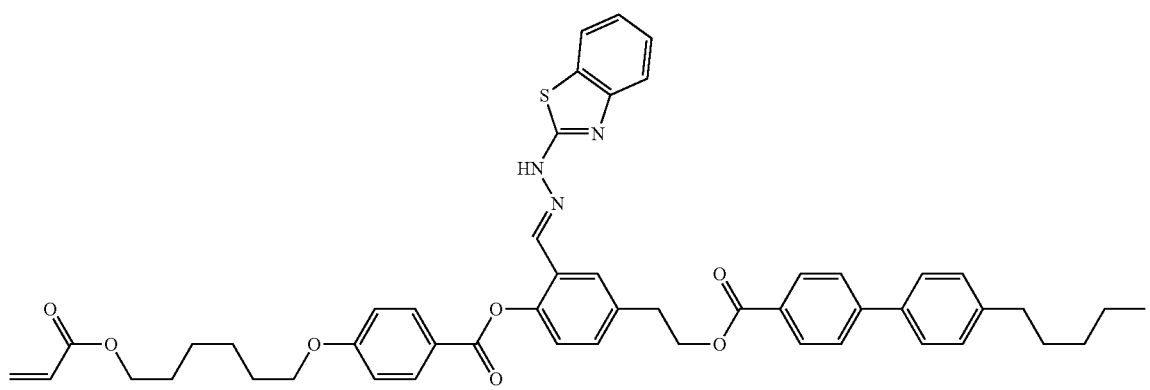

-continued
(1-1-8)
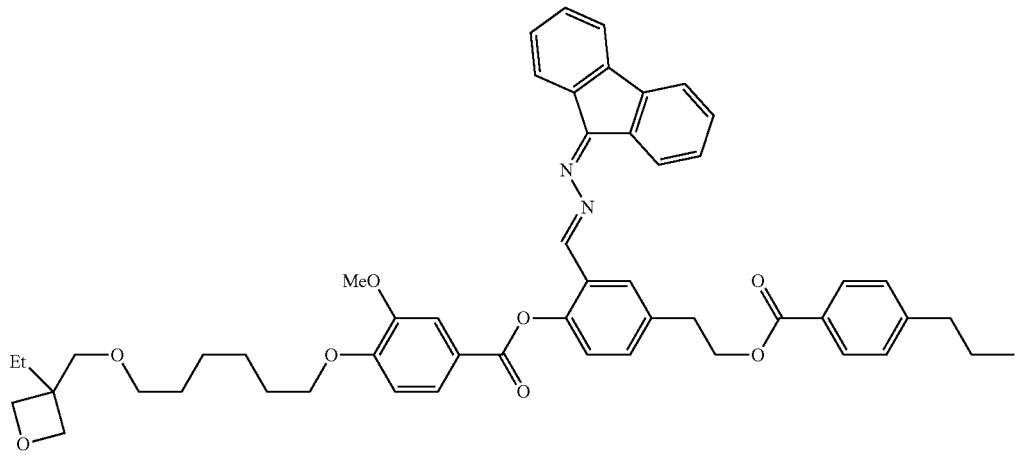
(1-1-9)
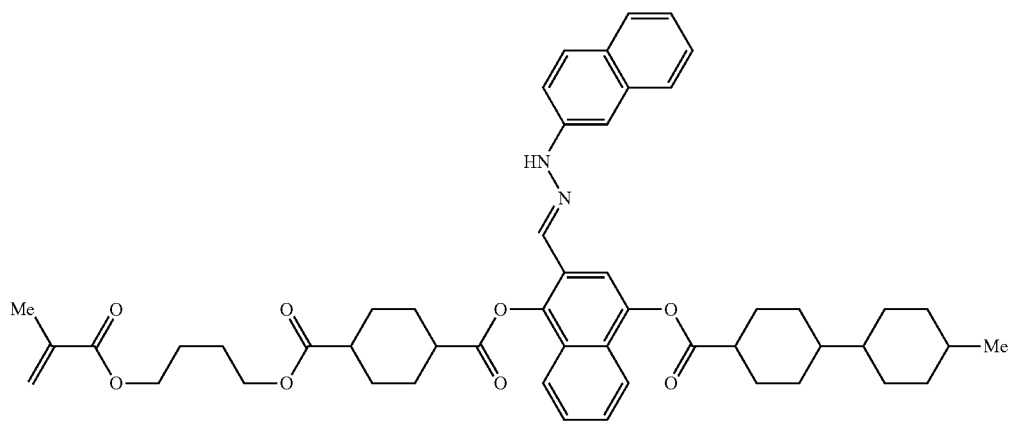
[Chem. 44]
(1-1-10)
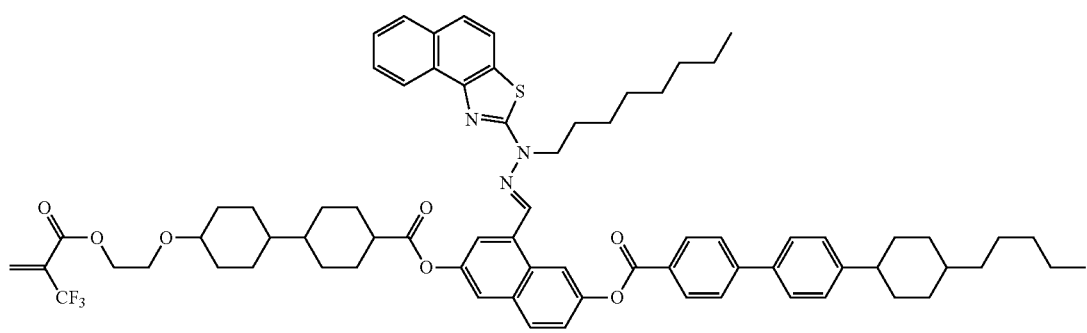
(1-1-11)
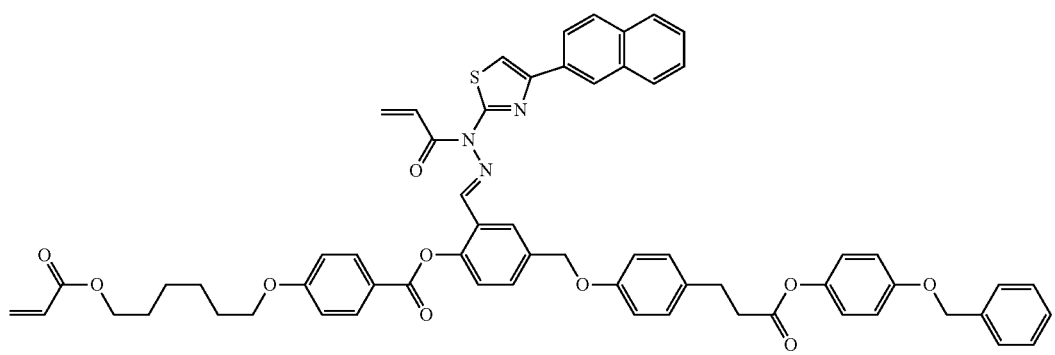

(1-1-12)
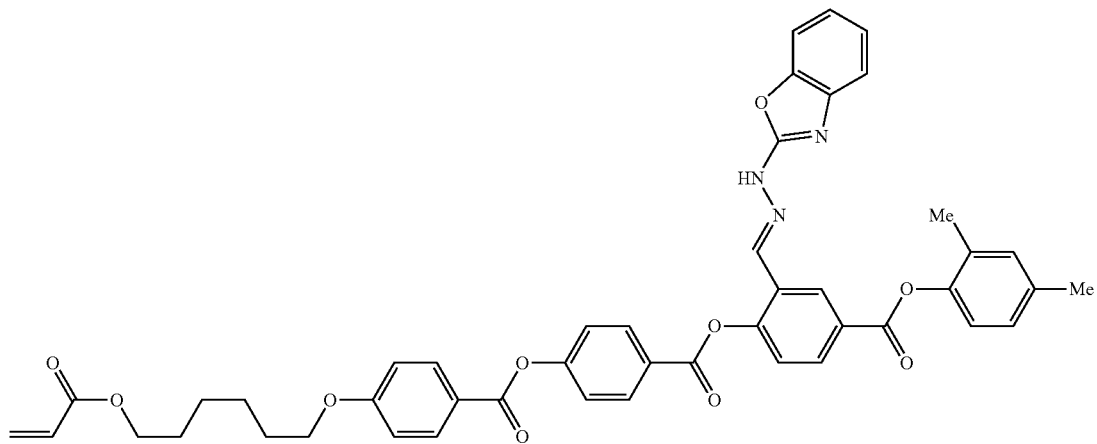
(1-1-13)
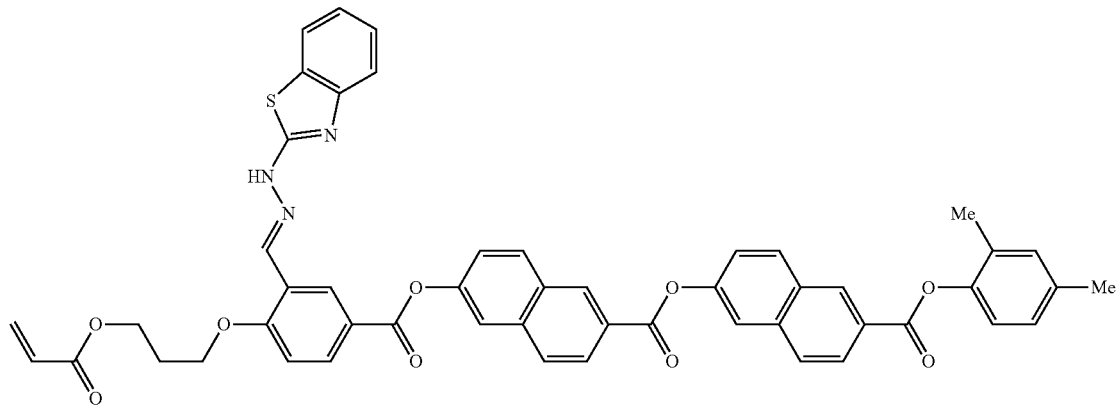
[Chem. 45]
(1-1-14)
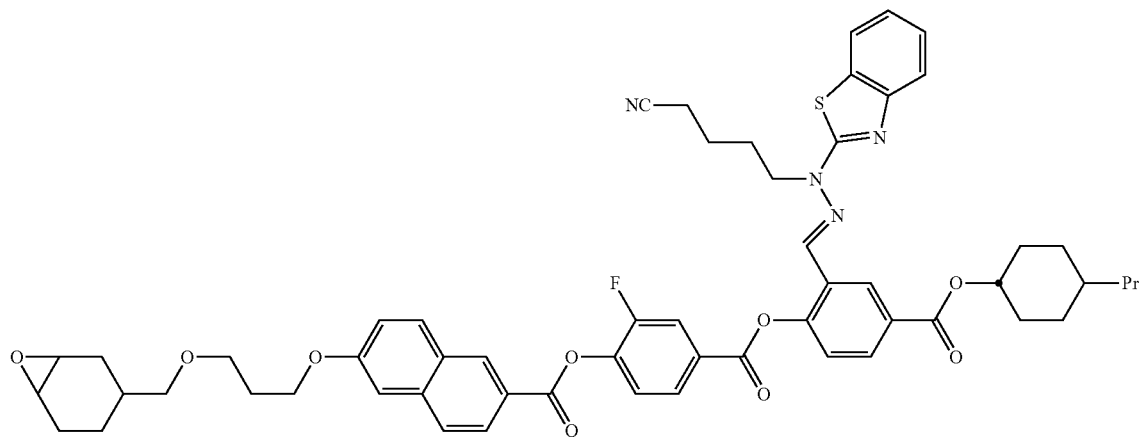

(1-1-15)
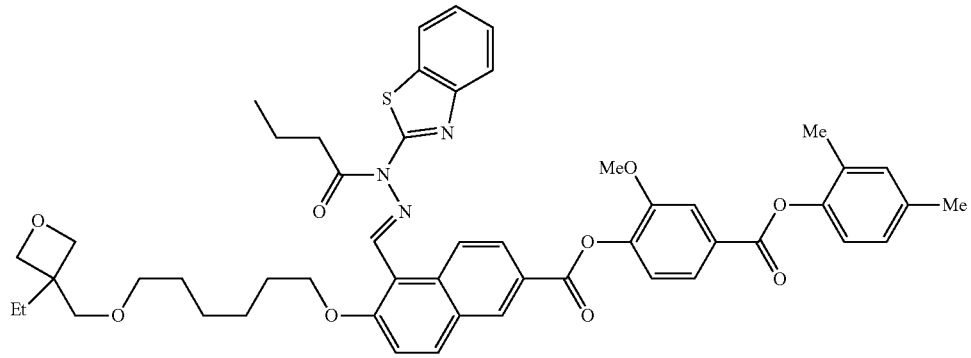
(1-1-16)
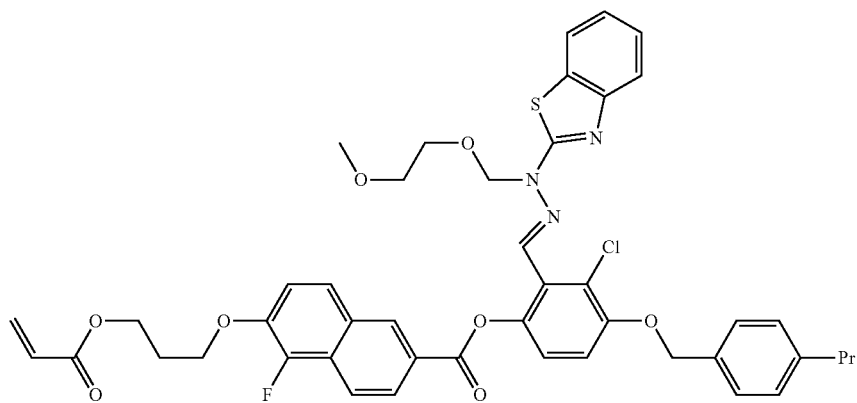
(1-1-17)
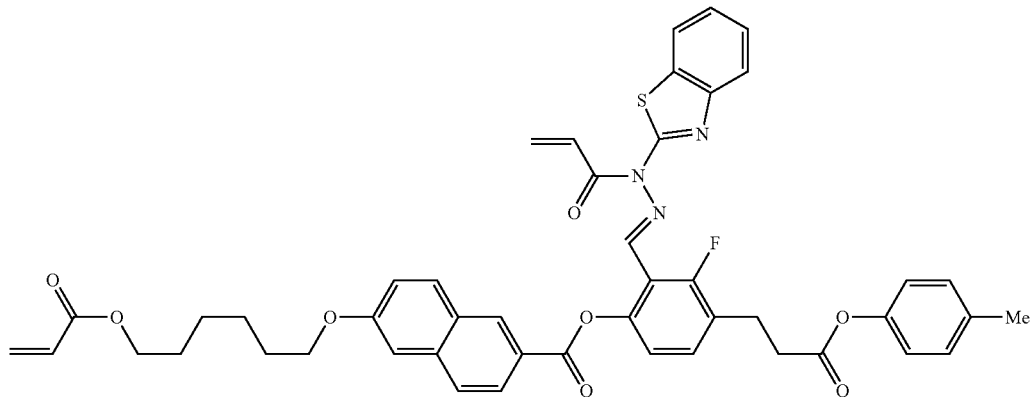

[Chem. 46]
(1-1-18)
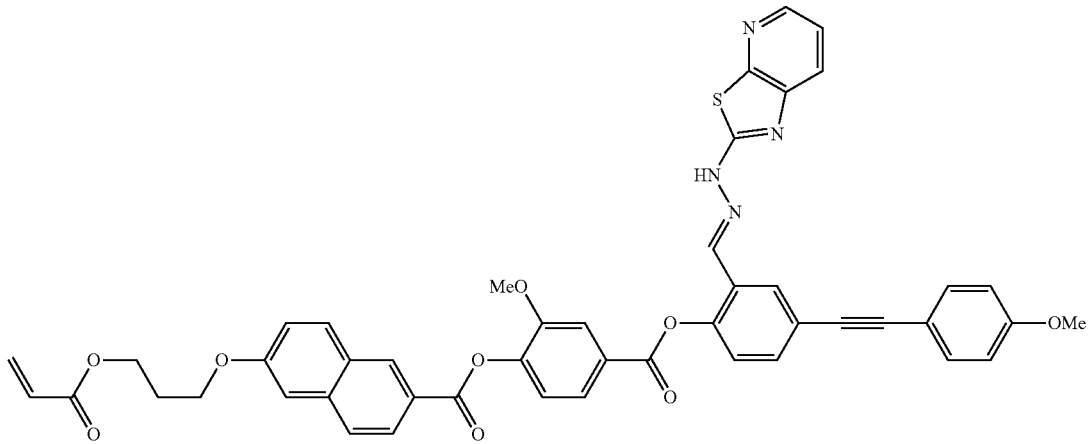
(1-1-19)
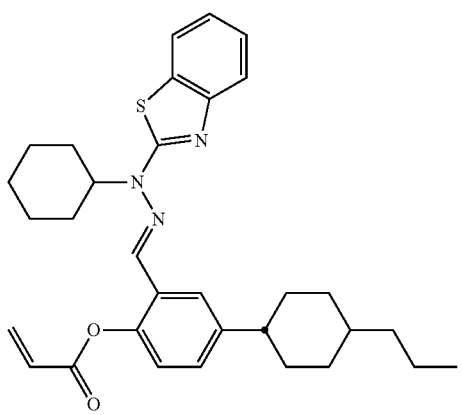
(1-1-20)
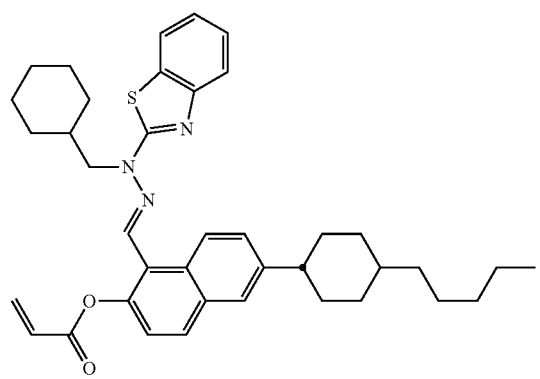
[Chem. 47]
(1-1-21)
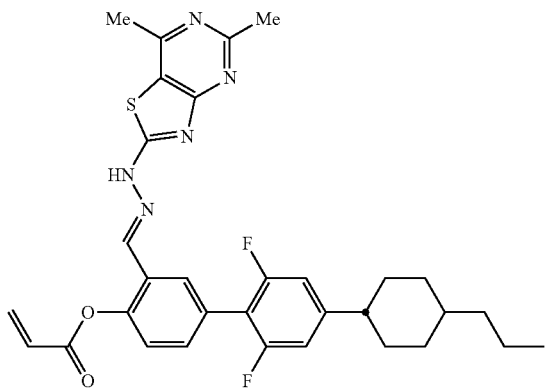
(1-1-22)
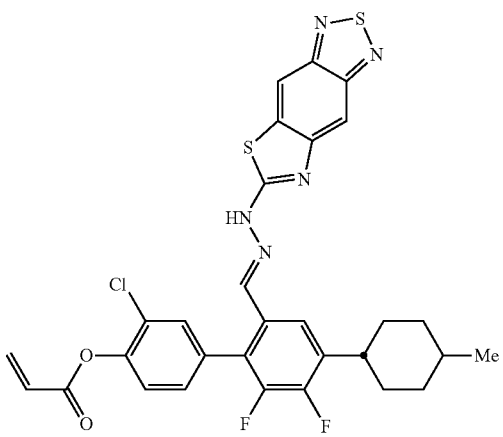

-continued
(1-1-23)
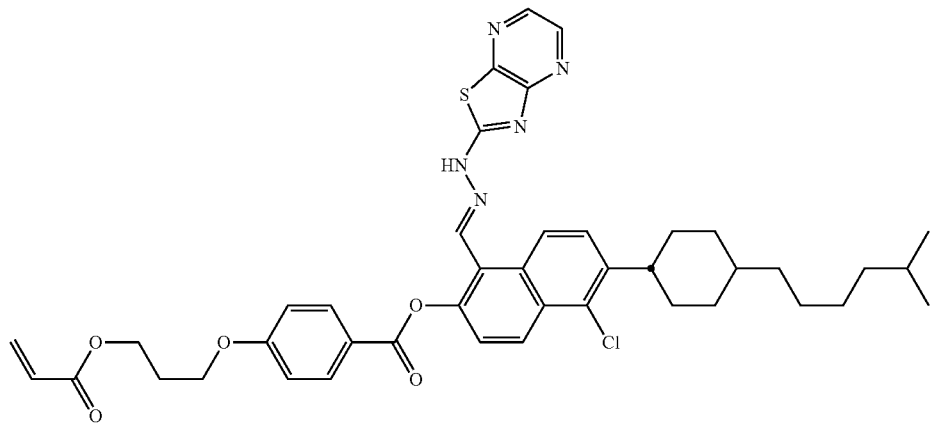
(1-1-24)
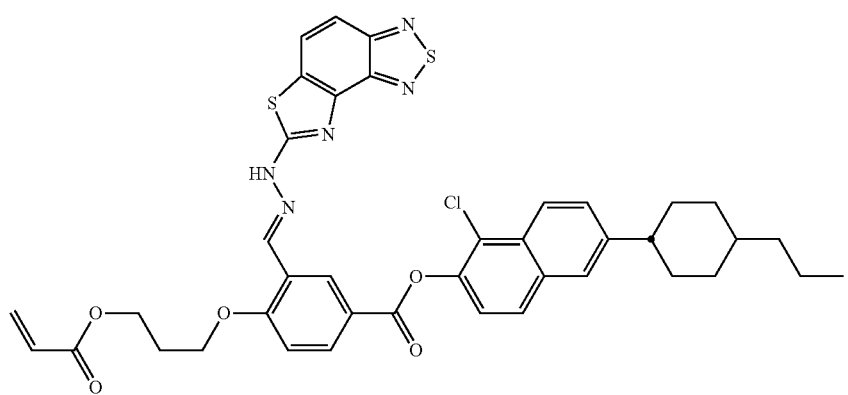
(1-1-25)
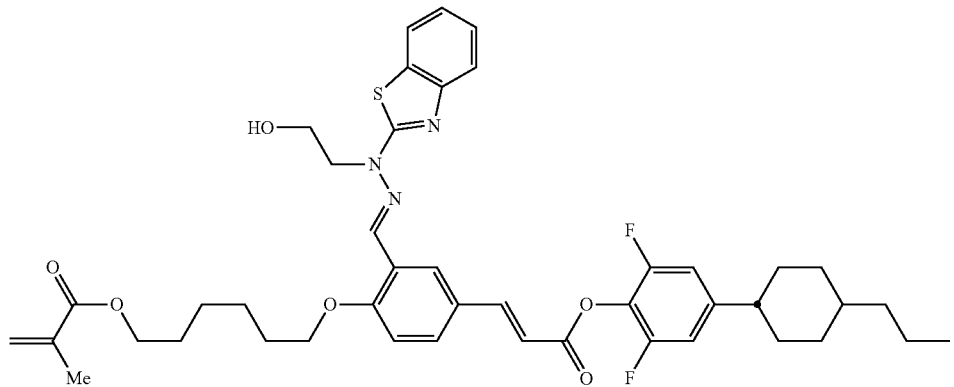
[Chem. 48]
(1-1-26)
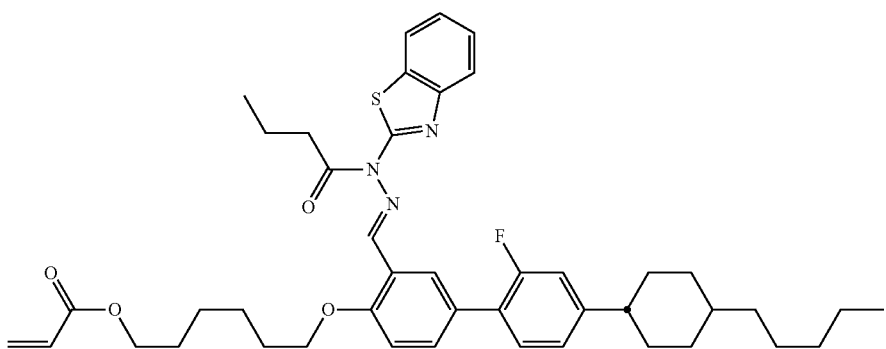

-continued
(1-1-27)
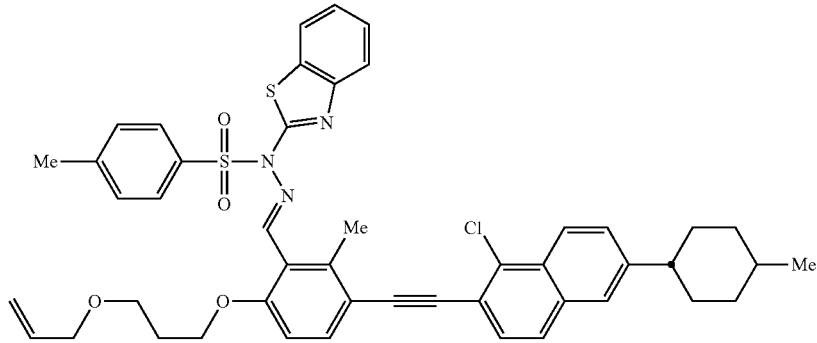
(1-1-28)
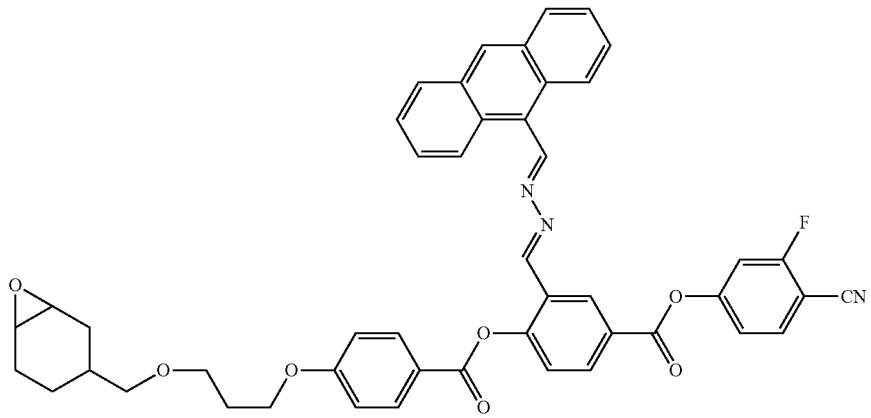
(1-1-29)
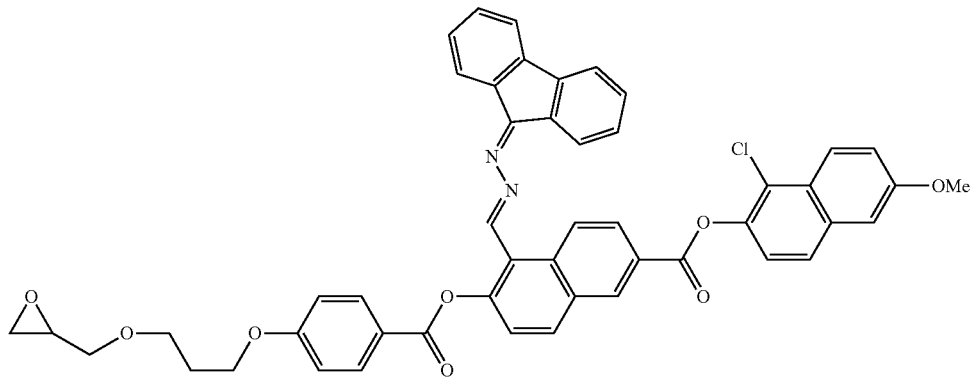
(1-1-30)
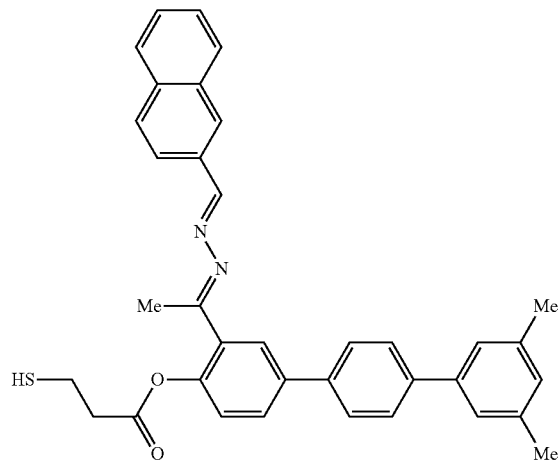

[Chem. 49]
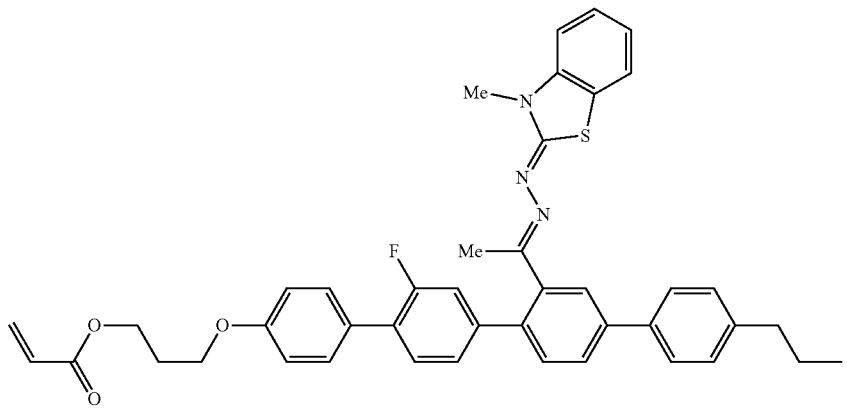
(1-1-31)
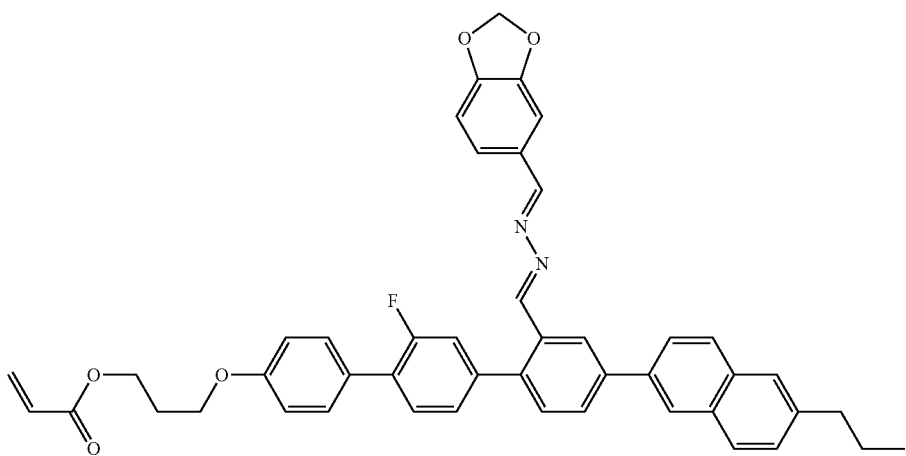
(1-1-32)
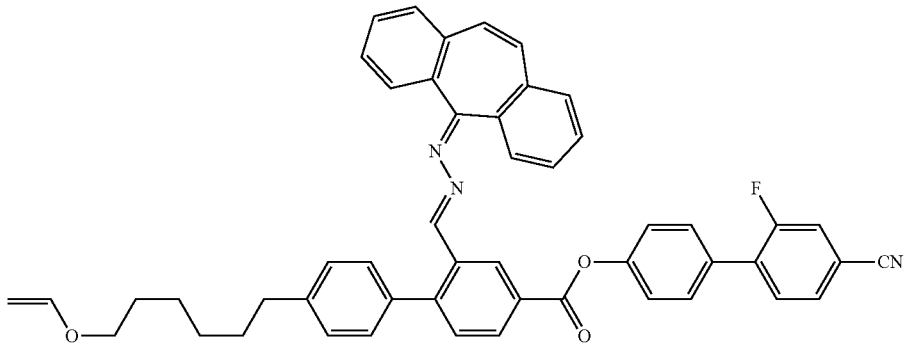
(1-1-33)

(1-1-34)
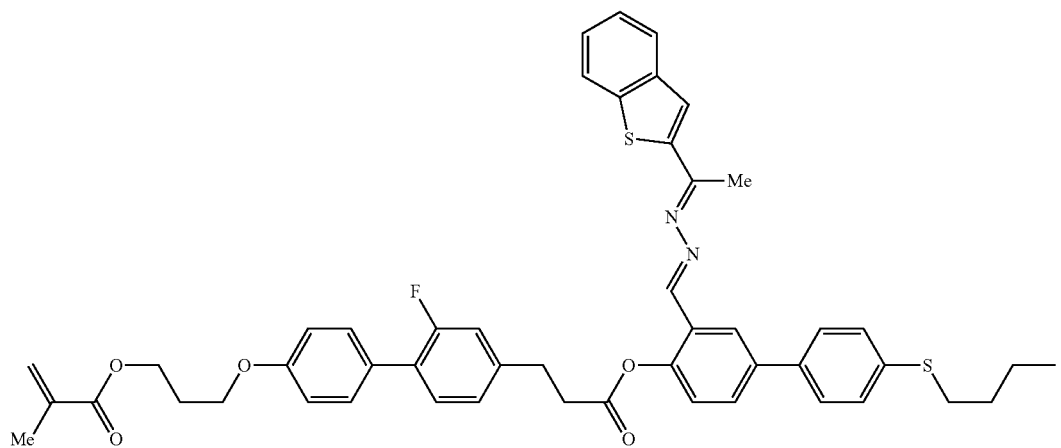
(1-1-35)
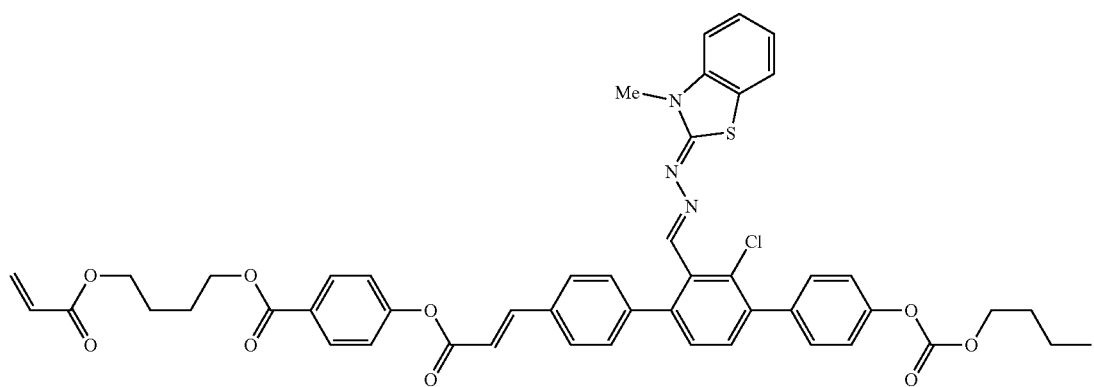
[Chem. 50]
(1-1-36)
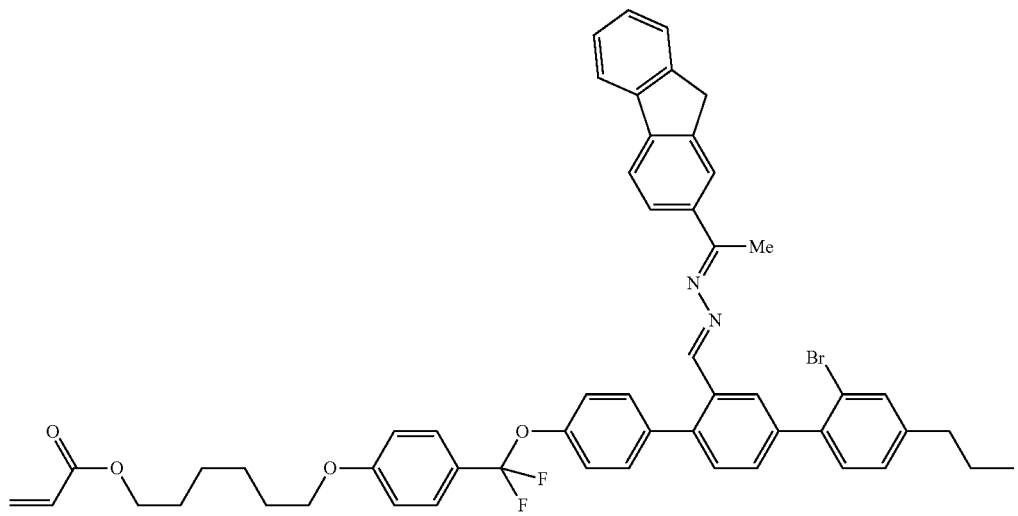

(1-1-37)
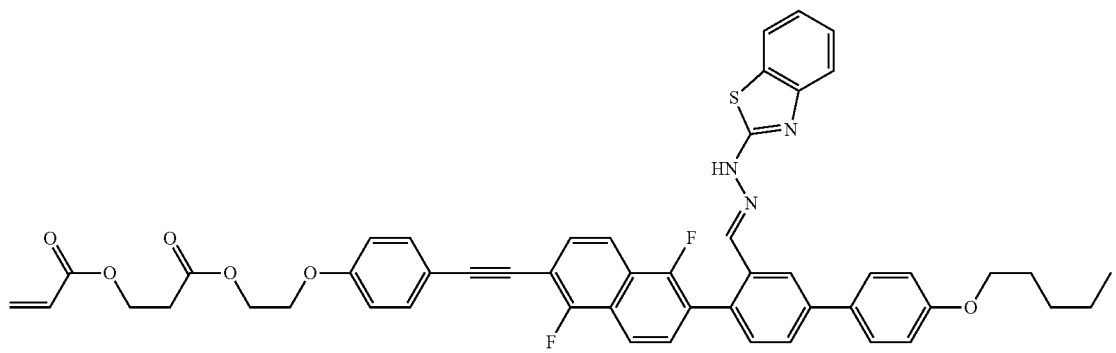
(1-1-38)
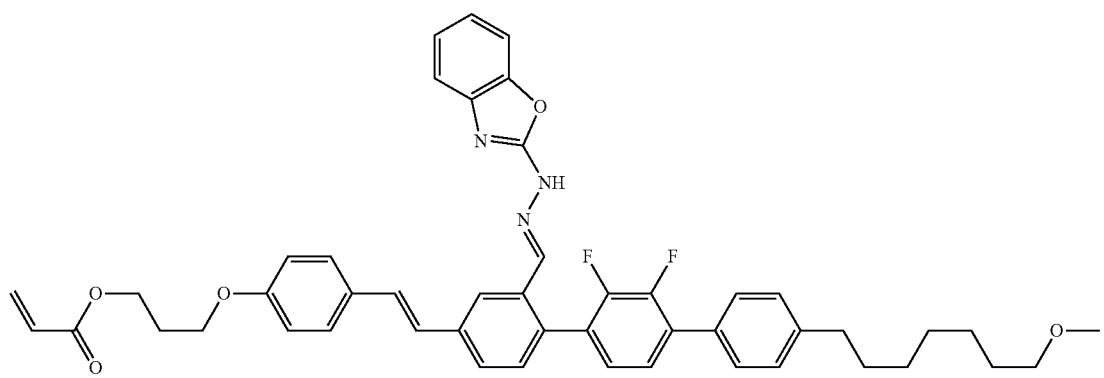
(1-1-39)
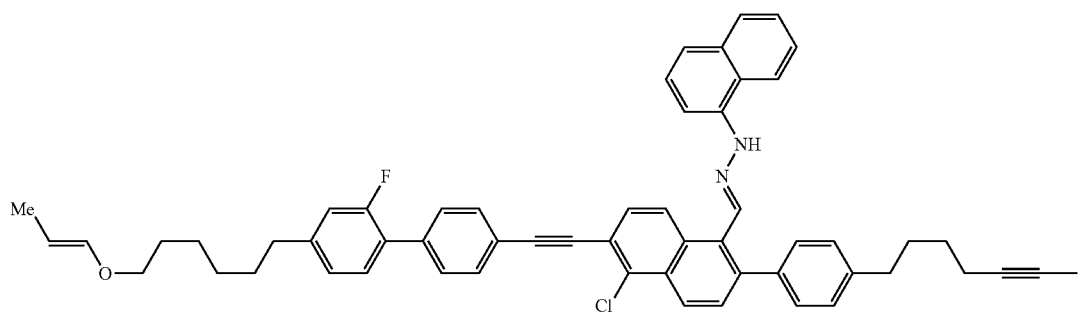
(1-1-40)
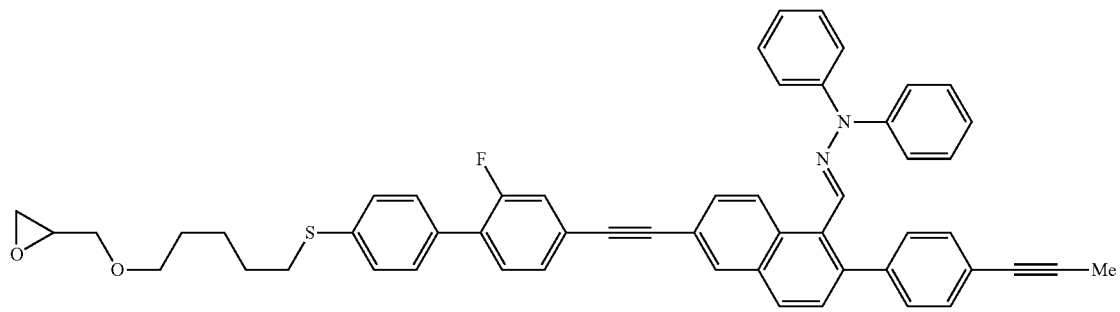

[Chem. 51]
(1-1-41)
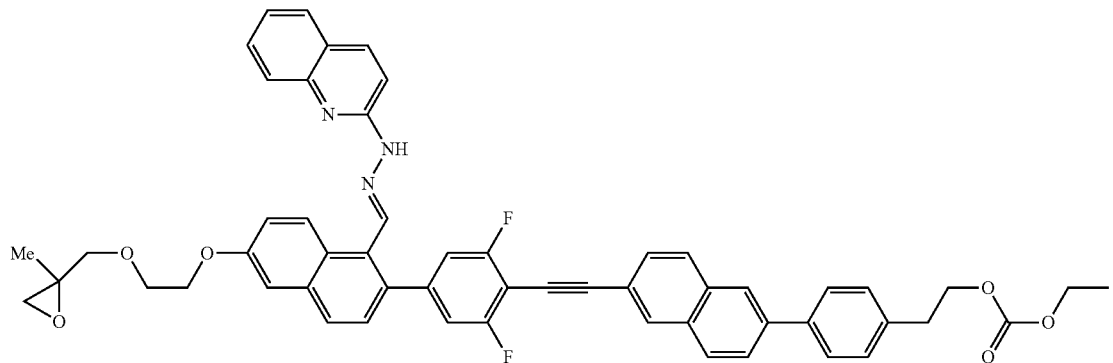
(1-1-42)
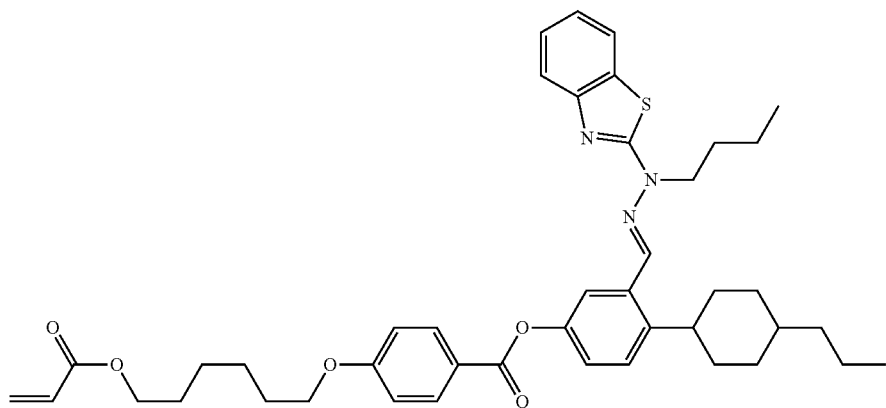
(1-1-43)
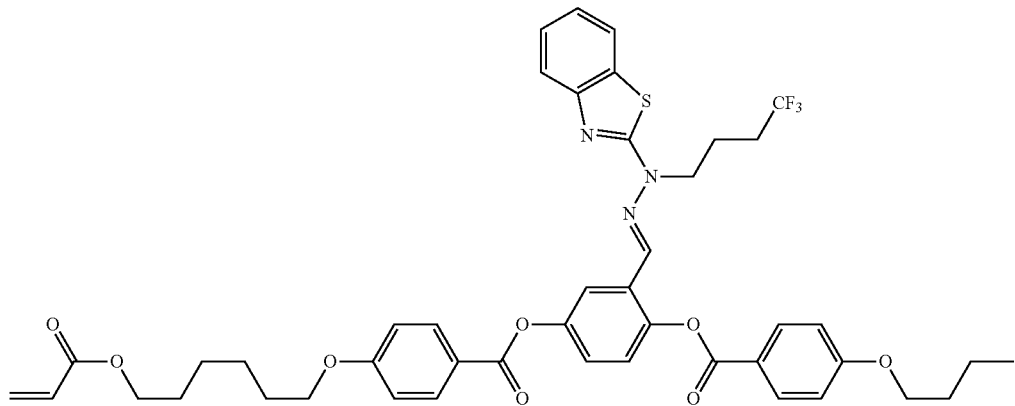

(1-1-44)
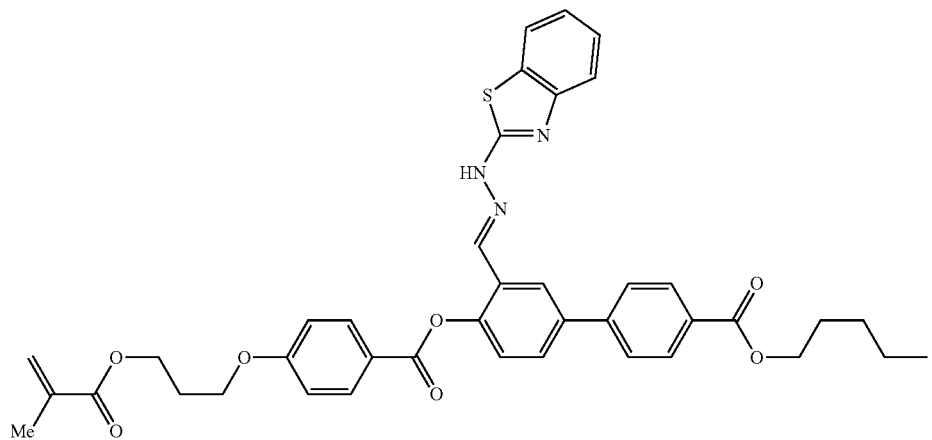
(1-1-45)
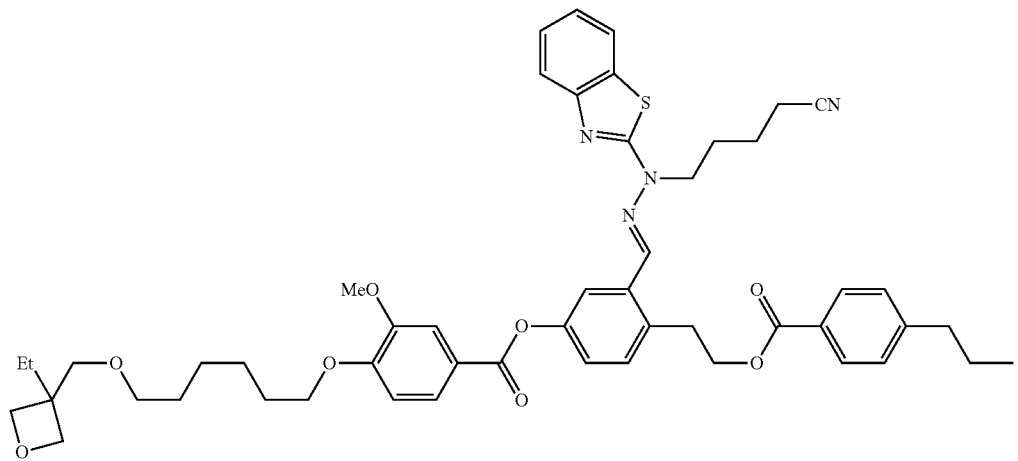
(1-1-46)
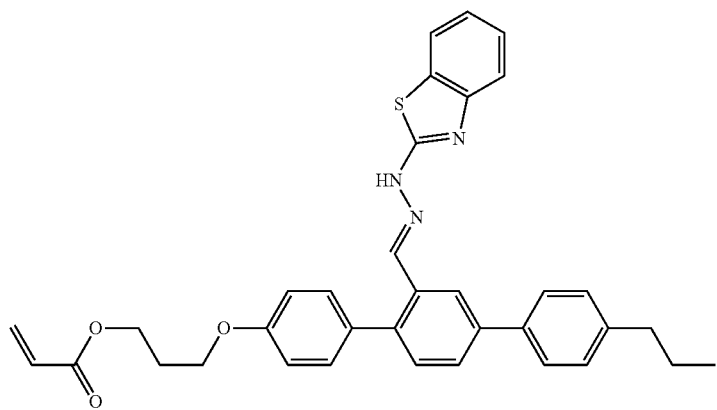

[Chem. 52]
(1-1-47)
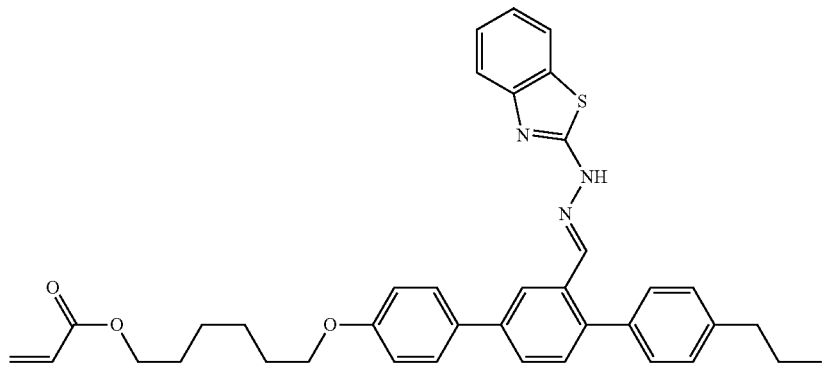
(1-1-48)
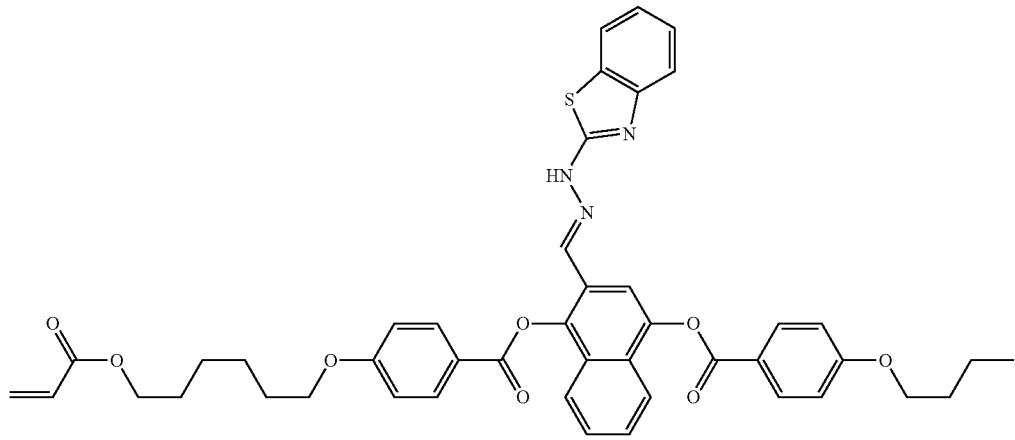
(1-1-49)
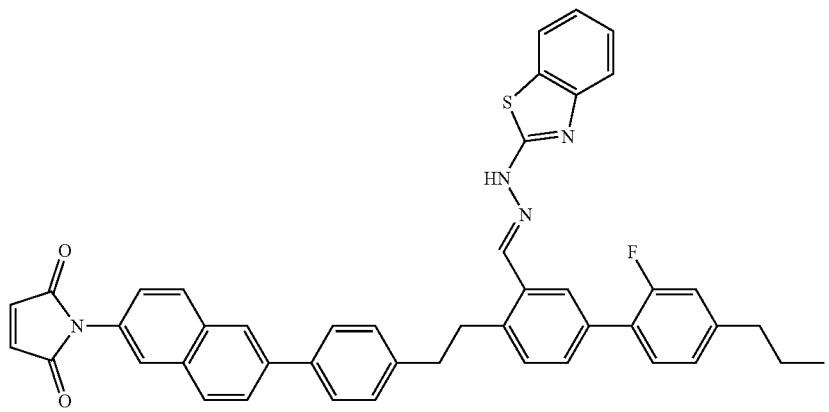
(1-1-50)
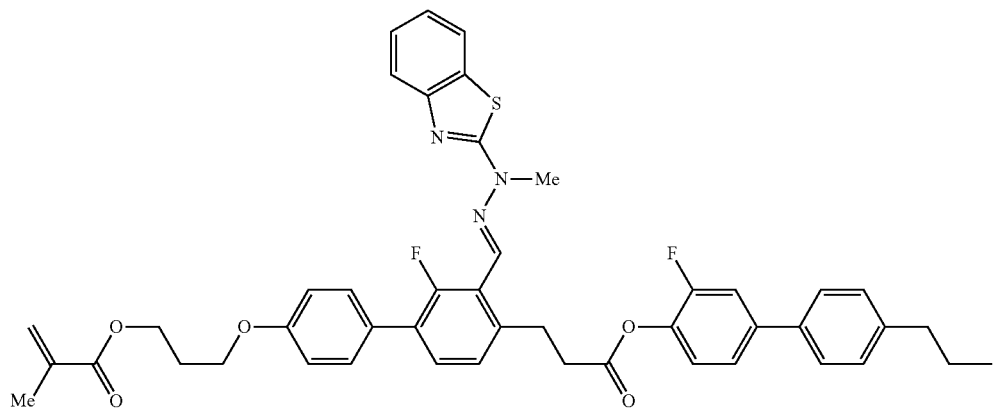

(1-1-51)
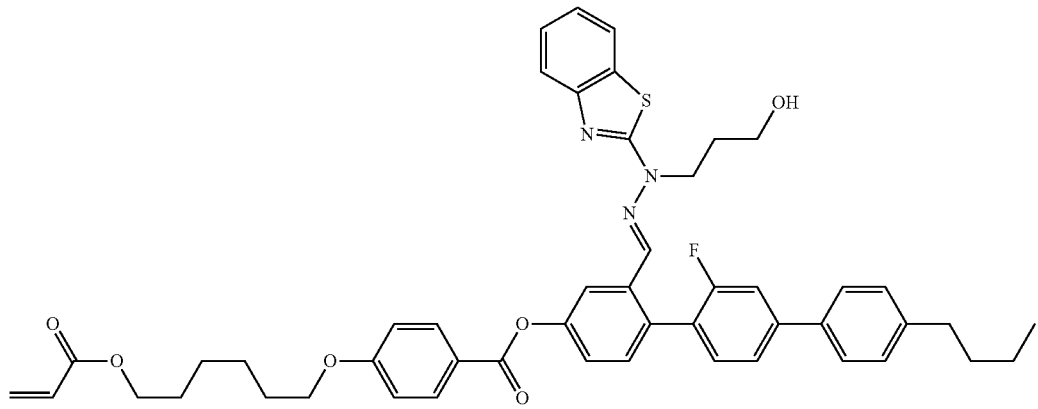
[Chem. 53]
(1-1-52)
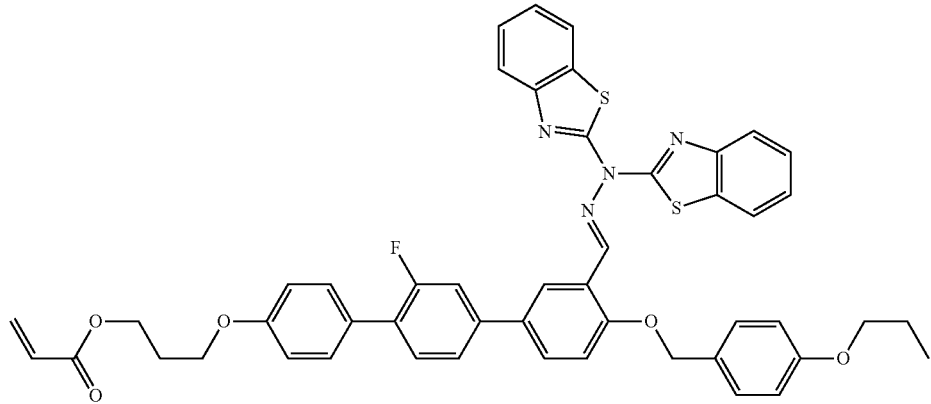
(1-1-53)
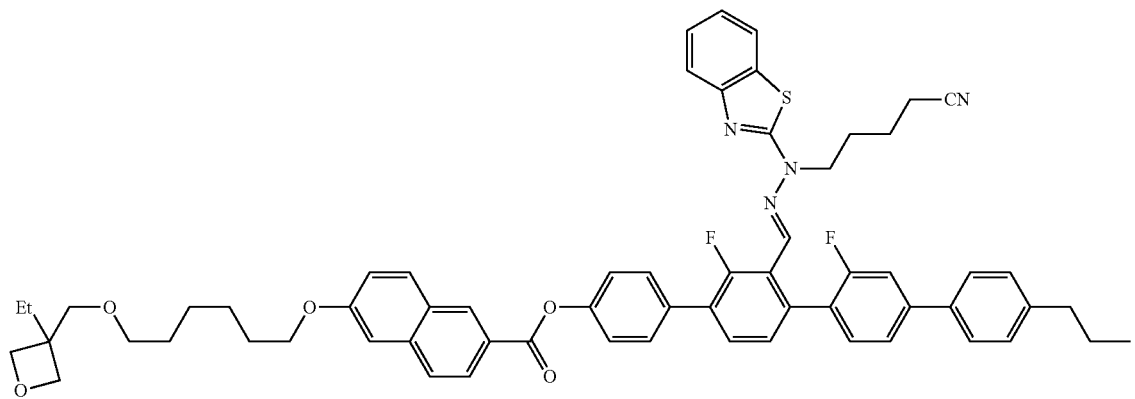

-continued
(1-1-54)
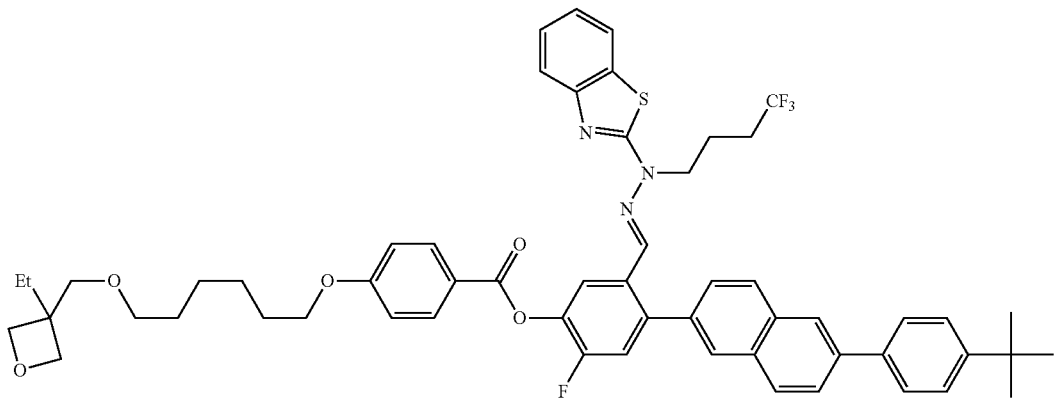
(1-1-55)
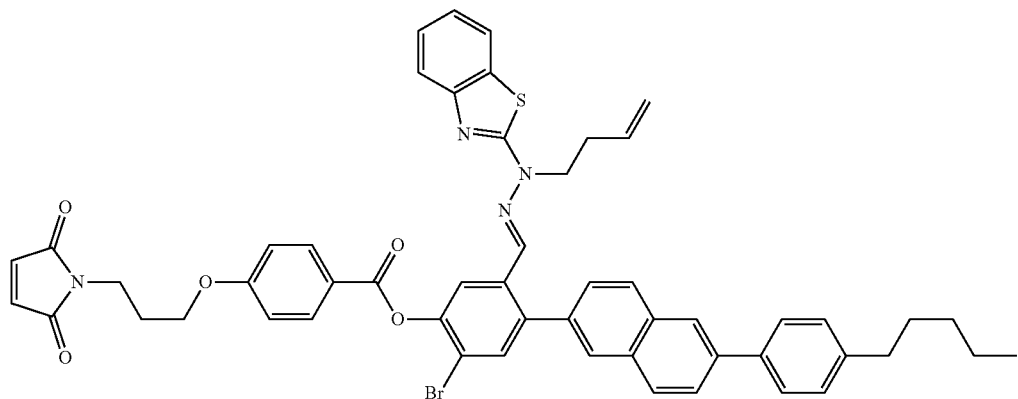
(1-1-56)
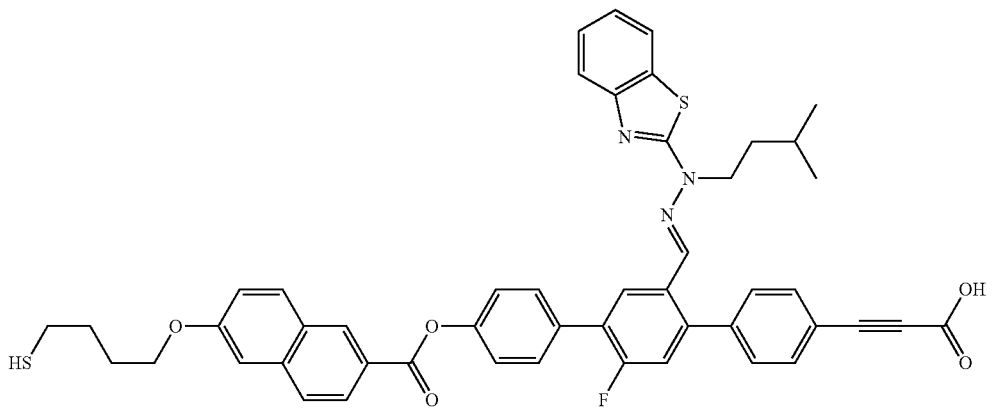
[Chem. 54]
(1-1-57)
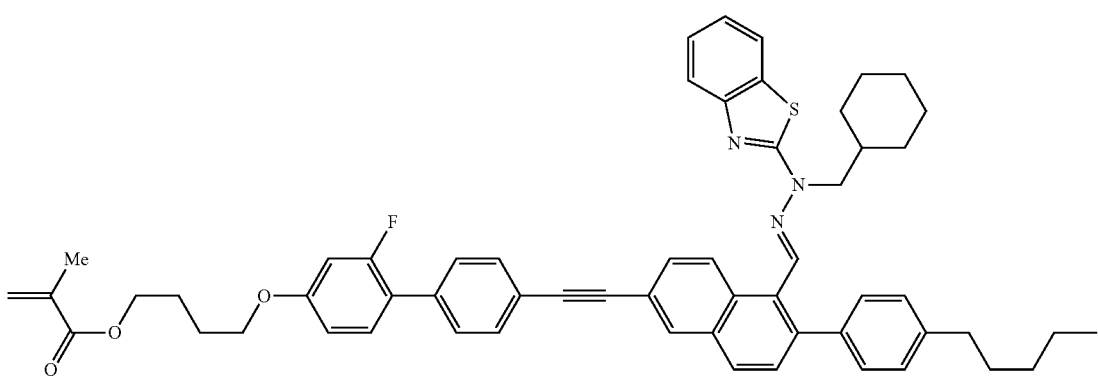

-continued
(1-1-58)
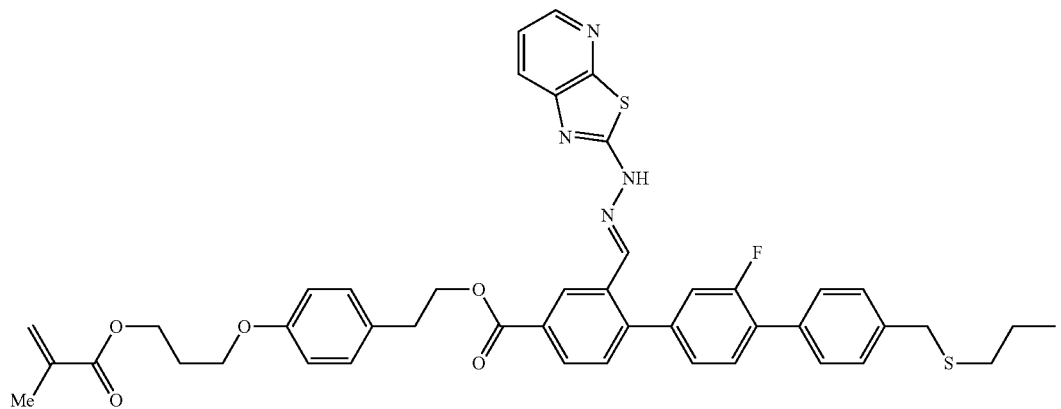
(1-1-59)
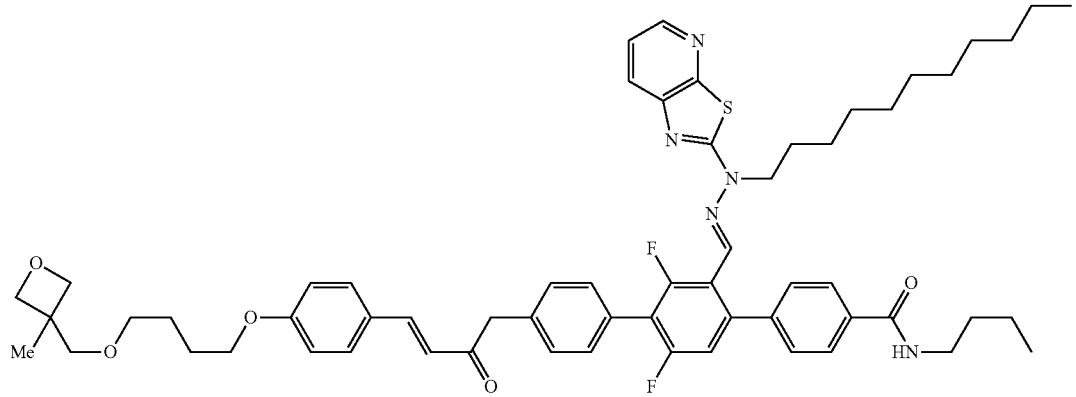
(1-1-60)
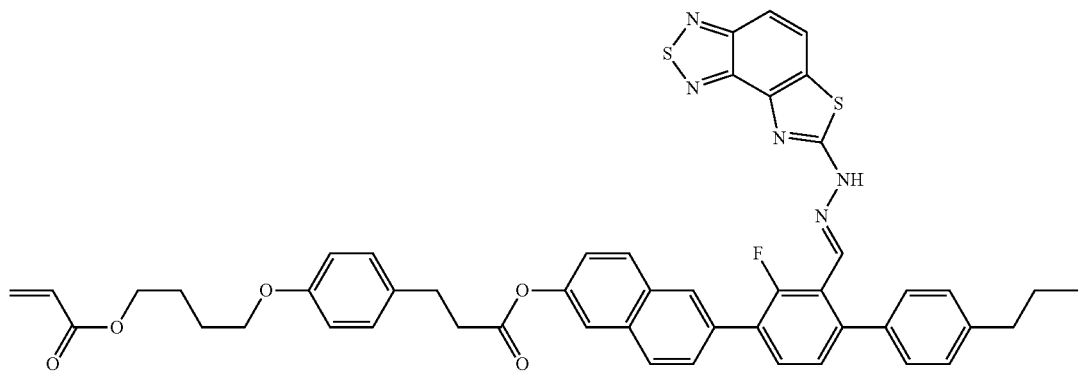
(1-1-61)
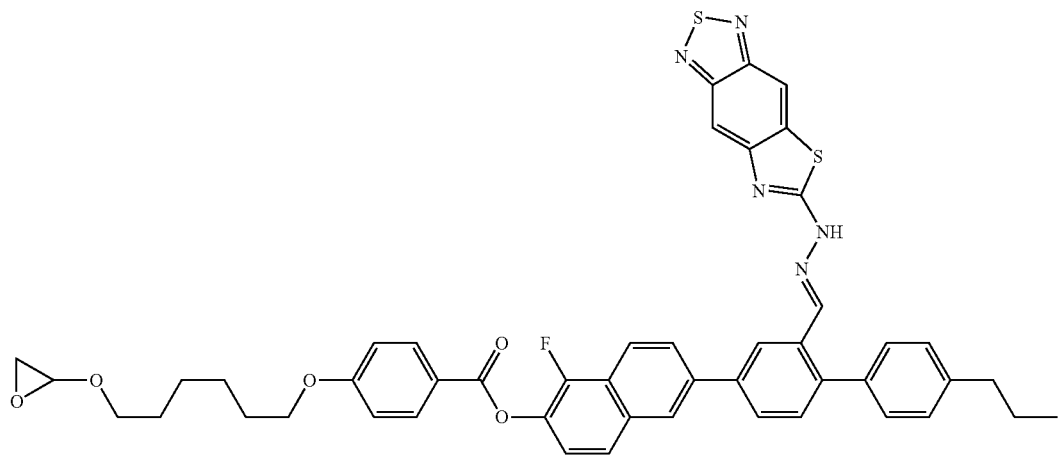

[Chem. 55]
(1-1-62)
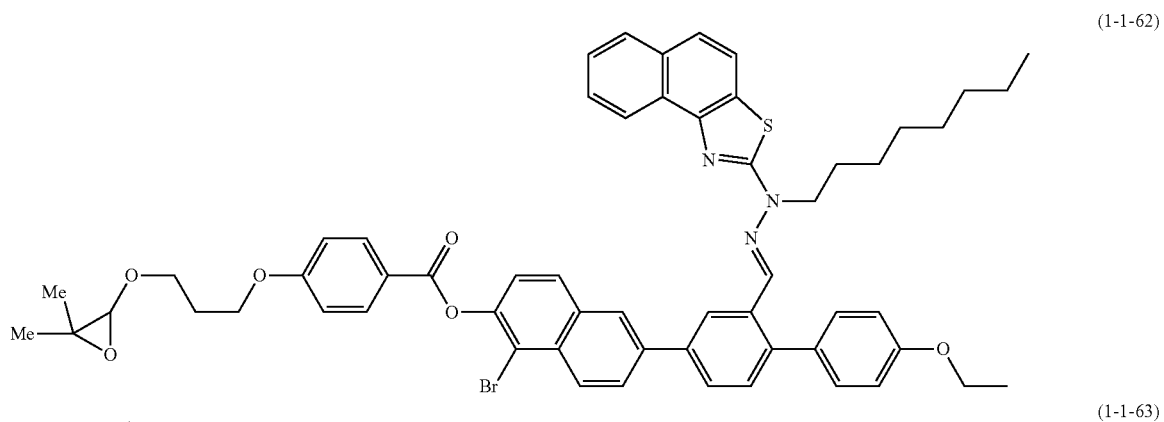
(1-1-63)
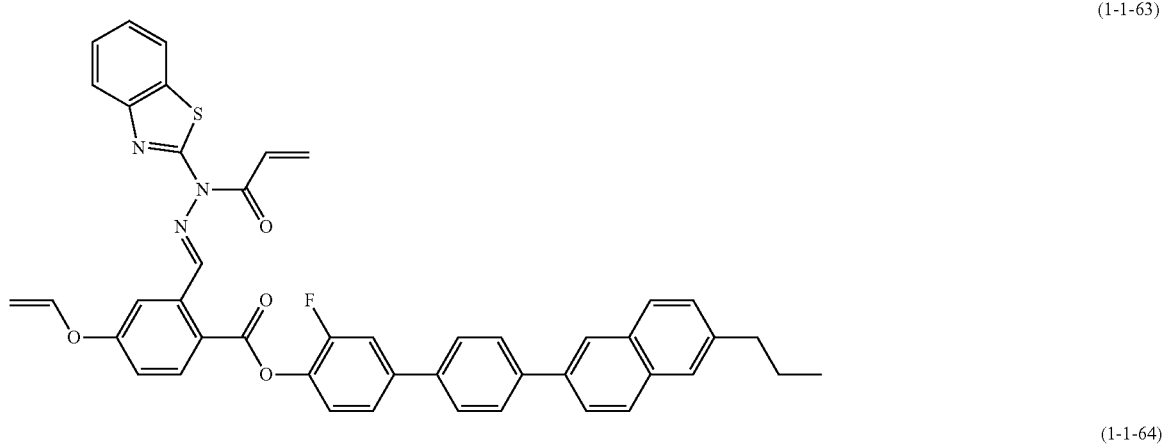
(1-1-64)
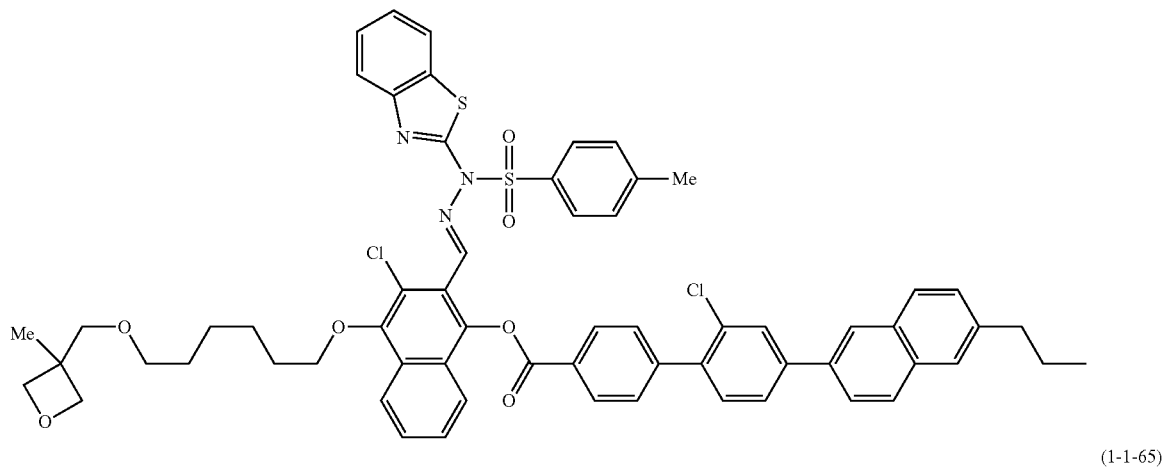
(1-1-65)
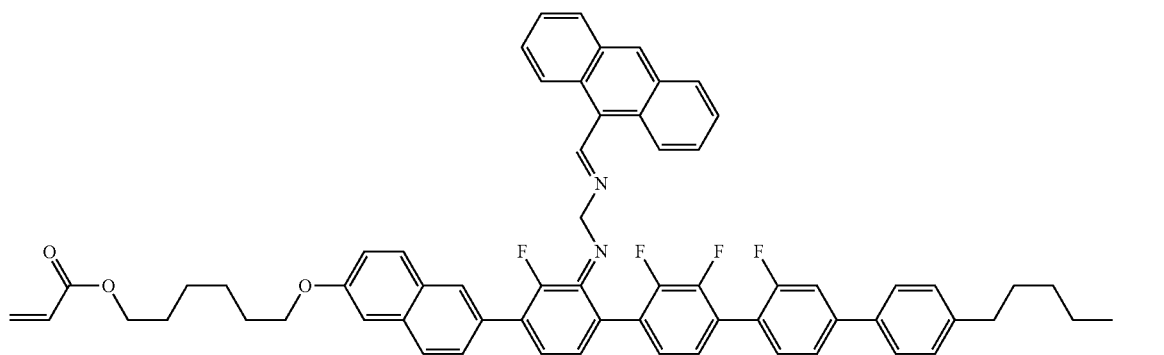

-continued
(1-1-66)
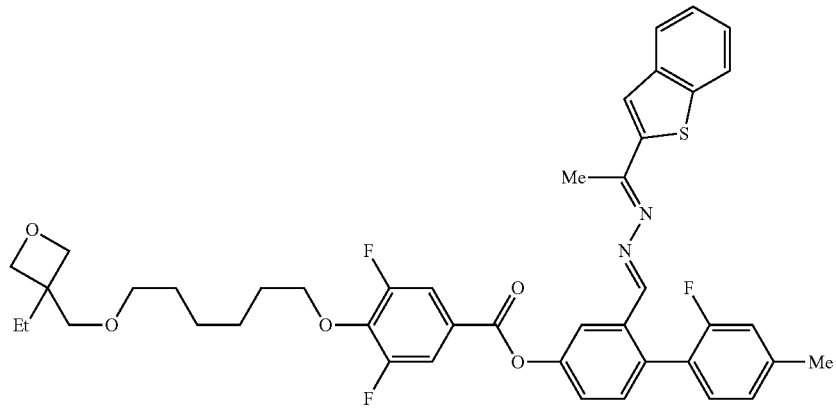
(1-1-67)
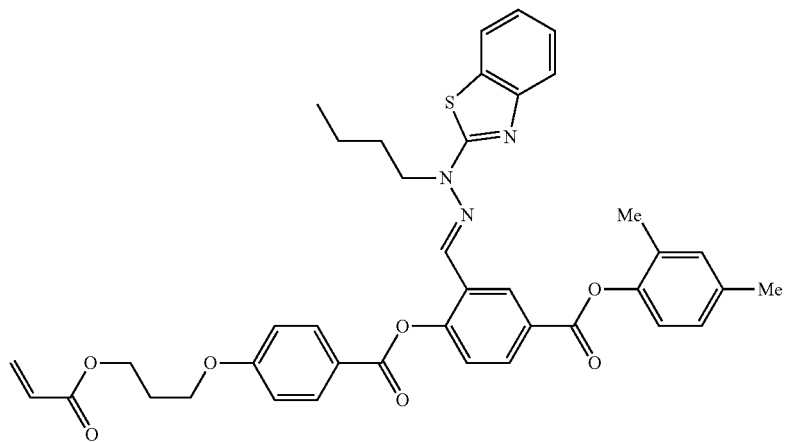
[Chem. 56]
(1-1-68)
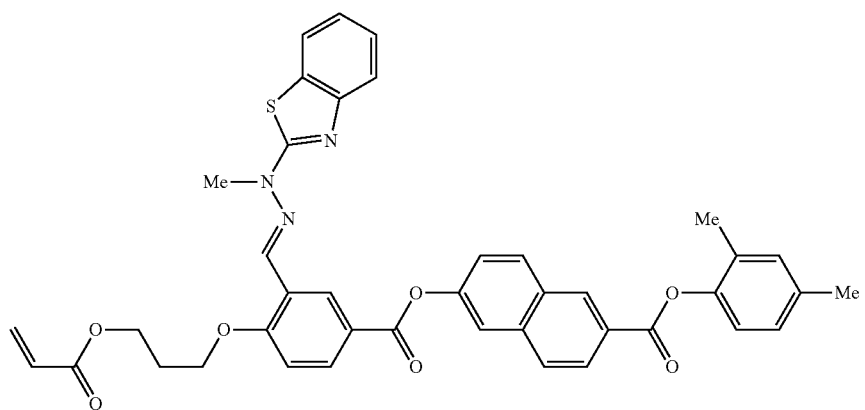

(1-1-69)
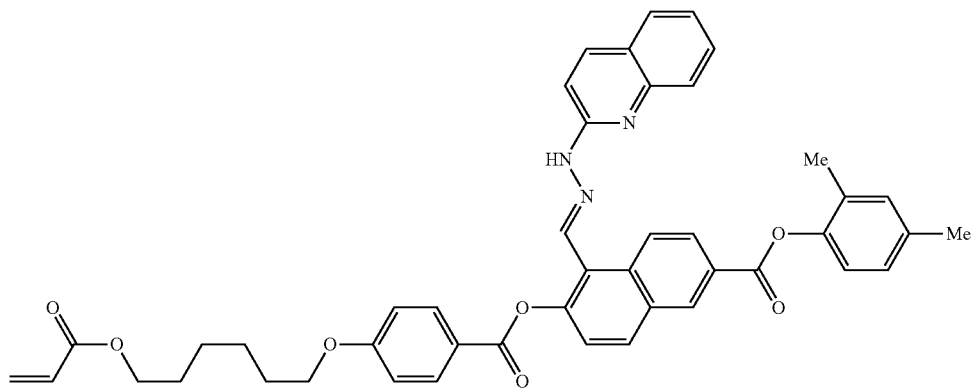
(1-1-70)
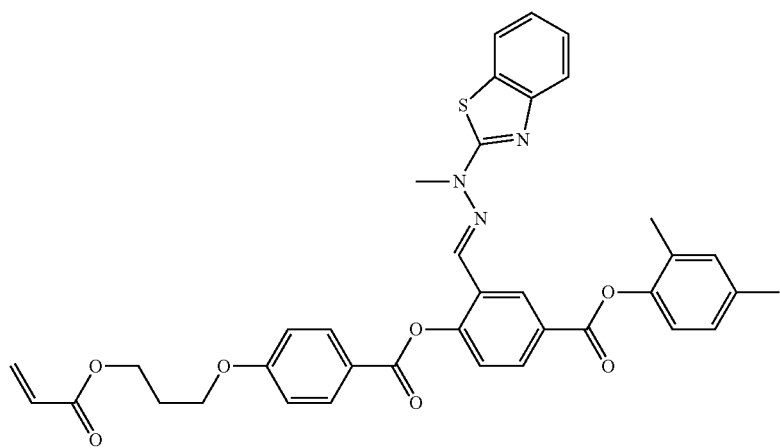
(1-1-71)
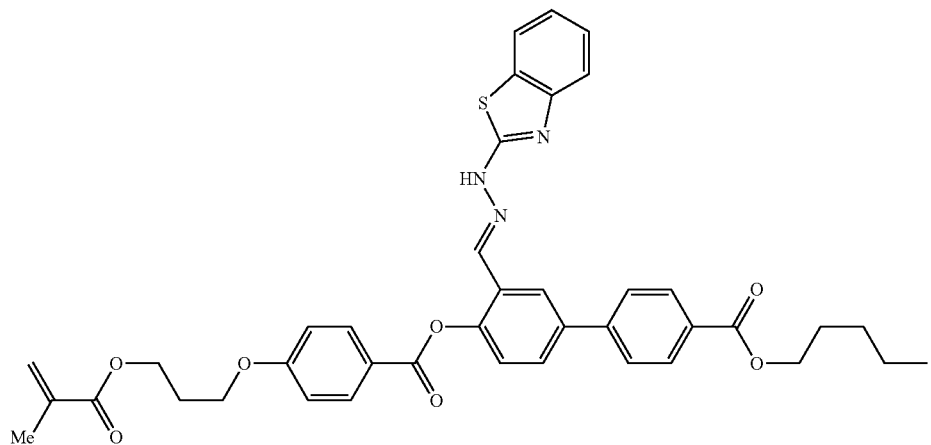

-continued
(1-1-72)
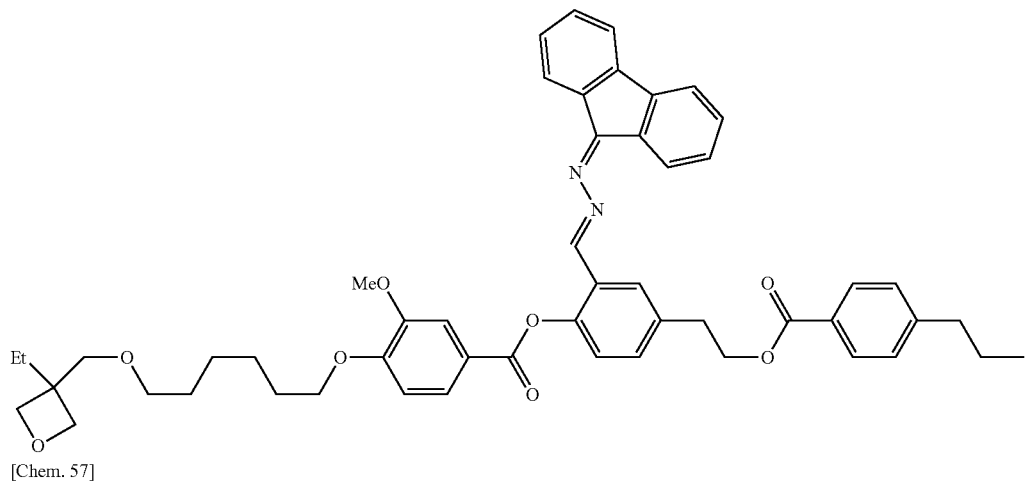
[Chem. 57]
(1-1-73)
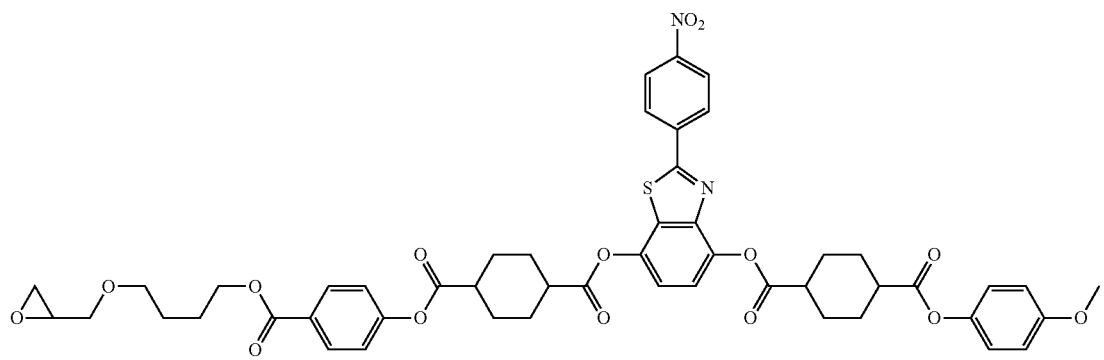
(1-1-74)
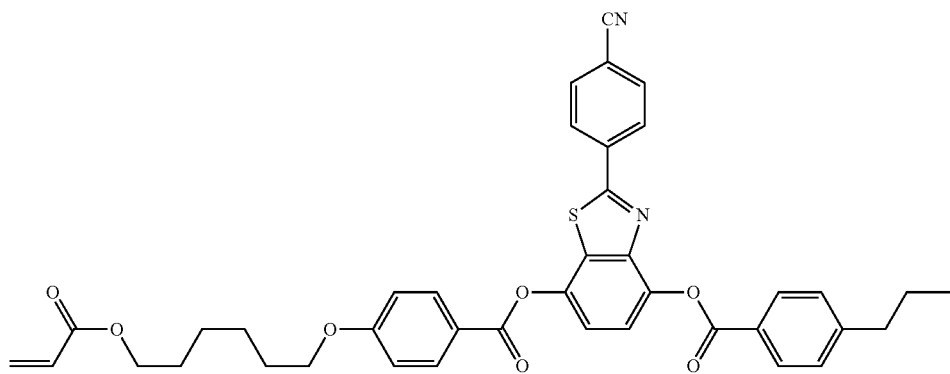
(1-1-75)
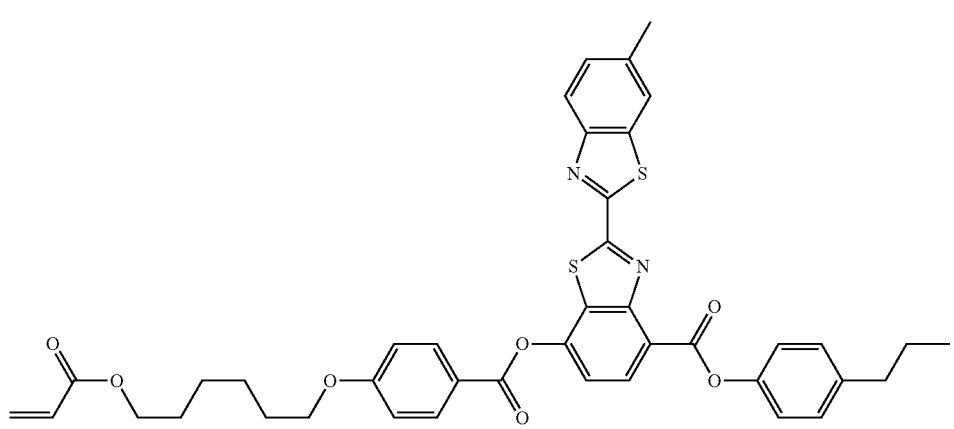

-continued
(1-1-76)
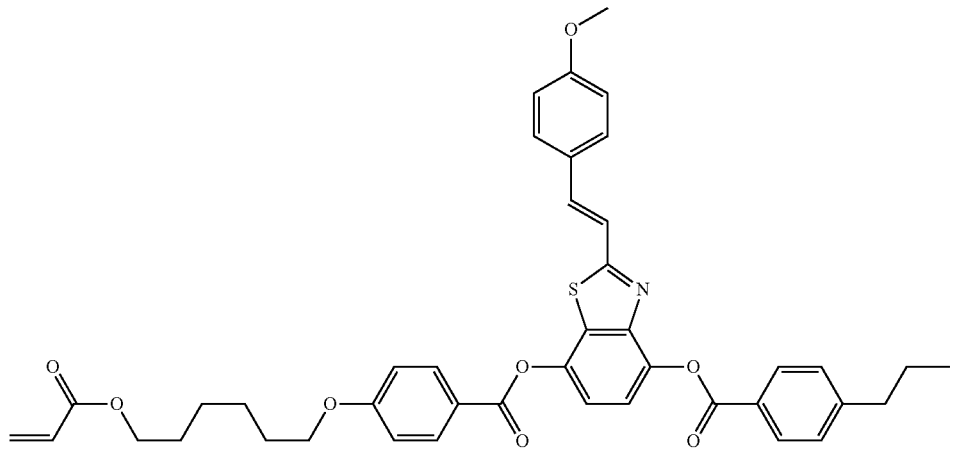
(1-1-77)
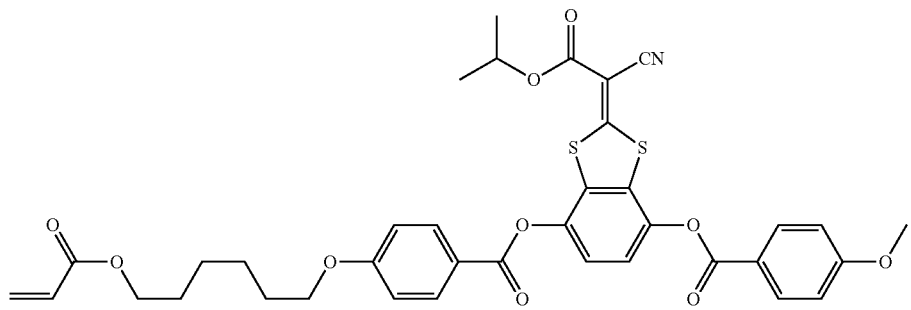
[Chem. 58]
(1-1-78)
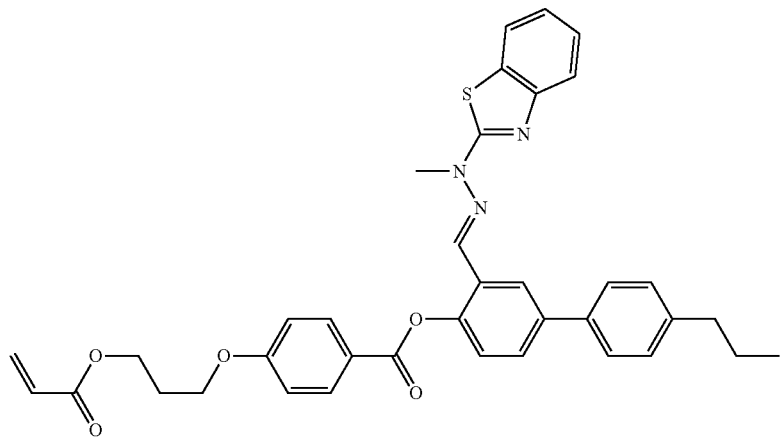

-continued
(1-1-79)
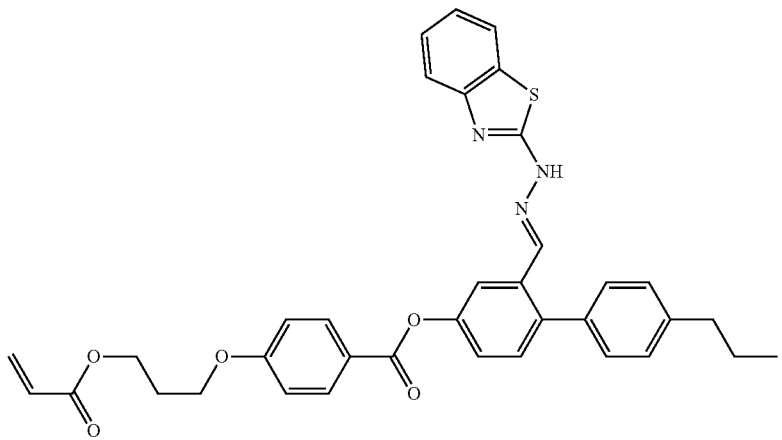
(1-1-80)
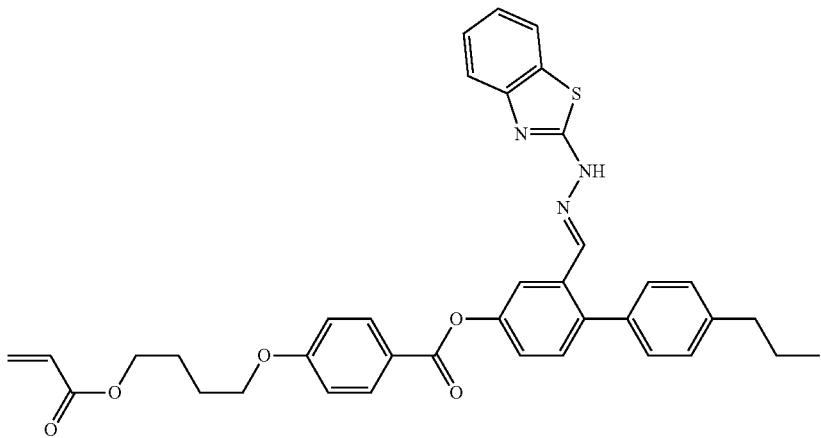
(1-1-81)
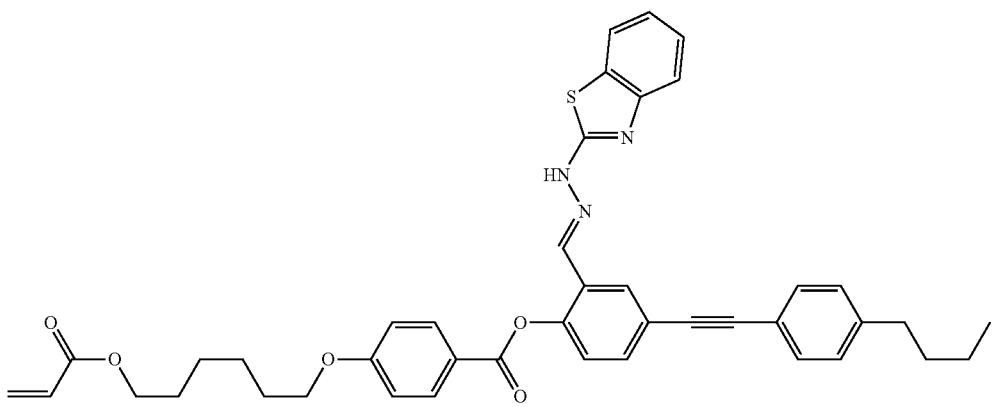

[Chem. 59]
(1-1-82)
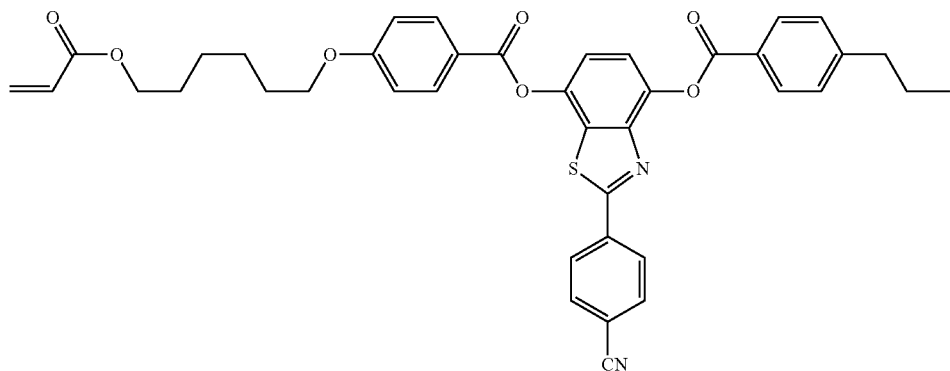
(1-1-83)
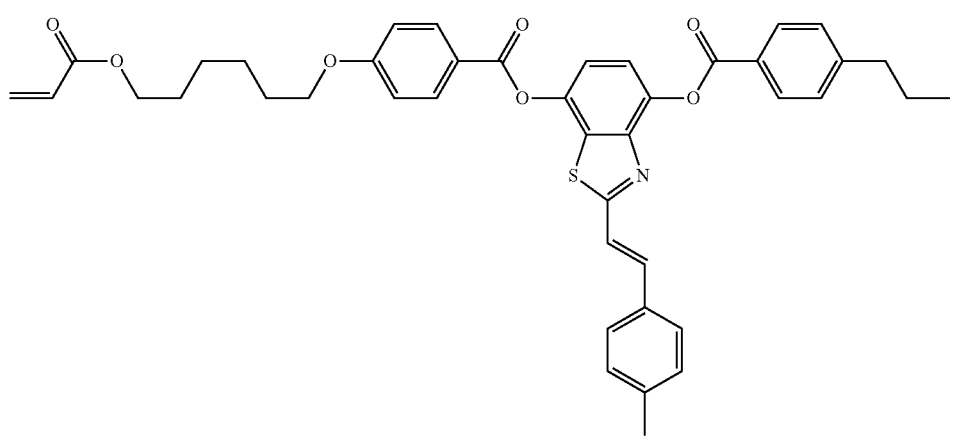
(1-1-84)
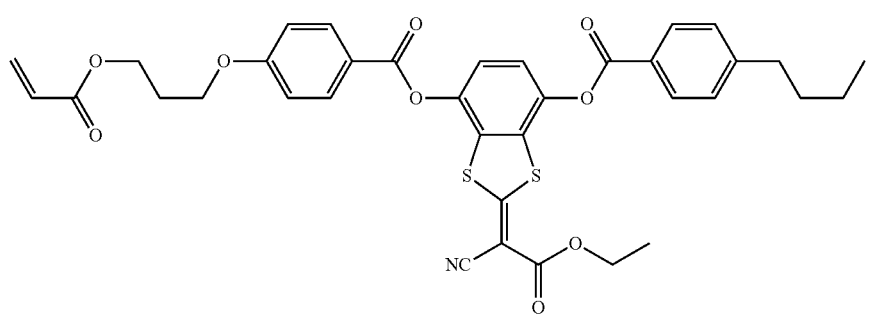
(1-1-85)
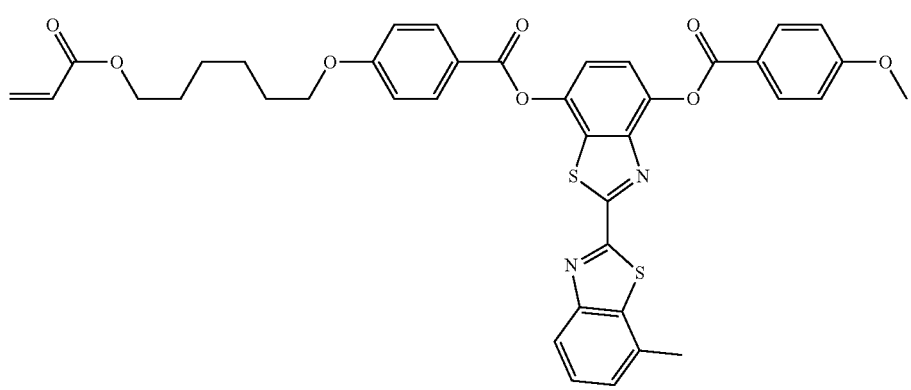

-continued
[Chem. 60]
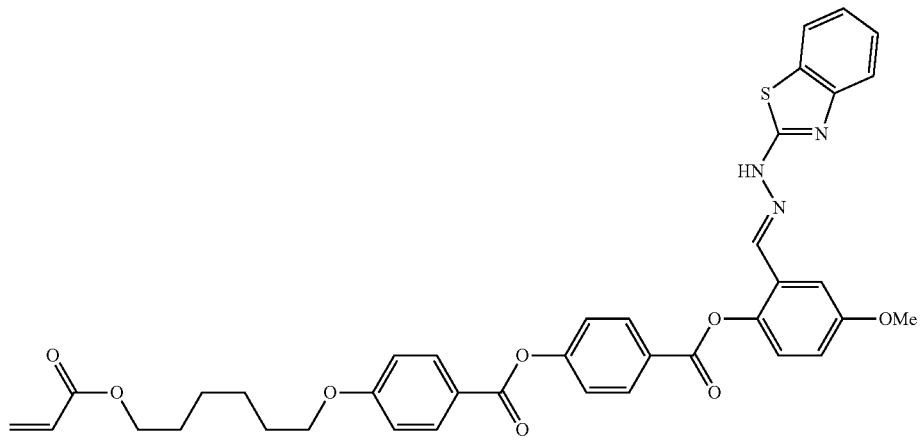
(1-1-86)
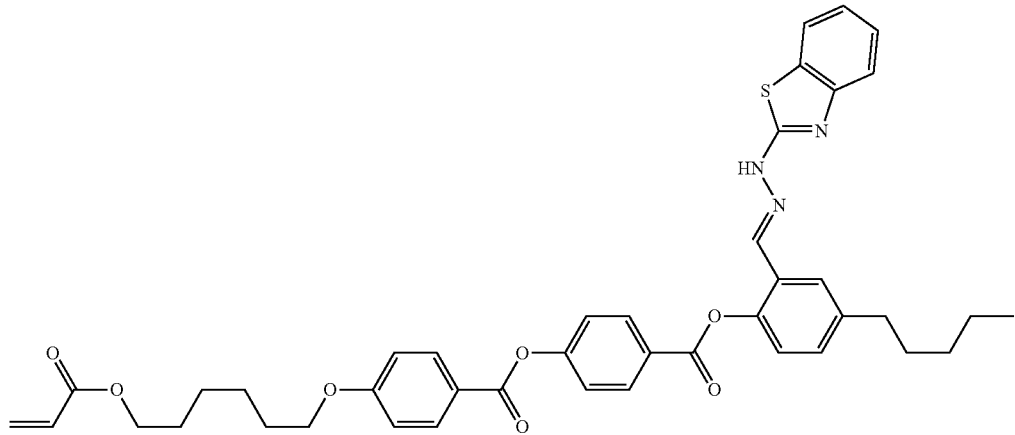
(1-1-87)
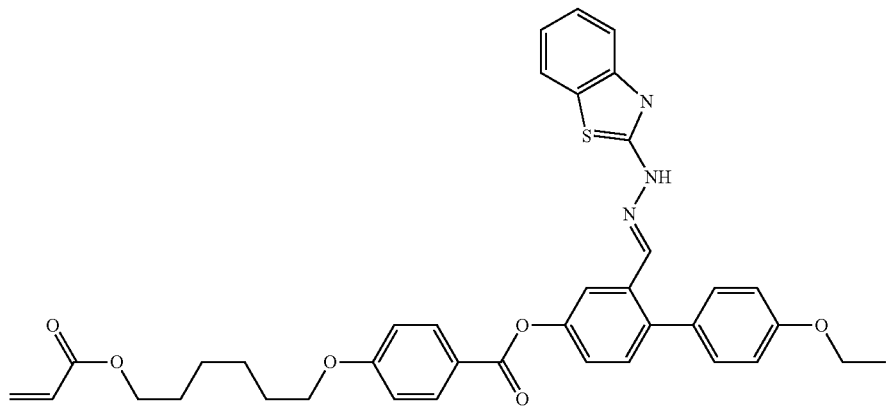
(1-1-88)

(1-1-89)
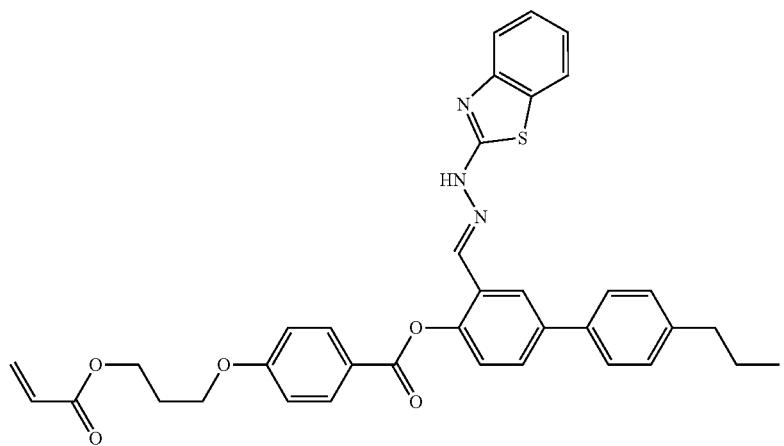
(1-1-90)
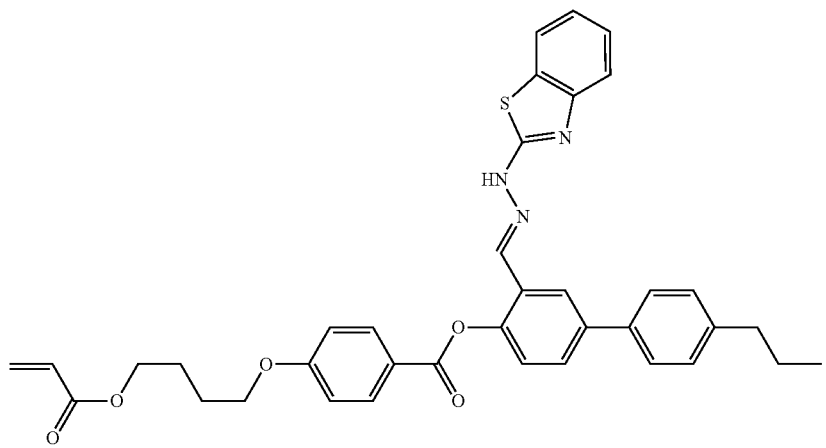
[Chem. 61]
(1-1-91)
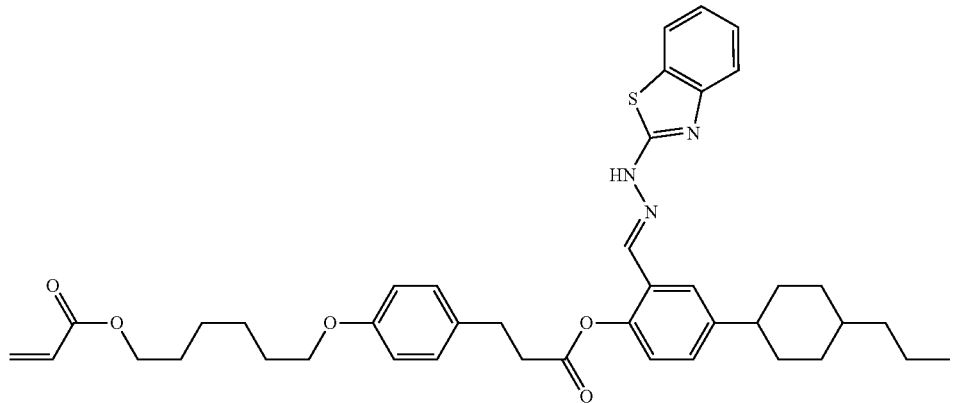

-continued
(1-1-92)
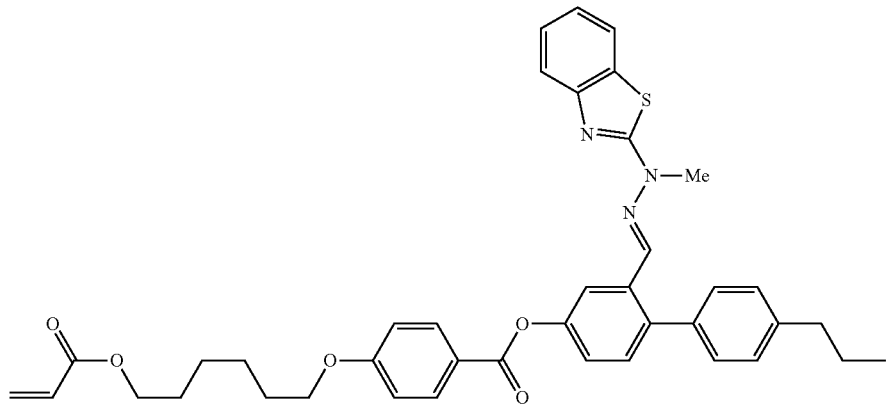
(1-1-93)
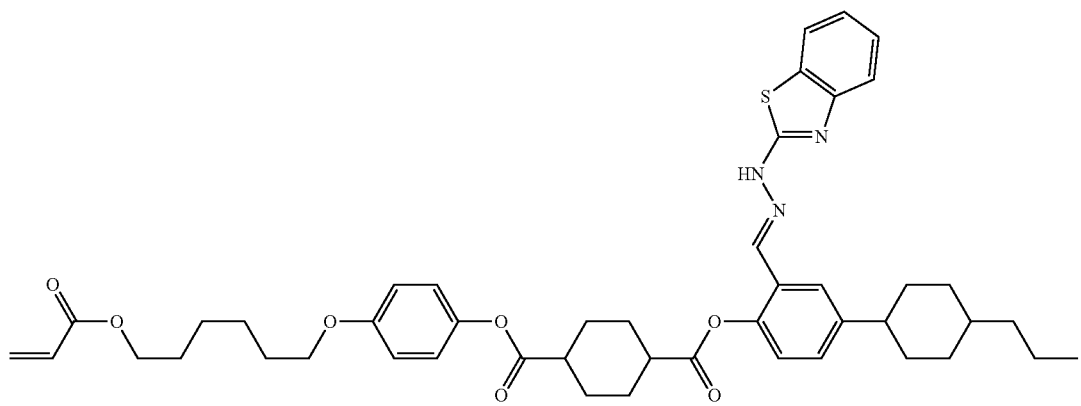
(1-1-94)
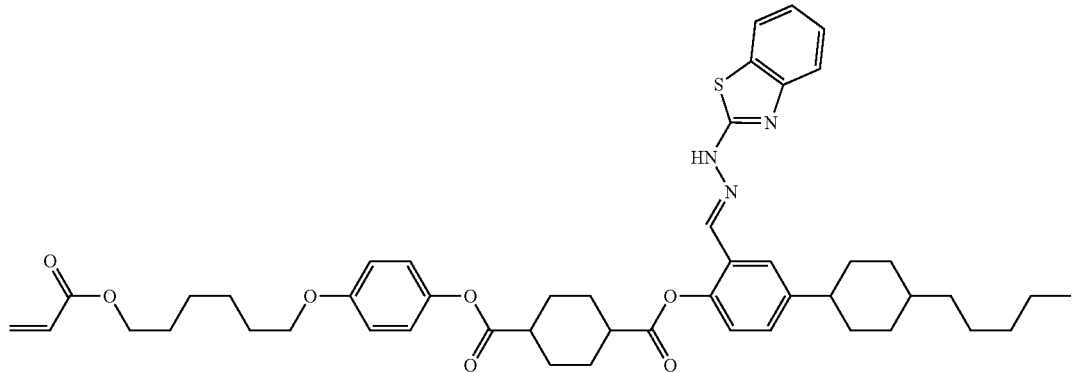
(1-1-95)
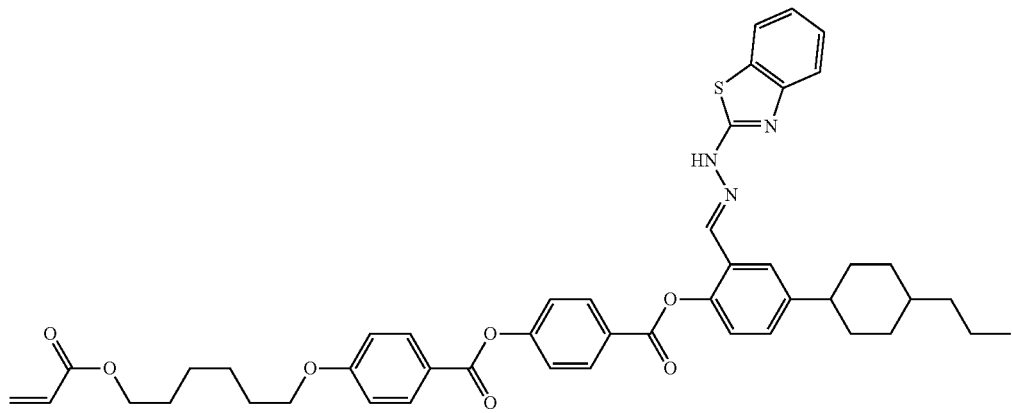

-continued
[Chem. 62]
(1-1-96)
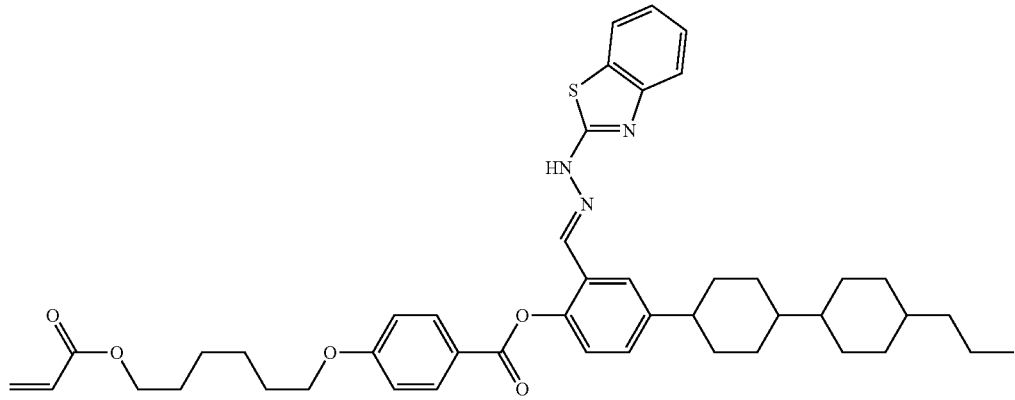
(1-1-97)
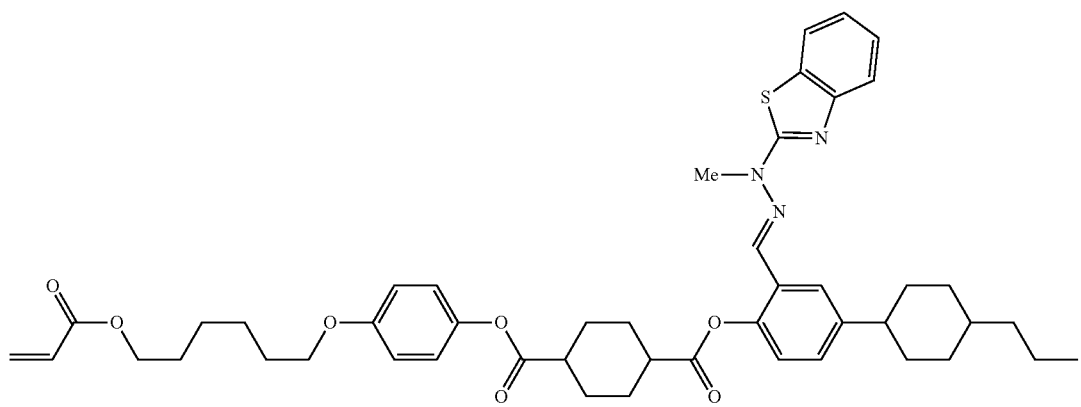
(1-1-98)
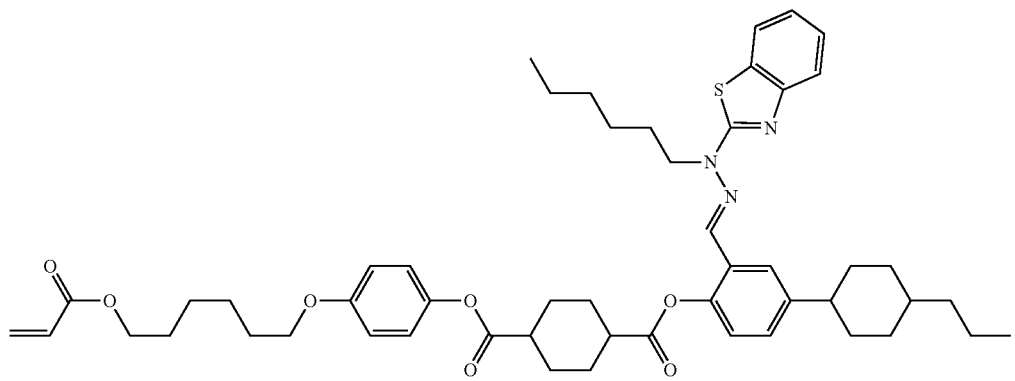
(1-1-99)
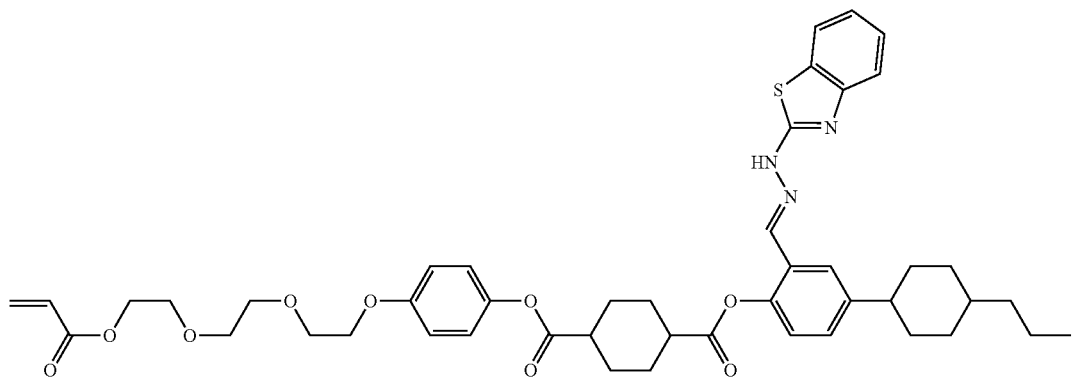

-continued
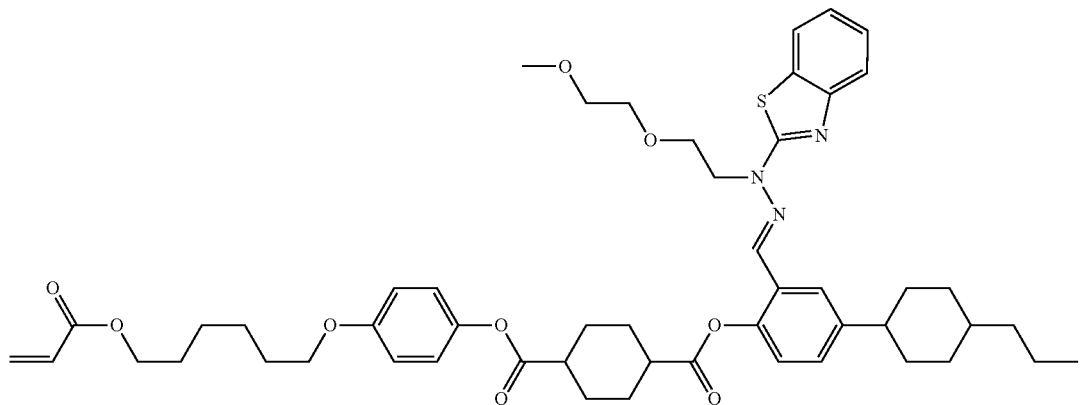
(1-1-100)
[Chem. 63]
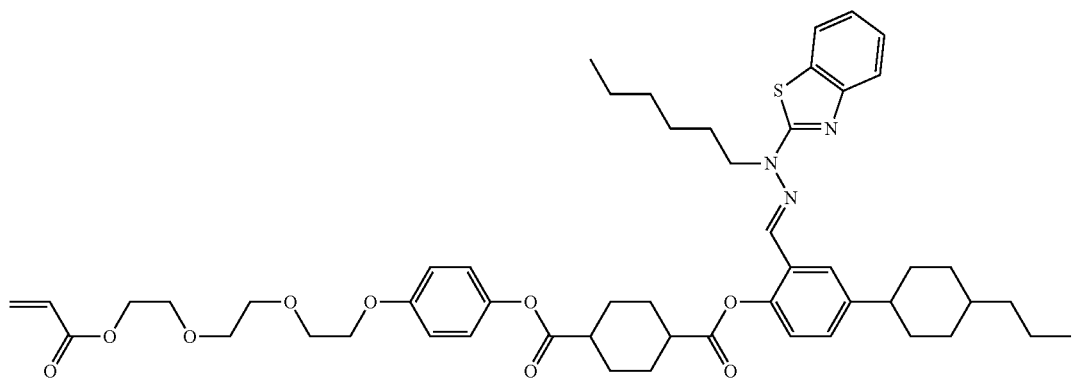
(1-1-101)
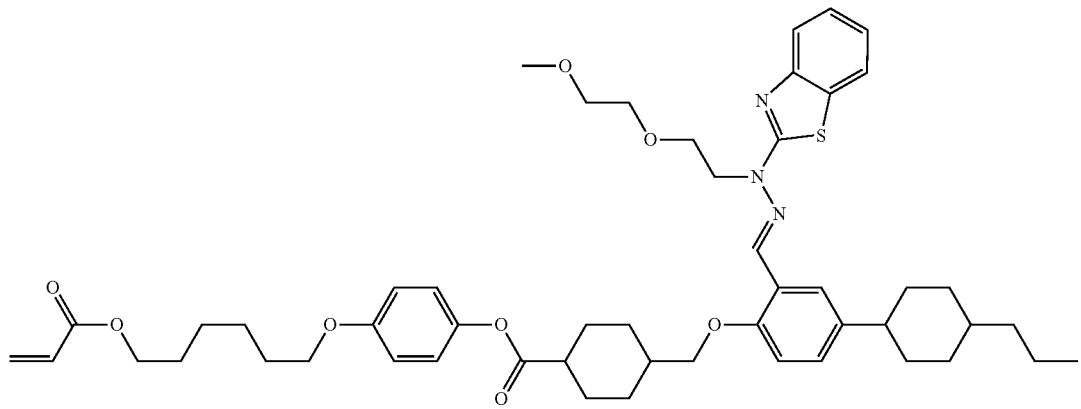
(1-1-102)
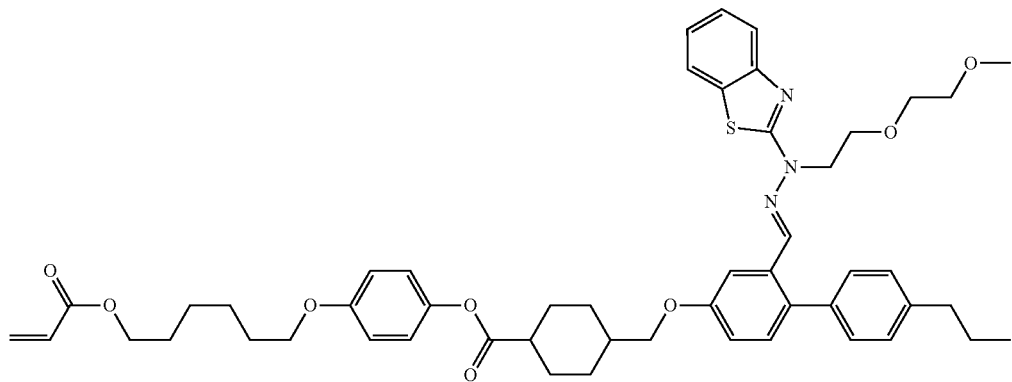
(1-1-103)

-continued

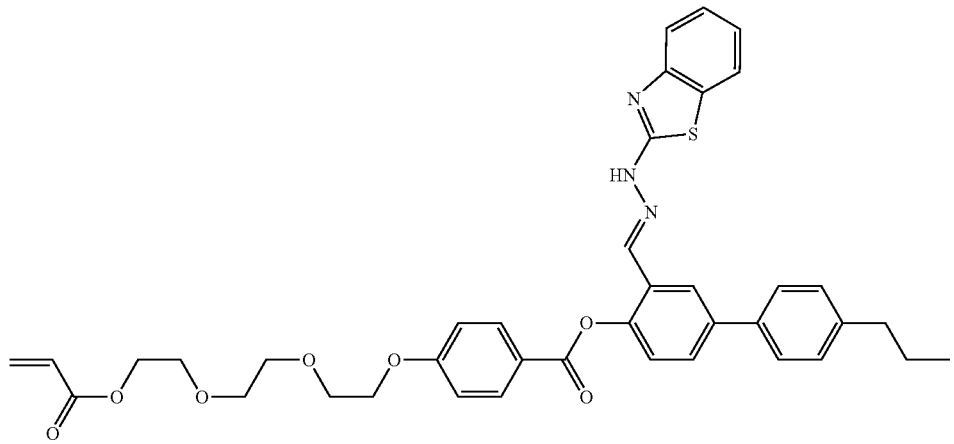
(1-1-104)

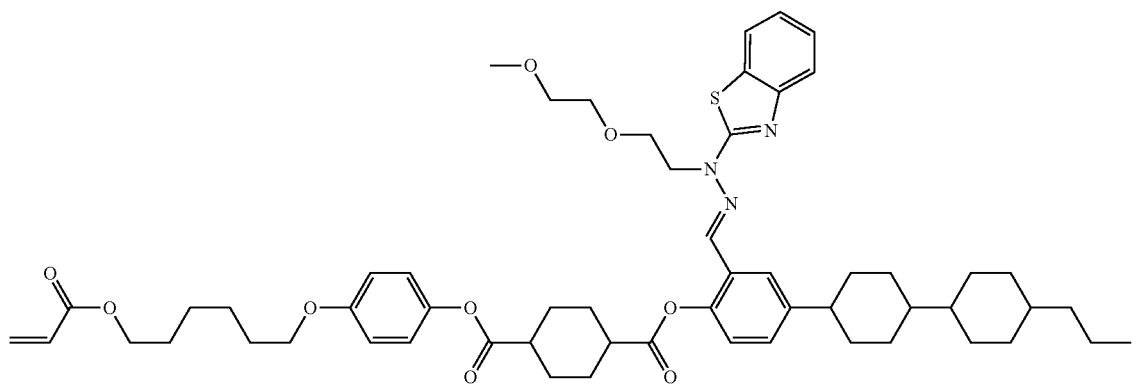
(1-1-105)

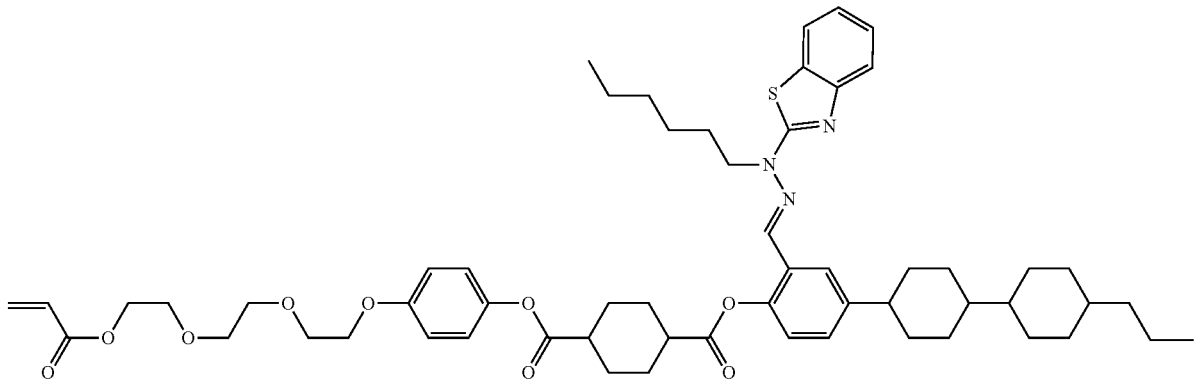
(1-1-106)

The total amount of the above reverse-wavelength dispersion monofunctional polymerizable compound is preferably 0% to 90% by mass, is more preferably 0% to 80% by mass, and is particularly preferably 0% to 70% by mass of the total amount of the polymerizable compounds included in the polymerizable composition.

In the case where primary importance is attached to the preservation stability of the polymerizable composition, the lower limit is preferably set to 5% by mass or more and is more preferably set to 10% by mass or more.

(Reverse-Wavelength Dispersion Difunctional Polymerizable Compound)

The reverse-wavelength dispersion difunctional polymerizable compound is preferably the polymerizable compound represented by General Formula (2-1):

[Chem. 64]

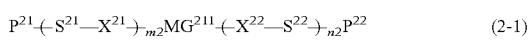
(2-1)

In General Formula (2-1), $P^{21}$ and $P^{22}$ each independently represent a polymerizable group.

In General Formula (2-1), $S^{21}$ and $S^{22}$ each independently represent a spacer group or a single bond; and, when a plurality of $S^{21}$ groups and/or a plurality of $S^{22}$ groups are present, they may be identical to or different from one another.

In General Formula (2-1), $X^{21}$ and $X^{22}$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; and, when a plurality of X$^{21}$ groups and/or a plurality of X$^{22}$ groups are present, they may be identical to or different from one another (the P—(S—X)— linkages do not include —O—O—).

In General Formula (2-1), MG$^{211}$ each independently represents a mesogenic group.

In General Formula (2-1), m2 and n2 each independently represent an integer of 0 to 5.

In General Formula (2-1) above, the spacer groups represented by S$^{21}$ and S$^{22}$ are alkylene groups having 1 to 18 carbon atoms. The alkylene groups may be substituted with one or more halogen atoms, CN groups, alkyl groups having 1 to 8 carbon atoms, or alkyl groups having 1 to 8 carbon atoms and including a polymerizable functional group. In the above groups, one CH$_2$ group or two or more CH$_2$ groups that are not adjacent to one another may be each independently replaced with —O—, —S—, —NH—, —N(CH$_3$)—, —CO—, —CH(OH)—, CH(COOH), —COO—, —OCO—, —OCOO—, —SCO—, —COS— —C≡C—, or Formula (S-1) or (S-2) such that any two oxygen atoms do not directly bind to each other.

[Chem. 65]

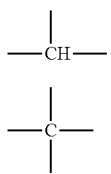

(S-1)

(S-2)

In consideration of alignment, among the above spacer groups, a linear alkylene group having 2 to 8 carbon atoms, an alkylene group having 2 to 6 carbon atoms substituted with a fluorine atom, and an alkylene group having 5 to 14 carbon atoms in which a part of the alkylene group is replaced with —O— are preferable.

In General Formula (2-1), the polymerizable groups represented by P$^{21}$ and P$^{22}$ are preferably selected from Formulae (P-1) to (P-20) below.

[Chem. 66]

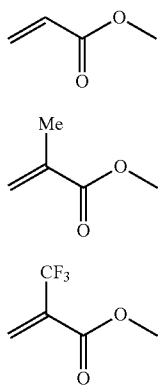

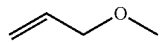
(P-4)

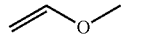
(P-5)

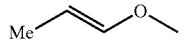
(P-6)

(P-7)

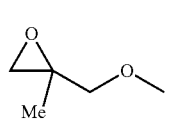
(P-8)

(P-9)

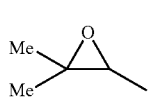
(P-10)

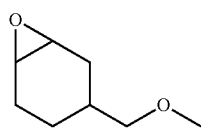
(P-11)

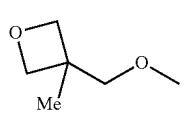
(P-12)

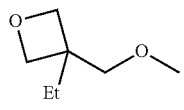
(P-13)

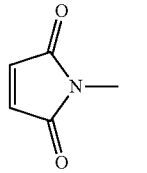
(P-14)

(P-15)

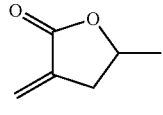
(P-16)

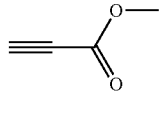
(P-17)

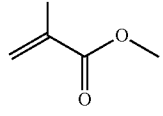
(P-18)

-continued (P-19)
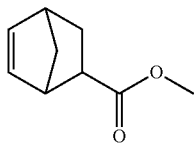

(P-20)
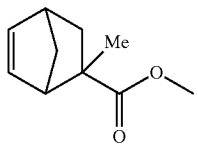

In order to enhance polymerizability and preservation stability, among the above polymerizable groups, Formulae (P-1), (P-2), (P-7), (P-12), and (P-13) are preferable; and Formulae (P-1), (P-7), and (P-12) are more preferable.

The mesogenic group represented by $MG^{21}$ in General Formula (2-1) is represented by Formula (8-a) below.

[Chem. 67]

(8-a)
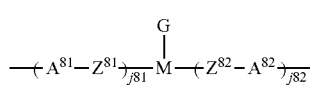

(in Formula (8-a), $A^{81}$ and $A^{82}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^2$ substituents, and, when a plurality of $A^{81}$ groups and/or a plurality of $A^{82}$ groups are present, they may be identical to or different from one another;

$Z^{81}$ and $Z^{82}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—, —N═CH—, —CH═N—N═CH—, —CF═CF—, —C≡C—, or a single bond, and, when a plurality of $Z^{81}$ groups and/or a plurality of $Z^{82}$ groups are present, they may be identical to or different from one another;

M represents a group selected from Formulae (M-81) to (M-813) below:

[Chem. 68]

(M-81)
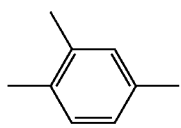

(M-82)
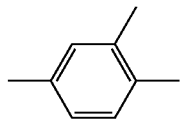

(M-83)
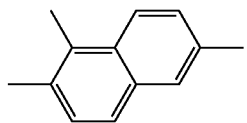

(M-84)
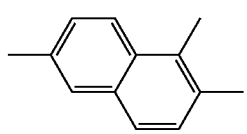

(M-85)
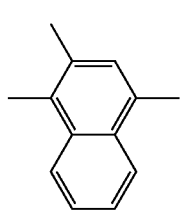

(M-86)
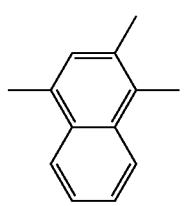

(M-87)
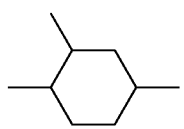

(M-88)
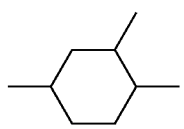

(M-89)
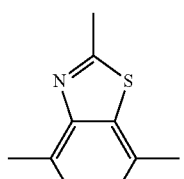

(M-810)
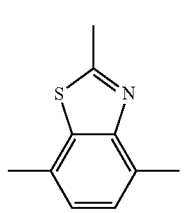

(M-811)

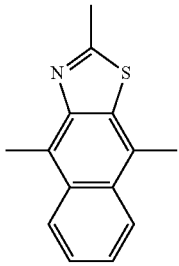

(M-812)

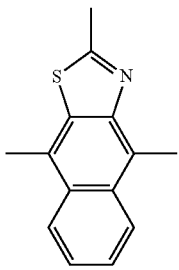

(M-813)

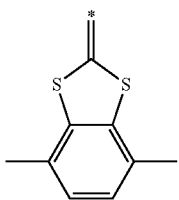

the above groups may be optionally substituted with one or more $L^2$ substituents;

G is selected from Formulae (G-81) to (G-86) below:

[Chem. 69]

(G-81)

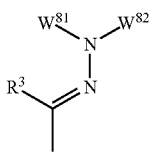

(G-82)

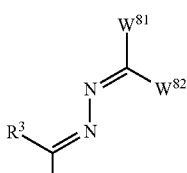

(G-83)

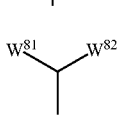

(G-84)

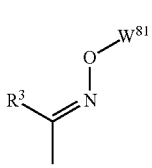

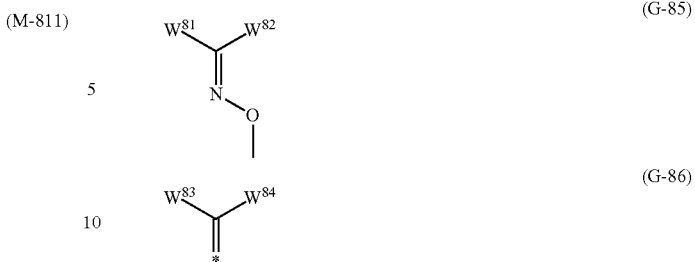

(in Formulae (G-81) to (G-86), $R^3$ represents a hydrogen atom or an alkyl group having 1 to 20 carbon atoms, the alkyl group may be linear or branched, a hydrogen atom included in the alkyl group may be replaced with a fluorine atom, and, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

$W^{81}$ represents a group having 5 to 30 carbon atoms, the group including at least one aromatic group, and the group may be optionally substituted with one or more $L^2$ substituents;

$W^{82}$ represents a hydrogen atom or an alkyl group having 1 to 20 carbon atoms, the alkyl group may be linear or branched, a hydrogen atom included in the alkyl group may be replaced with a fluorine atom and/or an —OH group, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, $W^{82}$ may represent the same thing as $W^{81}$, and $W^{81}$ and $W^{82}$ may be bonded to each other to form a ring structure; $W^{83}$ and $W^{84}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms and, in the alkyl group, the cycloalkyl group, the alkenyl group, the cycloalkenyl group, the alkoxy group, the acyloxy group, and the alkylcarbonyloxy group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

when M is selected from Formulae (M-81) to (M-812), G is selected from Formulae (G-81) to (G-85) and, when M is Formula (M-813), G represents Formula (G-86);

$L^2$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms, the alkyl group may be linear or branched, a hydrogen atom may be replaced with a fluorine atom, and, in the alkyl group, one —CH$_2$— group or two or more —CH$_2$— groups that are not adjacent to one another may be each independently replaced with a group selected from —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—; and j81 and j82 each independently represent an integer of 0 to 5, and j81+j82 is an integer of 1 to 5).

The compound represented by General Formula (2-1) above is preferably the compound represented by General Formula (2-a) below.

[Chem. 70]

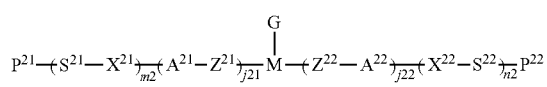

(2-a)

In General Formula (2-a) above, the polymerizable groups P$^{21}$ and P$^{22}$ are preferably each independently selected from Formulae (P-1) to (P-20) below:

[Chem. 71]

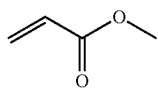 (P-1)

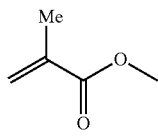 (P-2)

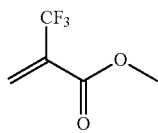 (P-3)

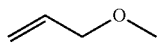 (P-4)

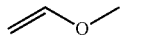 (P-5)

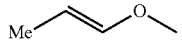 (P-6)

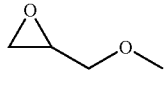 (P-7)

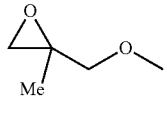 (P-8)

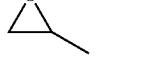 (P-9)

-continued

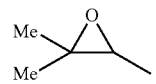 (P-10)

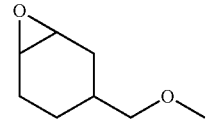 (P-11)

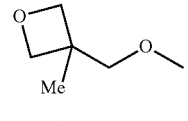 (P-12)

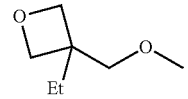 (P-13)

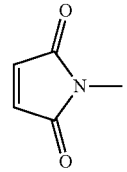 (P-14)

HS— (P-15)

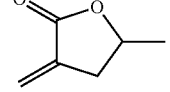 (P-16)

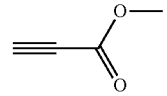 (P-17)

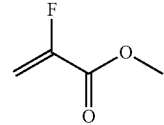 (P-18)

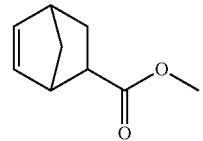 (P-19)

(P-20)

In order to enhance polymerizability and preservation stability, among the above polymerizable groups, Formulae (P-1), (P-2), (P-7), (P-12), and (P-13) are preferable; and Formulae (P-1), (P-7), and (P-12) are more preferable.

In General Formula (2-a), S$^{21}$ and S$^{22}$ each independently represent a spacer group or a single bond. When a plurality of S$^{21}$ groups and/or a plurality of S$^{22}$ groups are present, they may be identical to or different from one another. The spacer group is an alkylene group having 1 to 18 carbon atoms. The alkylene group may be substituted with one or more halogen atoms, CN groups, alkyl groups having 1 to 8 carbon atoms, or alkyl groups having 1 to 8 carbon atoms and including a polymerizable functional group. In the above groups, one CH$_2$ group or two or more CH$_2$ groups that are not adjacent to one another may be each independently replaced with —O—, —S—, —NH—, —N(CH$_3$)—, —CO—, —CH(OH)—, CH(COOH), —COO—, —OCO—, —OCOO—, —SCO—, —COS—, or —C≡C— such that any two oxygen atoms do not directly bind to each other. In consideration of alignment, among the above spacer groups, a linear alkylene group having 2 to 8 carbon atoms, an alkylene group having 2 to 6 carbon atoms substituted with a fluorine atom, and an alkylene group having 5 to 14 carbon atoms in which a part of the alkylene group is replaced with —O— are preferable.

In General Formula (2-a), X$^{21}$ and X$^{22}$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and, when a plurality of X$^{21}$ groups and/or a plurality of X$^{22}$ groups are present, they may be identical to or different from one another (the P—(S—X)$_k$— linkages do not include an —O—O— linkage). In consideration of the availability of raw materials and ease of synthesis, X$^{21}$ and X$^{22}$ preferably each independently represent —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond and, when a plurality of X$^{21}$ groups and/or a plurality of X$^{22}$ groups are present, they may be identical to or different from one another; more preferably each independently represent —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond; and particularly preferably each independently represent —O—, —COO—, —OCO—, or a single bond and, when a plurality of X$^{21}$ groups and/or a plurality of X$^{22}$ groups are present, they may be identical to or different from one another.

In General Formula (2-a), A$^{21}$ and A$^{22}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more L substituents. When a plurality of A$^{21}$ groups and/or a plurality of A$^{22}$ groups are present, they may be identical to or different from one another. In consideration of the availability of raw materials and ease of synthesis, A$^{21}$ and A$^{22}$ preferably each independently represent a 1,4-phenylene group, a 1,4-cyclohexylene group, or a naphthalene-2,6-diyl that may be optionally substituted with one or more L$^2$ substituents; and more preferably each independently represent a group selected from Formulae (A-1) to (A-11) below.

[Chem. 72]

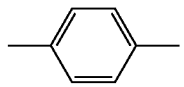
(A-1)

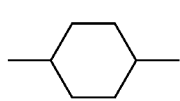
(A-2)

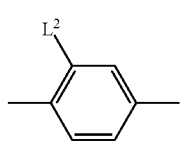
(A-3)

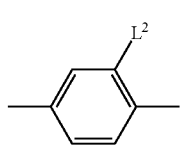
(A-4)

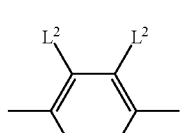
(A-5)

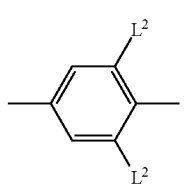
(A-6)

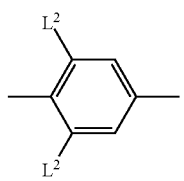
(A-7)

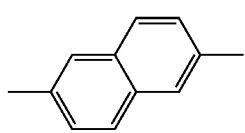
(A-8)

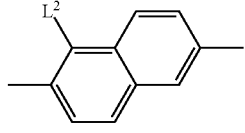
(A-9)

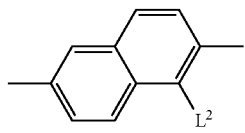
(A-10)

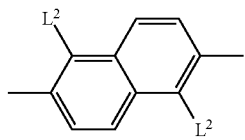
(A-11)

$A^{21}$ and $A^{22}$ further preferably each independently represent a group selected from Formulae (A-1) to (A-8) and particularly preferably each independently represent a group selected from Formulae (A-1) to (A-4).

In General Formula (2-a), $Z^{21}$ and $Z^{22}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond. When a plurality of $Z^{21}$ groups and/or a plurality of $Z^{22}$ groups are present, they may be identical to or different from one another. In consideration of the liquid crystal property of the compound, the availability of raw materials, and ease of synthesis, $Z^{21}$ and $Z^{22}$ preferably each independently represent a single bond, —OCH$_2$—, —CH$_2$O—, —COO—, —OCO—, —CF—O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond; more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond; further preferably each independently represent —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond; and particularly preferably each independently represent —CH$_2$CH$_2$—, —COO—, —OCO—, or a single bond.

In General Formula (2-a), M represents a group selected from Formulae (M-81) to (M-813) below.

[Chem. 73]

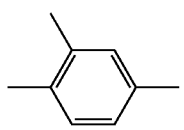

(M-81)

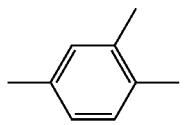

(M-82)

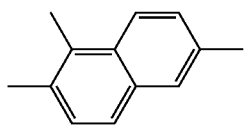

(M-83)

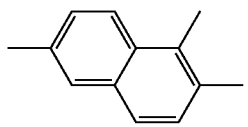

(M-84)

-continued

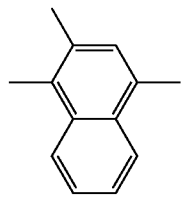

(M-85)

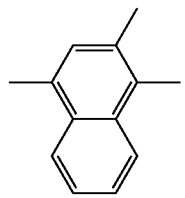

(M-86)

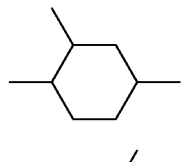

(M-87)

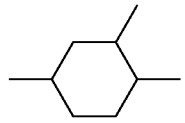

(M-88)

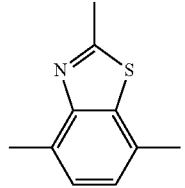

(M-89)

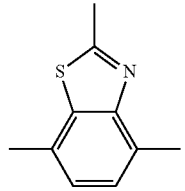

(M-810)

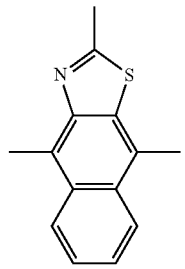

(M-811)

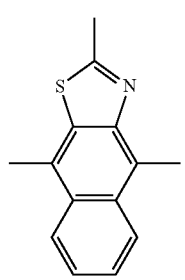

(M-812)

-continued (M-813)

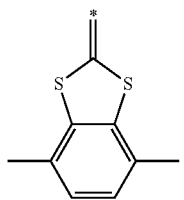

The above groups may be optionally substituted with one or more $L^2$ substituents. In consideration of the availability of raw materials and ease of synthesis, M preferably each independently represents Formula (M-81) or (M-82) that may be optionally substituted with one or more $L^2$ substituents or a group selected from Formulae (M-83) to (M-86) which is not substituted; more preferably represents a group selected from Formulae (M-81) and (M-82) which may be optionally substituted with one or more $L^2$ substituents; and particularly preferably represents a group selected from Formulae (M-81) and (M-82) which is not substituted.

In General Formula (2-a), G represents a group selected from Formulae (G-81) to (G-86) below.

[Chem. 74]

(G-81)
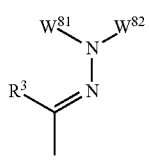

(G-82)
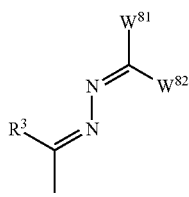

(G-83)
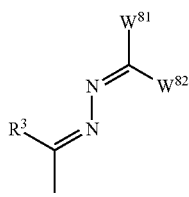

(G-84)
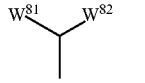

(G-85)
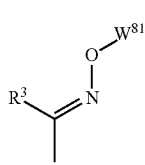

(G-86)
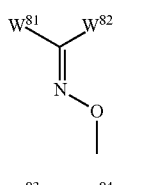

In Formulae (G-81) to (G-86), $R^3$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom;

$W^{81}$ represents a group having 5 to 30 carbon atoms, the group including at least one aromatic group, and the group may be optionally substituted with one or more $L^2$ substituents;

$W^{82}$ represents a hydrogen atom or an linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom and/or an —OH group; and $W^{82}$ may represent the same thing as $W^{81}$, and $W^{81}$ and $W^{82}$ may be bonded to each other to form a ring structure.

In consideration of liquid crystal property and ease of synthesis, $R^3$ preferably represents a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with —O—, —COO—, or —OCO—; more preferably represents a linear or branched alkyl group having 1 to 12 carbon atoms in which a hydrogen atom may be replaced with a fluorine atom; and particularly preferably represents a linear alkyl group having 1 to 12 carbon atoms.

$W^{83}$ and $W^{84}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms. In the alkyl group, the cycloalkyl group, the alkenyl group, the cycloalkenyl group, the alkoxy group, the acyloxy group, and the alkylcarbonyloxy group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—.

The aromatic group included in $W^{81}$ may be an aromatic hydrocarbon group, an aromatic hetero group, or a group including both aromatic hydrocarbon group and aromatic hetero group. The above aromatic groups may be bonded to one another with a single bond or a linking group (—OCO—, —COO—, —CO—, or —O—) or may form a condensed ring. $W^{81}$ may further include, in addition to an aromatic group, an acyclic structure and/or a cyclic structure other than an aromatic group. In consideration of the availability of raw materials and ease of synthesis, the aromatic group included in $W^{81}$ is preferably a group selected from Formulae (W-1) to (W-19) below which may be optionally substituted with one or more $L^2$ substituents:

[Chem. 75]

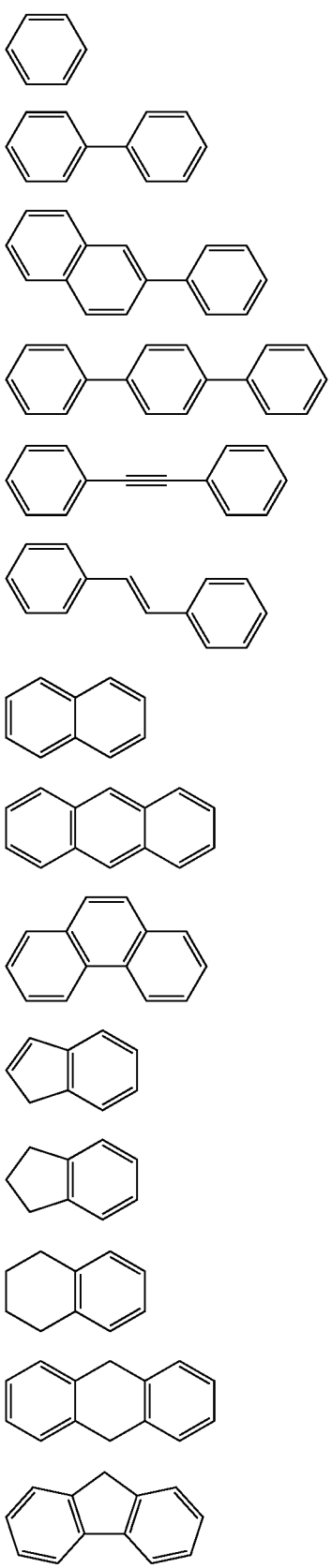

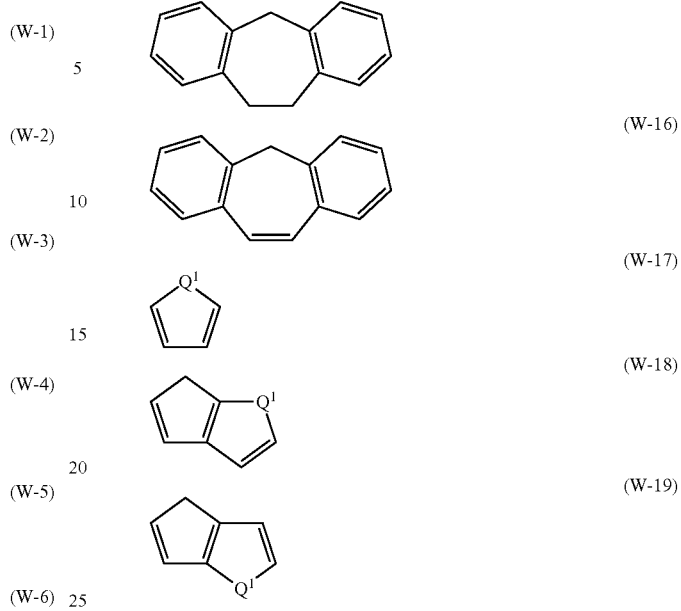

(in Formulae (W-1) to (W-19), the above groups may have a bond at any position; two or more aromatic groups selected from the above groups may be connected to one another with a single bond to form another group; $Q^1$ represents —O—, —S—, —NR$^5$— (where $R^5$ represents a hydrogen atom or an alkyl group having 1 to 8 carbon atoms), or —CO—; and, in the above aromatic groups, —CH= groups may be each independently replaced with —N=, and —CH$_2$— groups may be each independently replaced with —O—, —S—, —NR$^4$— (where $R^4$ represents a hydrogen atom or an alkyl group having 1 to 8 carbon atoms), or —CO— such that an —O—O— linkage is not included). The group represented by Formula (W-1) is preferably a group selected from Formulae (W-1-1) to (W-1-8) below which may be optionally substituted with one or more $L^2$ substituents:

[Chem. 76]

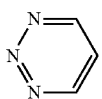 (W-1-6)

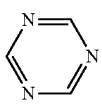 (W-1-7)

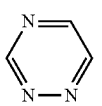 (W-1-8)

(in Formulae (W-1-1) to (W-1-8), the above groups may have a bond at any position). The group represented by Formula (W-7) is preferably a group selected from Formulae (W-7-1) to (W-7-7) below which may be optionally substituted with one or more $L^2$ substituents:

[Chem. 77]

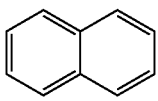 (W-7-1)

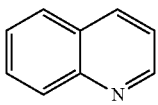 (W-7-2)

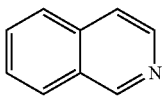 (W-7-3)

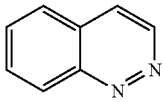 (W-7-4)

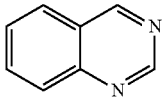 (W-7-5)

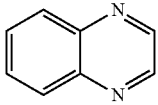 (W-7-6)

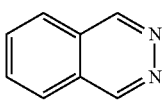 (W-7-7)

(in Formulae (W-7-1) to (W-7-7), the above groups may have a bond at any position). The group represented by Formula (W-10) is preferably a group selected from Formulae (W-10-1) to (W-10-8) below which may be optionally substituted with one or more $L^2$ substituents:

[Chem. 78]

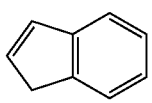 (W-10-1)

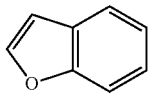 (W-10-2)

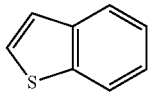 (W-10-3)

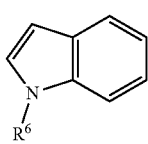 (W-10-4)

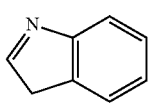 (W-10-5)

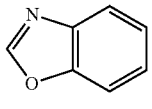 (W-10-6)

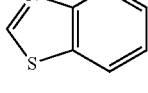 (W-10-7)

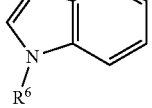 (W-10-8)

(in Formulae (W-10-1) to (W-10-8), the above groups may have a bond at any position; and $R^6$ represents a hydrogen atom or an alkyl group having 1 to 8 carbon atoms). The group represented by Formula (W-11) is preferably a group selected from Formulae (W-11-1) to (W-11-13) below which may be optionally substituted with one or more $L^2$ substituents:

[Chem. 79]

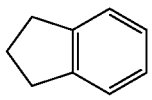 (W-11-1)

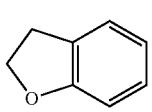 (W-11-2)

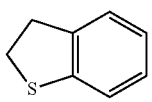 (W-11-3)

-continued
(W-11-4) 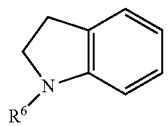
(W-11-5) 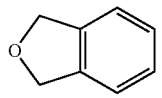
(W-11-6) 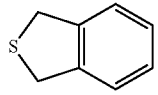
(W-11-7) 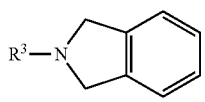
(W-11-8) 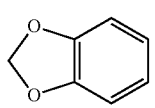
(W-11-9) 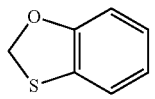
(W-11-10) 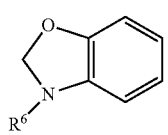
(W-11-11) 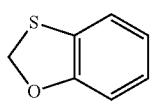
(W-11-12) 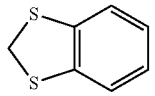
(W-11-13) 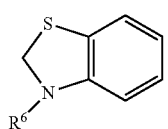
(in Formulae (W-11-1) to (W-11-13), the above groups may have a bond at any position; and $R^6$ represents a hydrogen atom or an alkyl group having 1 to 8 carbon atoms). The group represented by Formula (W-12) is preferably a group selected from Formulae (W-12-1) to (W-12-19) below which may be optionally substituted with one or more $L^2$ substituents:
[Chem. 80]
(W-12-1) 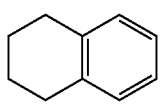
(W-12-2) 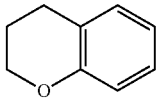
(W-12-3) 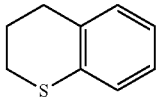
(W-12-4) 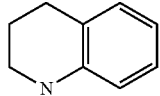
(W-12-5) 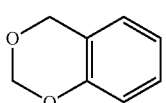
(W-12-6) 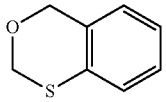
(W-12-7) 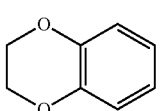
(W-12-8) 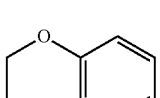
(W-12-9) 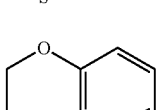
(W-12-10) 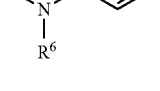
(W-12-11) 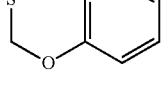
(W-12-12) 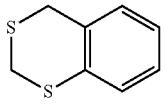
(W-12-13) 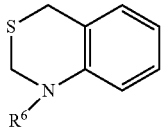

(W-12-14) 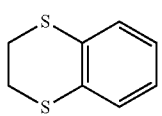

(W-12-15) 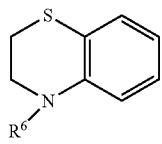

(W-12-16) 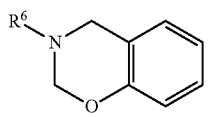

(W-12-17) 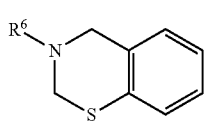

(W-12-18) 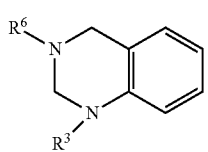

(W-12-19) 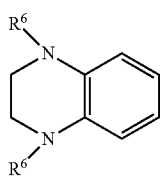

(in Formulae (W-12-1) to (W-12-19), the above groups may have a bond at any position; $R^6$ represents a hydrogen atom or an alkyl group having 1 to 8 carbon atoms; and, when a plurality of $R^6$ groups are present, they may be identical to or different from one another). The group represented by Formula (W-13) is preferably a group selected from Formulae (W-13-1) to (W-13-10) below which may be optionally substituted with one or more $L^2$ substituents:

[Chem. 81]

(W-13-1) 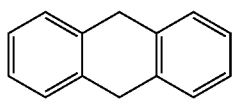

(W-13-2) 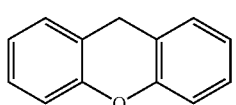

(W-13-3) 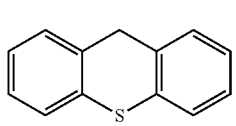

(W-13-4) 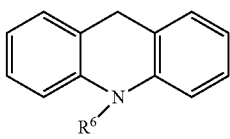

(W-13-5) 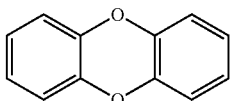

(W-13-6) 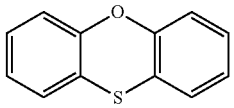

(W-13-7) 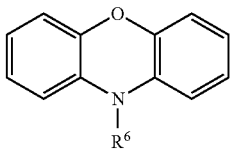

(W-13-8) 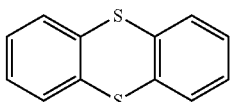

(W-13-9) 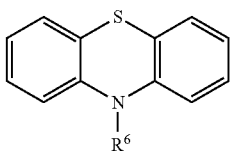

(W-13-10) 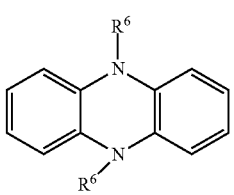

(in Formulae (W-13-1) to (W-13-10), the above groups may have a bond at any position; $R^6$ represents a hydrogen atom or an alkyl group having 1 to 8 carbon atoms; and, when a plurality of $R^6$ groups are present, they may be identical to or different from one another). The group represented by Formula (W-14) is preferably a group selected from Formulae (W-14-1) to (W-14-4) below which may be optionally substituted with one or more $L^2$ substituents:

[Chem. 82]

(W-14-1) 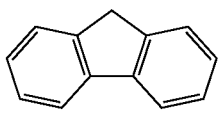

(W-14-2) 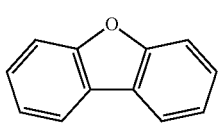

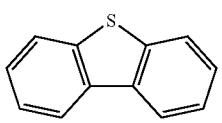
(W-14-3)

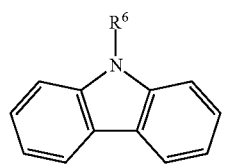
(W-14-4)

(in Formulae (W-14-1) to (W-14-4), the above groups may have a bond at any position; and R⁶ represents a hydrogen atom or an alkyl group having 1 to 8 carbon atoms). The group represented by Formula (W-15) is preferably a group selected from Formulae (W-15-1) to (W-15-18) below which may be optionally substituted with one or more L² substituents:

[Chem. 83]

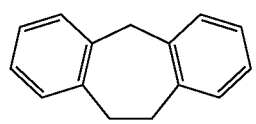
(W-15-1)

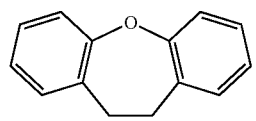
(W-15-2)

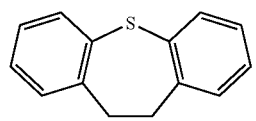
(W-15-3)

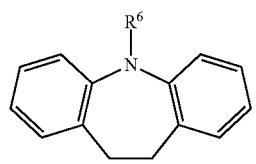
(W-15-4)

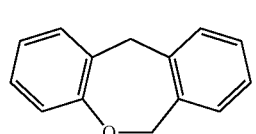
(W-15-5)

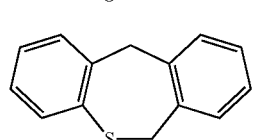
(W-15-6)

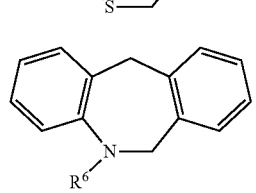
(W-15-7)

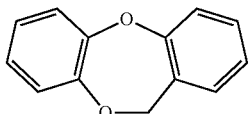
(W-15-8)

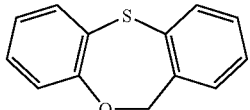
(W-15-11)

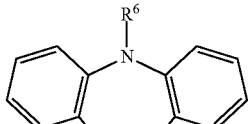
(W-15-12)

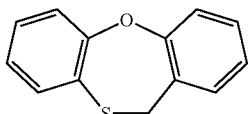
(W-15-13)

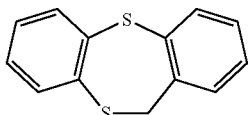
(W-15-14)

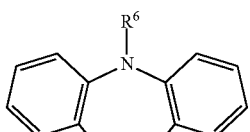
(W-15-15)

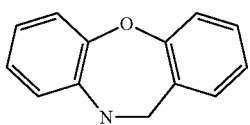
(W-15-16)

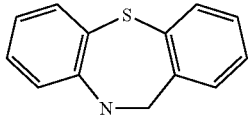
(W-15-17)

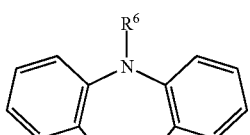
(W-15-18)

(in Formulae (W-15-1) to (W-15-18), the above groups may have a bond at any position; R⁶ represents a hydrogen atom or an alkyl group having 1 to 8 carbon atoms; and, when a plurality of R⁶ groups are present, they may be identical to or different from one another). The group represented by Formula (W-16) is preferably a group selected from Formulae (W-16-1) to (W-16-4) below which may be optionally substituted with one or more L² substituents:

[Chem. 84]

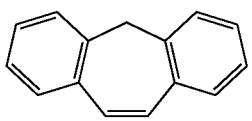
(W-16-1)

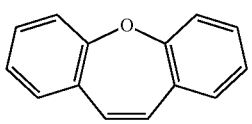
(W-16-2)

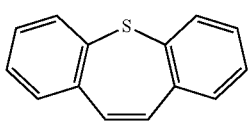
(W-16-3)

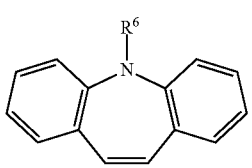
(W-16-4)

(in Formulae (W-16-1) to (W-16-4), the above groups may have a bond at any position; and $R^6$ represents a hydrogen atom or an alkyl group having 1 to 8 carbon atoms). The group represented by Formula (W-17) is preferably a group selected from Formulae (W-17-1) to (W-17-6) below which may be optionally substituted with one or more $L^2$ substituents:

[Chem. 85]

(W-17-1)

(W-17-2)

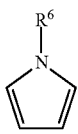
(W-17-3)

(W-17-4)

(W-17-5)

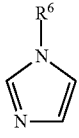
(W-17-6)

(in Formulae (W-17-1) to (W-17-6), the above groups may have a bond at any position; and $R^6$ represents a hydrogen atom or an alkyl group having 1 to 8 carbon atoms). The group represented by Formula (W-18) is preferably a group selected from Formulae (W-18-1) to (W-18-6) below which may be optionally substituted with one or more $L^2$ substituents:

[Chem. 86]

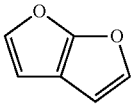
(W-18-1)

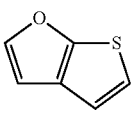
(W-18-2)

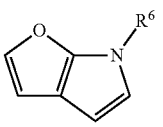
(W-18-3)

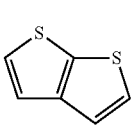
(W-18-4)

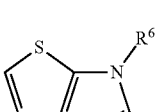
(W-18-5)

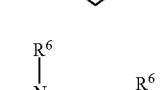
(W-18-6)

(in Formulae (W-18-1) to (W-18-6), the above groups may have a bond at any position; $R^6$ represents a hydrogen atom or an alkyl group having 1 to 8 carbon atoms; and, when a plurality of $R^6$ groups are present, they may be identical to or different from one another). The group represented by Formula (W-19) is preferably a group selected from Formulae (W-19-1) to (W-19-9) below which may be optionally substituted with one or more $L^2$ substituents:

[Chem. 87]

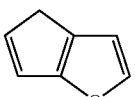
(W-19-1)

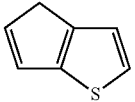
(W-19-2)

(W-19-3)
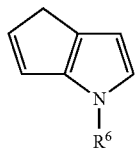

(W-19-4)
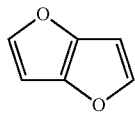

(W-19-5)
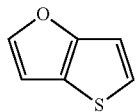

(W-19-6)
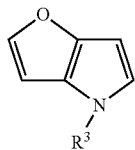

(W-19-7)
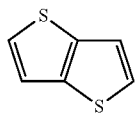

(W-19-8)
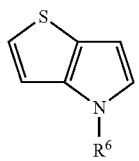

(W-19-9)
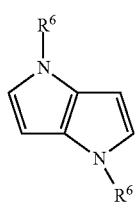

(in Formulae (W-19-1) to (W-19-9), the above groups may have a bond at any position; $R^6$ represents a hydrogen atom or an alkyl group having 1 to 8 carbon atoms; and, when a plurality of $R^6$ groups are present, they may be identical to or different from one another). The aromatic group included in $W^{81}$ is more preferably a group selected from Formulae (W-1-1), (W-7-1), (W-7-2), (W-7-7), (W-8), (W-10-6), (W-10-7), (W-10-8), (W-11-8), (W-11-9), (W-11-10), (W-11-11), (W-11-12), and (W-11-13) which may be optionally substituted with one or more $L^2$ substituents; and is particularly preferably a group selected from Formulae (W-1-1), (W-7-1), (W-7-2), (W-7-7), (W-10-6), (W-10-7), and (W-10-8) which may be optionally substituted with one or more L substituents. $W^{81}$ particularly preferably represents a group selected from Formulae (W-a-1) to (W-a-6) below:

[Chem. 88]

(W-a-1)
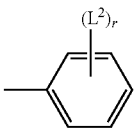

(W-a-2)
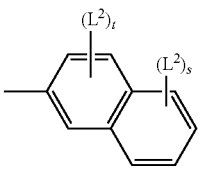

(W-a-3)
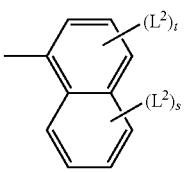

(W-a-4)
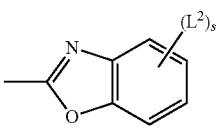

(W-a-5)
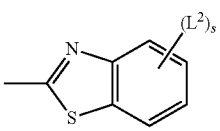

(W-a-6)
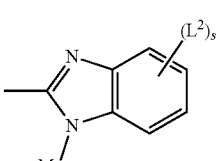

(in Formulae (W-a-1) to (W-a-6), r represents an integer of 0 to 5; s represents an integer of 0 to 4; and t represents an integer of 0 to 3).

$W^{82}$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. $W^{82}$ may represent the same thing as $W^{81}$. $W^{81}$ and $W^{82}$ may be bonded to each other to form a ring structure.

In consideration of the availability of raw materials and ease of synthesis, $W^{82}$ preferably represents a hydrogen atom or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —CO—, —COO—, —OCO—, —CH=CH—COO—, —OCO—CH=CH—, —CH=CH—, —CF=CF—, or —C≡C—; and more preferably represents a hydrogen atom or a linear or branched alkyl group having 1 to 20 carbon atoms in which one —CH$_2$— group or two or more —CH$_2$— groups that are not adjacent to one another may be each independently replaced with —O—.

In the case where W$^{82}$ represents the same thing as W$^{81}$, W$^{82}$ may be identical to or different from W$^{81}$, and the preferable groups are the same as those of W$^{81}$.

In the case where W$^{81}$ and W$^{82}$ are bonded to each other to form a ring structure, the cyclic group represented by —NW$^{81}$W$^{82}$ is preferably a group selected from Formulae (W-b-1) to (W-b-42) below which may be optionally substituted with one or more L$^2$ substituents:

[Chem. 89]

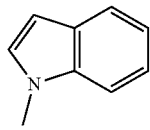 (W-b-1)

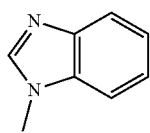 (W-b-2)

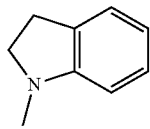 (W-b-3)

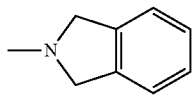 (W-b-4)

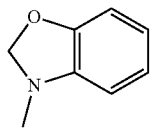 (W-b-5)

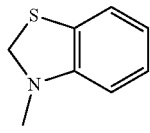 (W-b-6)

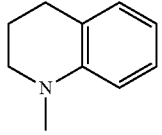 (W-b-7)

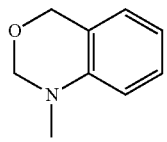 (W-b-8)

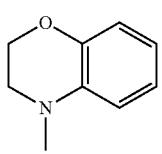 (W-b-9)

-continued

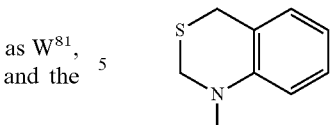 (W-b-9)

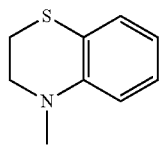 (W-b-10)

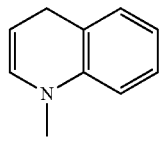 (W-b-11)

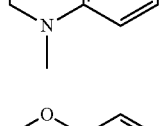 (W-b-11)

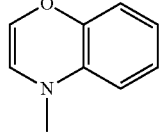 (W-b-12)

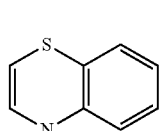 (W-b-13)

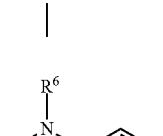 (W-b-14)

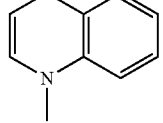 (W-b-15)

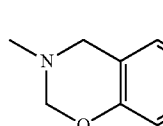 (W-b-16)

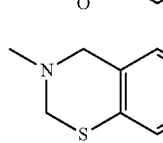 (W-b-17)

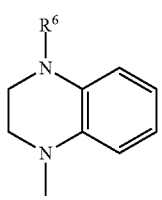 (W-b-18)
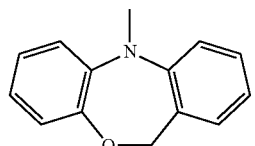 (W-b-27)
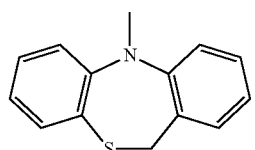 (W-b-28)
(W-b-19)
[Chem. 90]
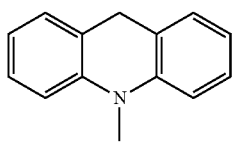 (W-b-20)
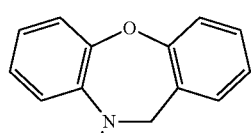 (W-b-29)
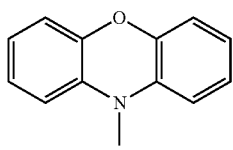 (W-b-21)
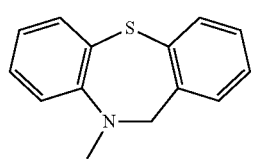 (W-b-30)
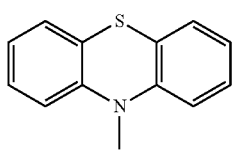 (W-b-22)
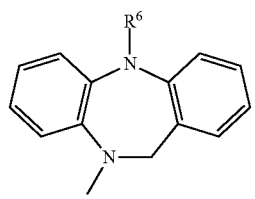 (W-b-31)
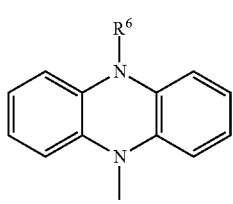 (W-b-23)
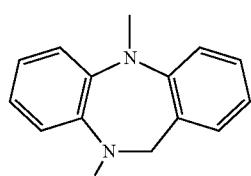 (W-b-32)
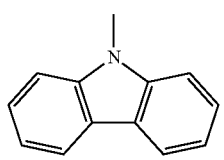 (W-b-24)
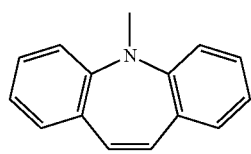 (W-b-33)
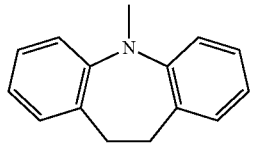 (W-b-25)
 (W-b-34)
 (W-b-35)
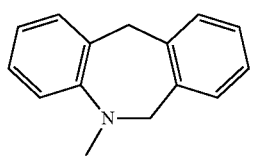 (W-b-26)
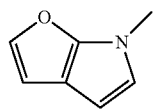 (W-b-36)

(W-b-37)
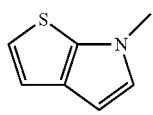

(W-b-38)
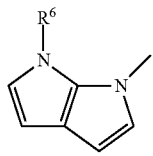

(W-b-39)
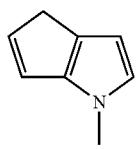

(W-b-40)
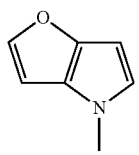

(W-b-41)
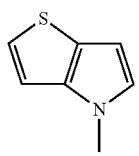

(W-b-42)
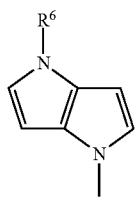

(in Formulae (W-b-1) to (W-b-42), $R^6$ represents a hydrogen atom or an alkyl group having 1 to 8 carbon atoms). In consideration of the availability of raw materials and ease of synthesis, the cyclic group represented by $-NW^{81}W^{82}$ is particularly preferably a group selected from Formulae (W-b-20), (W-b-21), (W-b-22), (W-b-23), (W-b-24), (W-b-25), and (W-b-33) which may be optionally substituted with one or more $L^2$ substituents.

The cyclic group represented by $=CW^{81}W^{82}$ is preferably a group selected from Formulae (W-c-1) to (W-c-81) below which may be optionally substituted with one or more $L^2$ substituents:

[Chem. 91]

(W-c-1)
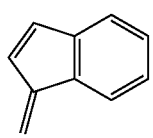

(W-c-2)
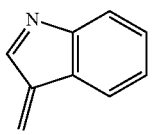

(W-c-3)
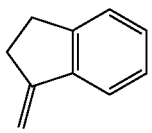

(W-c-4)
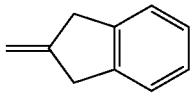

(W-c-5)
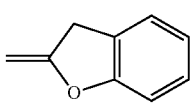

(W-c-6)
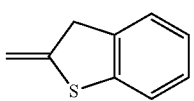

(W-c-7)
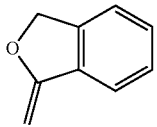

(W-c-8)
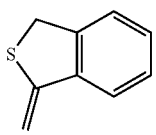

(W-c-9)
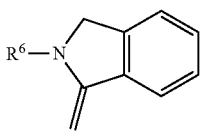

(W-c-10)
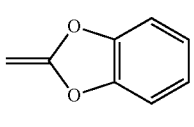

(W-c-11)
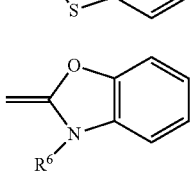

(W-c-12)
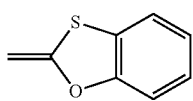
(W-c-13)
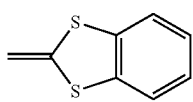
(W-c-14)
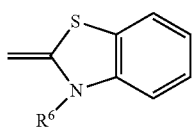
(W-c-15)
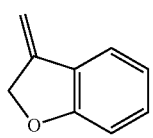
(W-c-16)
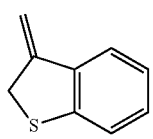
(W-c-17)
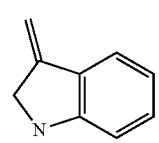
(W-c-18)
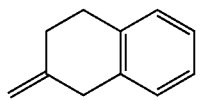
(W-c-19)
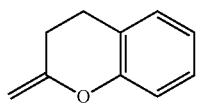
(W-c-20)
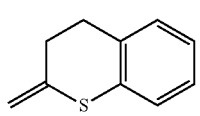
(W-c-21)
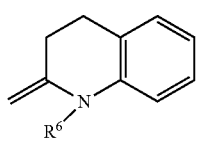
(W-c-22)
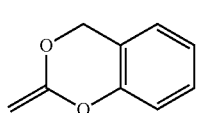
(W-c-23)
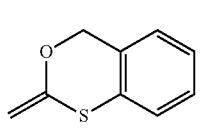
(W-c-24)
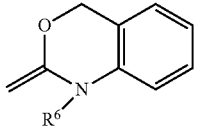
(W-c-25)
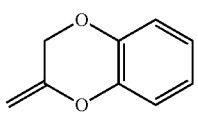
(W-c-26)
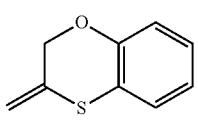
(W-c-27)
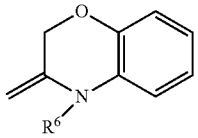
(W-c-28)
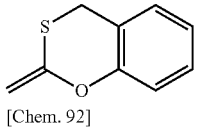
[Chem. 92]
(W-c-29)
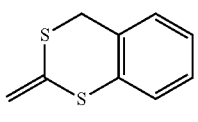
(W-c-30)
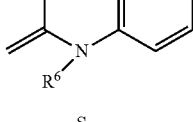
(W-c-31)
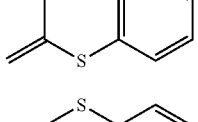
(W-c-32)
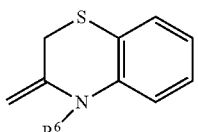
(W-c-33)
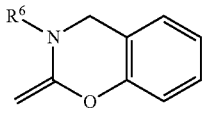
(W-c-34)
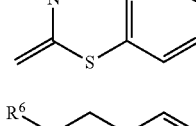
(W-c-35)
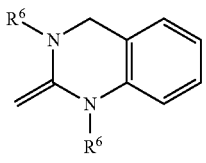

(W-c-36) 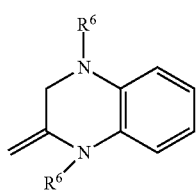
(W-c-37) 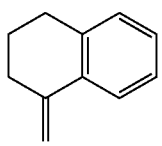
(W-c-38) 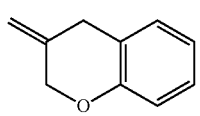
(W-c-39) 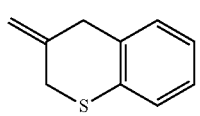
(W-c-40) 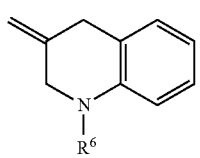
(W-c-41) 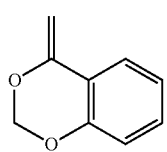
(W-c-42) 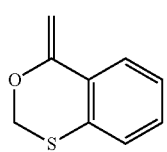
(W-c-43) 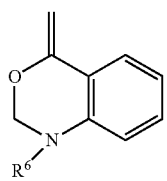
(W-c-44) 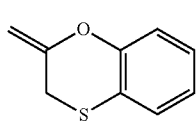
(W-c-45) 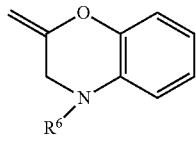
(W-c-46) 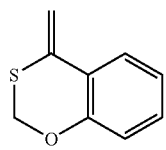
(W-c-47) 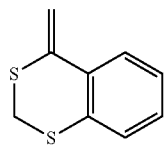
(W-c-48) 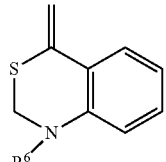
(W-c-49) 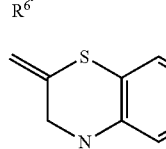
(W-c-50) 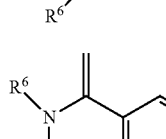
(W-c-51) 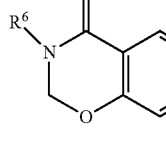
(W-c-52) 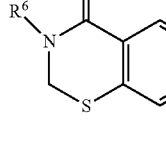
(W-c-53) 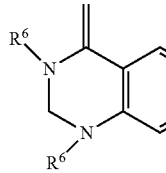
(W-c-54) 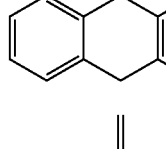
(W-c-55) 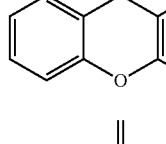

[Chem. 93]

-continued

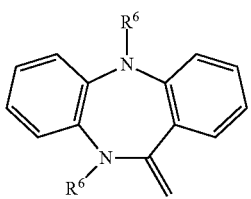
(W-c-74)

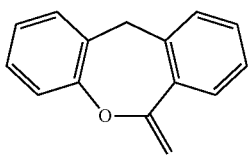
(W-c-75)

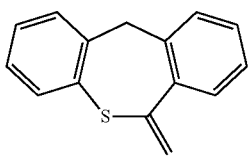
(W-c-76)

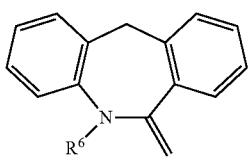
(W-c-77)

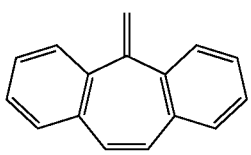
(W-c-78)

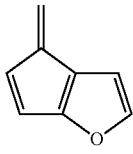
(W-c-79)

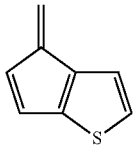
(W-c-80)

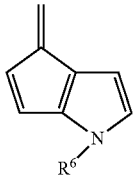
(W-c-81)

(in Formulae (W-c-1) to (W-c-81), $R^6$ represents a hydrogen atom or an alkyl group having 1 to 8 carbon atoms; and, when a plurality of $R^6$ groups are present, they may be identical to or different from one another). In consideration of the availability of raw materials and ease of synthesis, the cyclic group represented by $=CW^{81}W^{82}$ is particularly preferably a group selected from Formulae (W-c-11), (W-c-12), (W-c-13), (W-c-14), (W-c-53), (W-c-54), (W-c-55), (W-c-56), (W-c-57), and (W-c-78) which may be optionally substituted with one or more L substituents.

The total number of π electrons included in $W^{81}$ and $W^{82}$ is preferably 4 to 24 in consideration of wavelength dispersion property, preservation stability, liquid crystal property, and ease of synthesis.

$W^{83}$ and $W^{84}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms. In the alkyl group, the cycloalkyl group, the alkenyl group, the cycloalkenyl group, the alkoxy group, the acyloxy group, and the alkylcarbonyloxy group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—.

$W^{83}$ is more preferably a group selected from a cyano group, a nitro group, a carboxyl group, and an alkyl, alkenyl, acyloxy, or alkylcarbonyloxy group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—; and is particularly preferably a group selected from a cyano group, a carboxyl group, and an alkyl, alkenyl, acyloxy, or alkylcarbonyloxy group having 1 to 20 carbon atoms in which one —CH$_2$— group or two or more —CH$_2$— groups that are not adjacent to one another may be each independently replaced with —CO—, —COO—, —OCO—, —O—CO—O—, —CO—NH—, —NH—CO—, or —C≡C—.

$W^{84}$ is more preferably a group selected from a cyano group, a nitro group, a carboxyl group, and an alkyl, alkenyl, acyloxy, or alkylcarbonyloxy group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—; and is particularly preferably a group selected from a cyano group, a carboxyl group, and an alkyl, alkenyl, acyloxy, or alkylcarbonyloxy group having 1 to 20 carbon atoms in which one —CH$_2$— group or two or more —CH$_2$— groups that are not adjacent to one another may be each independently replaced with —CO—, —COO—, —OCO—, —O—CO—O—, —CO—NH—, —NH—CO—, or —C≡C—.

$L^2$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and a hydrogen atom included in the alkyl group may be replaced with a fluorine atom. In consideration of liquid crystal property and ease of synthesis, $L^2$ preferably represents a fluorine atom, a chlorine atom, a pentafluorosulfanyl group, a nitro group, a methylamino group, a dimethylamino group, a diethylamino group, a diisopropylamino group, or a linear or branched alkyl group having 1 to 20 carbon atoms in which a hydrogen atom may be replaced with a fluorine atom and one —CH$_2$— group or two or more —CH$_2$— groups that are not adjacent to one another may be each independently replaced with —O—, —S—, —CO—, —COO—, —OCO—, —O—CO—O—, —CH=CH—, —CF=CF—, or —C≡C—; more preferably represents a fluorine atom, a chlorine atom, or a linear or branched alkyl group having 1 to 12 carbon atoms in which a hydrogen atom may be replaced with a fluorine atom and one —CH$_2$— group or two or more —CH$_2$— groups that are not adjacent to one another may be each independently replaced with —O—, —COO—, or —OCO—; further preferably represents a fluorine atom, a chlorine atom, or a linear or branched alkyl or alkoxy group having 1 to 12 carbon atoms in which a hydrogen atom may be replaced with a fluorine atom; and particularly preferably represents a fluorine atom, a chlorine atom, or a linear alkyl or alkoxy group having 1 to 8 carbon atoms.

In General Formula (2-a), G more preferably represents a hydrogen atom, a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—.

In General Formula (2-a), j21 and j22 each independently represent an integer of 0 to 5, and j21+j22 is an integer of 1 to 5. In consideration of liquid crystal property, ease of synthesis, and preservation stability, j21 and j22 preferably each independently represent an integer of 1 to 4, more preferably each independently represent an integer of 1 to 3, and particularly preferably each independently represent 1 or 2; and j21+j22 is preferably an integer of 1 to 4 and is particularly preferably 2 or 3.

Specifically, the compound represented by General Formula (2-a) above is preferably selected from the compounds represented by Formulae (2-a-1) to (2-a-61) below:

[Chem. 94]

(2-a-1)

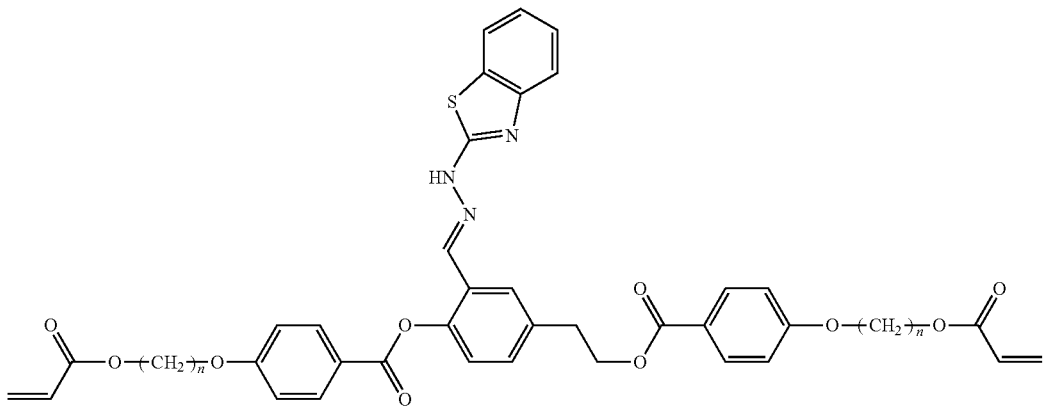

(2-a-2)

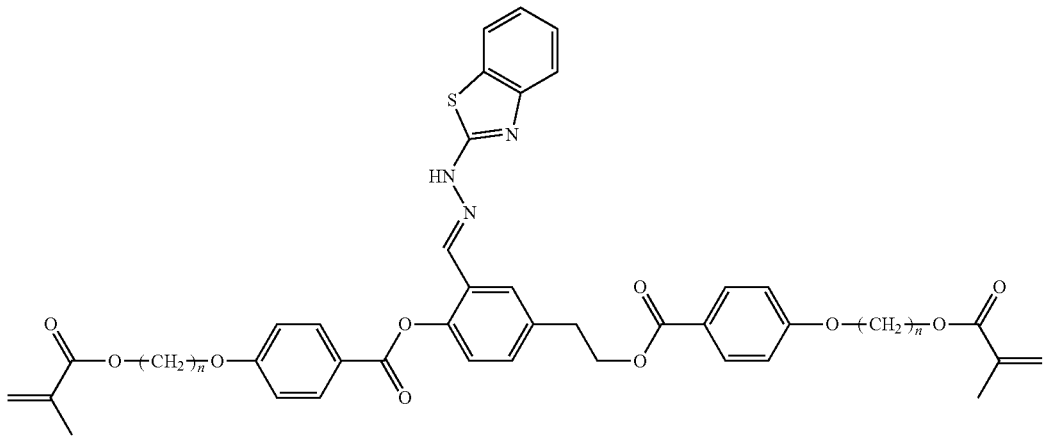

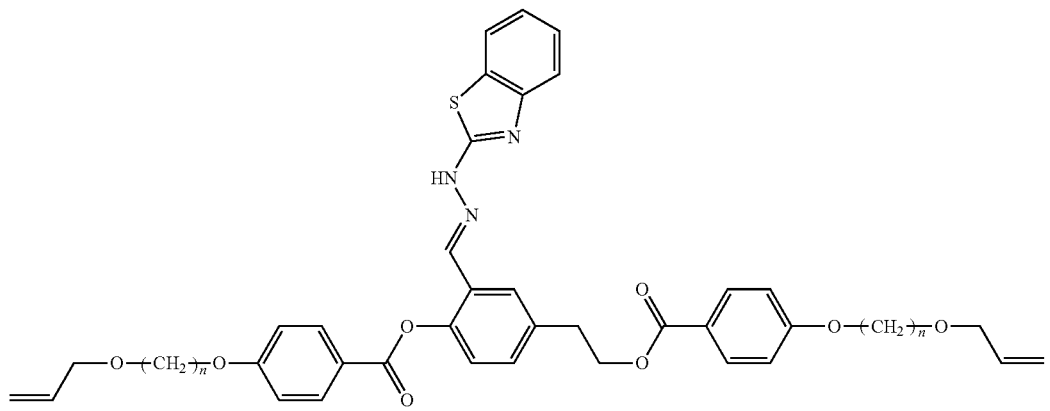
(2-a-3)
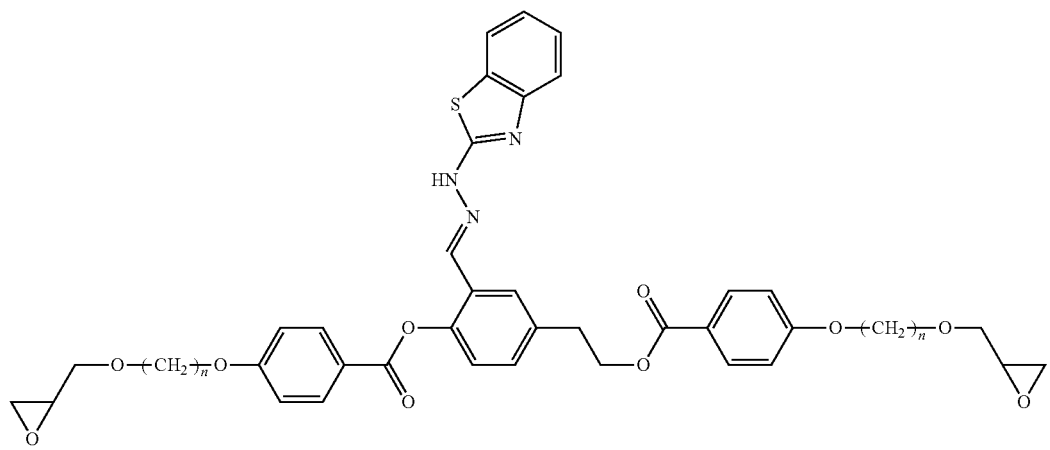
(2-a-4)
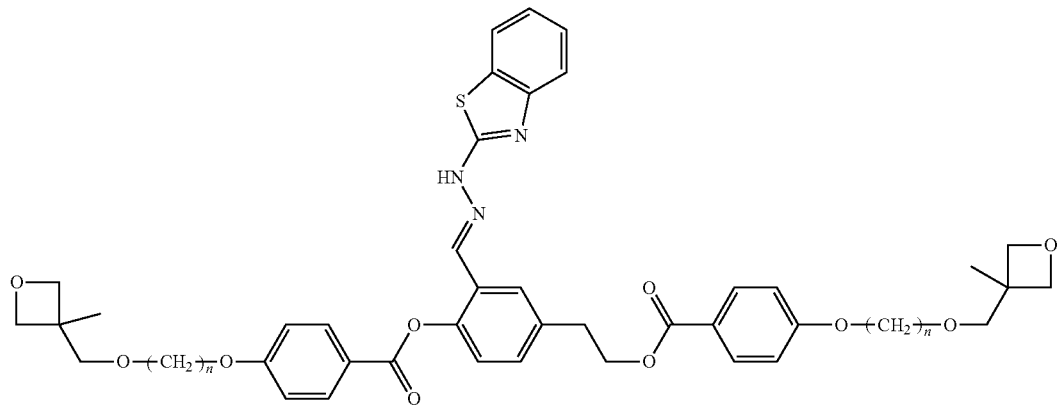
(2-a-5)

[Chem. 95]
(2-a-6)
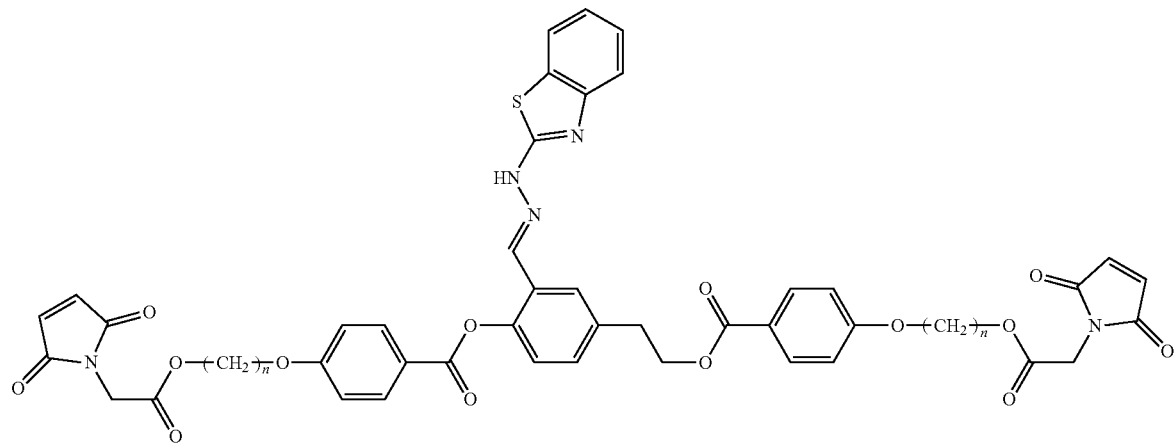
(2-a-7)
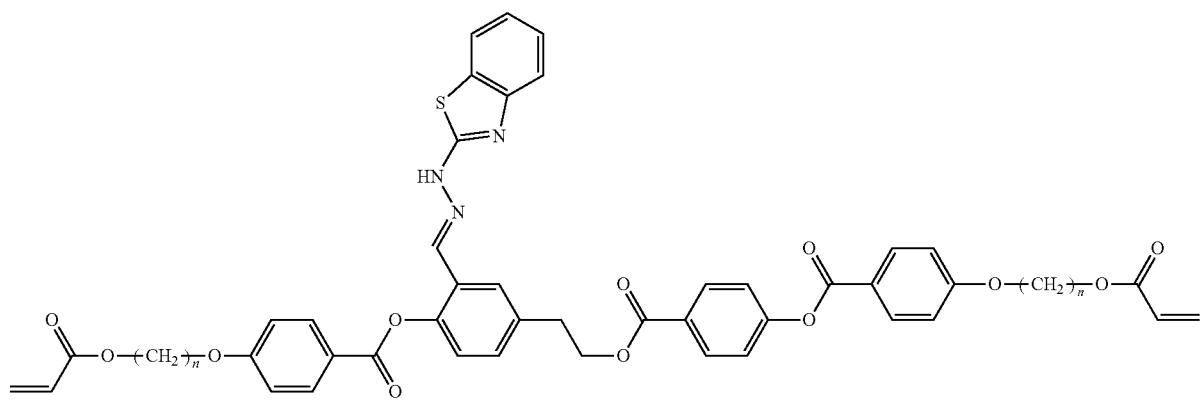
(2-a-8)
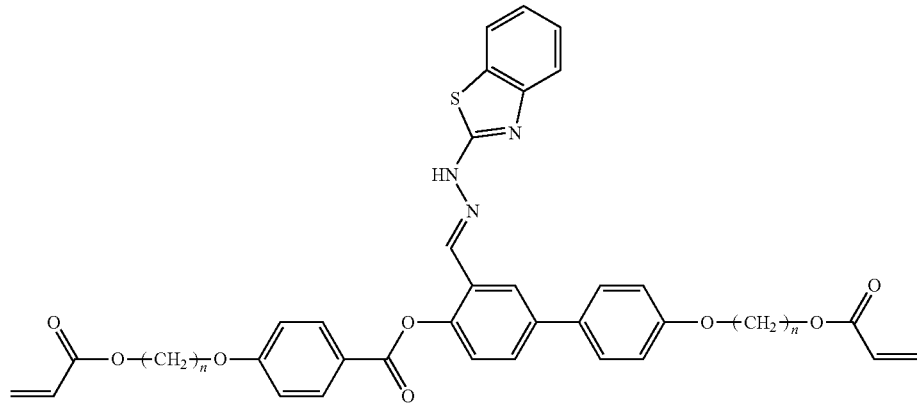

-continued
(2-a-9)
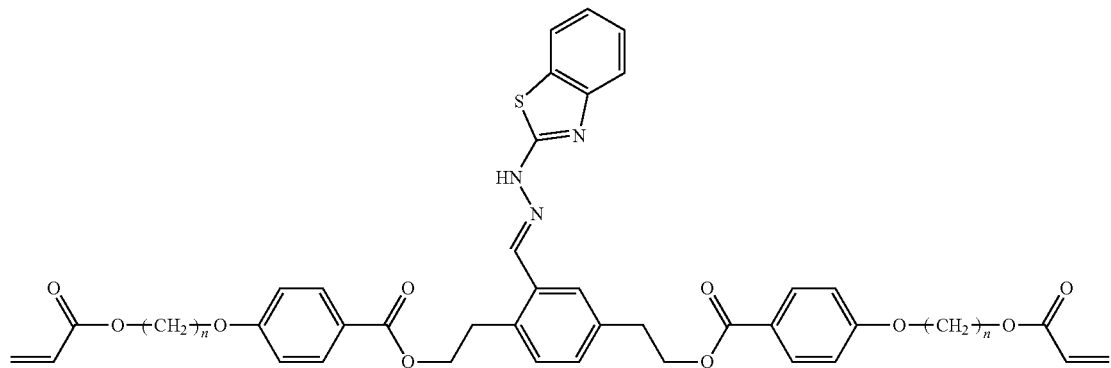
(2-a-10)
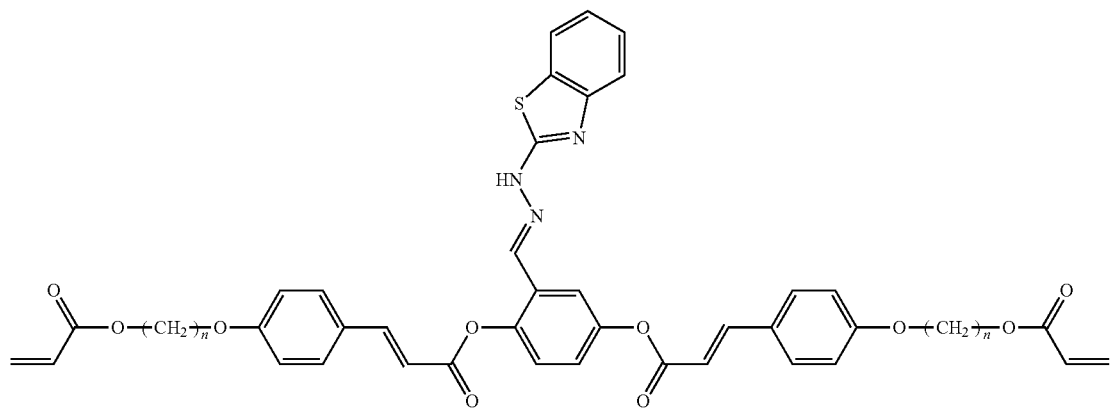
[Chem. 96]
(2-a-11)
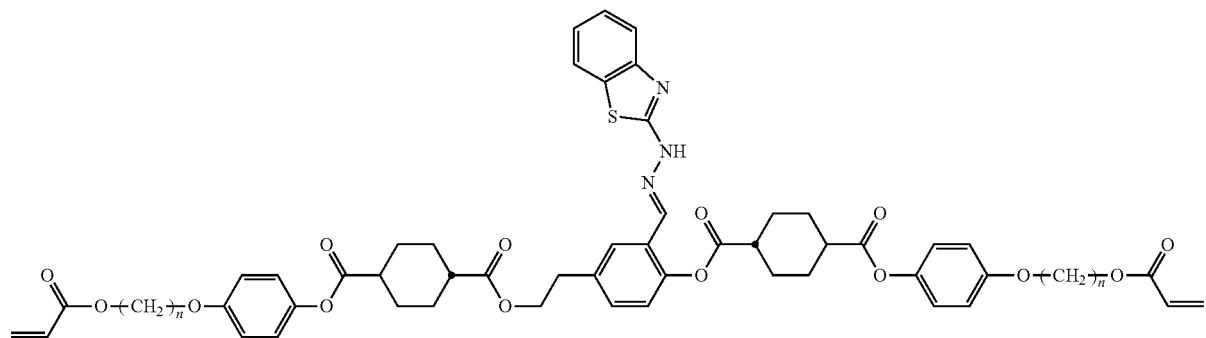

-continued
(2-a-12)
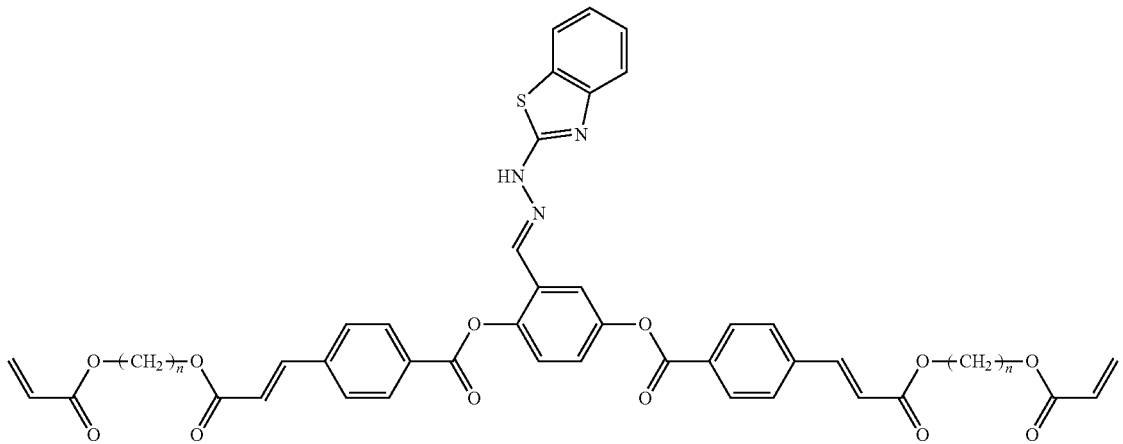
(2-a-13)
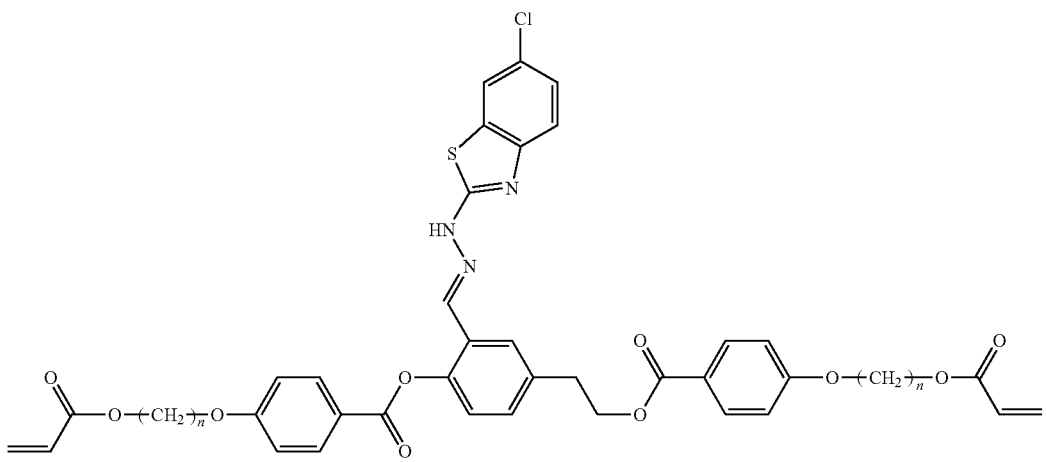
(2-a-14)
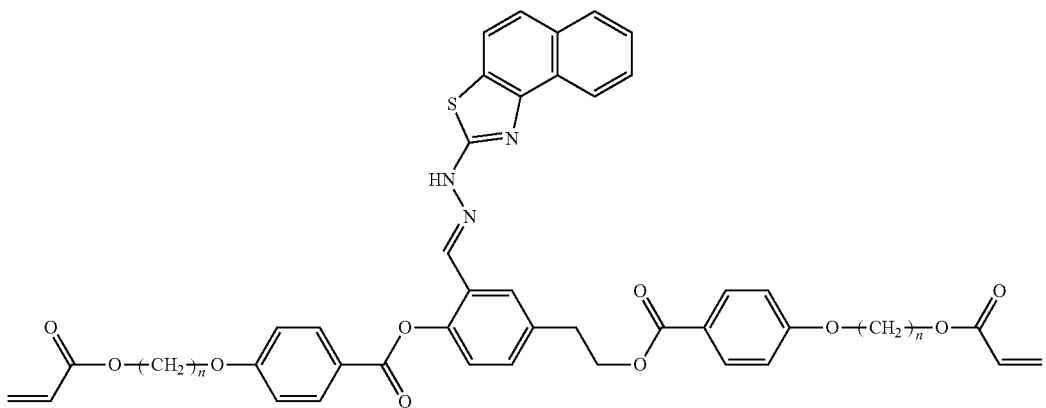

(2-a-15)
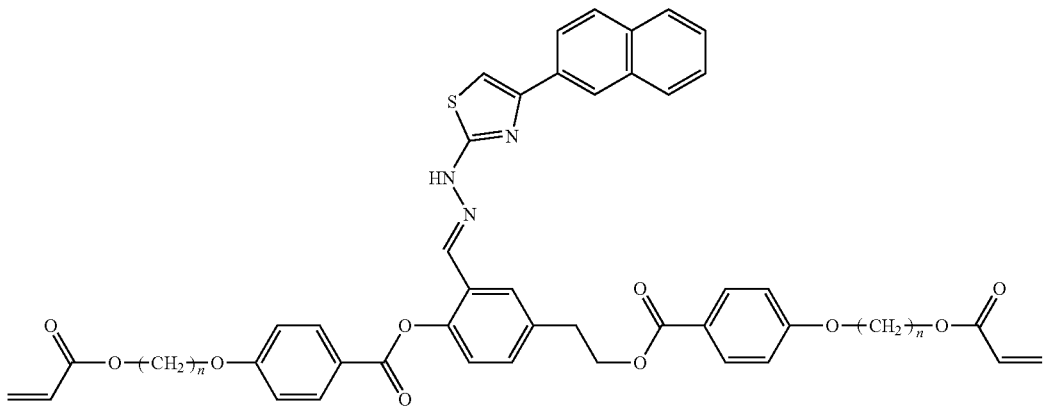
[Chem. 97]
(2-a-16)
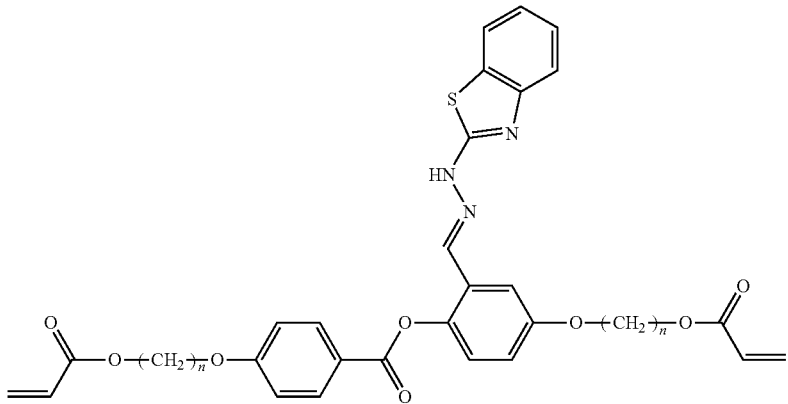
(2-a-17)
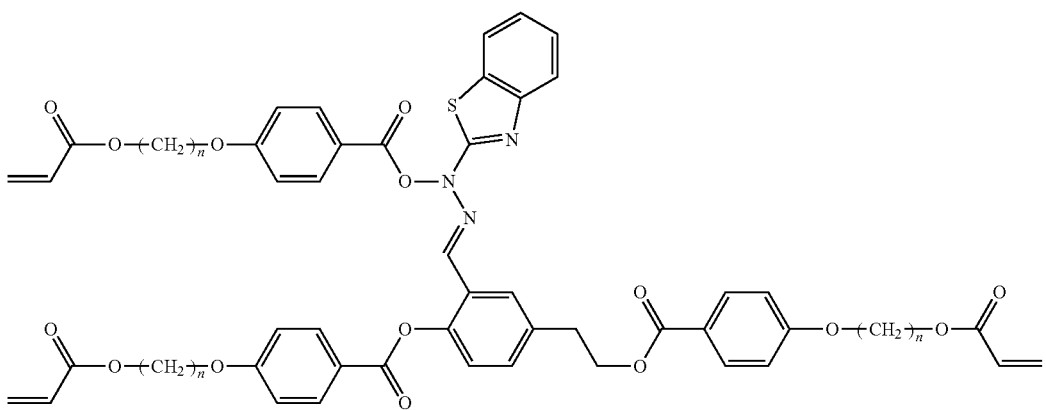

(2-a-18)
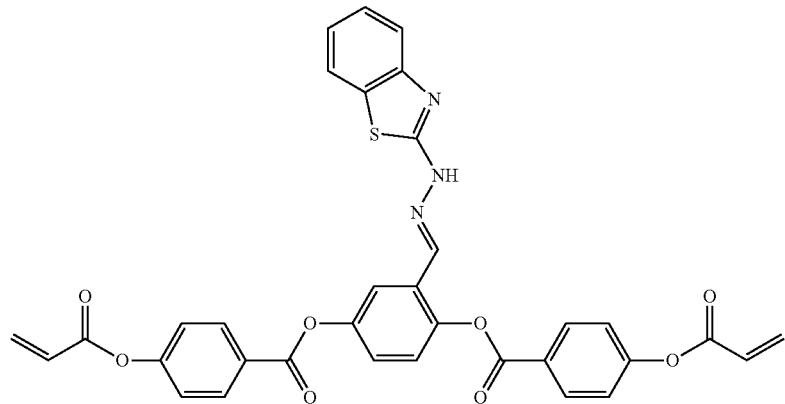
(2-a-19)
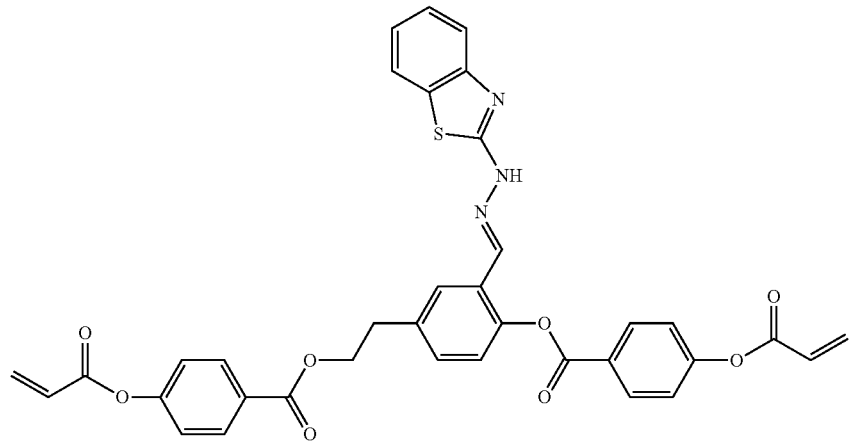
(2-a-20)
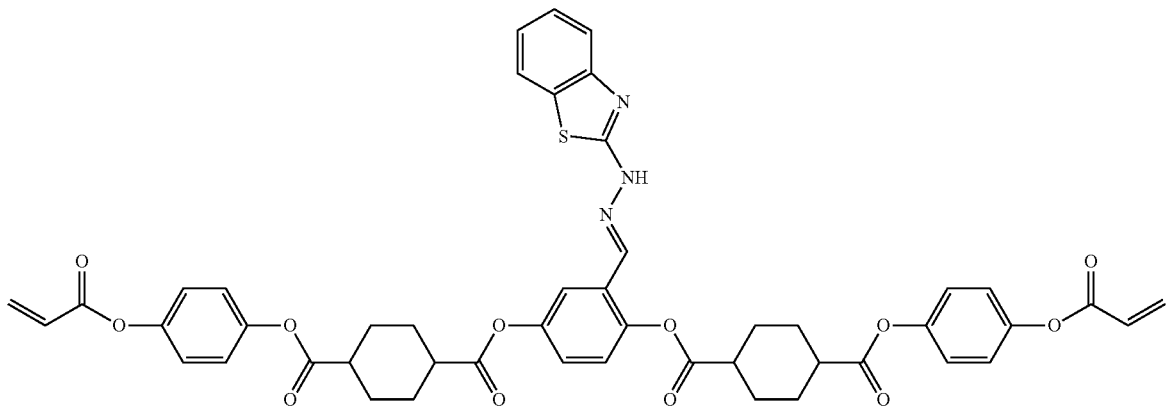

[Chem. 98]
(2-a-21)
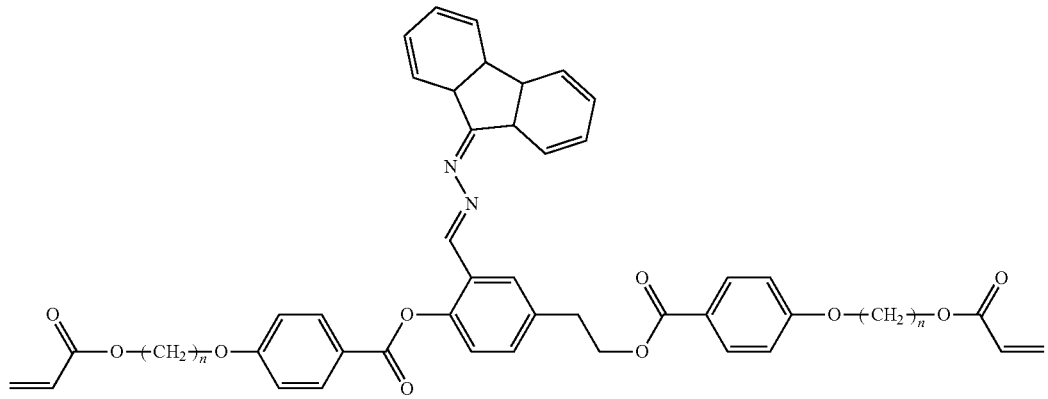
(2-a-22)
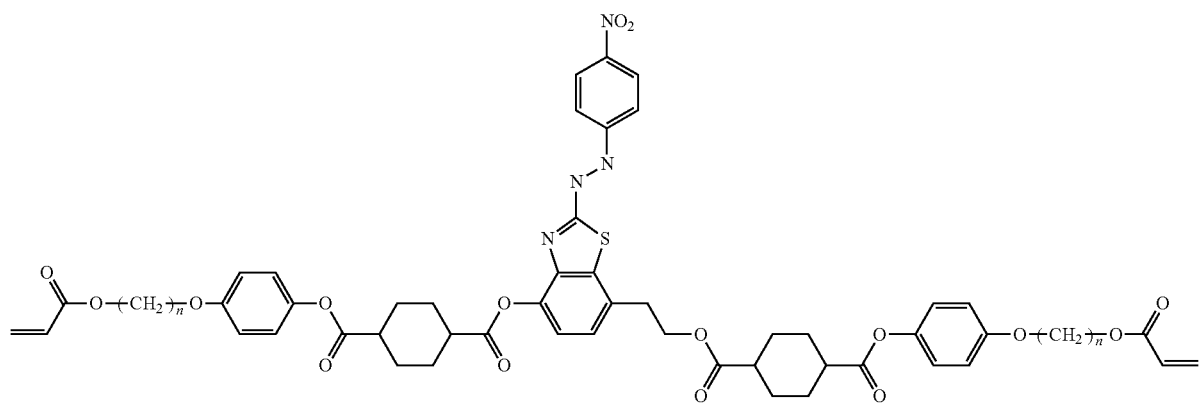
(2-a-23)
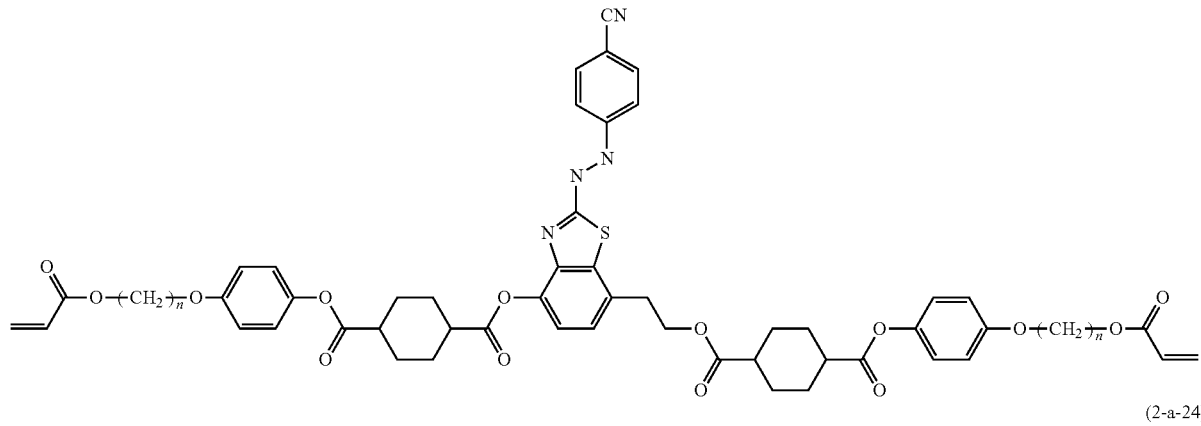
(2-a-24)
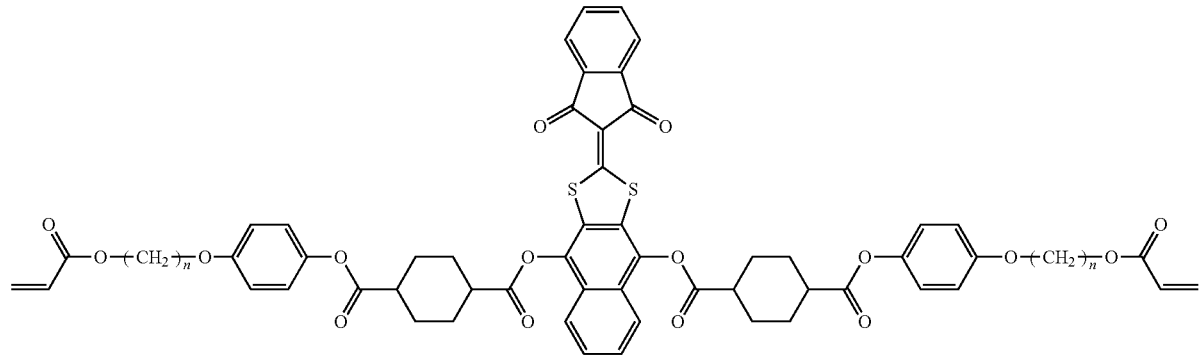

-continued
(2-a-25)
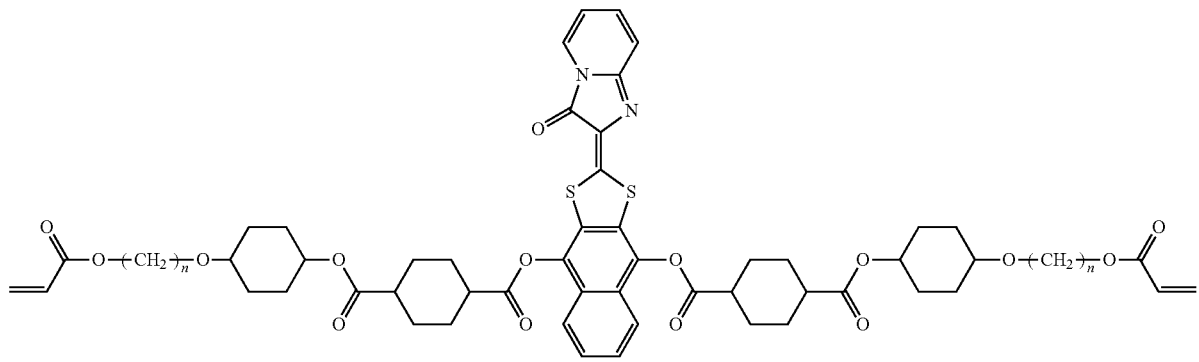
[Chem. 99]
(2-a-26)
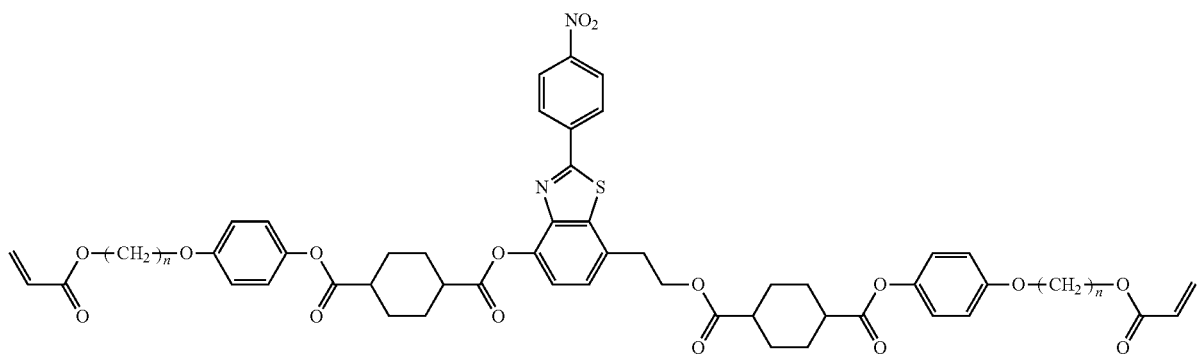
(2-a-27)
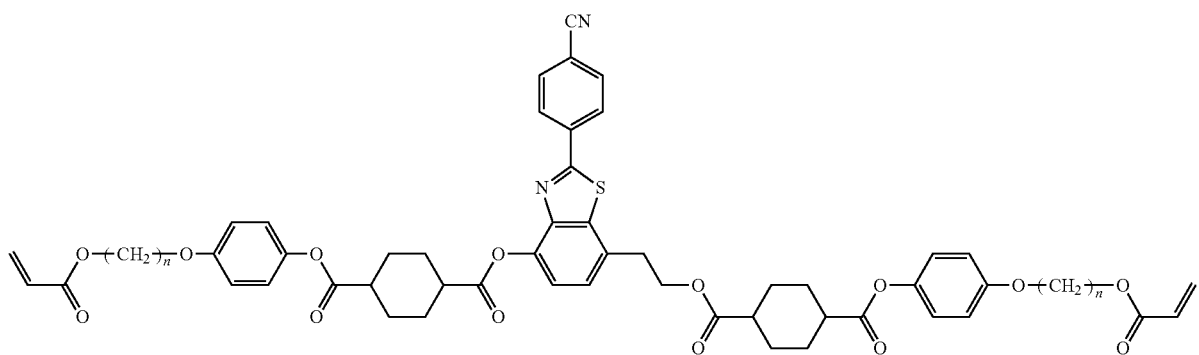
(2-a-28)
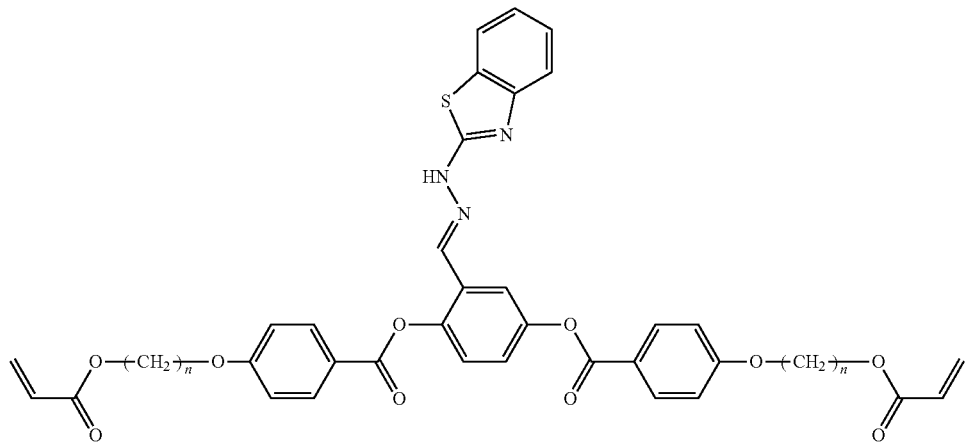

-continued
(2-a-29)
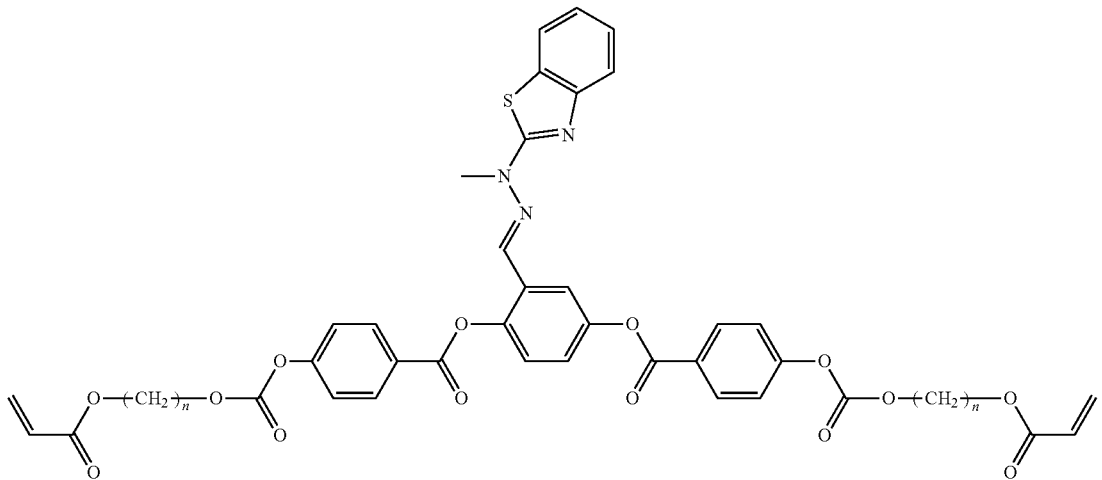
[Chem. 100]
(2-a-30)
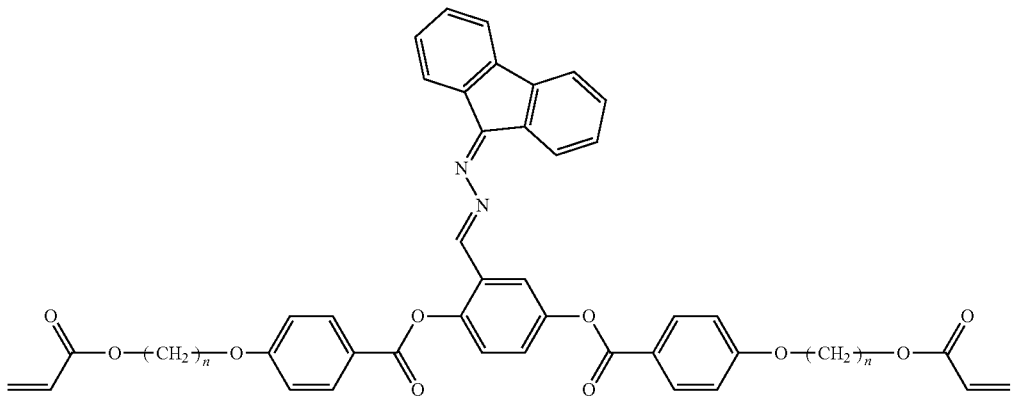
(2-a-31)
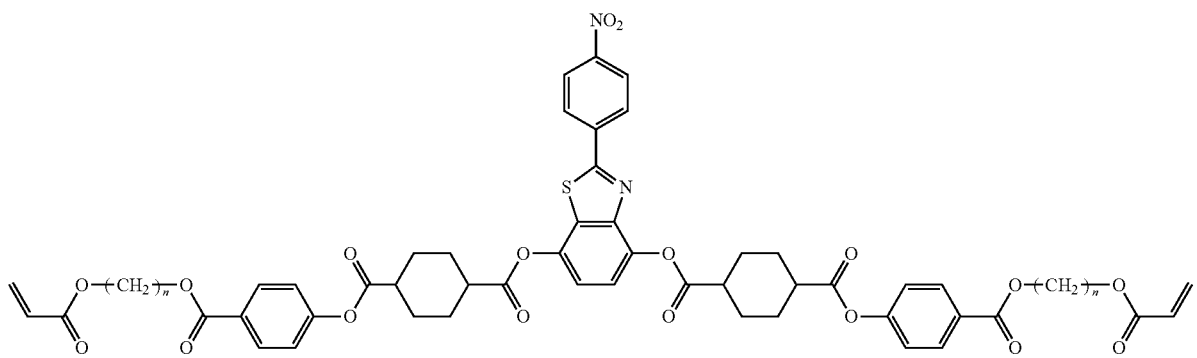

-continued
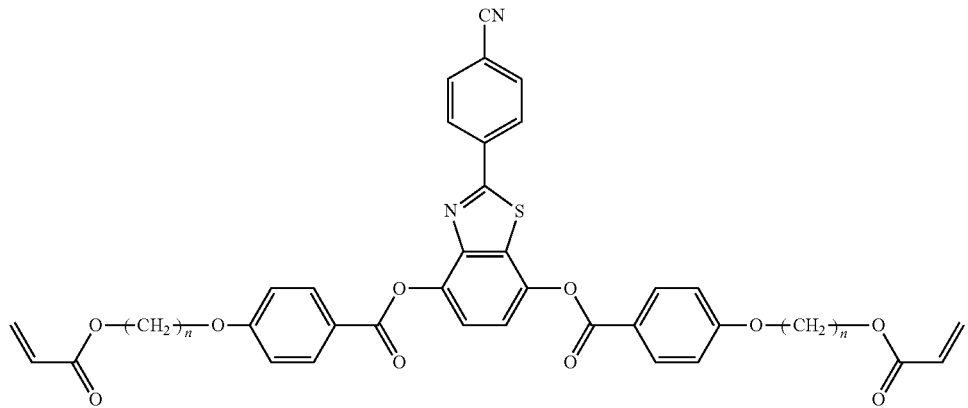
(2-a-32)
[Chem. 101]
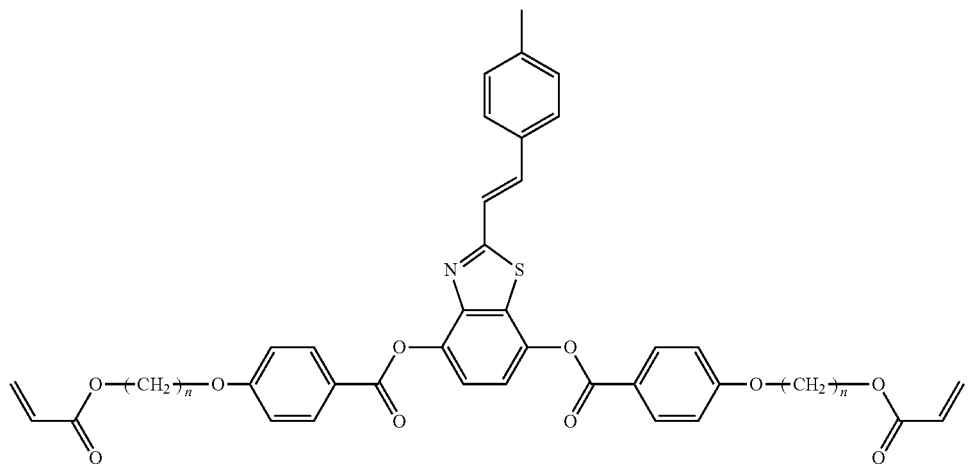
(2-a-33)
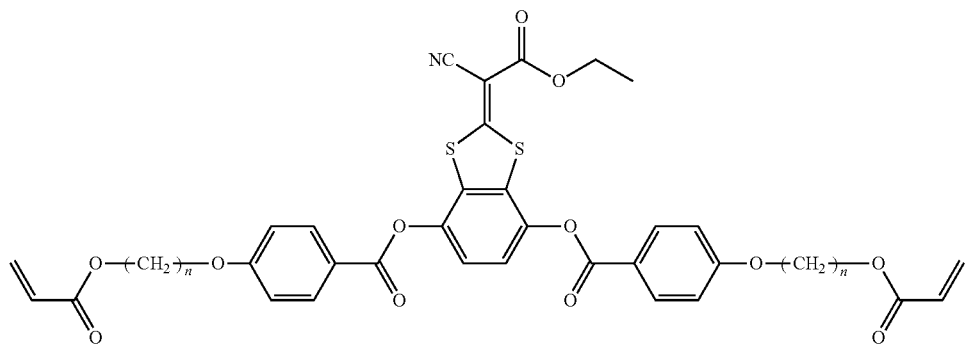
(2-a-34)

(2-a-35)
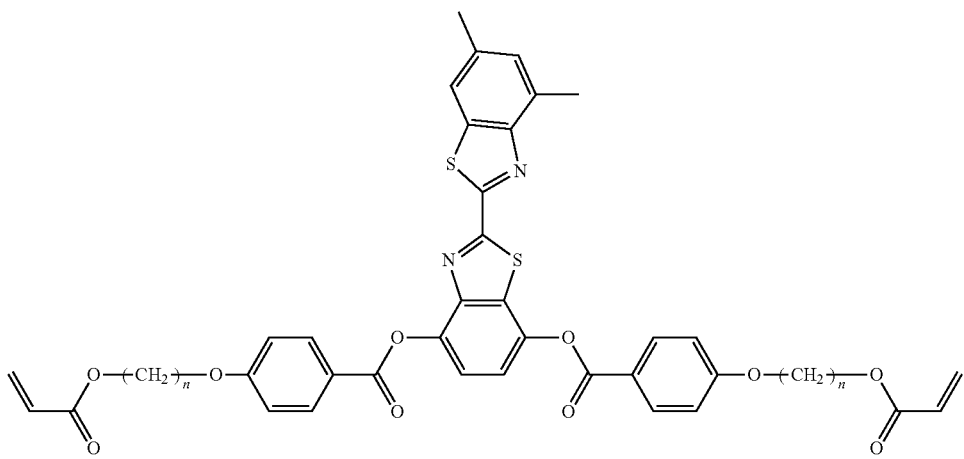
(2-a-36)
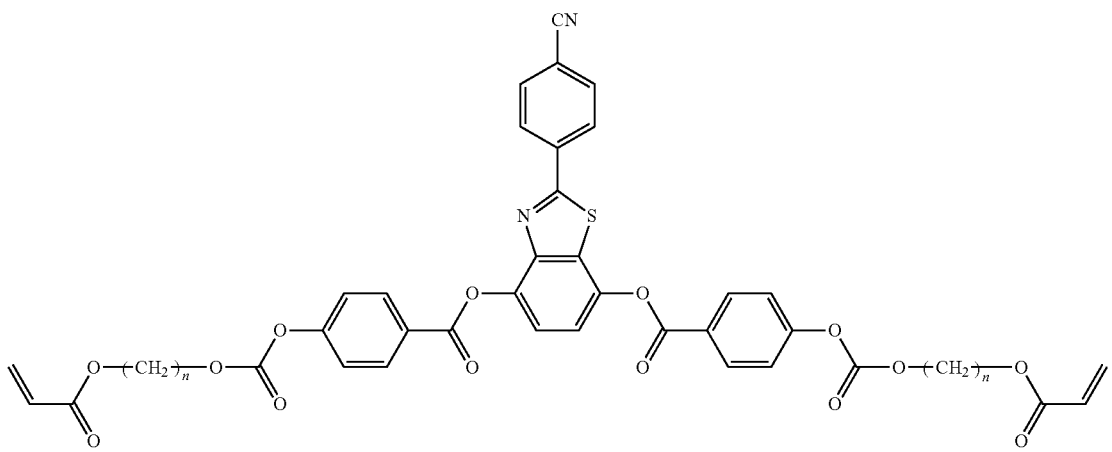
[Chem. 102]
(2-a-37)
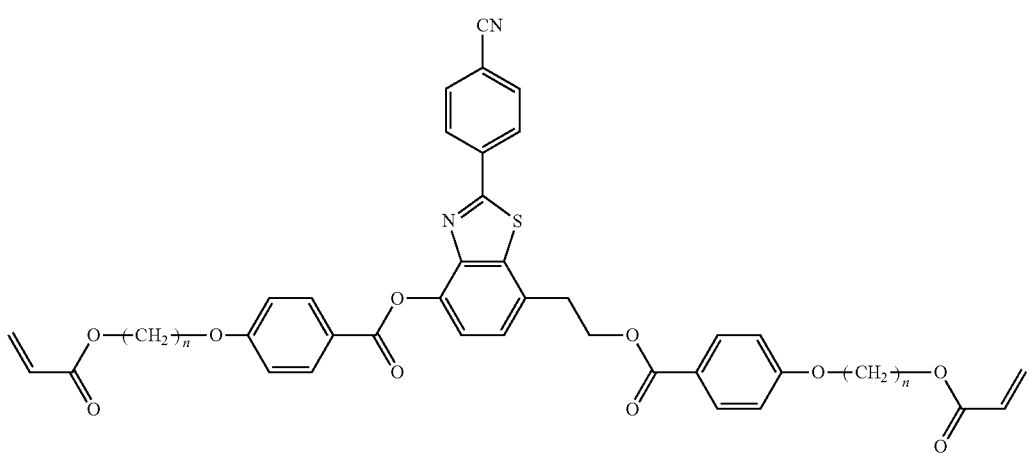

-continued
(2-a-38)
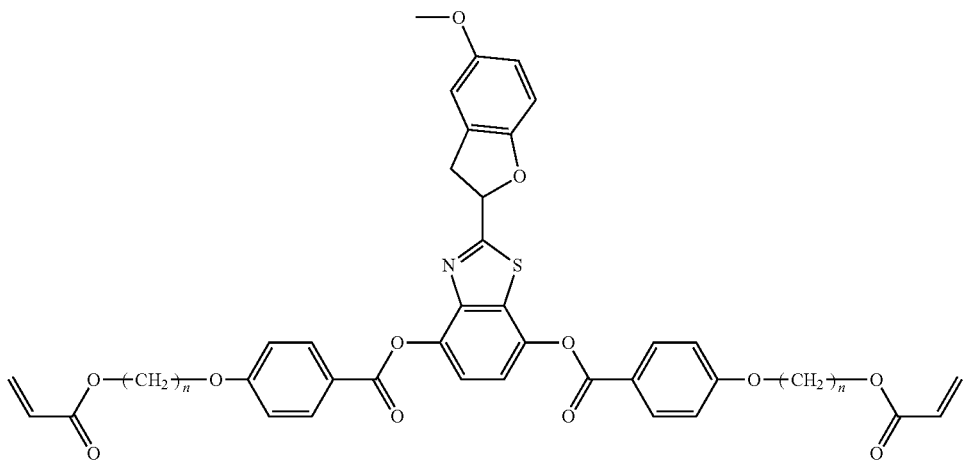
(2-a-39)
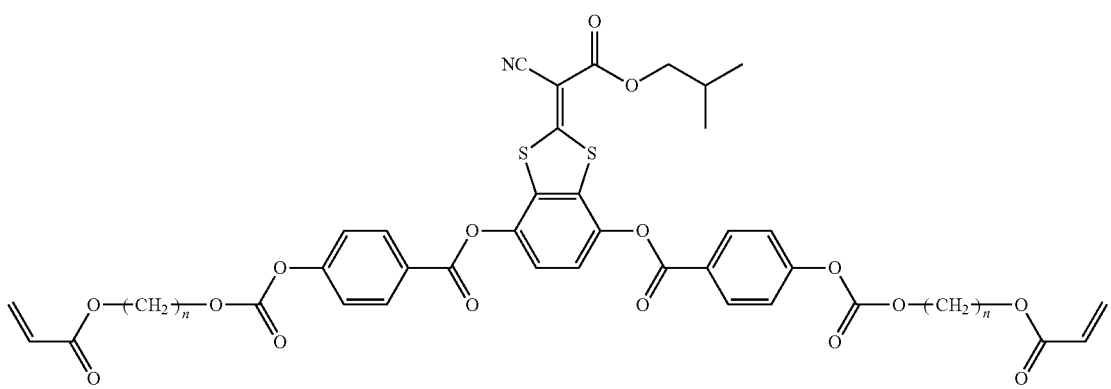
(2-a-40)
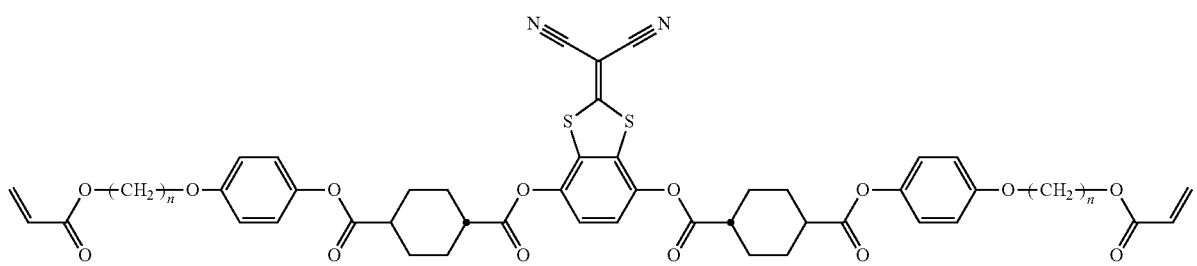
[Chem. 103]
(2-a-41)
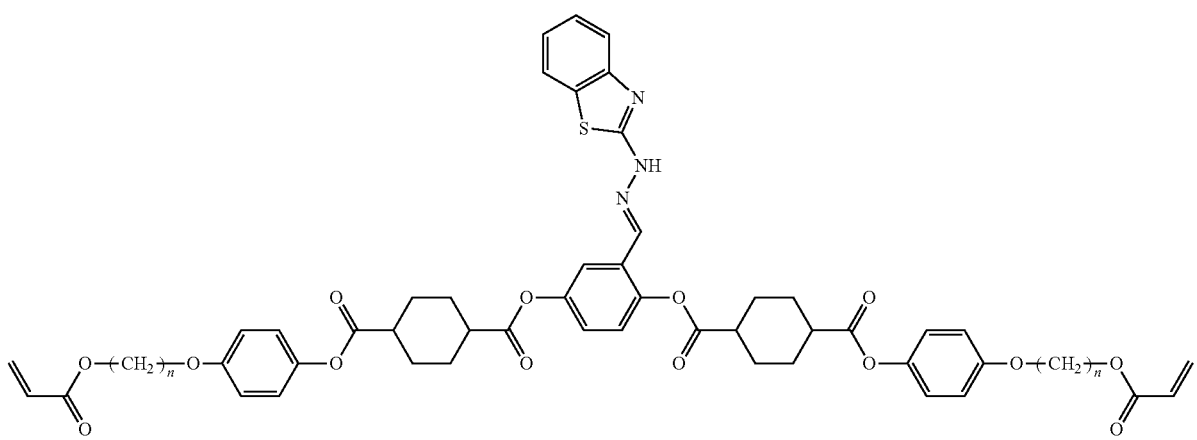

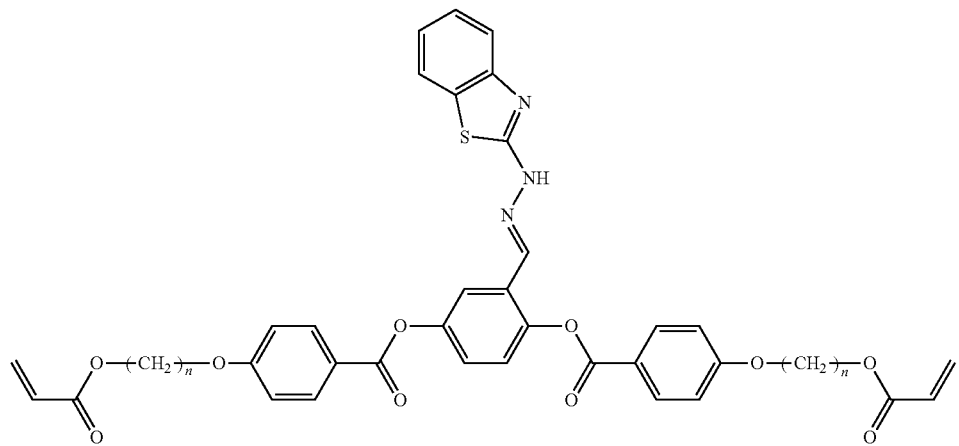
(2-a-42)
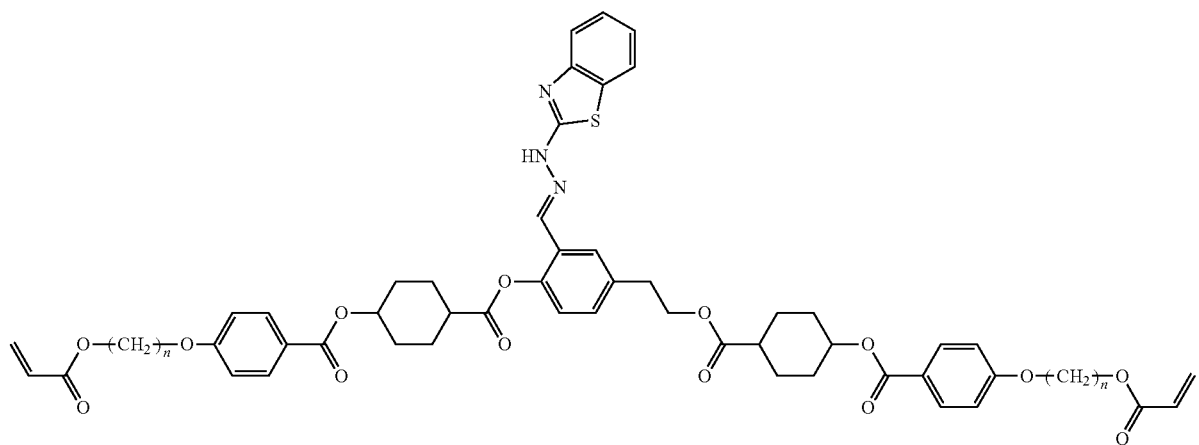
(2-a-43)
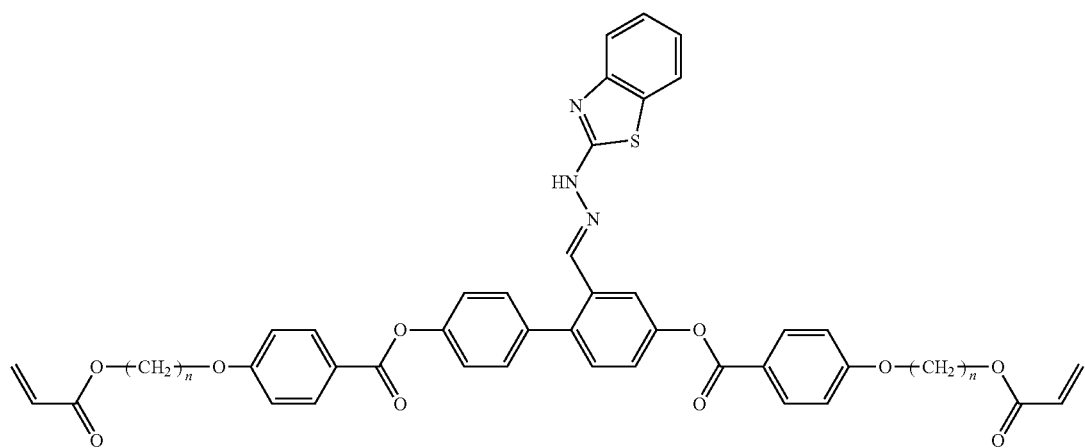
(2-a-44)

-continued
[Chem. 104]
(2-a-45)
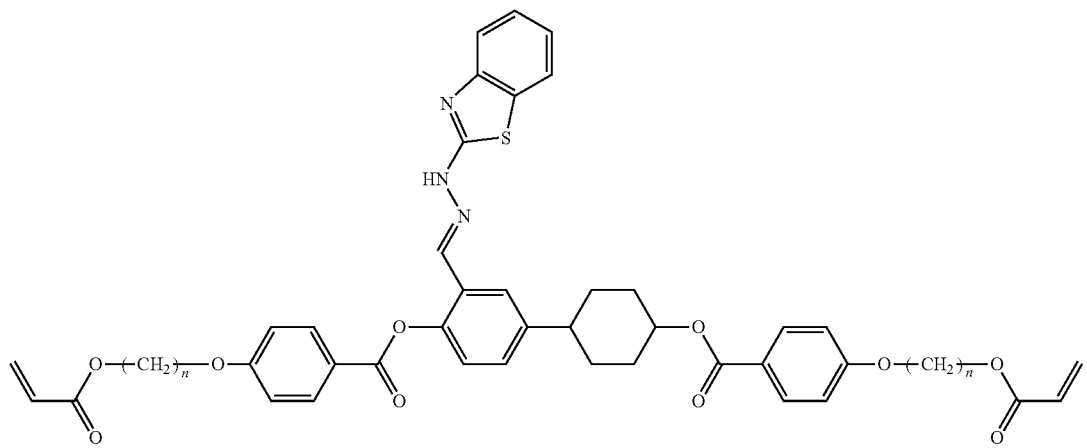
(2-a-46)
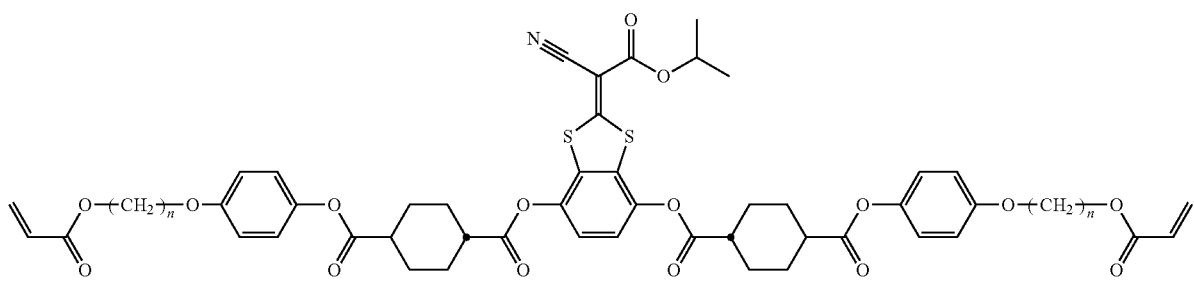
[Chem. 105]
(2-a-47)
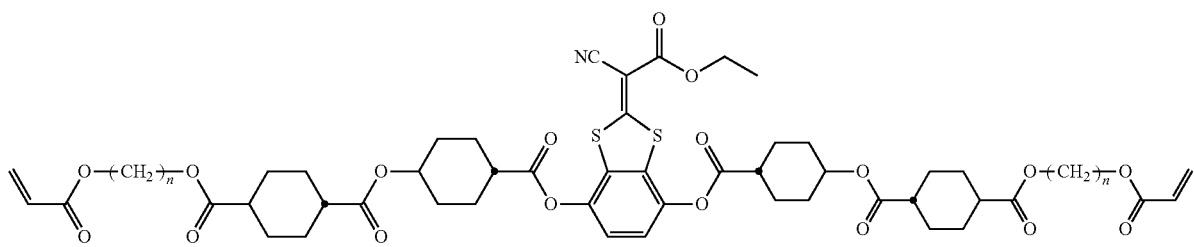
(2-a-48)
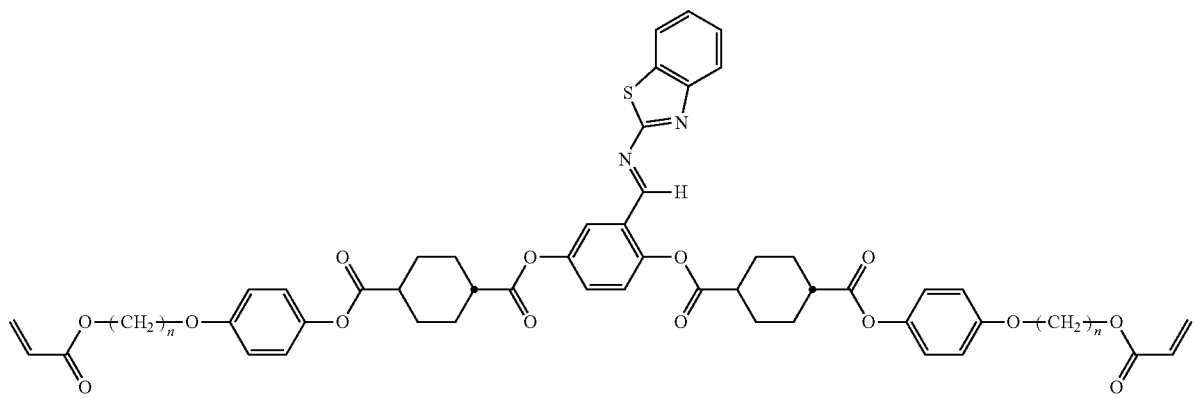

(2-a-49)
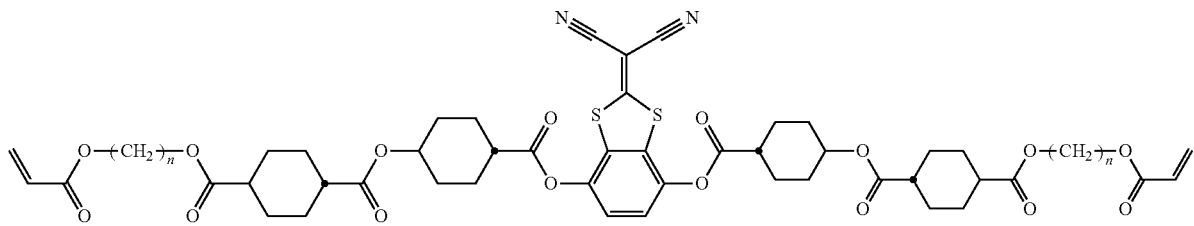
[Chem. 106]
(2-a-50)
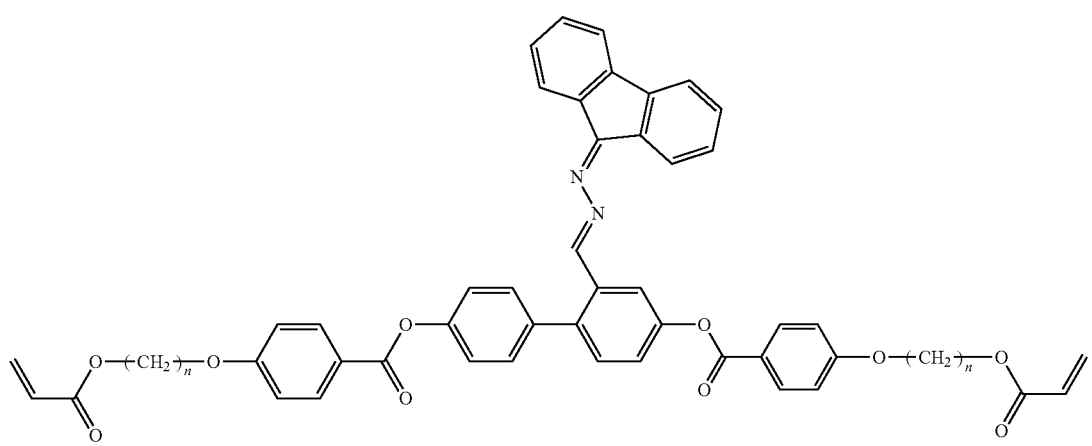
(2-a-51)
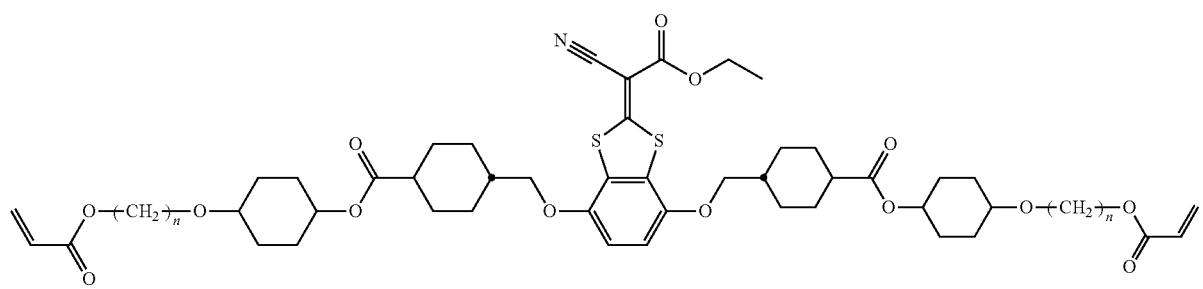
(2-a-52)
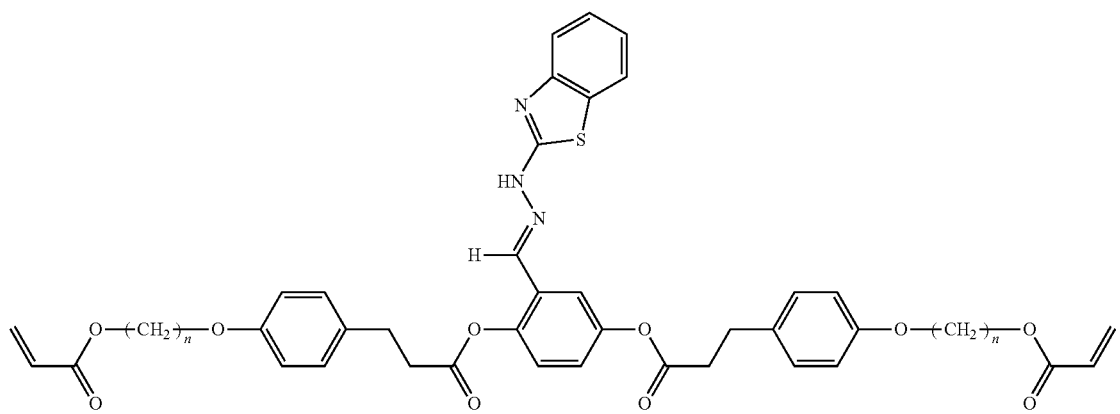

-continued
[Chem. 107]
(2-a-53)
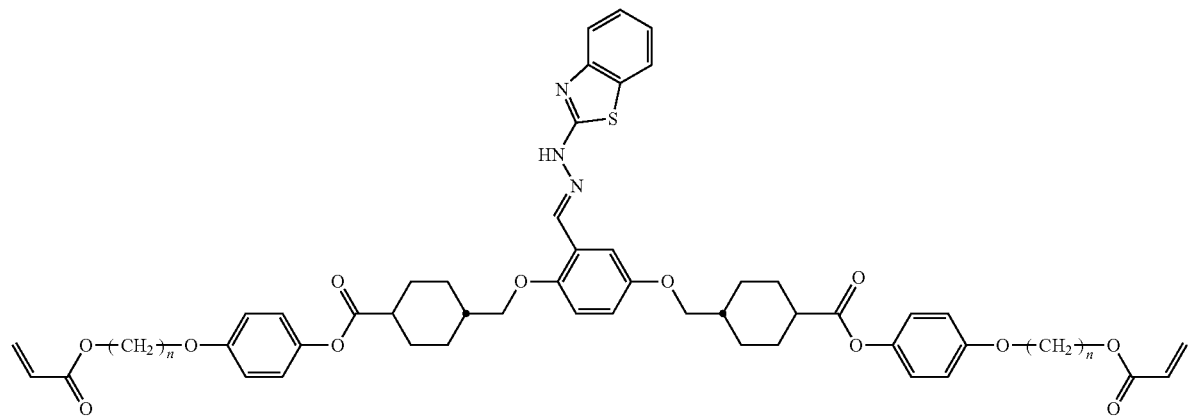
(2-a-54)
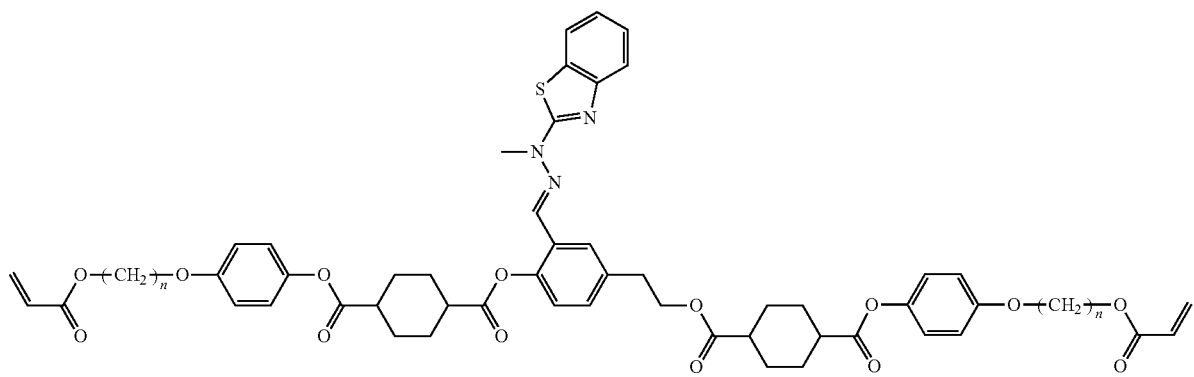
(2-a-55)
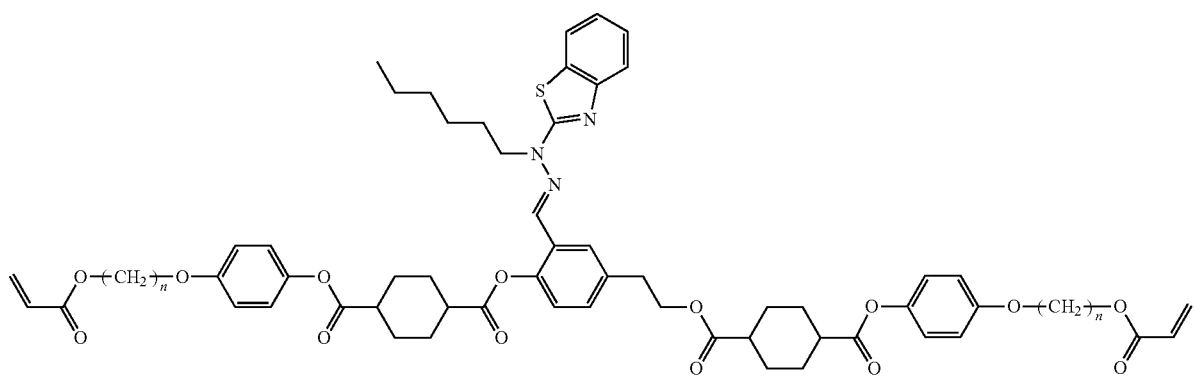

-continued
[Chem. 108]
(2-a-56)
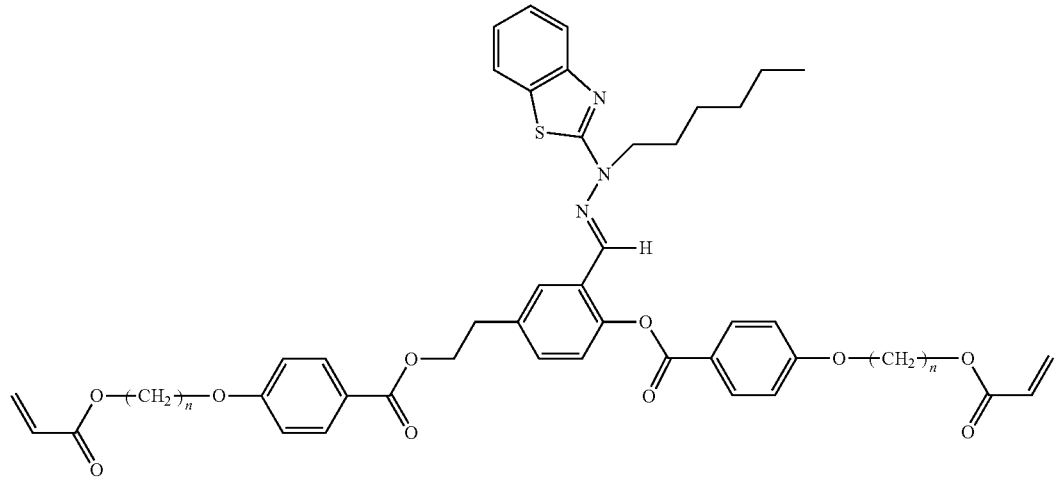
(2-a-57)
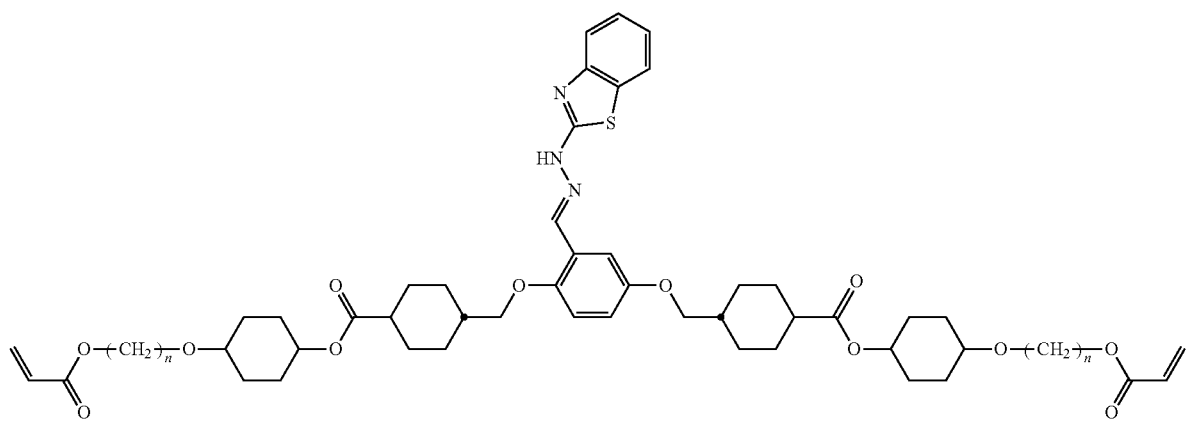
[Chem. 109]
(2-a-58)
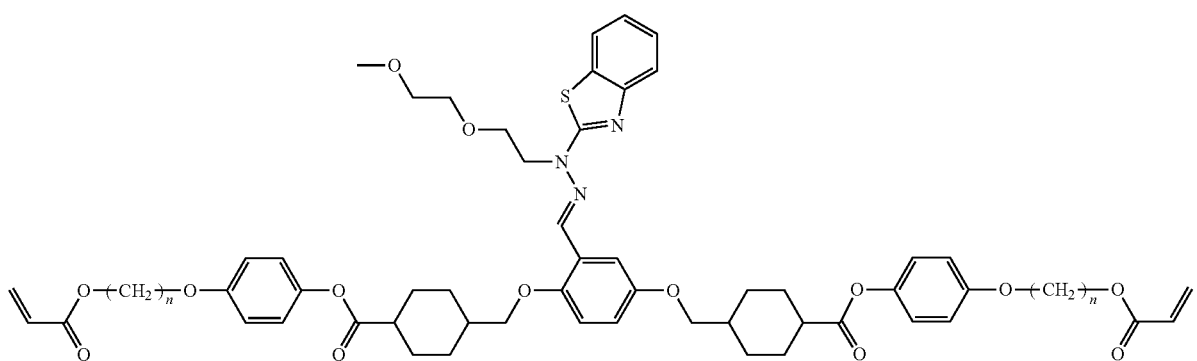

(2-a-59)

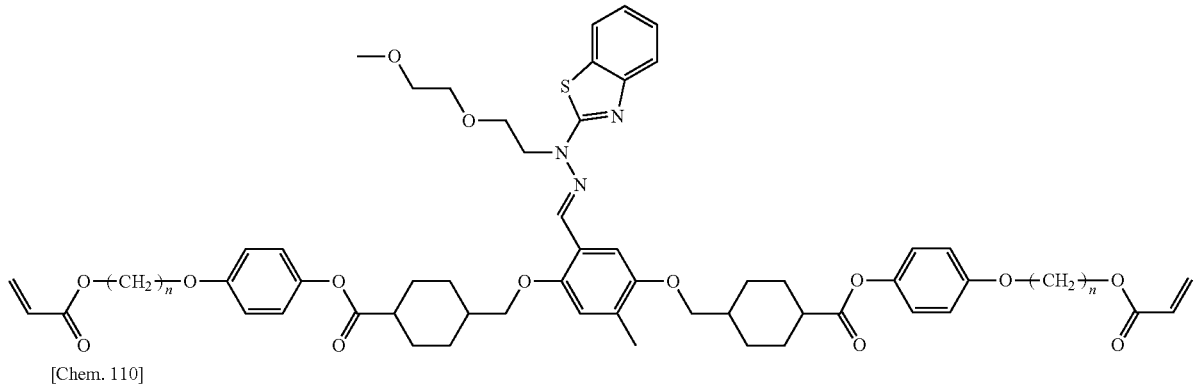

[Chem. 110]

(2-a-60)

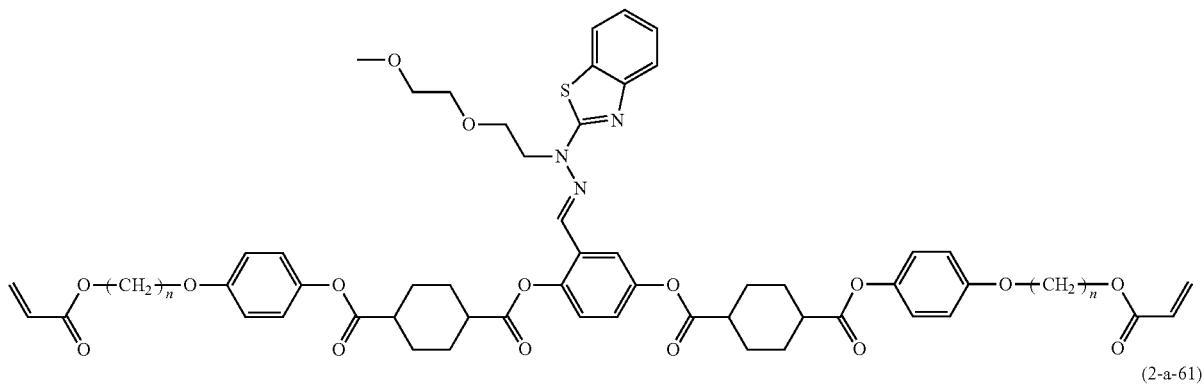

(2-a-61)

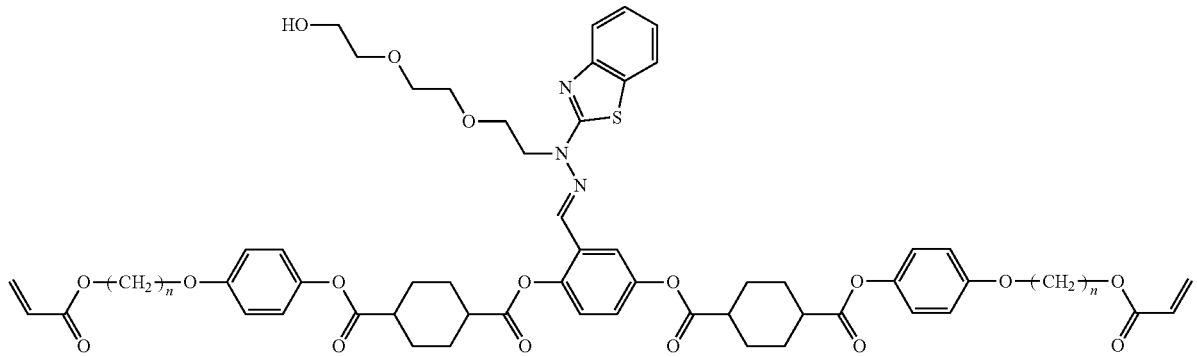

(in Formulae (2-a-1) to (2-a-65), n represents an integer of 1 to 10).

The total amount of the above reverse-wavelength dispersion difunctional polymerizable compound is preferably 0% to 90% by mass, is more preferably 0% to 80% by mass, and is particularly preferably 0% to 70% by mass of the total amount of the polymerizable compounds included in the polymerizable composition.

In the case where primary importance is attached to the preservation stability of the polymerizable composition, the lower limit is preferably set to 5% by mass or more and is more preferably set to 10% by mass or more.

(Positive Wavelength Dispersion Difunctional Polymerizable Compound)

The polymerizable composition according to the present invention may further include, in addition to the above-described reverse-wavelength dispersion polymerizable compounds, a positive-wavelength dispersion polymerizable compound represented by General Formula (2-2) which has two polymerizable groups such that the properties of the polymerizable composition do not become degraded.

[Chem. 111]

$$P^{212}(\!-\!S^{212}\!-\!X^{212}\!)_{m22}MG^{212}(\!-\!X^{222}\!-\!S^{222}\!)_{n22}P^{222} \quad (2\text{-}2)$$

In General Formula (2-2) above, $P^{212}$ and $P^{222}$ each independently represent a polymerizable group.

In General Formula (2-2), $S^{212}$ and $S^{212}$ each independently represent a spacer group or a single bond; and, when a plurality of $S^{212}$ groups and/or a plurality of $S^{222}$ groups are present, they may be identical to or different from one another.

In General Formula (2-2), $X^{212}$ and $X^{222}$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond; and, when a plurality of $X^{212}$ groups and/or a plurality of $X^{222}$ groups are present, they may be identical to or different from one another (the P—(S—X)— linkages do not include —O—O—).

In General Formula (2-2), $MG^{212}$ represents a mesogenic group.

In General Formula (2-2), m22 and n22 each independently represent an integer of 0 to 5.

In General Formula (2-2) above, the spacer groups represented by $S^{212}$ and $S^{222}$ are alkylene groups having 1 to 18 carbon atoms. The alkylene groups may be substituted with one or more halogen atoms, CN groups, alkyl groups having 1 to 8 carbon atoms, or alkyl groups having 1 to 8 carbon atoms which include a polymerizable functional group. In the above groups, one CH$_2$ group or two or more CH$_2$ groups that are not adjacent to one another may be each independently replaced with —O—, —S—, —NH—, —N(CH$_3$)—, —CO—, —CH(OH)—, CH(COOH), —COO—, —OCO—, —OCOO—, —SCO—, —COS—C≡C—, or Formula (S-1) or (S-2) such that any two oxygen atoms do not directly bind to each other.

[Chem. 112]

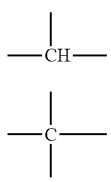

(S-1)

(S-2)

In consideration of alignment, among the above spacer groups, a linear alkylene group having 2 to 8 carbon atoms, an alkylene group having 2 to 6 carbon atoms substituted with a fluorine atom, and an alkylene group having 5 to 14 carbon atoms in which a part of the alkylene group is replaced with —O— are preferable.

The polymerizable groups represented by $P^{212}$ and $P^{222}$ are preferably selected from Formulae (P-1) to (P-20) below.

[Chem. 113]

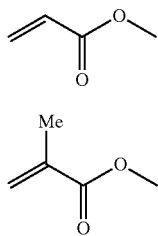

(P-1)

(P-2)

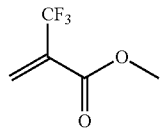 (P-3)

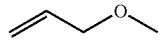 (P-4)

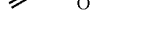 (P-5)

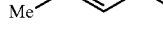 (P-6)

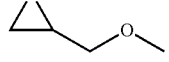 (P-7)

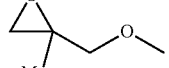 (P-8)

 (P-9)

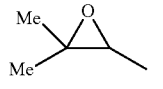 (P-10)

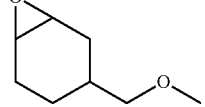 (P-11)

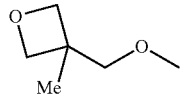 (P-12)

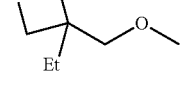 (P-13)

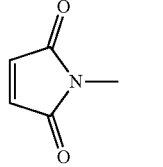 (P-14)

 (P-15)

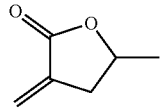 (P-16)

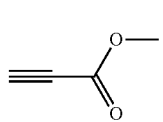 (P-17)

-continued

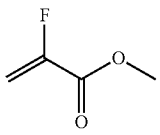
(P-18)

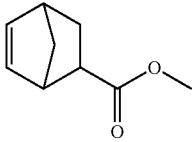
(P-19)

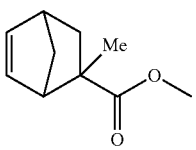
(P-20)

In order to enhance polymerizability and preservation stability, among the above polymerizable groups, Formulae (P-1), (P-2), (P-7), (P-12), and (P-13) are preferable; and Formulae (P-1), (P-7), and (P-12) are more preferable. The mesogenic group represented by $MG^{212}$ is represented by General Formula (8-b):

[Chem. 114]

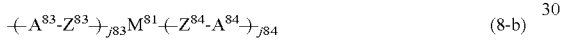
(8-b)

(in Formula (8-b), $A^{83}$ and $A^{84}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^2$ substituents, and, when a plurality of $A^{83}$ groups and/or a plurality of $A^{84}$ groups are present, they may be identical to or different from one another;

$Z^{83}$ and $Z^{84}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, and, when a plurality of $Z^{83}$ groups and/or a plurality of $Z^{84}$ groups are present, they may be identical to or different from one another;

$M^{81}$ represents a group selected from a 1,4-phenylene group, a 1,4-cyclohexylene group, a 1,4-cyclohexenyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a thiophene-2,5-diyl group-, a 1,2,3,4-tetrahydronaphthalene-2,6-diyl group, a naphthylene-1,4-diyl group, a naphthylene-1,5-diyl group, a naphthylene-1,6-diyl group, a naphthylene-2,6-diyl group, a phenanthrene-2,7-diyl group, a 9,10-dihydrophenanthrene-2,7-diyl group, a 1,2,3,4,4a,9,10a-octahydrophenanthrene-2,7-diyl group, a benzo[1,2-b:4,5-b']dithiophene-2,6-diyl group, a benzo[1,2-b:4,5-b']diselenophene-2,6-diyl group, a [1]benzothieno[3,2-b]thiophene-2,7-diyl group, a [1]benzoselenopheno[3,2-b]selenophene-2,7-diyl group, and a fluorene-2,7-diyl group, and the above groups may be optionally substituted with one or more $L^2$ substituents;

$L^2$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom; and j83 and j84 each independently represent an integer of 0 to 5, and j83+j84 is an integer of 1 to 5).

General Formula (2-2) above is represented by General Formula (2-b) below.

[Chem. 115]

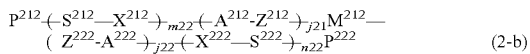
(2-b)

In General Formula (2-b) above, the polymerizable groups $P^{212}$ and $P^{222}$ preferably each independently represent a group selected from Formulae (P-1) to (P-20) below:

[Chem. 116]

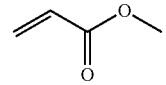
(P-1)

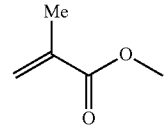
(P-2)

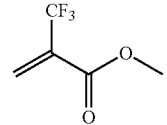
(P-3)

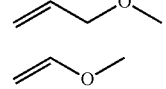
(P-4)

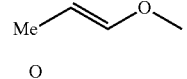
(P-5)

(P-6)

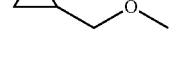
(P-7)

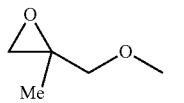 (P-8)

 (P-9)

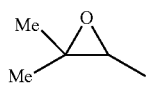 (P-10)

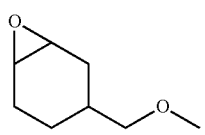 (P-11)

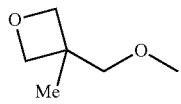 (P-12)

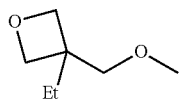 (P-13)

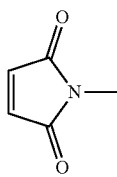 (P-14)

 (P-15)

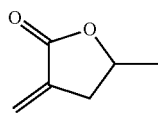 (P-16)

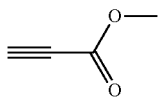 (P-17)

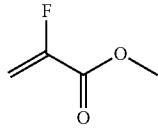 (P-18)

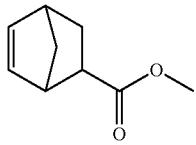 (P-19)

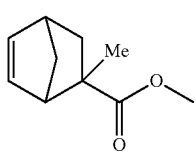 (P-20)

In order to enhance polymerizability and preservation stability, among the above polymerizable groups, Formulae (P-1), (P-2), (P-7), (P-12), and (P-13) are preferable; and Formulae (P-1), (P-7), and (P-12) are more preferable.

In General Formula (2-b), $S^{212}$ and $S^{222}$ each independently represent a spacer group or a single bond. When a plurality of $S^{212}$ groups and/or a plurality of $S^{222}$ groups are present, they may be identical to or different from one another. The spacer group is an alkylene group having 1 to 18 carbon atoms. The alkylene group may be substituted with one or more halogen atoms, CN groups, alkyl groups having 1 to 8 carbon atoms, or alkyl groups having 1 to 8 carbon atoms and including a polymerizable functional group. In the above groups, one $CH_2$ group or two or more $CH_2$ groups that are not adjacent to one another may be each independently replaced with —O—, —S—, —NH—, —N(CH$_3$)—, —CO—, —CH(OH)—, CH(COOH), —COO—, —OCO—, —OCOO—, —SCO—, —COS—, or —C≡C— such that any two oxygen atoms do not directly bind to each other. In consideration of alignment, among the above spacer groups, a linear alkylene group having 2 to 8 carbon atoms, an alkylene group having 2 to 6 carbon atoms substituted with a fluorine atom, and an alkylene group having 5 to 14 carbon atoms in which a part of the alkylene group is replaced with —O— are preferable.

In General Formula (2-b), $X^{212}$ and $X^{222}$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, and, when a plurality of $X^{212}$ groups and/or a plurality of $X^{222}$ groups are present, they may be identical to or different from one another (the P—(S—X)— linkages do not include an —O—O— linkage). In consideration of the availability of raw materials and ease of synthesis, $X^{212}$ and $X^{222}$ preferably each independently represent —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond and, when a plurality of $X^{212}$ groups and/or a plurality of $X^{222}$ groups are present, they may be identical to or different from one another; more preferably each independently represent —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond; and particularly preferably each independently represent —O—, —COO—, —OCO—, or a single bond and, when a plurality of $X^{212}$ groups and/or a plurality of $X^{222}$ groups are present, they may be identical to or different from one another.

In General Formula (2-b), $A^{212}$ and $A^{222}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more $L^2$ substituents. When a plurality of $A^{212}$ groups and/or a plurality of $A^{222}$ groups are present, they may be identical to or different from one another. In consideration of the availability of raw materials and ease of synthesis, $A^{12}$ and $A^{222}$ preferably each independently represent a 1,4- phenylene group, a 1,4-cyclohexylene group, or a naphthalene-2,6-diyl that may be optionally substituted with one or more $L^2$ substituents; and more preferably each independently represent a group selected from Formulae (A-1) to (A-11) below.

[Chem. 117]

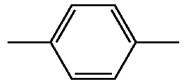 (A-1)

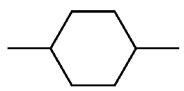 (A-2)

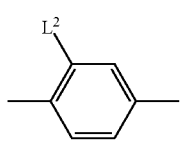 (A-3)

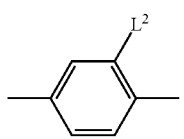 (A-4)

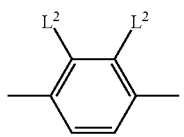 (A-5)

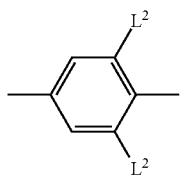 (A-6)

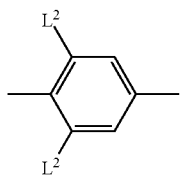 (A-7)

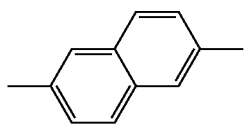 (A-8)

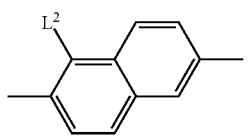 (A-9)

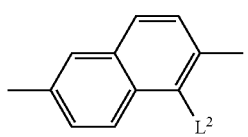 (A-10)

-continued

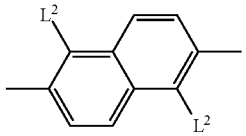 (A-11)

$A^{212}$ and $A^{222}$ further preferably each independently represent a group selected from Formulae (A-1) to (A-8) and particularly preferably each independently represent a group selected from Formulae (A-1) to (A-4).

In General Formula (2-b), $Z^{212}$ and $Z^{222}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond. When a plurality of $Z^{212}$ groups and/or a plurality of $Z^{222}$ groups are present, they may be identical to or different from one another. In consideration of the liquid crystal property of the compound, the availability of raw materials, and ease of synthesis, $Z^{212}$ and $Z^{222}$ preferably each independently represent —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond; more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond; further preferably each independently represent —CH$_2$CH—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond; and particularly preferably each independently represent —CH$_2$CH$_2$—, —COO—, —OCO—, or a single bond.

In General Formula (2-b), $M^{212}$ represents a group selected from a 1,4-phenylene group, a 1,4-cyclohexylene group, a 1,4-cyclohexenyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a thiophene-2,5-diyl group-, a 1,2,3,4-tetrahydronaphthalene-2,6-diyl group, a naphthylene-1,4-diyl group, a naphthylene-1,5-diyl group, a naphthylene-1,6-diyl group, a naphthylene-2,6-diyl group, a phenanthrene-2,7-diyl group, a 9,10-dihydrophenanthrene-2,7-diyl group, a 1,2,3,4,4a,9,10a-octahydrophenanthrene-2,7-diyl group, a benzo[1,2-b:4,5-b']dithiophene-2,6-diyl group, a benzo[1,2-b:4,5-b']diselenophene-2,6-diyl group, a [1]benzothieno[3,2-b]thiophene-2,7-diyl group, a [1]benzoselenopheno[3,2-b]selenophene-2,7-diyl group, and a fluorene-2,7-diyl group. The above groups may be optionally substituted with one or more $L^2$ substituents. In consideration of the availability of raw materials and ease of synthesis, $M^{212}$ preferably each independently represents a 1,4-phenylene group, a naphthylene-1,4-diyl group, or a naphthylene-2,6-diyl group that may be optionally substituted with one or more $L^2$ substituents; and more preferably represents a group selected from 1,4-phenylene groups that may be optionally substituted with one or more $L^2$ substituents.

In General Formula (2-b), $L^2$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom. In consideration of liquid crystal property and ease of synthesis, $L^2$ preferably represents a fluorine atom, a chlorine atom, a pentafluorosulfanyl group, a nitro group, a methylamino group, a dimethylamino group, a diethylamino group, a diisopropylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —S—, —CO—, —COO—, —OCO—, —O—CO—O—, —CH=CH—, —CF=CF—, or —C≡C—; more preferably represents a fluorine atom, a chlorine atom, or a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with —O—, —COO—, or —OCO—; further preferably represents a fluorine atom, a chlorine atom, or a linear or branched alkyl or alkoxy group having 1 to 12 carbon atoms in which a hydrogen atom may be replaced with a fluorine atom; and particularly preferably represents a fluorine atom, a chlorine atom, or a linear alkyl or alkoxy group having 1 to 8 carbon atoms.

In General Formula (2-b), m22 and n22 each independently represent an integer of 0 to 5. In consideration of liquid crystal property, the availability of raw materials, and ease of synthesis, m22 and n22 preferably represent an integer of 0 to 4, more preferably represent an integer of 0 to 2, and further preferably represent 0 or 1.

In General Formula (2-b), j21 and j22 each independently represent an integer of 0 to 5; and j21+j22 is an integer of 1 to 5. In consideration of liquid crystal property, ease of synthesis, and preservation stability, j21 and j22 preferably each independently represent an integer of 1 to 4, more preferably each independently represent an integer of 1 to 3, and particularly preferably each independently represent 1 or 2; and j21+j22 is preferably an integer of 1 to 4 and is particularly preferably 2 or 3.

Specifically, the compound represented by General Formula (2-b) is preferably selected from the compounds represented by Formulae (2-b-1) to (2-b-33) below:

[Chem. 118]

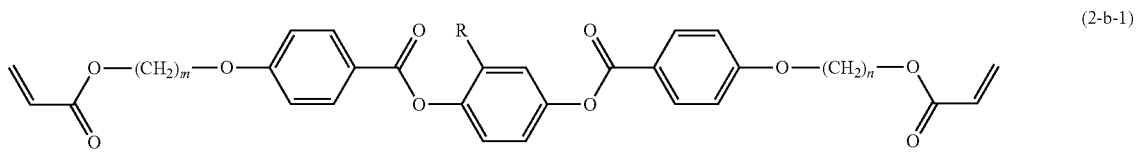

(2-b-1)

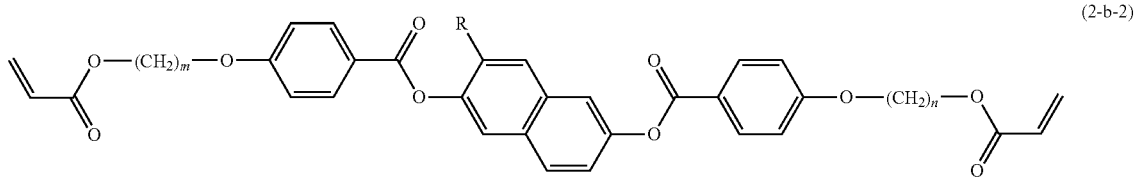

(2-b-2)

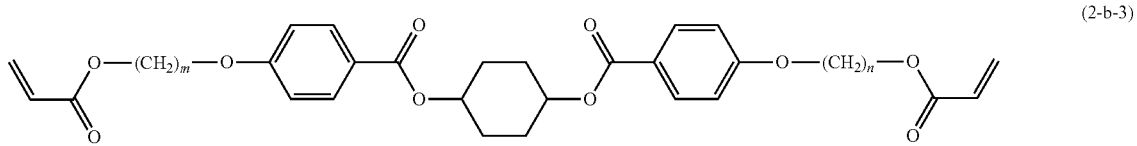

(2-b-3)

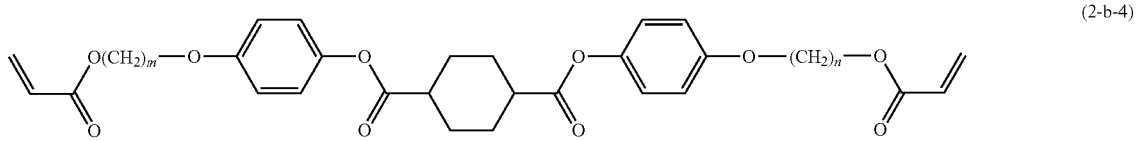

(2-b-4)

-continued
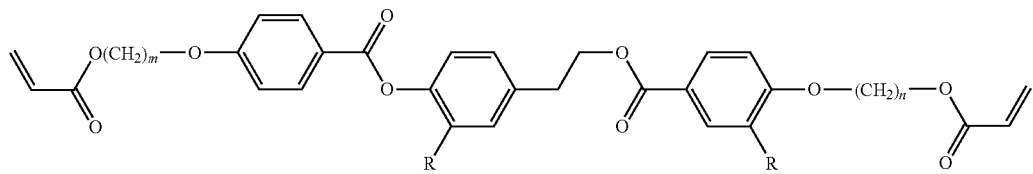
(2-b-5)
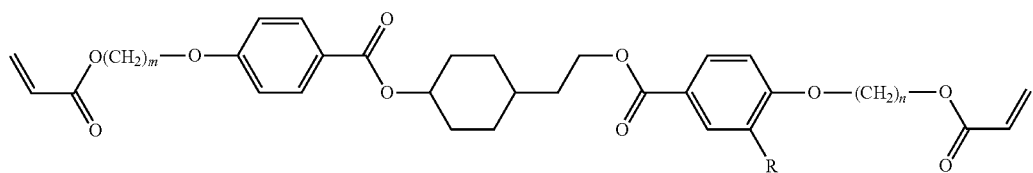
(2-b-6)
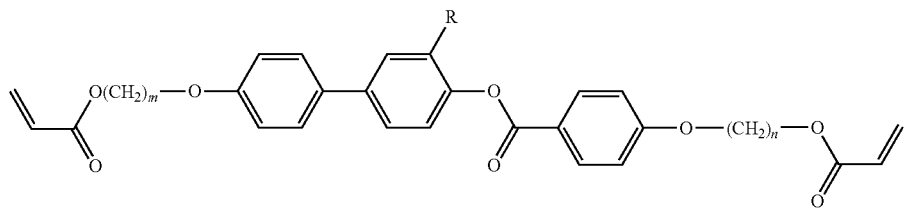
(2-b-7)
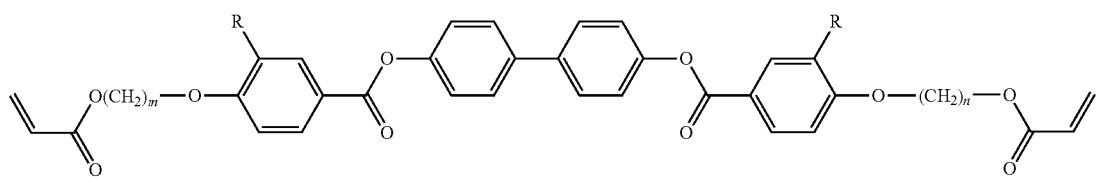
(2-b-8)
[Chem. 119]
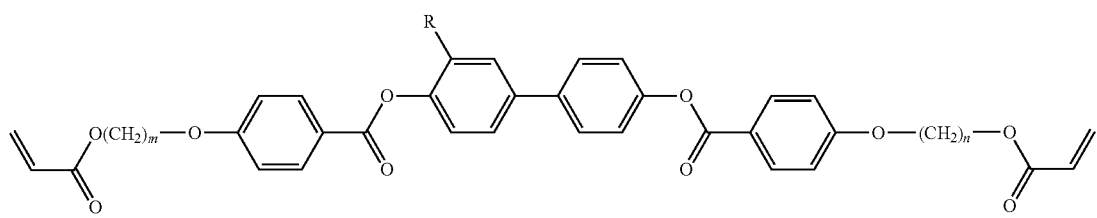
(2-b-9)
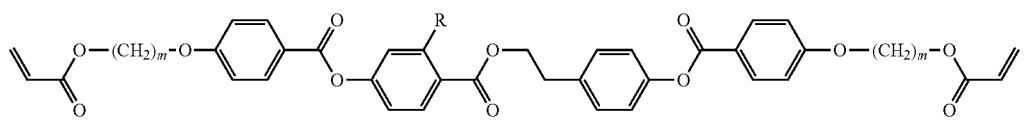
(2-b-10)
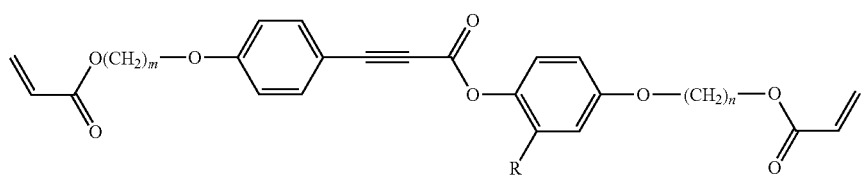
(2-b-11)
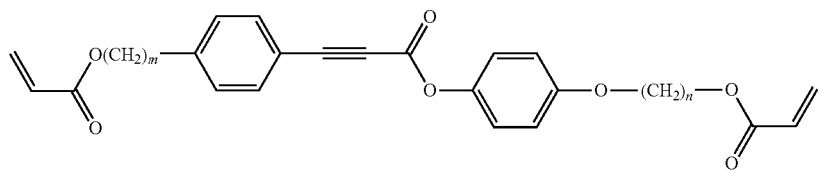
(2-b-12)

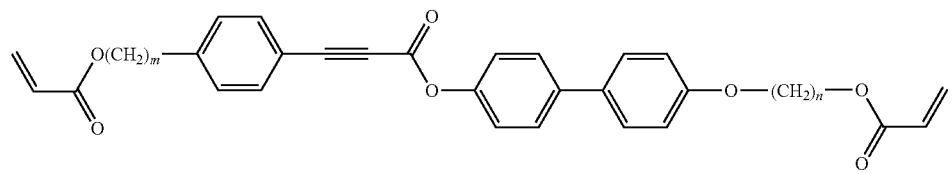
(2-b-13)
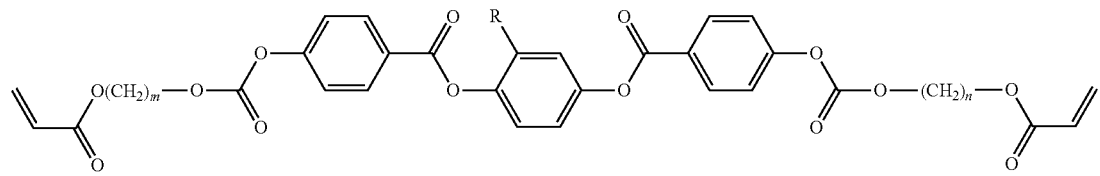
(2-b-14)
[Chem. 120]
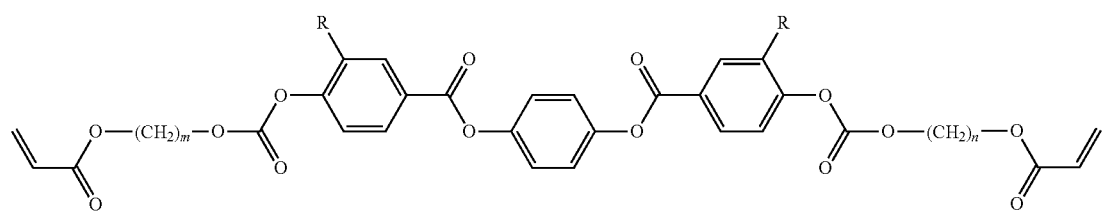
(2-b-15)
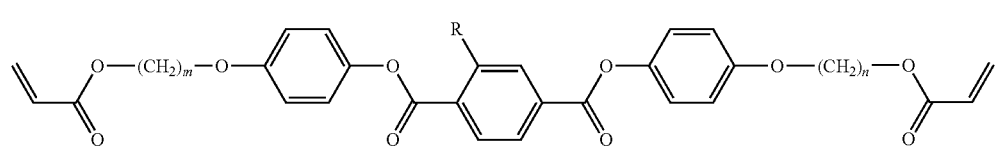
(2-b-16)
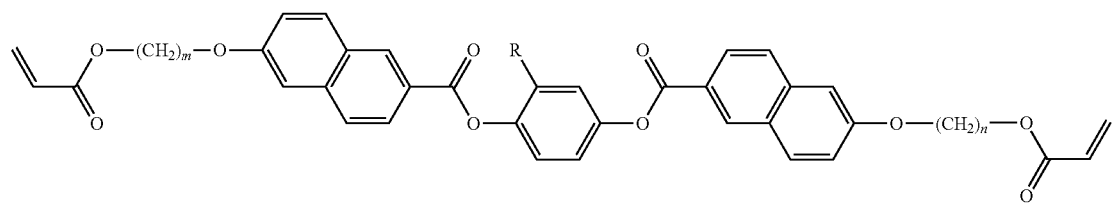
(2-b-17)
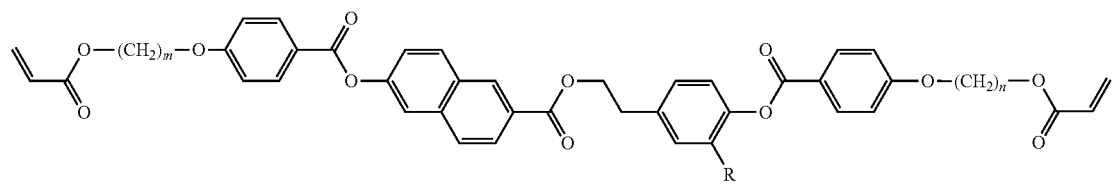
(2-b-18)
[Chem. 121]
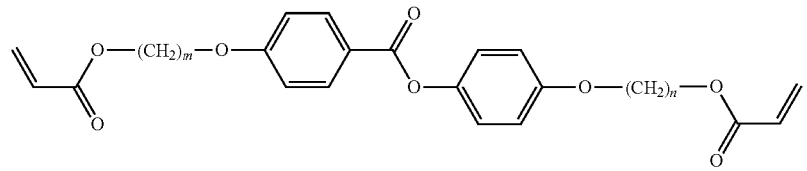
(2-b-19)
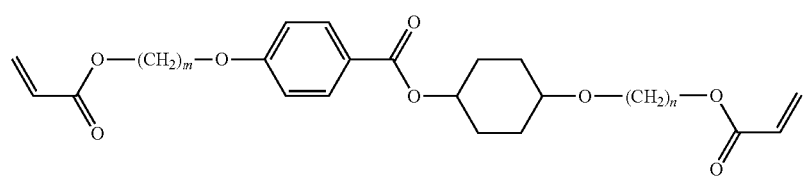
(2-b-20)

-continued
(2-b-21)
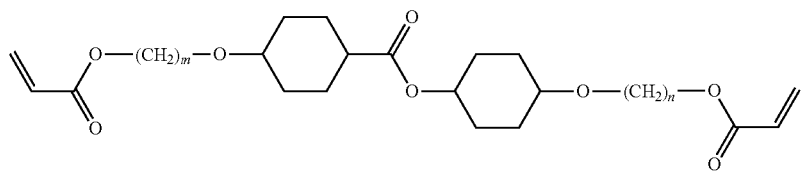
(2-b-22)
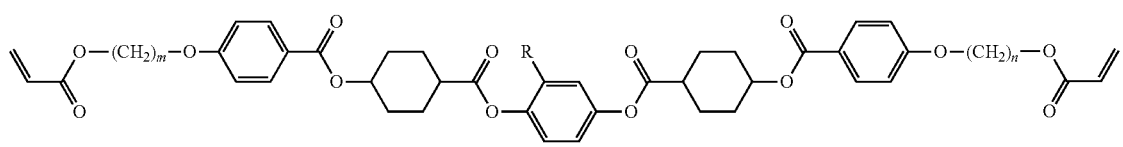
(2-b-23)
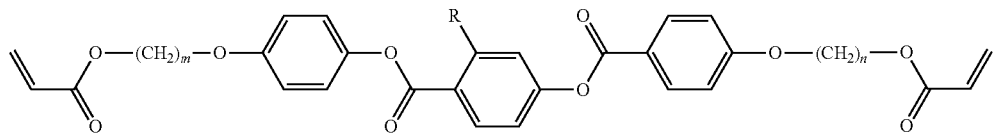
(2-b-24)
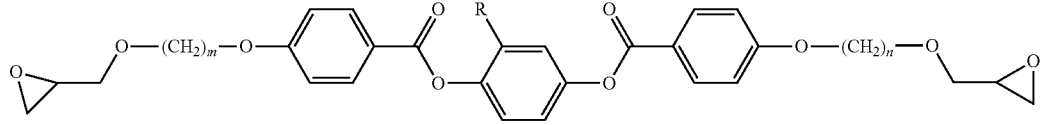
(2-b-25)
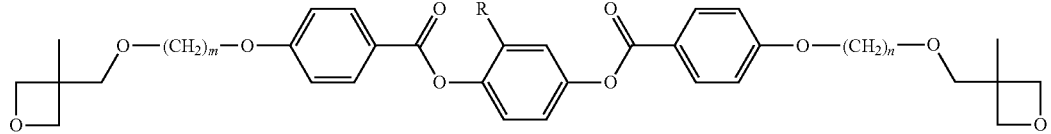
(2-b-26)
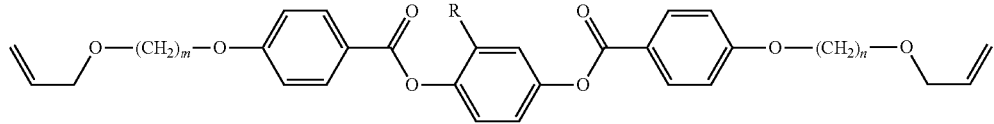
[Chem. 122]
(2-b-27)
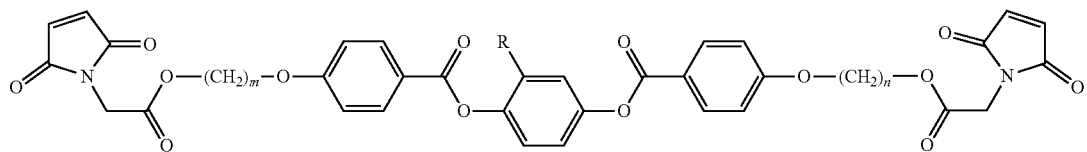
(2-b-28)
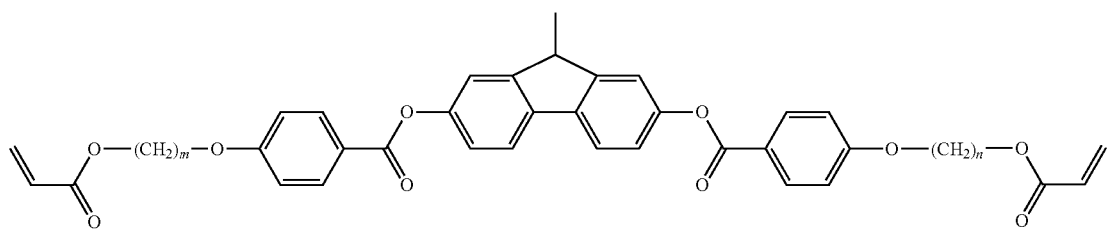
(2-b-29)
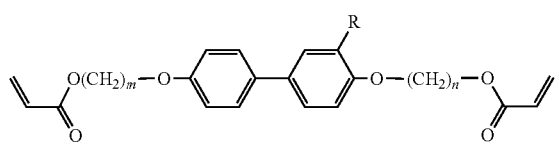
(2-b-30)
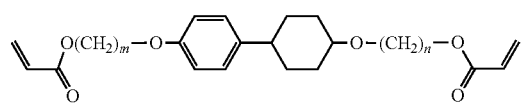

-continued

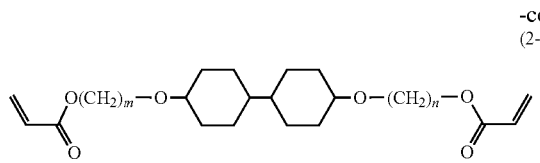
(2-b-31)

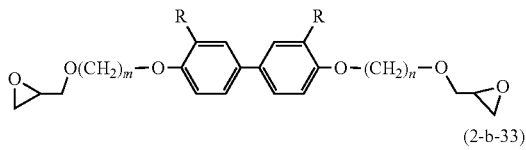
(2-b-32)

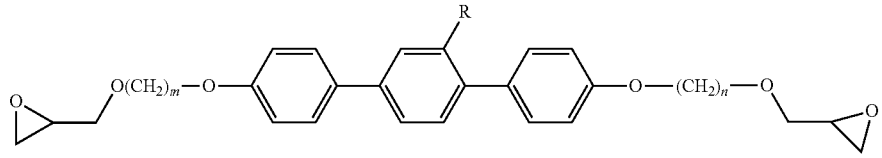
(2-b-33)

(in Formulae (2-b-1) to (2-b-33), m and n each independently represent an integer of 1 to 18; R represents a hydrogen atom, a halogen atom, an alkyl group having 1 to 6 carbon atoms, an alkoxy group having 1 to 6 carbon atoms, or a cyano group; and, in the case where these groups are the alkyl group having 1 to 6 carbon atoms or the alkoxy group having 1 to 6 carbon atoms, the entirety may be unsubstituted or may be substituted with one or two or more halogen atoms). The above liquid crystal compounds may be used alone or in a mixture of two or more.

The total amount of the above positive wavelength dispersion difunctional polymerizable compound is preferably 0% to 30% by mass, is more preferably 0% to 20% by mass, and is particularly preferably 0% to 15% by mass of the total amount of the polymerizable compounds included in the polymerizable composition.

In the case where primary importance is attached to the preservation stability of the polymerizable composition, the lower limit is preferably set to 5% by mass or more and is more preferably set to 10% by mass or more.

(Initiator)

The polymerizable composition according to the present invention may include an initiator as needed. The polymerization initiator included in the polymerizable composition according to the present invention is used for polymerizing the polymerizable composition according to the present invention. The photopolymerization initiator used when the polymerization is performed by light radiation is not limited; publicly known and commonly used photopolymerization initiators may be used in an amount with which the alignment of the polymerizable compound does not become degraded.

Examples of the photopolymerization initiator include 1-hydroxycyclohexyl phenyl ketone "Irgacure 184", 1-(4-isopropylphenyl)-2-hydroxy-2-methylpropan-1-one "Darocur 1116", 2-methyl-1-[(methylthio)phenyl]-2-morpholinopropane-1 "Irgacure 907", 2,2-dimethoxy-1,2-diphenylethan-1-one "Irgacure 651", 2-benzyl-2-dimethylamino-1-(4-morpholinophenyl)-butanone "Irgacure 369"), 2-dimethylamino-2-(4-methylbenzyl)-1-(4-morpholino-phenyl)butan-1-one "Irgacure 379", 2,2-dimethoxy-1,2-diphenylethan-1-one, bis(2,4,6-trimethylbenzoyl)-diphenylphosphine oxide "Lucirin TPO", 2,4,6-trimethylbenzoyl-phenyl-phosphine oxide "Irgacure 819", 1,2-octanedione, 1-[4-(phenylthio)-,2-(O-benzoyloxime)], ethanone "Irgacure OXE01"), 1-[9-ethyl-6-(2-methylbenzoyl)-9H-carbazol-3-yl]-,1-(O-acetyloxime) "Irgacure OXE02", and "Irgacure OXE04" (produced by BASF SE; a mixture of 2,4-diethylthioxanthone ("KAYACURE DETX" produced by Nippon Kayaku Co., Ltd.) and ethyl p-dimethylaminobenzoate ("KAYACURE EPA" produced by Nippon Kayaku Co., Ltd.); a mixture of isopropylthioxanthone ("Cantacure-ITX" produced by Wordprekinsop) and ethyl p-dimethylaminobenzoate; "Esacure ONE", "Esacure KIP150", "Esacure KIP160", "Esacure 1001M", "Esacure A198", "Esacure KIP IT", "Esacure KTO46", and "Esacure TZT" (produced by Lamberti S.p.A.); and "Speedcure BMS", "Speedcure PBZ", and "benzophenone" produced by Lambson Limited. A photo acid generator may be used as a photo cationic initiator. Examples of the photo acid generator include diazodisulfone compounds, triphenylsulfonium compounds, phenylsulfone compounds, sulfonylpyridine compounds, triazine compounds, and diphenyliodonium compounds.

The amount of the photopolymerization initiator is preferably 0.1 to 10 parts by mass and is particularly preferably 1 to 8 parts by mass relative to 100 parts by mass of the total amount of polymerizable compounds included in the polymerizable composition. The above photopolymerization initiators may be used alone or in a mixture of two or more.

In the case where thermal polymerization is performed, publicly known and commonly used thermal polymerization initiators may be used. Examples of such thermal polymerization initiators include organic peroxides, such as methyl acetoacetate peroxide, cumene hydroperoxide, benzoyl peroxide, bis(4-t-butylcyclohexyl)peroxydicarbonate, t-butyl peroxybenzoate, methyl ethyl ketone peroxide, 1,1-bis(t-hexylperoxy)3,3,5-trimethylcyclohexane, p-pentahydroperoxide, t-butyl hydroperoxide, dicumyl peroxide, isobutyl peroxide, di(3-methyl-3-methoxybutyl) peroxydicarbonate, and 1,1-bis(t-butylperoxy)cyclohexane; azonitrile compounds, such as 2,2'-azobisisobutyronitrile and 2,2'-azobis (2,4-dimethyl)valeronitrile); azoamidine compounds, such as 2,2'-azobis(2-methyl-N-phenylpropion amidine)dihydrochloride; azoamide compounds, such as 2,2'azobis{2-methyl-N-[1,1-bis(hydroxymethyl)-2-hydroxyethyl]propionamide}; and alkyl azo compounds, such as 2,2'azobis(2,4,4-trimethylpentane). The amount of the thermal polymerization initiator is preferably 0.1 to 10 parts by mass and is particularly preferably 1 to 6 parts by mass relative to 100 parts by mass of the total amount of polymerizable compounds included in the polymerizable composition. The above thermal polymerization initiators may be used alone or in a mixture of two or more.

(Organic Solvent)

The polymerizable composition according to the present invention may include an organic solvent as needed. The organic solvent is not limited but preferably an organic solvent in which the polymerizable compounds are readily soluble and which can be removed by drying at a temperature of 100° C. or less. Examples of such a solvent include aromatic hydrocarbons, such as toluene, xylene, cumene, and mesitylene; ester solvents, such as methyl acetate, ethyl acetate, propyl acetate, butyl acetate, cyclohexyl acetate, 3-butoxymethyl acetate, and ethyl lactate; ketone solvents, such as methyl ethyl ketone, methyl isobutyl ketone, cyclohexanone, and cyclopentanone; ether solvents, such as tetrahydrofuran, 1,2-dimethoxyethane, and anisole; amide solvents, such as N,N-dimethylformamide and N-methyl-2-pyrrolidone; and ethylene glycol monomethyl ether acetate, propylene glycol monomethyl ether acetate, propylene glycol monomethyl ether, propylene glycol diacetate, propylene glycol monomethyl propyl ether, diethylene glycol monomethyl ether acetate, γ-butyrolactone, and chlorobenzene. The above organic solvents may be used alone or in a mixture of two or more. It is preferable to use one or more organic solvents selected from a ketone solvent, an ether solvent, an ester solvent, and an aromatic hydrocarbon solvent in consideration of solution stability.

The proportion of the organic solvent is not limited and may be set appropriately such that the properties of the resulting coating film do not become degraded significantly, because the polymerizable composition used in the present invention is normally used for coating. The amount of the organic solvent is preferably 50 to 700 parts by mass, is further preferably 100 to 650 parts by mass, and is particularly preferably 150 to 600 parts by mass relative to 100 parts by mass of the total amount of polymerizable compounds included in the polymerizable composition.

When the polymerizable liquid crystalline compounds are dissolved in the organic solvent, it is preferable to heat and stir the solvent in order to prepare a uniform solution. The heating temperature at which the solvent is heated and stirred may be adjusted appropriately with consideration of the solubility of the polymerizable liquid crystal compounds in the organic solvent. The heating temperature is preferably 15° C. to 130° C., is further preferably 30° C. to 110° C., and is particularly preferably 50° C. to 100° C. in consideration of productivity.

(Additive)

The polymerizable composition according to the present invention may include general-purpose additives in order to achieve uniform coating and other intended purposes. For example, the following additives may be used in amounts with which the alignment of liquid crystal does not become degraded significantly: a polymerization inhibitor, an antioxidant, an ultraviolet absorber, a leveling agent, an alignment control agent, a chain-transfer agent, an infrared absorber, a thixotropic agent, an antistatic agent, a colorant, a filler, a chiral compound, a non-liquid crystalline compound including a polymerizable group, another liquid crystal compound, and an alignment material.

(Polymerization Inhibitor)

The polymerizable composition according to the present invention may include a polymerization inhibitor as needed. The polymerization inhibitor is not limited; publicly known and commonly used polymerization inhibitors may be used.

Examples of such polymerization inhibitors include phenol compounds, such as p-methoxyphenol, cresol, t-butylcatechol, 3.5-di-t-butyl-4-hydroxytoluene, 2.2'-methylenebis(4-methyl-6-t-butylphenol), 2.2'-methylenebis(4-ethyl-6-t-butylphenol), 4.4'-thiobis(3-methyl-6-t-butylphenol), 4-methoxy-1-naphthol, and 4,4'-dialkoxy-2,2'-bi-1-naphthol; quinone compounds, such as hydroquinone, methylhydroquinone, tert-butylhydroquinone, p-benzoquinone, methyl-p-benzoquinone, tert-butyl-p-benzoquinone, 2,5-diphenylbenzoquinone, 2-hydroxy-1,4-naphthoquinone, 1,4-naphthoquinone, 2,3-dichloro-1,4-naphthoquinone, anthraquinone, and diphenoquinone; amine compounds, such as p-phenylenediamine, 4-aminodiphenylamine, N.N'-diphenyl-p-phenylenediamine, N-i-propyl-N'-phenyl-p-phenylenediamine, N-(1.3-dimethylbutyl)-N'-phenyl-p-phenylenediamine, N.N'-di-2-naphthyl-p-phenylenediamine, diphenylamine, N-phenyl-β-naphthylamine, 4.4'-dicumyldiphenylamine, and 4.4'-dioctyl-diphenylamine; thioether compounds, such as phenothiazine and distearyl thiodipropionate; and nitroso compounds, such as N-nitrosodiphenylamine, N-nitrosophenylnaphthylamine, N-nitrosodinaphthylamine, p-nitrosophenol, nitrosobenzene, p-nitrosodiphenylamine, α-nitroso-β-naphthol, and the like, N,N-dimethyl p-nitrosoaniline, p-nitrosodiphenylamine, p-nitrosodimethylamine, p-nitroso-N,N-diethylamine, N-nitrosoethanolamine, N-nitrosodi-n-butylamine, N-nitroso-N-n-butyl-4-butanolamine, N-nitroso-diisopropanolamine, N-nitroso-N-ethyl-4-butanolamine, 5-nitroso-8-hydroxyquinoline, N-nitrosomorpholine, an N-nitroso-N-phenylhydroxylamine ammonium salt, nitrosobenzene, 2,4,6-tri-tert-butylnitrosobenzene, N-nitroso-N-methyl-p-toluenesulfonamide, N-nitroso-N-ethylurethane, N-nitroso-N-n-propylurethane, 1-nitroso-2-naphthol, 2-nitroso-1-naphthol, sodium 1-nitroso-2-naphthol-3,6-sulfonate, sodium 2-nitroso-1-naphthol-4-sulfonate, 2-nitroso-5-methylaminophenol hydrochloride, and 2-nitroso-5-methylaminophenol hydrochloride.

The amount of the polymerization inhibitor is preferably 0.01 to 2.0 parts by mass and is more preferably 0.05 to 1.0 parts by mass relative to 100 parts by mass of the total amount of polymerizable compounds included in the polymerizable composition.

(Antioxidant) The polymerizable composition according to the present invention may include an antioxidant and the like as needed. Examples of such compounds include a hydroquinone derivative, a nitrosoamine polymerization inhibitor, and a hindered phenol antioxidant. Specific examples thereof include tert-butyl hydroquinone, "Q-1300" and "Q-1301" produced by Wako Pure Chemical Industries, Ltd.; pentaerythritol tetrakis[3-(3,5-di-tert-butyl-4-hydroxyphenyl)propionate "IRGANOX 1010", thiodiethylene bis[3-(3,5-di-tert-butyl-4-hydroxyphenyl)propionate "IRGANOX 1035", octadecyl-3-(3,5-di-tert-butyl-4-hydroxyphenyl)propionate "IRGANOX 1076", "IRGANOX 1135", "IRGANOX 1330", 4,6-bis(octylthiomethyl)-o-cresol "IRGANOX 1520L", "IRGANOX 1726", "IRGANOX 245", "IRGANOX 259", "IRGANOX 3114", "IRGANOX 3790", "IRGANOX 5057", and "IRGANOX 565" (produced by BASF SE); ADK STAB AO-20, AO-30, AO-40, AO-50, AO-60, and AO-80 produced by ADEKA CORPORATION; and SUMILIZER BHT, SUMILIZER BBM-S, and SUMILIZER GA-80 produced by Sumitomo Chemical Co., Ltd.

The amount of the antioxidant is preferably 0.01 to 2.0 parts by mass and is more preferably 0.05 to 1.0 parts by mass relative to 100 parts by mass of the total amount of polymerizable compounds included in the polymerizable composition.

(Ultraviolet Absorber)

The polymerizable composition according to the present invention may include an ultraviolet absorber and a light stabilizer as needed. The ultraviolet absorber and the light stabilizer are not limited but preferably capable of enhancing the lightfastness of an optically anisotropic body, an optical film, and the like.

Examples of the ultraviolet absorber include 2-(2-hydroxy-5-t-butylphenyl)-2H-benzotriazole "TINUVIN PS", "TINUVIN 99-2", "TINUVIN 109", "TINUVIN 213", "TINUVIN 234", "TINUVIN 326", "TINUVIN 328", "TINUVIN 329", "TINUVIN 384-2", "TINUVIN 571", 2-(2H-benzotriazol-2-yl)-4,6-bis(1-methyl-1-phenylethyl) phenol "TINUVIN 900", 2-(2H-benzotriazol-2-yl)-6-(1-methyl-1-phenylethyl)-4-(1,1,3,3-tetramethylbutyl)phenol "TINUVIN 928", "TINUVIN 1130", "TINUVIN 400", "TINUVIN 405", 2,4-bis[2-hydroxy-4-butoxyphenyl]-6-(2, 4-dibutoxyphenyl)-1,3,5-triazine "TINUVIN 460", "TINUVIN 479", and "TINUVIN 5236" (produced by BASF SE); and "ADK STAB LA-32", "ADK STAB LA-34", "ADK STAB LA-36", "ADK STAB LA-31", "ADK STAB 1413", and "ADK STAB LA-51" (produced by ADEKA CORPORATION).

Examples of the light stabilizer include "TINUVIN 111 FDL", "TINUVIN 123", "TINUVIN 144", "TINUVIN 152", "TINUVIN 292", "TINUVIN 622", "TINUVIN 770", "TINUVIN 765", "TINUVIN 780", "TINUVIN 905", "TINUVIN 5100", "TINUVIN 5050", "TINUVIN 5060", "TINUVIN 5151", "CHIMASSORB 119FL", "CHIMASSORB 944FL", and "CHIMASSORB 944LD" (produced by BASF SE); and "ADK STAB LA-52", "ADK STAB LA-57", "ADK STAB LA-62", "ADK STAB LA-67", "ADK STAB LA-63P", "ADK STAB LA-68LD", "ADK STAB LA-77", "ADK STAB LA-82", and "ADK STAB LA-87" (produced by ADEKA CORPORATION).

(Leveling Agent)

The polymerizable composition according to the present invention may include a leveling agent as needed. The leveling agent is not limited but preferably capable of reducing inconsistencies in the thickness of a thin film, such as an optically anisotropic body or an optical film. Examples of the leveling agent include an alkyl carboxylate, an alkyl phosphate, an alkyl sulfonate, a fluoroalkyl carboxylate, a fluoroalkyl phosphate, a fluoroalkyl sulfonate, a polyoxyethylene derivative, a fluoroalkyl ethylene oxide derivative, a polyethylene glycol derivative, an alkyl ammonium salt, and a fluoroalkyl ammonium salt.

Specific examples thereof include "MEGAFACE F-114", "MEGAFACE F-251", "MEGAFACE F-281", "MEGAFACE F-410", "MEGAFACE F-430", "MEGAFACE F-444", "MEGAFACE F-472SF", "MEGAFACE F-477", "MEGAFACE F-510", "MEGAFACE F-511", "MEGAFACE F-552", "MEGAFACE F-553", "MEGAFACE F-554", "MEGAFACE F-555", "MEGAFACE F-556", "MEGAFACE F-557", "MEGAFACE F-558", "MEGAFACE F-559", "MEGAFACE F-560", "MEGAFACE F-561", "MEGAFACE F-562", "MEGAFACE F-563", "MEGAFACE F-565", "MEGAFACE F-567", "MEGAFACE F-568", "MEGAFACE F-569", "MEGAFACE F-570", "MEGAFACE F-571", "MEGAFACE R-40", "MEGAFACE R-41", "MEGAFACE R-43", "MEGAFACE R-94", "MEGAFACE RS-72-K", "MEGAFACE RS-75", "MEGAFACE RS-76-E", "MEGAFACE RS-76-NS", "MEGAFACE RS-90", "MEGAFACE EXP.TF-1367", "MEGAFACE EXP.TF1437", "MEGAFACE EXP.TF1537", "MEGAFACE EXP.TF-2066", and "MEGAFACE DS-21" (produced by DIG Corporation);

"FTERGENT 100", "FTERGENT 100C", "FTERGENT 110", "FTERGENT 150", "FTERGENT 150CH", "FTERGENT 100A-K", "FTERGENT 300", "FTERGENT 310", "FTERGENT 320", "FTERGENT 400SW", "FTERGENT 251", "FTERGENT 215M", "FTERGENT 212M", "FTERGENT 215M", "FTERGENT 250", "FTERGENT 222F", "FTERGENT 212D", "FTX-218", "FTERGENT 209F", "FTERGENT 245F", "FTERGENT 208G", "FTERGENT 240G", "FTERGENT 2122", "FTERGENT 220P", "FTERGENT 2282", "DFX-18", "FTERGENT 601AD", "FTERGENT 602A", "FTERGENT 650A", "FTERGENT 750FM", "FTX-730FM", "FTERGENT 730FL", "FTERGENT 710FS", "FTERGENT 710FM", "FTERGENT 710FL", "FTERGENT 750LL", "FTX-730LS", and "FTERGENT 730LM" (produced by NEOS COMPANY LIMITED);

"BYK-300", "BYK-302", "BYK-306", "BYK-307", "BYK-310", "BYK-315", "BYK-320", "BYK-322", "BYK-323", "BYK-325", "BYK-330", "BYK-331", "BYK-333", "BYK-337", "BYK-340", "BYK-344", "BYK-370", "BYK-375", "BYK-377", "BYK-350", "BYK-352", "BYK-354", "BYK-355", "BYK-356", "BYK-358N", "BYK-361N", "BYK-357", "BYK-390", "BYK-392", "BYK-UV3500", "BYK-UV3510", "BYK-UV3570", and "BYK-Silclean3700" (produced by BYK);

"TEGO Rad2100", "TEGO Rad2011", "TEGO Rad2200N", "TEGO Rad2250", "TEGO Rad2300", "TEGO Rad2500", "TEGO Rad2600", "TEGO Rad2650", "TEGO Rad2700", "TEGO Flow300", "TEGO Flow370", "TEGO Flow425", "TEGO Flow ATF2", "TEGO Flow ZFS460", "TEGO Glide100", "TEGO Glide110", "TEGO Glide130", "TEGO Glide410", "TEGO Glide411", "TEGO Glide415", "TEGO Glide432", "TEGO Glide440", "TEGO Glide450", "TEGO Glide482", "TEGO Glide A115", "TEGO Glide B1484", "TEGO Glide ZG400", "TEGO Twin4000", "TEGO Twin4100", "TEGO Twin4200", "TEGO Wet240", "TEGO Wet250", "TEGO Wet260", "TEGO Wet265", "TEGO Wet270", "TEGO Wet280", "TEGO Wet500", "TEGO Wet505", "TEGO Wet510", "TEGO Wet520", and "TEGO Wet KL245" (produced by Evonik Industries AG); "FC-4430" and "FC-4432" (produced by 3M Japan Limited.); "UNIDYNE NS" (produced by Daikin Industries, Ltd.); "SURFLON S-241", "SURFLON S-242", "SURFLON S-243", "SURFLON S-420", "SURFLON S-611", "SURFLON S-651", and "SURFLON S-386" (produced by AGC Seimi Chemical Co., Ltd.); "DISPARLON OX-880EF", "DISPARLON OX-881", "DISPARLON OX-883", "DISPARLON OX-77EF", "DISPARLON OX-710", "DISPARLON 1922", "DISPARLON 1927", "DISPARLON 1958", "DISPARLON P-410EF", "DISPARLON P-420", "DISPARLON P-425", "DISPARLON PD-7", "DISPARLON 1970", "DISPARLON 230", "DISPARLON LF-1980", "DISPARLON LF-1982", "DISPARLON LF-1983", "DISPARLON LF-1084", "DISPARLON LF-1985", "DISPARLON LHP-90", "DISPARLON LHP-91", "DISPARLON LHP-95", "DISPARLON LHP-96", "DISPARLON OX-715", "DISPARLON 1930N", "DISPARLON 1931", "DISPARLON 1933", "DISPARLON 1934", "DISPARLON 1711EF", "DISPARLON 1751N", "DISPARLON 1761", "DISPARLON LS-009", "DISPARLON LS-001", and "DISPARLON LS-050" (produced by Kusumoto Chemicals, Ltd.); "PF-151N", "PF-636", "PF-6320", "PF-656", "PF-6520", "PF-652-NF", and "PF-3320" (produced by OMNOVA Solutions Inc.); "POLYFLOW No. 7", "POLYFLOW No. 50E", "POLYFLOW No. 50EHF", "POLYFLOW No. 54N", "POLYFLOW No. 75", "POLYFLOW No. 77", "POLYFLOW No. 85", "POLYFLOW No. 85HF", "POLYFLOW No. 90", "POLYFLOW No. 90D-50", "POLYFLOW No. 95", "POLYFLOW No. 99C", "POLYFLOW KL-400K", "POLYFLOW KL-400HF", "POLYFLOW KL-401", "POLYFLOW KL-402", "POLYFLOW KL-403", "POLYFLOW KL-404", "POLYFLOW KL-100", "POLYFLOW LE-604", "POLYFLOW KL-700", "FLOWLEN AC-300", "FLOWLEN AC-303", "FLOWLEN AC-324", "FLOWLEN AC-326F", "FLOWLEN AC-530", "FLOWLEN AC-903", "FLOWLEN AC-903HF", "FLOWLEN AC-1160", "FLOWLEN AC-1190", "FLOWLEN AC-2000", "FLOWLEN AC-2300C", "FLOWLEN AO-82", "FLOWLEN AO-98", and "FLOWLEN AO-108" (produced by KYOEISHA CHEMICAL Co., LTD.); and "L-7001", "L-7002", "8032ADDITIVE", "57ADDTIVE", "L-7064", "FZ-2110", "FZ-2105", "67ADDTIVE", and "8616ADDTIVE" (produced by Dow Corning Toray Silicone Co., Ltd.).

The amount of the leveling agent is preferably 0.01 to 2.0 parts by mass and is more preferably 0.05 to 0.5 parts by mass relative to 100 parts by mass of the total amount of polymerizable compounds included in the polymerizable composition.

The above leveling agents may effectively reduce the tilt angle at air interface in the case where an optically anisotropic body is produced using the polymerizable composition according to the present invention.

(Alignment Control Agent)

The polymerizable composition according to the present invention may include an alignment control agent in order to control the alignment of the liquid crystalline compounds. Examples of the alignment control agent include an alignment control agent that enables the liquid crystalline compounds to be aligned substantially horizontally, vertically, or in a hybrid manner, with respect to the substrate and an alignment control agent that provides planar alignment in the case where a chiral compound is used. While some surfactants may induce horizontal alignment or planar alignment as described above, the alignment control agent is not limited and any publicly known and commonly used alignment control agent that induces intended alignment may be used.

An example of such an alignment control agent is a compound that includes a repeating unit represented by General Formula (8) below and has a weight-average molecular weight of 100 or more and 1000000 or less, the compound being capable of effectively reducing the tilt angle at air interface in the case where an optically anisotropic body is produced using the polymerizable composition:

[Chem. 123]

 (8)

(in General Formula (8), $R^{11}$, $R^{12}$, $R^{13}$, and $R^{14}$ each independently represent a hydrogen atom, a halogen atom, or a hydrocarbon group having 1 to 20 carbon atoms, and a hydrogen atom included in the hydrocarbon group may be replaced with one or more halogen atoms).

Other examples of such an alignment control agent include rod-like and disc-like liquid crystalline compounds modified with a fluoroalkyl group; and a polymerizable compound that includes a long-chain aliphatic alkyl group that may have a branched structure.

Examples of an alignment control agent capable of effectively increasing the tilt angle at air interface in the case where an optically anisotropic body is produced using the polymerizable composition include cellulose nitrate; cellulose acetate; cellulose propionate; cellulose butyrate; a rod-like liquid crystalline compound modified with a heteroaromatic ring salt; and a rod-like liquid crystalline compound modified with a cyano group or a cyanoalkyl group.

(Chain-Transfer Agent)

The polymerizable composition according to the present invention may include a chain-transfer agent in order to enhance the adhesion of the polymer or optically anisotropic body to the substrate. Examples of the chain-transfer agent include aromatic hydrocarbons; halogenated hydrocarbons, such as chloroform, carbon tetrachloride, carbon tetrabromide, and bromotrichloromethane;

mercaptan compounds, such as octyl mercaptan, n-butyl mercaptan, n-pentyl mercaptan, n-hexadecyl mercaptan, n-tetradecyl mercaptan, n-dodecyl mercaptan, t-tetradecyl mercaptan, and t-dodecyl mercaptan; thiol compounds, such as hexanedithiol, decanedithiol, 1,4-butanediol bisthiopropionate, 1,4-butanediol bisthioglycolate, ethylene glycol bisthioglycolate, ethylene glycol bisthiopropionate, trimethylolpropane tristhioglycolate, trimethylolpropane tristhiopropionate, trimethylolpropane tris(3-mercaptobutyrate), pentaerythritol tetrakisthioglycolate, pentaerythritol tetrakisthiopropionate, trimercaptopropionic acid tris(2-hydroxyethyl)isocyanurate, 1,4-dimethylmercaptobenzene, 2,4,6-trimercapto-s-triazine, and 2-(N,N-dibutylamino)-4,6-dimercapto-s-triazine; sulfide compounds, such as dimethyl xanthogen disulfide, diethyl xanthogen disulfide, diisopropyl xanthogen disulfide, tetramethylthiuram disulfide, tetraethylthiuram disulfide, and tetrabutylthiuram disulfide; and N,N-dimethylaniline, N,N-divinylaniline, pentaphenylethane, α-methylstyrene dimer, acrolein, allyl alcohol, terpynoren, α-terpinene, γ-terpinene, and dipentene. Among these, 2,4-diphenyl-4-methyl-1-pentene and the thiol compounds are more preferable.

Specifically, the compounds represented by General Formulae (9-1) to (9-12) below are preferable.

[Chem. 124]

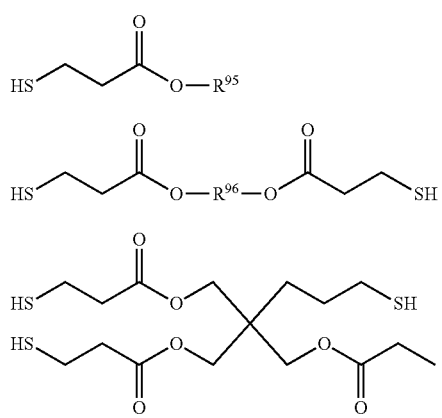

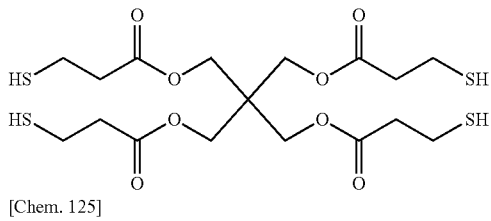

(9-7)

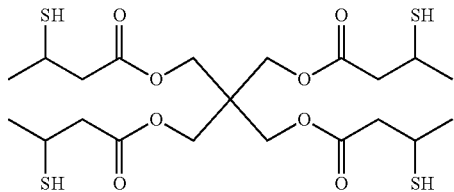

(9-8)

[Chem. 125]

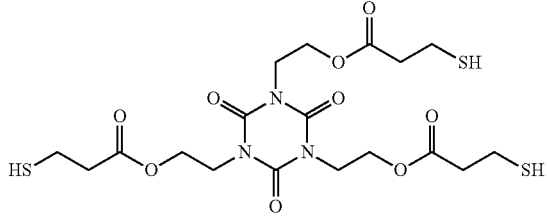

(9-9)

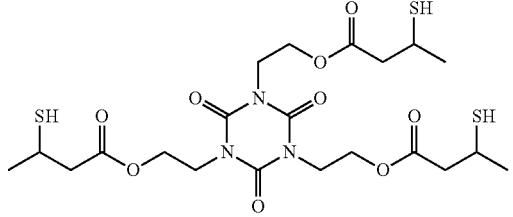

(9-10)

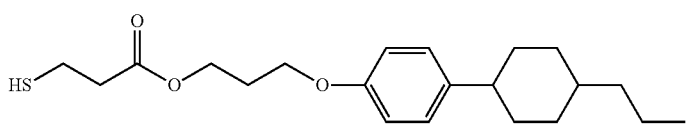

(9-11)

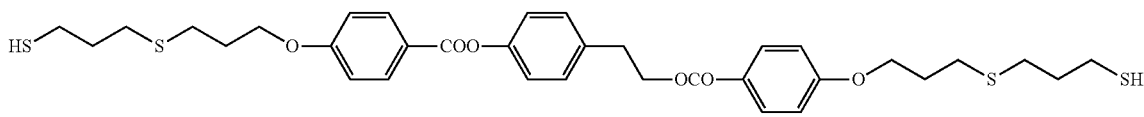

(9-12)

In General Formulae (9-1) to (9-12), $R^{95}$ represents an alkyl group having 2 to 18 carbon atoms, the alkyl group may be linear or branched, and, in the alkyl groups, one or more methylene groups may be replaced with an oxygen atom, a sulfur atom, —CO—, —OCO—, —COO—, or —CH=CH— such that any two oxygen or sulfur atoms do not directly bind to each other; $R^{96}$ represents an alkylene group having 2 to 18 carbon atoms, and one or more methylene groups included in the alkylene group may be replaced with an oxygen atom, a sulfur atom, —CO—, —OCO—, —COO—, or —CH=CH— such that any two oxygen or sulfur atoms do not directly bind to each other.

The chain-transfer agent is preferably used in a step in which the polymerizable liquid crystal compounds are mixed with the organic solvent and the resulting mixture is stirred while being heated to form a polymerizable solution. Alternatively, the chain-transfer agent may be used in a subsequent step in which the polymerization initiator is mixed with the polymerizable solution. In another case, the chain-transfer agent may be used in both of the above steps.

The amount of the chain-transfer agent is preferably 0.5 to 10 parts by mass and is more preferably 1.0 to 5.0 parts by mass relative to 100 parts by mass of the total amount of polymerizable compounds included in the polymerizable composition.

Furthermore, a nonpolymerizable liquid crystal compound and the like may be used as needed in order to adjust physical properties. A polymerizable compound that does not have a liquid crystal property is preferably used in a step in which the polymerizable compounds are mixed with the organic solvent and the resulting mixture is stirred while being heated to form a polymerizable solution. Alternatively, the nonpolymerizable liquid crystal compound and the like may be used in a subsequent step in which the polymerization initiator is mixed with the polymerizable solution. In another case, the nonpolymerizable liquid crystal compound and the like may be used in both of the above steps. The amount of the above compounds are preferably 20 parts by mass or less, is more preferably 10 parts by mass or less, and is further preferably 5 parts by mass or less relative to 100 parts by mass of the total amount of polymerizable compounds included in the polymerizable composition.

(Infrared Absorber)

The polymerizable composition according to the present invention may include an infrared absorber as needed. The infrared absorber is not limited; publicly known and commonly used infrared absorbers may be used in an amount with which alignment does not become degraded.

Examples of the infrared absorber include a cyanine compound, a phthalocyanine compound, a naphthoquinone compound, a dithiol compound, a diimmonium compound, an azo compounds, and an aluminum salt.

Specific examples thereof include diimmonium salt-type "NIR-IM1" and aluminum salt-type "NIR-AM1" (produced by Nagase ChemteX Corporation); "Karenz IR-T" and "Karenz IR-13F" (produced by Showa Denko K.K.); "YKR-2200" and "YKR-2100" (produced by Yamamoto Chemicals, Inc.); and "IRA908", "IRA931", "IRA955", and "IRA1034" (produced by INDECO).

(Antistatic Agent)

The polymerizable composition according to the present invention may include an antistatic agent as needed. The antistatic agent is not limited; publicly known and commonly used antistatic agents may be used in an amount with which alignment does not become degraded.

Examples of such antistatic agents include a high-molecular compound that includes at least one sulfonate or phosphate group in the molecule; a compound that includes a quaternary ammonium salt; and a surfactant that includes a polymerizable group.

Among these, a surfactant that includes a polymerizable group is preferable. Examples of the surfactant that includes a polymerizable group include the following anionic surfactants: alkyl ether surfactants, such as "Antox SAD" and "Antox MS-2N" (produced by NIPPON NYUKAZAI CO., LTD.), "Aqualon KH-05", "Aqualon KH-10", "Aqualon KH-20", "Aqualon KH-0530", and "Aqualon KH-1025" (produced by DKS Co. Ltd.), "ADEKA REASOAP SR-10N" and "ADEKA REASOAP SR-20N" (produced by ADEKA CORPORATION), and "LATEMUL PD-104" (produced by Kao Corporation); sulfosuccinic acid ester surfactants, such as "LATEMUL S-120", "LATEMUL S-120A", "LATEMUL S-180P", and "LATEMUL S-180A" (produced by Kao Corporation), and "ELEMINOL JS-2" (produced by Sanyo Chemical Industries, Ltd.); alkyl phenyl ether and alkyl phenyl ester surfactants, such as "Aqualon H-2855A", "Aqualon H-3855B", "Aqualon H-3855C", "Aqualon H-3856", "Aqualon HS-05", "Aqualon HS-10", "Aqualon HS-20", "Aqualon HS-30", "Aqualon HS-1025", "Aqualon BC-05", "Aqualon BC-10", "Aqualon BC-20", "Aqualon BC-1025", and "Aqualon BC-2020" (produced by DKS Co. Ltd.), and "ADEKA REASOAP SDX-222", "ADEKA REASOAP SDX-223", "ADEKA REASOAP SDX-232", "ADEKA REASOAP SDX-233", "ADEKA REASOAP SDX-259", "ADEKA REASOAP SE-10N", and "ADEKA REASOAP SE-20N" (produced by ADEKA CORPORATION); (meth)acrylate sulfuric acid ester surfactants, such as "Antox MS-60" and "Antox MS-2N" (produced by NIPPON NYUKAZAI CO., LTD.) and "ELEMINOL RS-30" (produced by Sanyo Chemical Industries, Ltd.); and phosphoric acid ester surfactants, such as "H-3330P" (produced by DKS Co. Ltd.) and "ADEKA REASOAP PP-70" (produced by ADEKA CORPORATION).

Examples of the surfactant that includes a polymerizable group also include the following nonionic surfactants: alkyl ether surfactants, such as "Antox LMA-20", "Antox LMA-27", "Antox EMH-20", "Antox LMH-20, and "Antox SMH-20" (produced by NIPPON NYUKAZAI CO., LTD.), "ADEKA REASOAP ER-10", "ADEKA REASOAP ER-20", "ADEKA REASOAP ER-30", and "ADEKA REASOAP ER-40" (produced by ADEKA CORPORATION), and "LATEMUL PD-420", "LATEMUL PD-430", and "LATEMUL PD-450" (produced by Kao Corporation); alkyl phenyl ether and alkyl phenyl ester surfactants, such as "Aqualon RN-10", "Aqualon RN-20", "Aqualon RN-30", "Aqualon RN-50", and "Aqualon RN-2025" (produced by DKS Co. Ltd.), and "ADEKA REASOAP NE-10", "ADEKA REASOAP NE-20", "ADEKA REASOAP NE-30", and "ADEKA REASOAP NE-40" (produced by ADEKA CORPORATION); and (meth)acrylate sulfuric acid ester surfactants, such as "RMA-564", "RMA-568", and "RMA-1114" (produced by NIPPON NYUKAZAI CO., LTD.).

Other examples of the antistatic agent include polyethylene glycol (meth)acrylate, methoxypolyethylene glycol (meth)acrylate, ethoxypolyethylene glycol (meth)acrylate, propoxypolyethylene glycol (meth)acrylate, n-butoxypolyethylene glycol (meth)acrylate, n-pentaxypolyethylene glycol (meth)acrylate, phenoxypolyethylene glycol (meth)acrylate, polypropylene glycol (meth)acrylate, methoxypolypropylene glycol (meth)acrylate, ethoxypolypropylene glycol (meth)acrylate, propoxypolypropylene glycol (meth)acrylate, n-butoxypolypropylene glycol (meth)acrylate, n-pentaxypolypropylene glycol (meth)acrylate, phenoxypolypropylene glycol (meth)acrylate, polytetramethylene glycol (meth)acrylate, methoxy polytetramethylene glycol (meth)acrylate, phenoxy tetraethylene glycol (meth)acrylate, hexaethylene glycol (meth)acrylate, and methoxy hexaethylene glycol (meth)acrylate.

The above antistatic agents may be used alone or in combination of two or more. The amount of the antistatic agent is preferably 0.001 to 10 parts by weight and is more preferably 0.01 to 5 parts by weight relative to 100 parts by mass of the total amount of polymerizable compounds included in the polymerizable composition.

(Colorant)

The polymerizable composition according to the present invention may include a colorant as needed. The colorant is not limited; publicly known and commonly used colorants may be used in an amount with which alignment does not become degraded.

Examples of the colorant include dichroic dyes and fluorescent colorants. Examples of such colorants include polyazo colorants, anthraquinone colorants, cyanine colorants, phthalocyanine colorants, perylene colorants, perinone colorants, and squarylium colorants. The colorant preferably has a liquid crystal property in consideration of addition.

Examples of the colorant include the colorants described in the following documents: U.S. Pat. No. 2,400,877, Dreyer J. F., Phys. and Colloid Chem., 1948, 52, 808., "The Fixing of MolecularOrientation", Dreyer J. F., Journal de Physique, 1969, 4, 114., "LightPolarization from Films of Lyotropic Nematic Liquid Crystals", and J. Lydon, "Chromonics" in "Handbook of Liquid Crystals Vol. 2B: Low Molecular-Weight Liquid Crystals II", D. Demus, J. Goodby, G. W. Gray, H. W. Spiessm, V. Vill ed, Willey-VCH, P.981-1007 (1998), Dichroic Dyes for Liquid Crystal Display A. V. Ivashchenko CRC Press, 1994, and "Kinousei Shikiso Shijyo no Shin-Tenkai (New Development of Functional Colorants Market)", Chapter 1, p. 1, 1994, CMC Corporation.

Examples of the dichroic dye include Formulae (d-1) to (d-9) below.

[Chem. 126]
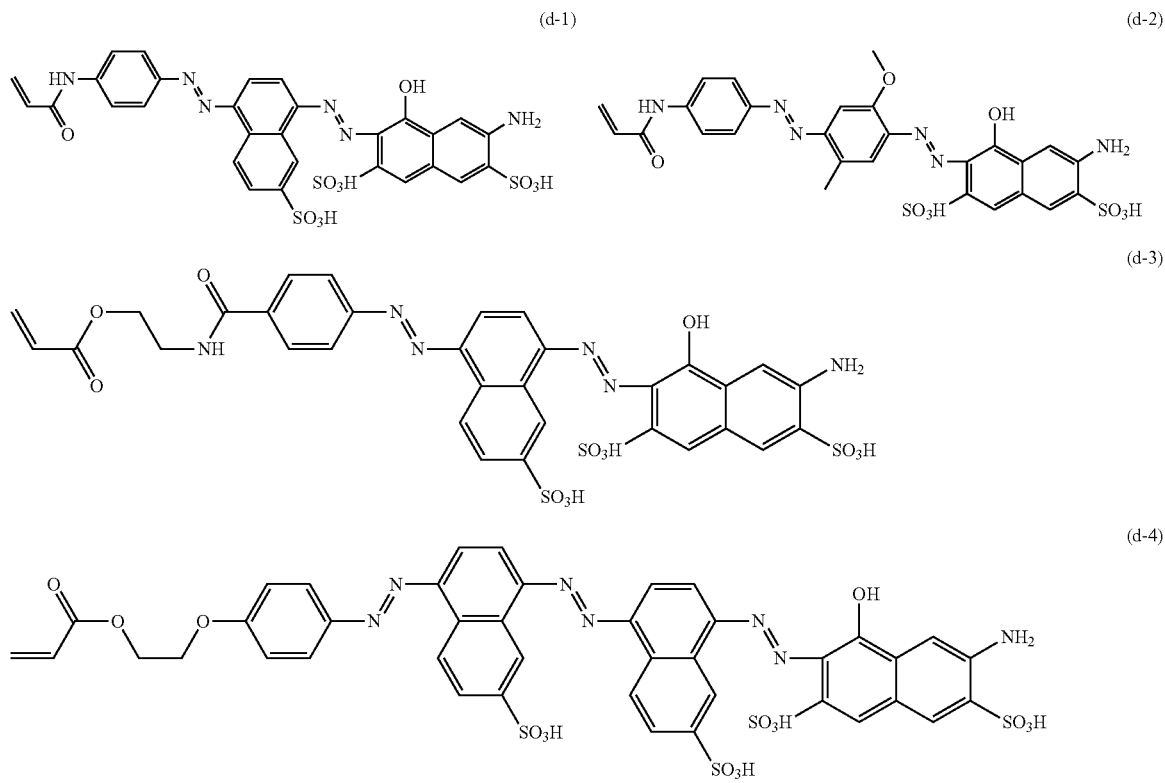
[Chem. 127]
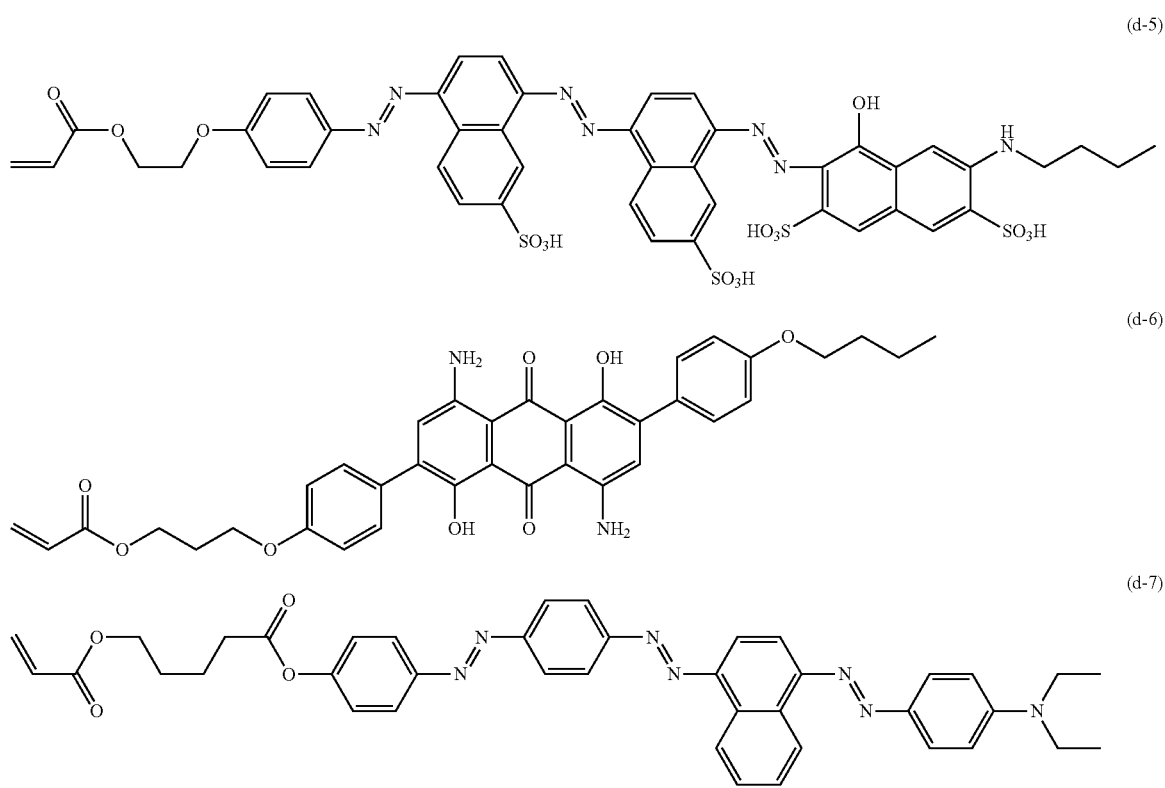

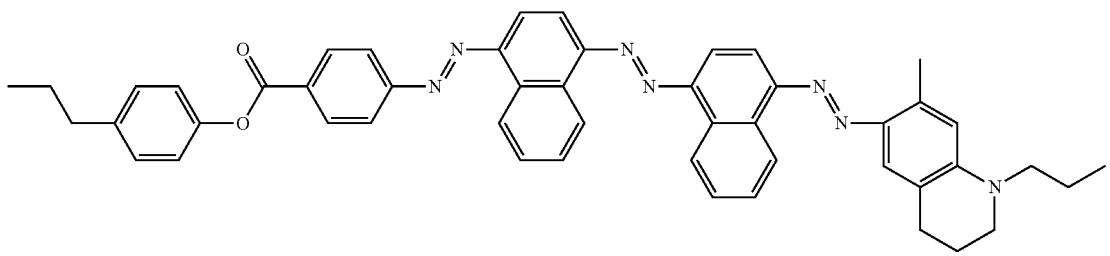

(d-8)

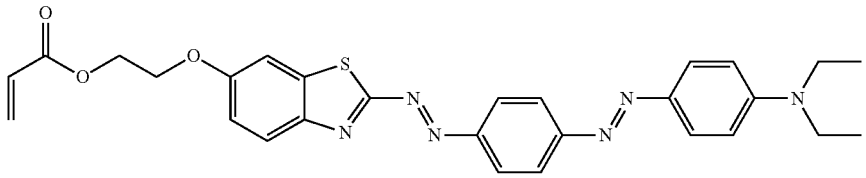

(d-9)

The amount of the colorant, such as the above dichroic dye, is preferably 0.001 to 20 parts by weight and is more preferably 0.01 to 10 parts by weight relative to 100 parts by mass of the total amount of polymerizable compounds included in the polymerizable composition.

(Filler)

The polymerizable composition according to the present invention may include a filler as needed. The filler is not limited; publicly known and commonly used fillers may be used in an amount with which the thermal conductivity of the resulting polymer does not become degraded.

Examples of the filler include inorganic fillers, such as alumina, titanium white, aluminum hydroxide, talc, clay, mica, barium titanate, zinc oxide, and glass fibers; metal powders, such as a silver powder and a copper powder; thermally conductive fillers, such as aluminum nitride, boron nitride, silicon nitride, gallium nitride, silicon carbide, magnesia (aluminum oxide), silica, crystalline silica (silicon oxide), fused silica (silicon oxide), graphite, and carbon fibers that include carbon nanofibers; and silver nanoparticles.

Specific examples of the filler include, as alumina, DAM-70, DAM-45, DAM-07, DAM-05, DAW-45, DAW-05, DAW-03, and ASFP-20 (produced by Denki Kagaku Kogyo Kabushiki Kaisha), AL-43-KT, AL-47-H, AL-47-1, AL-160SG-3, AL-43-BE, AS-30, AS-40, AS-50, AS-400, CB-P02, and CB-P05 (produced by Showa Denko K.K.), A31, A31B, A32, A33F, A41A, A43A, MM-22, MM-26, MM-P, MM-23B, LS-110F, LS-130, LS-210, LS-242C, LS-250, and AHP300 (produced by Nippon Light Metal Company, Ltd.), AA-03, AA-04, AA-05, AA-07, AA-2, AA-5, AA-10, and AA-18 (produced by Sumitomo Chemical Co., Ltd.); as titanium white, G-1, G-10, F-2, F-4, and F-6 (produced by Showa Denko K.K.), TAF-520, TAF-500, TAF-1500, TM-1, TA-100C, and TA-100CT (produced by Fuji Titanium Industry Co., Ltd.), MT-01, MT-10EX, MT-05, MT-100S, MT-100TV, MT-100Z, MT-150EX, MT-100AQ, MT-100WP, MT-100SA, MT-100HD, MT-300HD, MT-500SA, MT-600SA, and MT-700HD (produced by TAYCA CORPORATION), TTO-51(A), TTO-51 (C), TTO-55(A), TTO-55(B), TTO-55(C), TTO-55(D), TTO-S-1, TTO-S-2, TTO-S-3, TTO-S-4, MPT-136, and TTO-V-3 (produced by Ishihara Sangyo Kaisha, Ltd.); as aluminum hydroxide, B-309 (produced by TOMOE Engineering Co., Ltd.), BA173, BA103, B703, B1403, BF013, BE033, BX103, and BX043 (produced by Nippon Light Metal Company, Ltd.); as talc, NANO ACE D-1000, NANO ACE D-800, MICRO ACE SG-95, MICRO ACE P-8, and MICRO ACE P-6 (produced by Nippon Talc Co., Ltd.), FH104, FH105, FL108, FG106, MG115, FH104S, and ML112S (produced by FUJI TALC INDUSTRIAL CO., LTD.); as mica, Y-1800, TM-10, A-11, and SJ-005 (produced by YAMAGUCHI MICA CO., LTD.); as barium titanate, BT-H9DX, HF-9, HF-37N, HF-90D, HF-120D, and HT-F (produced by KCM Corporation), BT-100 and HPBT Series (produced by Fuji Titanium Industry Co., Ltd.), BT Series (produced by Sakai Chemical Industry Co., Ltd.), and Pal Serum BT (produced by Nippon Chemical Industrial Co., Ltd.); as zinc oxide, FINEX-30, FINEX-30W-LP2, FINEX-50, FINEX-50S-LP2, and XZ-100F (produced by Sakai Chemical Industry Co., Ltd.), FZO-50 (produced by Ishihara Sangyo Kaisha, Ltd.), and MZ-300, MZ-306X, MZY-505S, MZ-506X, and MZ-510HPSX (produced by TAYCA CORPORATION); as glass fiber, CS6SK-406, CS13C-897, CS3PC-455, and CS3LCP-256 (produced by Nitto Boseki Co., Ltd.), ECS03-615, ECS03-650, EFDE50-01, EFDE50-31 (produced by Central Glass Co., Ltd.), and ACS6H-103 and ACS6S-750 (produced by Nippon Electric Glass Co., Ltd.); as a silver powder, spherical silver powders AG3 and AG4, flake silver powders FA5 and FA2 (produced by DOWA HIGHTECH CO., LTD.), SPQ03R, SPN05N, SPN08S, and Q03R (produced by Mitsui Mining & Smelting Co., Ltd.), AY-6010 and AY-6080 (produced by TANAKA KIKINZOKU KOGYO K. K.), ASP-100 (produced by Aida Chemical Industries Co., Ltd.), and an Ag-coated powder AG/SP (produced by Mitsubishi Materials Electronic Chemicals Co., Ltd.); as copper powder, MA-0015K, MA-002K, and MA-O025K (produced by Mitsui Mining & Smelting Co., Ltd.), electrolytic copper powders #52-C and #6 (produced by JX Nippon Mining & Metals Corp.), 10% Ag-coated Cu-HWQ (produced by Fukuda Metal Foil & Powder Co., Ltd.), copper powders Type-A and Type-B (produced by DOWA Electronics Materials Co., Ltd.), and UCP-030 (produced by Sumitomo Metal Mining Co., Ltd.);

as aluminum nitride, Grade H, Grade E, and Grade H-T (produced by Tokuyama Corporation), TOYAL TecFiller TFS-A05P and TOYAL TecFiller TFZ-A02P (produced by TOYO ALUMINIUM K.K.), ALN020BF, ALN050BF, ALN020AF, ALN050AF, and ALN020SF (produced by TOMOE Engineering Co., Ltd.), and FAN-f05 and FAN-f30 (produced by FURUKAWA DENSHI CO., LTD.); as boron nitride, DENKA BORON NITRIDE SGP, DENKA BORON NITRIDE MGP, DENKA BORON NITRIDE GP, DENKA BORON NITRIDE HGP, DENKA BORON NITRIDE SP-2, and DENKA BORON NITRIDE SGPS (produced by Denki Kagaku Kogyo Kabushiki Kaisha), and UHP-S1, UHP-1K, UHP-2, and UHP-EX (produced by Showa Denko K.K.); as silicon nitride, SN-9, SN-9S, SN-9FWS, SN-F1, and SN-F2 (produced by Denki Kagaku Kogyo Kabushiki Kaisha) and CF0027, CF0093, CF0018, and CF0033 (produced by NIPPON FRIT CO., LTD.); as silicon carbide, Type GMF-H, Type GMF-H2, and TYPE GMF-LC (produced by Pacific Rundum Co., Ltd.) and HSC1200, HSC1000, HSC059, HSC059I, and HSC007 (produced by TOMOE Engineering Co., Ltd.); as silica, SYLYSIA (Fuji Silysia Chemical, Ltd.), AEROSIL R972, AEROSIL R104, AEROSIL R202, AEROSIL 805, AEROSIL R812, and AEROSIL R7200 (produced by Nippon Aerosil Co., Ltd.), and REOSIL Series (produced by Tokuyama Corporation); as crystalline silica (silicon oxide), CMC-12, VX-S, and VX-SR (produced by TATSUMORI LTD.); as fused silica (silicon oxide), FB-3SDC, FB-3SDX, SFP-30M, SFP-20M, SFP-30MHE, SFP-130MC, and UFP-30 (produced by Denki Kagaku Kogyo Kabushiki Kaisha) and EXCELICA Series (produced by Tokuyama Corporation); as aluminum oxide, AEROXIDE Alu C and AEROXIDE Alu 65 (produced by Nippon Aerosil Co., Ltd.); and, as carbon fibers and graphite, TORAYCA MILDFIBER MLD-30 and TORAYCA MILDFIBER MLD-300 (produced by Toray Industries, Inc.), CFMP-30X and CFMP-150X (produced by Nippon Polymer Sangyo Co., Ltd.), XN-100 and HC-600 (produced by Nippon Graphite Fiber Corporation), and SWeNT SG65, SWeNT SGi, IsoNanoTubes-M, IsoNanoTubes-S, PureTubes, Pyrograf PR-25-XT-PS, and PR-25XT-LHT (produced by Sigma-Aldrich).

The above fillers may be used alone or in combination of two or more. The amount of the filler is preferably 0.01 to 80 parts by weight and is more preferably 0.1 to 50 parts by weight relative to 100 parts by mass of the total amount of polymerizable compounds included in the polymerizable composition.

(Chiral Compound)

The polymerizable composition according to the present invention may include a chiral compound in order to form a chiral nematic phase. The chiral compound does not necessarily have a liquid crystal property. The chiral compound may, but does not necessarily, include a polymerizable group. The direction of the helix of the chiral compound may be selected appropriately in accordance with the use of the polymer.

A chiral compound including a polymerizable group is not limited and publicly known and commonly used chiral compounds including a polymerizable group may be used. Chiral compounds having a high helical twisting power (HTP) are preferable. The polymerizable group is preferably a vinyl group, a vinyloxy group, an allyl group, an allyloxy group, an acryloyloxy group, a methacryloyloxy group, a glycidyl group, or an oxetanyl group; and is particularly preferably an acryloyloxy group, a glycidyl group, or an oxetanyl group.

The content of the chiral compound needs to be adjusted appropriately in accordance with the helix-inducing power of the compound. The amount of the chiral compound is preferably 0.5 to 80 parts by mass, is more preferably 3 to 50 parts by mass, and is particularly preferably 5 to 30 parts by mass of the total amount of liquid crystalline compounds and chiral compounds that include a polymerizable group.

Specific examples of the chiral compound include, but are not limited to, the compounds represented by General Formulae (10-1) to (10-4) below.

[Chem.128]

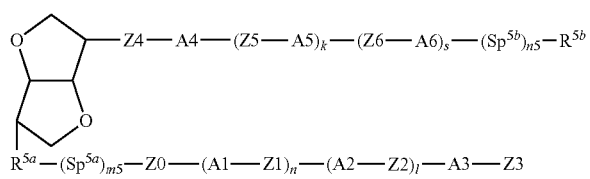

(10-1)

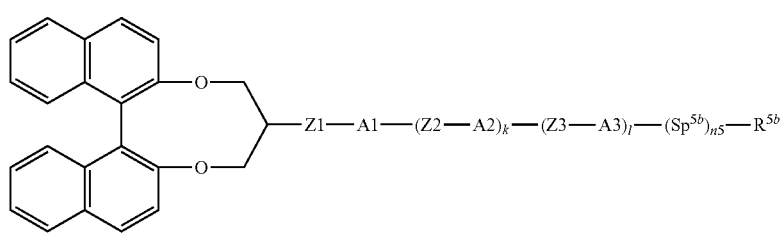

(10-2)

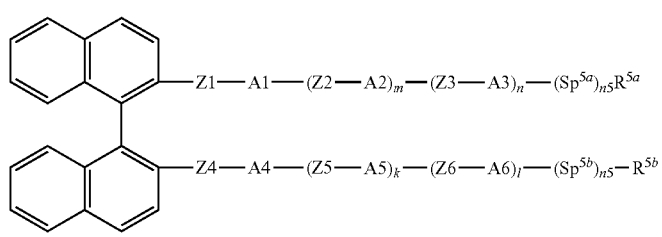

(10-3)

-continued $$R^{5a}-(Sp^{5a})_{m5}-Z0-(A1-Z1)_n-(A2-Z2)_l-A3-Z3-A4-Z4-A5-Z5-CH_2CH(R^{5a})R^{5b} \quad (10\text{-}4)$$

In the General Formulae (10-1) to (10-4) above, $Sp^{5a}$ and $Sp^{5b}$ each independently represent an alkylene group having 0 to 18 carbon atoms, the alkylene group may be substituted with one or more halogen atoms, CN groups, or alkyl groups having 1 to 8 carbon atoms and including a polymerizable functional group, and, in the above groups, one CH₂ group or two or more CH₂ groups that are not adjacent to one another may be each independently replaced with —O—, —S—, —NH—, —N(CH₃)—, —CO—, —COO—, —OCO—, —OCOO—, —SCO—, —COS—, or —C≡C— such that any two oxygen atoms do not directly bind to each other;

A1, A2, A3, A4, A5, and A6 each independently represent a 1,4-phenylene group, a 1,4-cyclohexylene group, a 1,4-cyclohexenyl group, a tetrahydropyran-2,5-diyl group, a 1,3-dioxane-2,5-diyl group, tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a thiophene-2,5-diyl group-, a 1,2,3,4-tetrahydronaphthalene-2,6-diyl group, a 2,6-naphthylene group, a phenanthrene-2,7-diyl group, a 9,10-dihydrophenanthrene-2,7-diyl group, a 1,2,3,4,4a,9,10a-octahydrophenanthrene-2,7-diyl group, a 1,4-naphthylene group, a benzo[1,2-b:4,5-b']dithiophene-2,6-diyl group, a benzo[1,2-b:4,5-b']diselenophene-2,6-diyl group, a [1]benzothieno[3,2-b]thiophene-2,7-diyl group, a [1]benzoselenopheno[3,2-b]selenophene-2,7-diyl group, or a fluorene-2,7-diyl group; n, l, and k each independently represent 0 or 1, where 0 n+l+k≤3;

m5 represents 0 or 1;

Z0, Z1, Z2, Z3, Z4, Z5, and Z6 each independently represent —COO—, —OCO—, —CH₂CH₂—, —OCH₂—, —CH₂O—, —CH=CH—, —C≡C—, —CH=CHCOO—, —OCOCH=CH—, —CH₂CH₂COO—, —CH₂CH₂OCO—, —COOCH₂CH₂—, —OCOCH₂CH₂—, —CONH—, —NHCO—, or an alkyl group that has 2 to 10 carbon atoms and may include a halogen atom, or a single bond;

$R^{5A}$ and $R^{5b}$ represent a hydrogen atom, a halogen atom, a cyano group, or an alkyl group having 1 to 18 carbon atoms, the alkyl group may be substituted with one or more halogen atoms or CN groups, and, in the above groups, one CH₂ group or two or more CH₂ groups that are not adjacent to one another may be each independently replaced with —O—, —S—, —NH—, —N(CH₃)—, —CO—, —COO—, —OCO—, —OCOO—, —SCO—, —COS—, or —C≡C— such that any two oxygen atoms do not directly bind to each other; and, in another case, $R^{5a}$ and $R^{5b}$ may be General Formula (10-a):

[Chem. 129]

$$-P^{5a} \quad (10\text{-}a)$$

(in General Formula (10-a), $P^{5a}$ represents a polymerizable functional group; and $Sp^{5a}$ represents the same thing as $Sp^1$).

$P^{5a}$ represents a substituent group selected from the polymerizable groups represented by Formulae (P-1) to (P-20) below.

[Chem. 130]

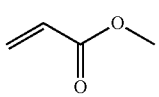 (P-1)

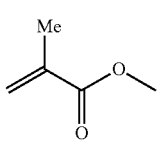 (P-2)

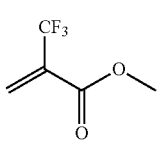 (P-3)

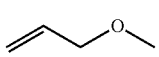 (P-4)

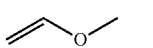 (P-5)

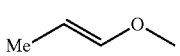 (P-6)

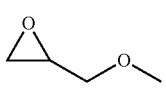 (P-7)

 (P-8)

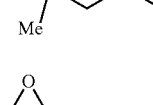 (P-9)

 (P-10)

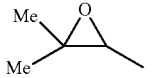 (P-11)

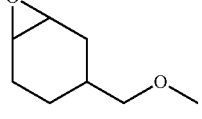 (P-12)

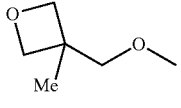 (P-13)

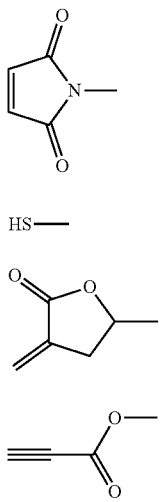
(P-14)
(P-15)
(P-16)
(P-17)
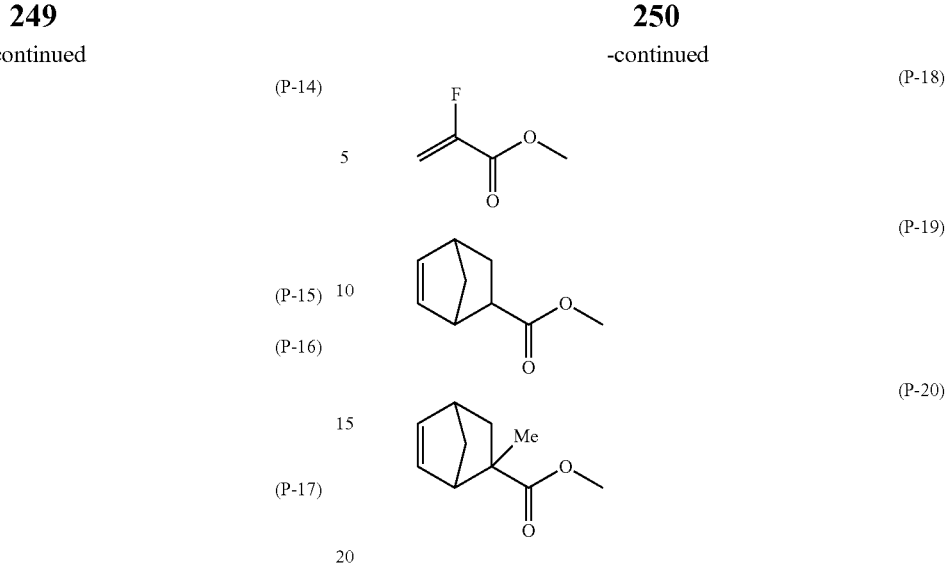
(P-18)
(P-19)
(P-20)
Further specific examples of the above chiral compound include the compounds represented by General Formulae (10-5) to (10-38) below.
[Chem. 131]
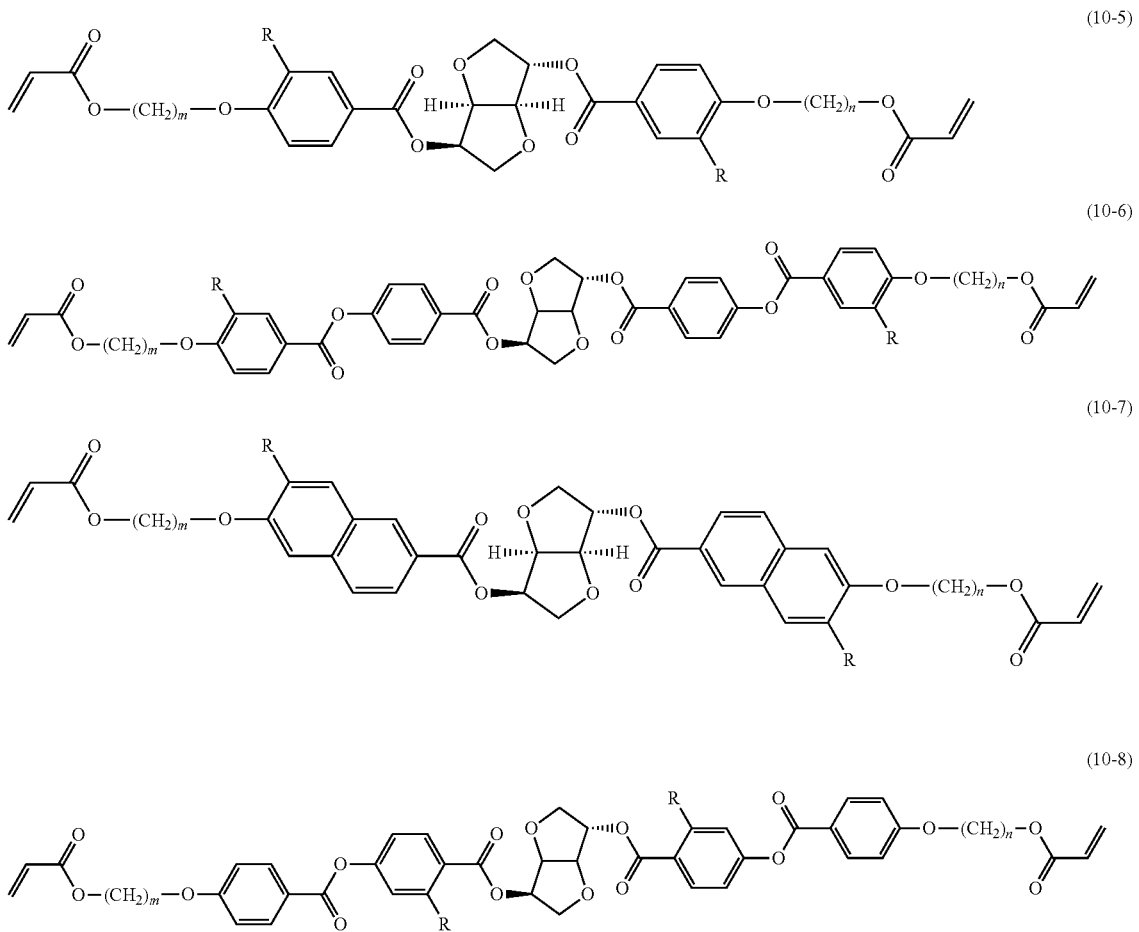
(10-5)
(10-6)
(10-7)
(10-8)

-continued
[Chem. 132]
(10-9)
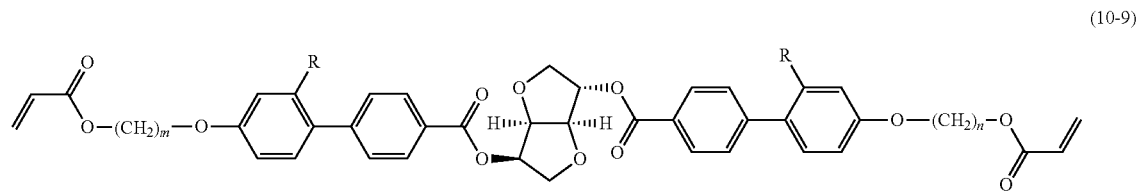
(10-10)
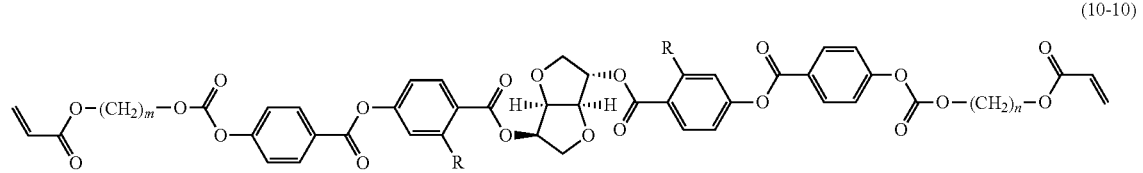
(10-11)
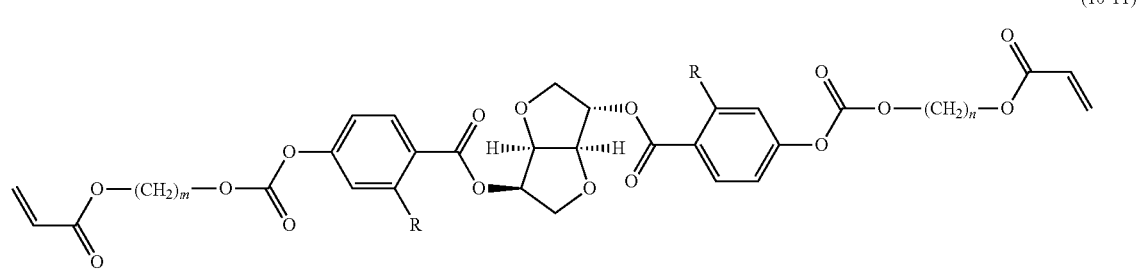
(10-12)
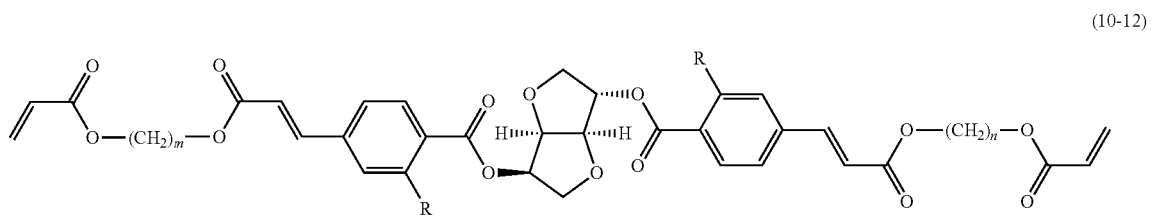
(10-13)
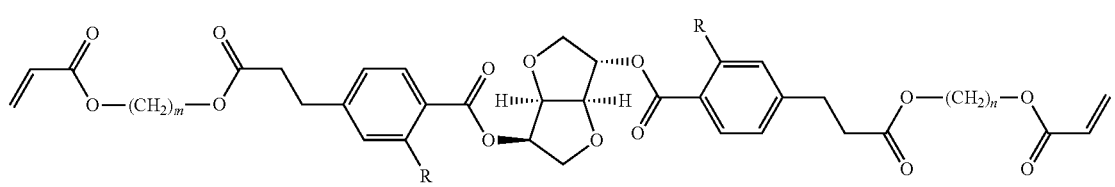
[Chem. 133]
(10-14)
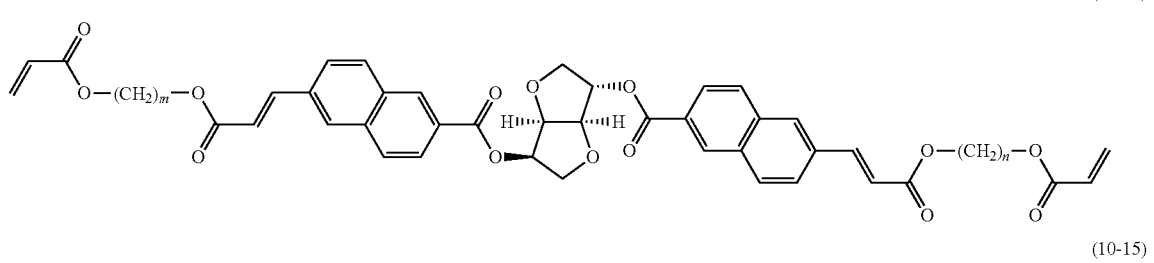
(10-15)
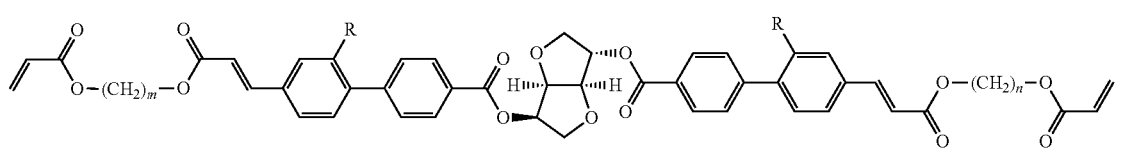

(10-16)
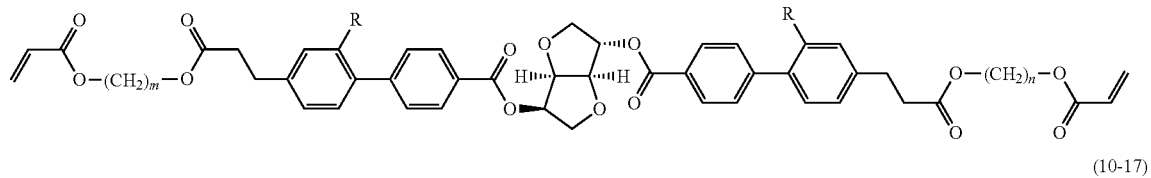
(10-17)
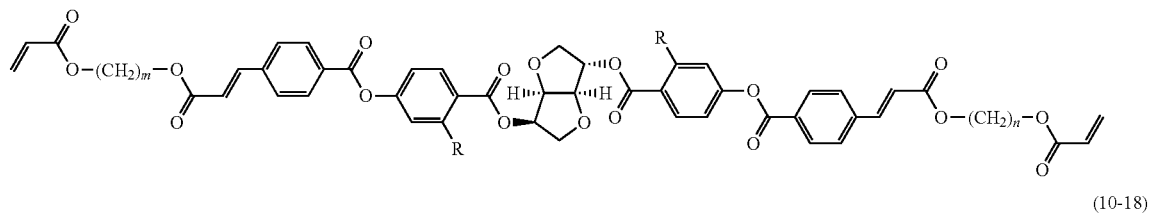
(10-18)
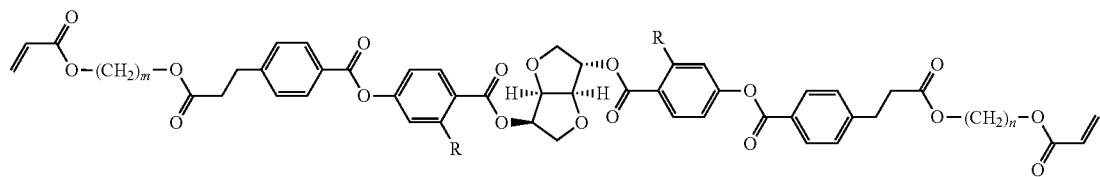
[Chem. 134]
(10-19)
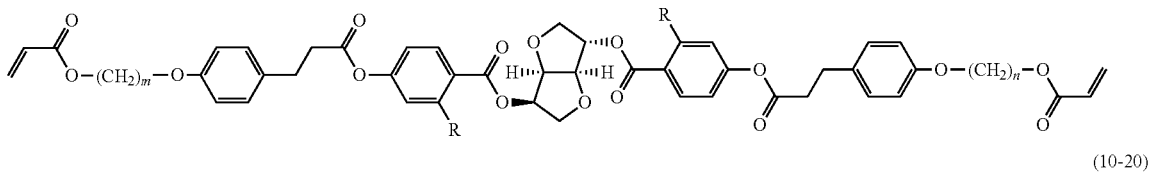
(10-20)
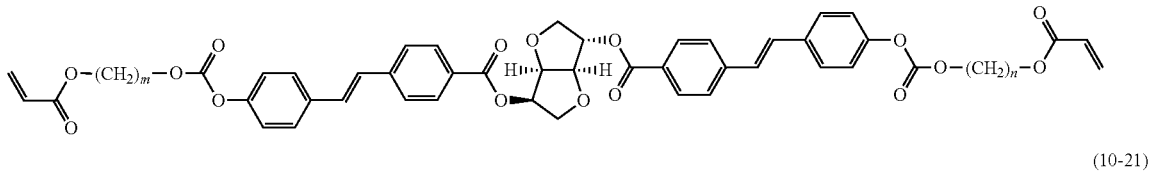
(10-21)
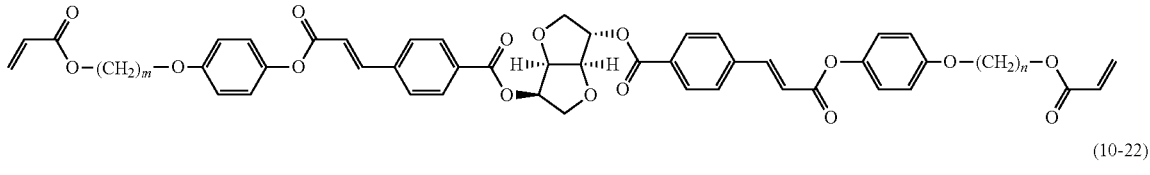
(10-22)
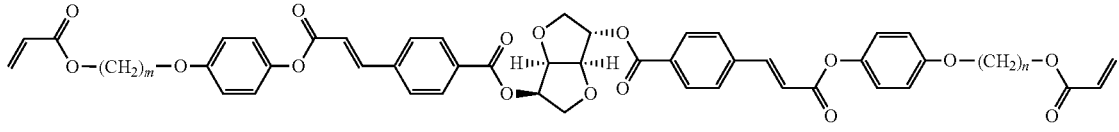
[Chem. 135]
(10-23)
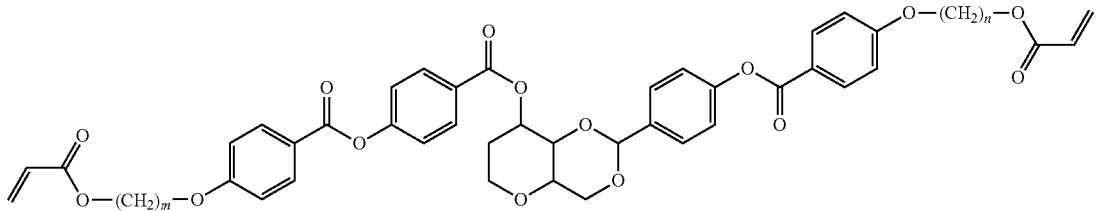

(10-24)
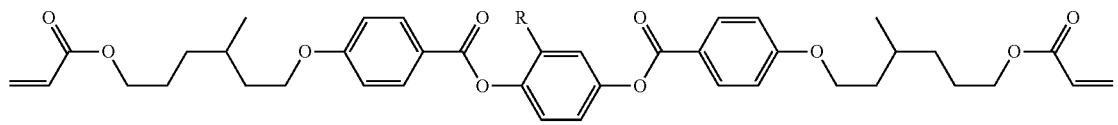
(10-25) (10-26)
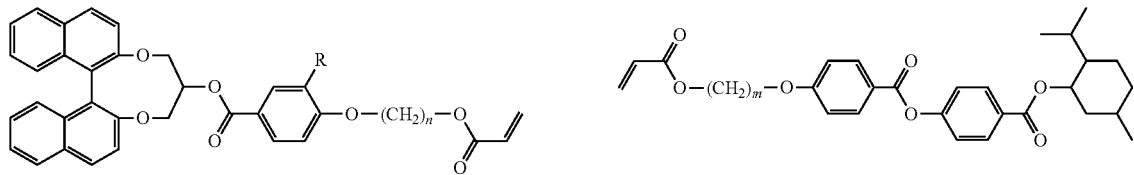
(10-27)
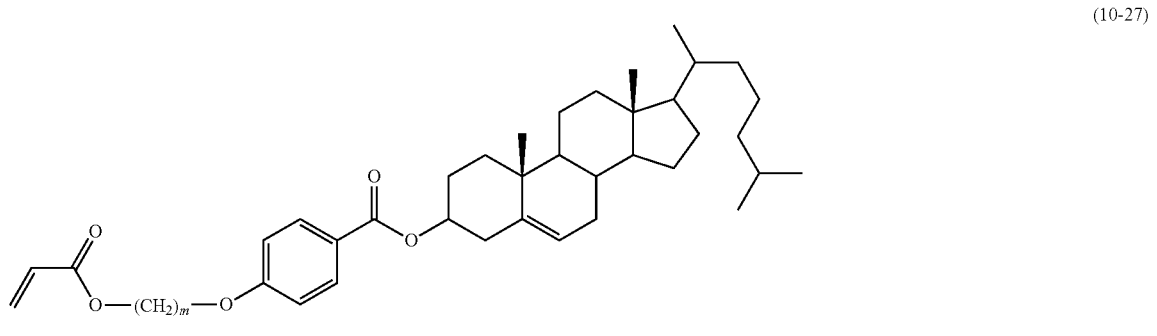
(10-28)
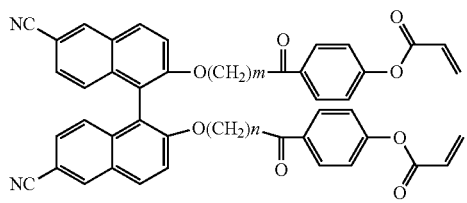
[Chem. 136]
(10-29) (10-30)
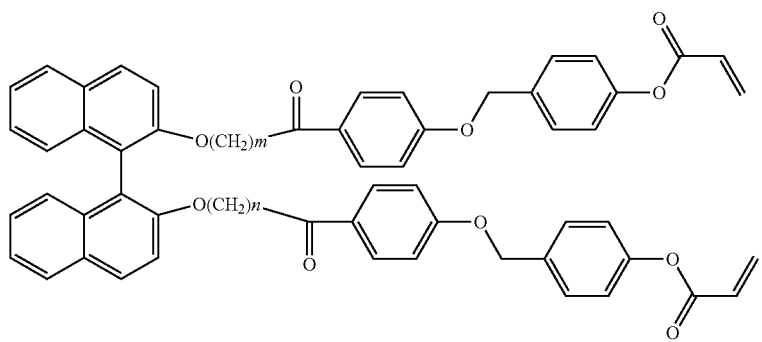
(10-31)

[Chem. 137]
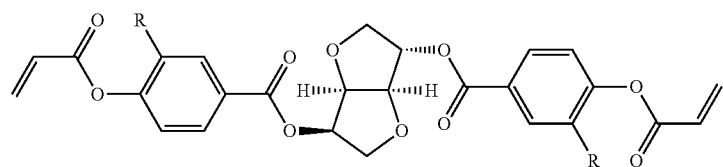
(10-32)
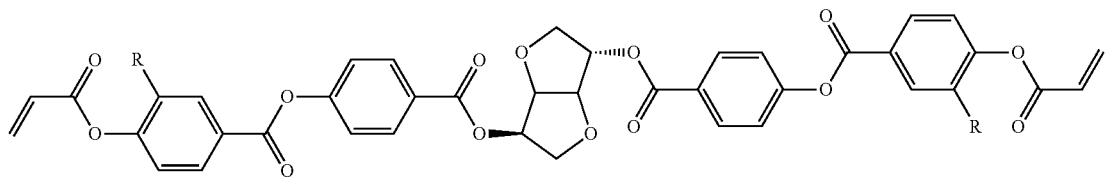
(10-33)
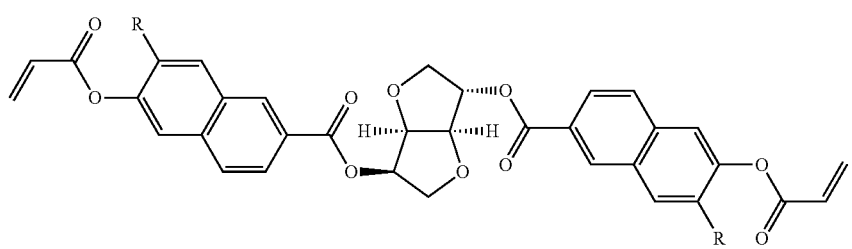
(10-33)
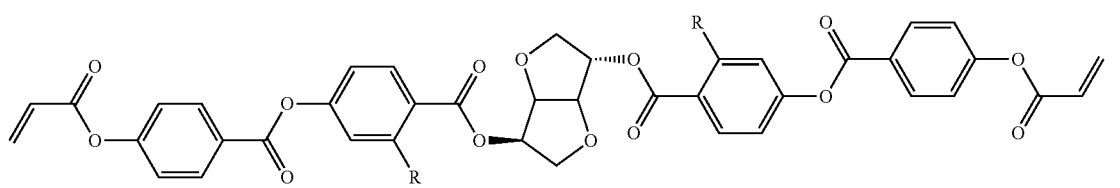
(10-34)
[Chem. 138]
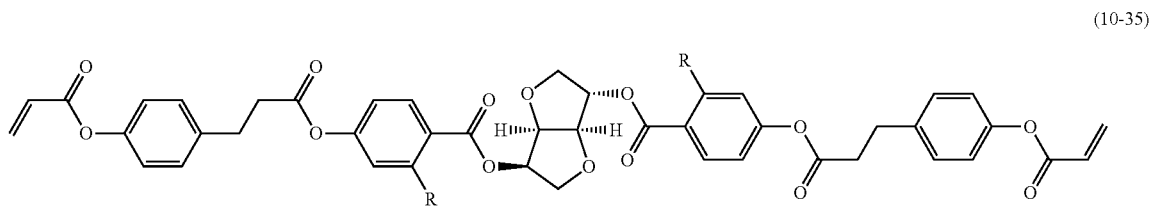
(10-35)
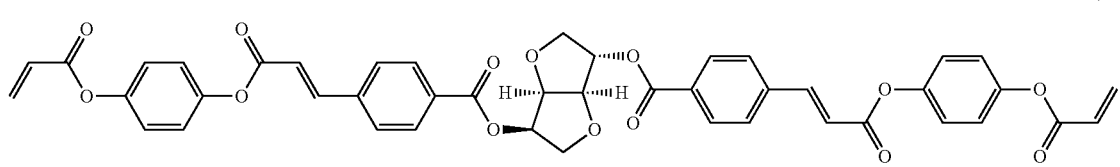
(10-36)
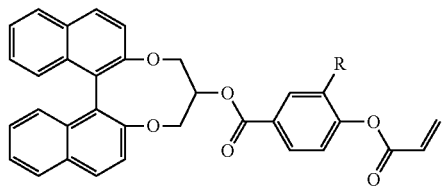
(10-37)
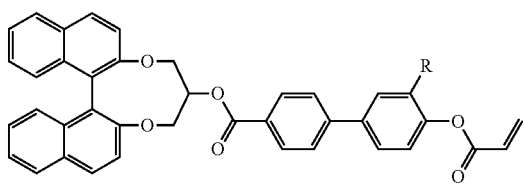
(10-38)

In General Formulae (10-5) to (10-38) above, m and n each independently represent an integer of 1 to 10; and R represents a hydrogen atom, an alkyl group having 1 to 10 carbon atoms, or a fluorine atom, and, when a plurality of R groups are present, they may be identical to or different from one another.

Specific examples of a chiral compound that does not include a polymerizable group include cholesteryl pelargonate and cholesteryl stearate that include a cholesteryl group serving as a chiral group; "CB-15" and "C-15" produced by BDH, "S-1082" produced by Merck, and "CM-19", "CM-20", and "CM" produced by Chisso Corporation, which include a 2-methylbutyl group serving as a chiral group; and "S-811" produced by Merck and "CM-21" and "CM-22" produced by Chisso Corporation, which include a 1-methylheptyl group serving as a chiral group.

In the case where the chiral compound is used, the amount of chiral compound is set in accordance with the use of the polymer produced using the polymerizable liquid crystal composition according to the present invention. The amount of chiral compound is preferably set such that the value (d/P) calculated by dividing the thickness (d) of the polymer by the pitch (P) of the helix of the polymer falls within the range of 0.1 to 100 and is further preferably set such that the value (d/P) falls within the range of 0.1 to 20.

(Non-Liquid Crystalline Compound Including Polymerizable Group)

The polymerizable composition according to the present invention may include a compound that includes a polymerizable group but is not a liquid crystal compound. Such a compound is not limited; any compounds commonly known as a polymerizable monomer or a polymerizable oligomer in the related art may be used. In the case where such a compound is used, the amount of the compound is preferably 15 parts by mass or less and is further preferably 10 parts by mass or less relative to 100 parts by mass of the total amount of polymerizable compounds included in the polymerizable composition.

Specific examples thereof include mono(meth)acrylates, such as methyl (meth)acrylate, ethyl (meth)acrylate, 2-hydroxyethyl acrylate, propyl (meth)acrylate, 2-hydroxypropyl (meth)acrylate, butyl (meth)acrylate, isobutyl (meth)acrylate, 4-hydroxybutyl (meth)acrylate, 2-hydroxybutyl (meth)acrylate, octyl (meth)acrylate, 2-ethylhexyl (meth)acrylate, dodecyl (meth)acrylate, stearyl (meth)acrylate, cyclohexyl (meth)acrylate, dicyclopentanyloxylethyl (meth)acrylate, isobornyloxylethyl (meth)acrylate, isobornyl (meth)acrylate, adamantyl (meth)acrylate, dimethyladamantyl (meth)acrylate, dicyclopentanyl (meth)acrylate, dicyclopentenyl (meth)acrylate, methoxyethyl (meth)acrylate, ethylcarbitol (meth)acrylate, tetrahydrofurfuryl (meth)acrylate, benzyl (meth)acrylate, phenoxyethyl (meth)acrylate, 2-phenoxydiethylene glycol (meth)acrylate, 2-hydroxy-3-phenoxyethyl (meth)acrylate, (2-methyl-2-ethyl-1,3-dioxolan-4-yl)methyl (meth)acrylate, (3-ethyloxetan-3-yl)methyl (meth)acrylate, o-phenylphenolethoxy (meth)acrylate, dimethylamino (meth)acrylate, diethylamino (meth)acrylate, 2,2,3,3,3-pentafluoropropyl (meth)acrylate, 2,2,3,4,4,4-hexafluorobutyl (meth)acrylate, 2,2,3,3,4,4,4-heptafluorobutyl (meth)acrylate, 2-(perfluorobutyl)ethyl (meth)acrylate, 2-(perfluorohexyl)ethyl (meth)acrylate, 1H, 1H,3H-tetrafluoropropyl (meth)acrylate, 1H,1H,5H-octafluoropentyl (meth)acrylate, 1H,1H,7H-dodecafluoroheptyl (meth)acrylate, 1H-1-(trifluoromethyl)trifluoroethyl (meth)acrylate, 1H,1H,3H-hexafluorobutyl (meth)acrylate, 1,2,2,2-tetrafluoro-1-(trifluoromethyl)ethyl (meth)acrylate, 1H,1H-pentadecafluorooctyl (meth)acrylate, 1H,1H,2H,2H-tridecafluorooctyl (meth)acrylate, 2-(meth)acryloyloxyethyl phthalic acid, 2-(meth)acryloyloxyethyl hexahydro phthalic acid, glycidyl (meth)acrylate, 2-(meth)acryloyloxyethyl phosphoric acid, acryloylmorpholine, dimethylacrylamide, dimethylaminopropyl acrylamide, iropropylacrylamide, diethylacrylamide, hydroxyethyl acrylamide, and N-acryloyloxyethylhexahydrophthalimide; diacrylates, such as 1,4-butanediol di(meth)acrylate, 1,6-hexanediol di(meth)acrylate, 1,9-nonanediol di(meth)acrylate, neopentyl diol di(meth)acrylate, tripropylene glycol di(meth)acrylate, ethylene glycol di(meth)acrylate, diethylene glycol di(meth)acrylate, triethylene glycol di(meth)acrylate, ethylene oxide-modified bisphenol A di(meth)acrylate, tricyclodecane dimethanol di(meth)acrylate, 9,9-bis[4-(2-acryloyloxyethoxy)phenyl]fluorene, glycerin di(meth)acrylate, 2-hydroxy-3-acroyloxypropyl methacrylate, an acrylic acid-adduct of 1,6-hexanediol diglycidyl ether, and an acrylic acid-adduct of 1,4-butanediol diglycidyl ether; tri(meth)acrylates, such as trimethylolpropane tri(meth)acrylate, ethoxylated isocyanuric acid triacrylate, pentaerythritol tri(meth)acrylate, and ε-caprolactone-modified tris-(2-acryloyloxyethyl)isocyanurate; tetra(meth)acrylates, such as pentaerythritol tetra(meth)acrylate and ditrimethylolpropane tetra(meth)acrylate; dipentaerythritol hexa(meth)acrylate; (meth)acrylate oligomers; urethane acrylates; macromonomers; epoxy compounds, such as ethylene glycol diglycidyl ether, diethylene glycol diglycidyl ether, propylene glycol diglycidyl ether, neopentyl glycol diglycidyl ether, 1,6-hexanediol diglycidyl ether, glycerin diglycidyl ether, and bisphenol A diglycidyl ether; and maleimide. The above compounds may be used alone or in a mixture of two or more.

(Other Liquid Crystalline Compounds)

The polymerizable composition according to the present invention may further include, in addition to the above polymerizable compounds, a polymerizable compound that includes one polymerizable group. However, if such a polymerizable compound is used in an excessively large amount, the optical properties of the resulting optically anisotropic body may become degraded. Therefore, in the case where such a polymerizable compound is used, the amount of the polymerizable compound is preferably 30 parts by mass or less, is further preferably 10 parts by mass or less, and is particularly preferably 5 parts by mass or less relative to 100 parts by mass of the total amount of polymerizable compounds included in the polymerizable composition.

Examples of such a liquid crystalline compound include Formulae (11-1) to (11-39) below.

[Chem. 139]
(11-1)
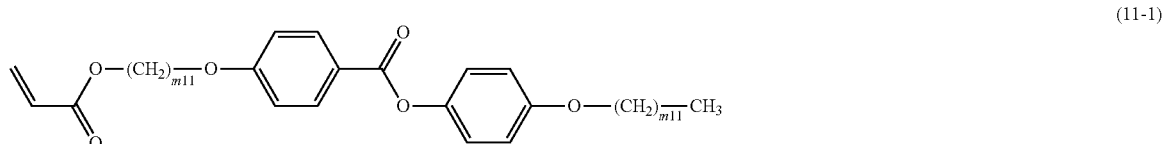
(11-2) (11-3)
(11-4) (11-5)
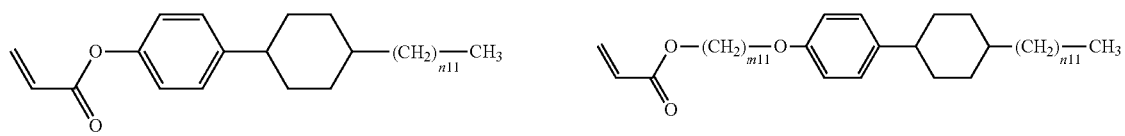
(11-6) (11-7)
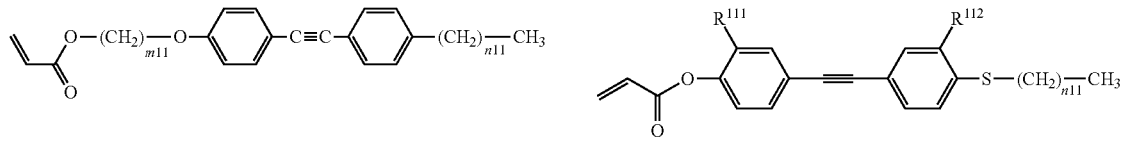
(11-8)
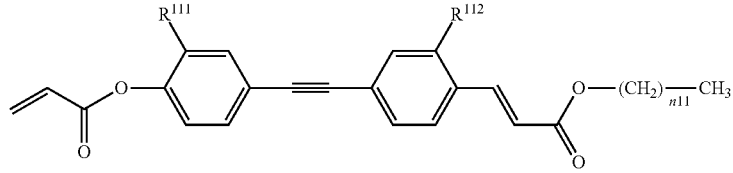
(11-9)
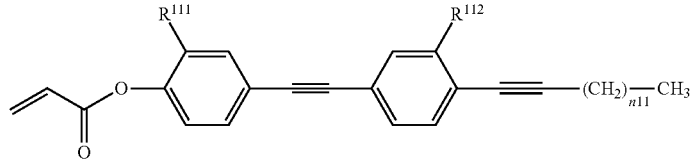
[Chem. 140]
(11-10)
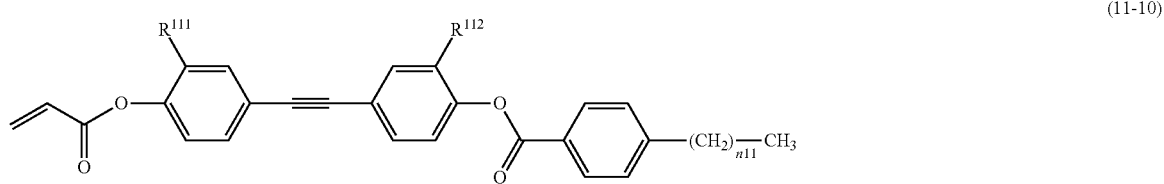
(11-11)
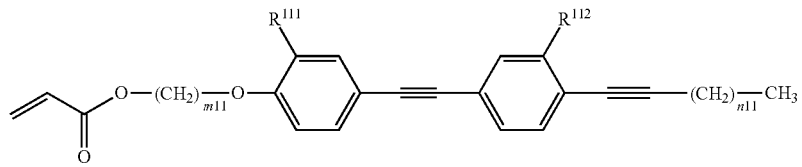
(11-12)
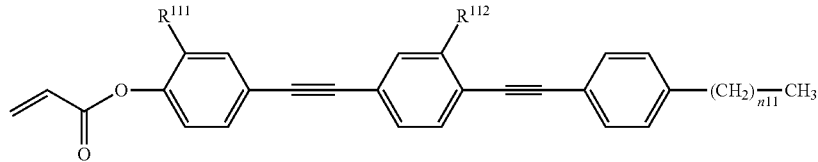

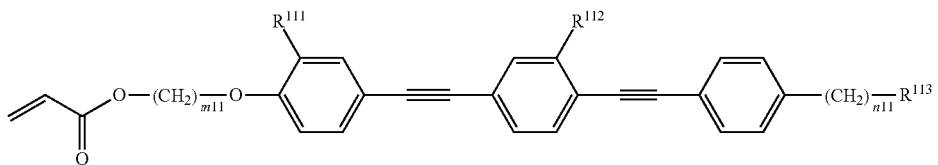
(11-13)
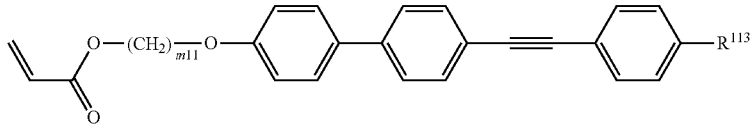
(11-14)
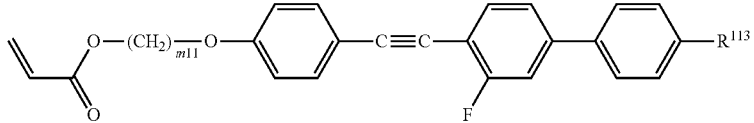
(11-15)
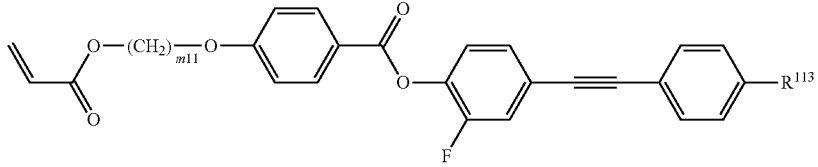
(11-16)
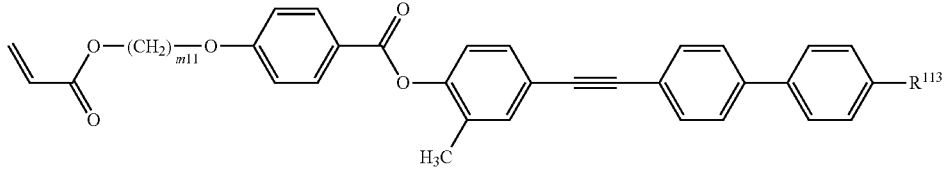
(11-17)
[Chem. 141]
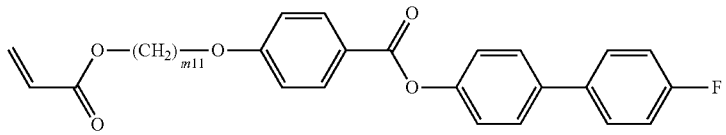
(11-18)
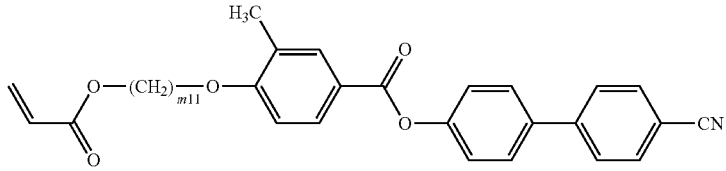
(11-19)
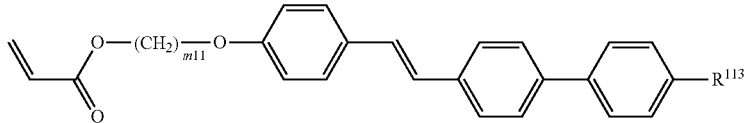
(11-20)
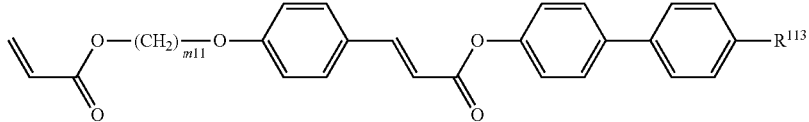
(11-21)

(11-22)
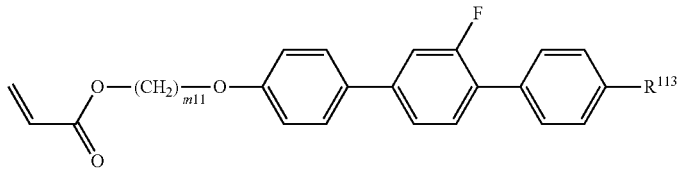
(11-23)
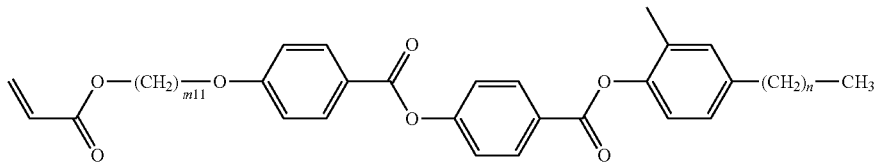
(11-24)
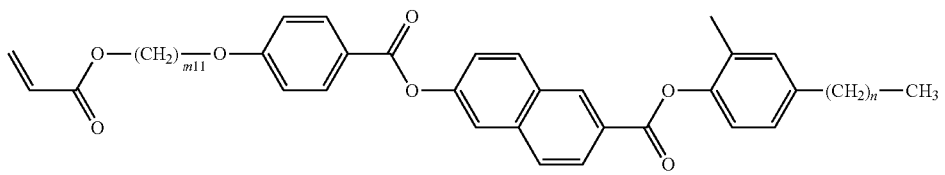
(11-25)
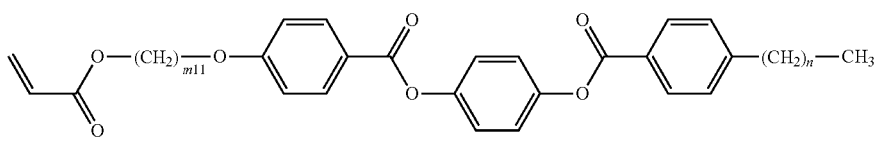
[Chem. 142]
(11-26)
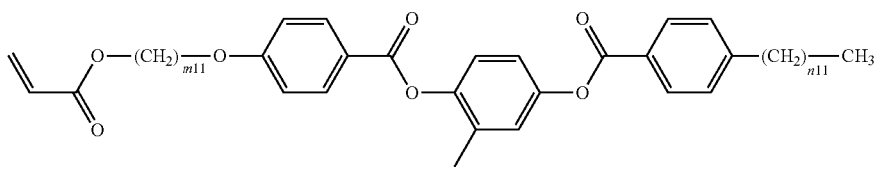
(11-27)
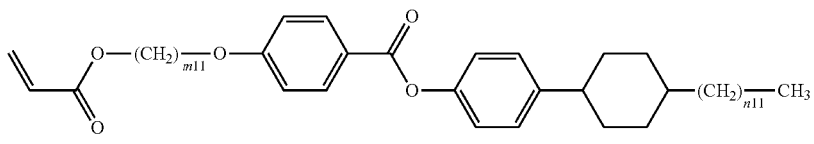
(11-28)
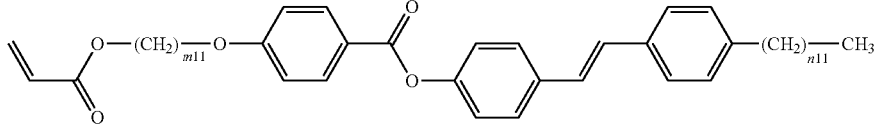
(11-29)
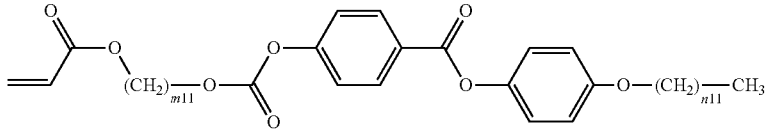
(11-30)
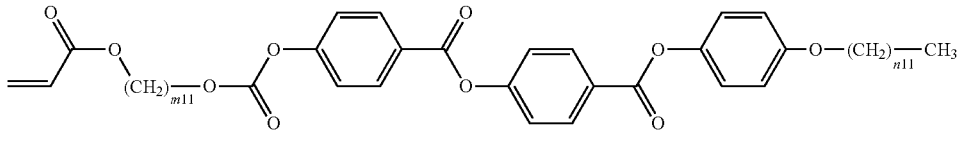
(11-31)
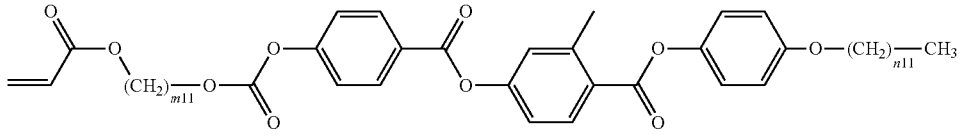

-continued (11-32)
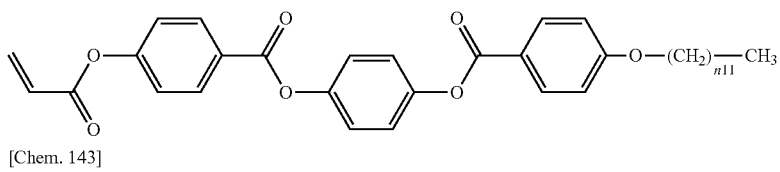

[Chem. 143]

(11-33)
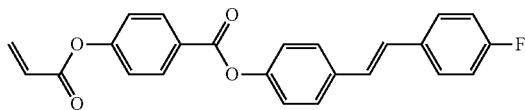

(11-34)
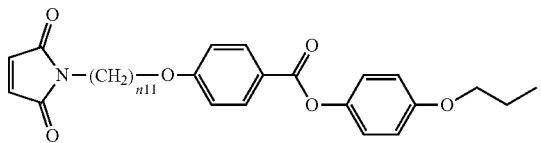

(11-35)
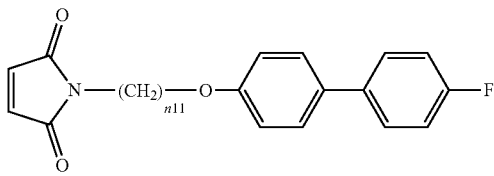

(11-36)
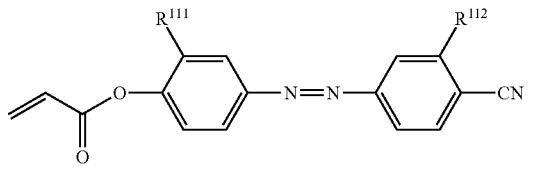

(11-37)
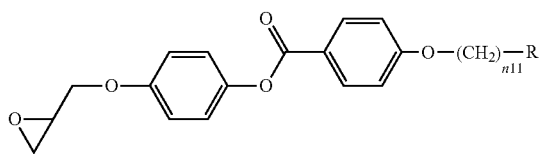

(11-38)
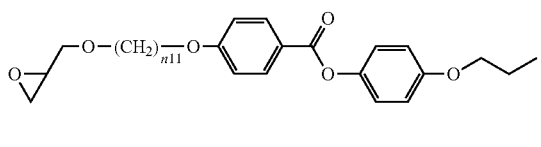

(11-39)
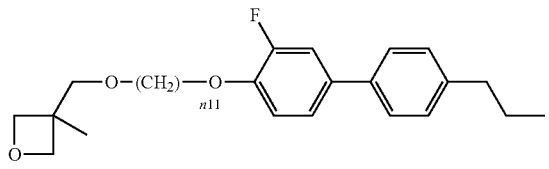

In Formulae (11-1) to (11-39) above, m11 and n11 each independently represent an integer of 1 to 10; $R^{111}$ and $R^{112}$ each independently represent a hydrogen atom, an alkyl group having 1 to 10 carbon atoms, or a fluorine atom; and $R^{113}$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom.

(Alignment Material)

In order to enhance alignment, the polymerizable composition according to the present invention may include an alignment material that enhances alignment. The alignment material may be any publicly known and commonly used alignment material soluble in the solvent included in the polymerizable composition according to the present invention, in which the liquid crystalline compounds that include a polymerizable group can be dissolved. The amount of the alignment material is set such that the alignment does not become degraded. Specifically, the amount of the alignment material is preferably 0.05 to 30 parts by weight, is further preferably 0.5 to 15 parts by weight, and is particularly preferably 1 to 10 parts by weight relative to 100 parts by mass of the total amount of polymerizable compounds included in the polymerizable composition.

Specific examples of the alignment material include photoisomerizable or photodimerizable compounds, such as polyimide, polyamide, BCB (benzocyclobutene polymer), polyvinyl alcohol, polycarbonate, polystyrene, polyphenylene ether, polyarylate, polyethylene terephthalate, polyether sulfone, an epoxy resin, an epoxy acrylate resin, an acrylic resin, a coumarin compound, a chalcone compound, a cinnamate compound, a fulgide compound, an anthraquinone compound, an azo compound, and an arylethene compound. Materials that become aligned upon being irradiated with ultraviolet or visible light (i.e., photoalignment materials) are preferable.

Examples of the photoalignment materials include a polyimide that includes a cyclic cycloalkane; wholly aromatic polyarylate; polyvinyl cinnamate and para-methoxycinnamic acid polyvinyl ester as described in Japanese Unexamined Patent Application Publication No. 5-232473; cinnamate derivatives as described in Japanese Unexamined Patent Application Publication Nos. 6-287453 and 6-289374; and maleimide derivatives as described in Japanese Unexamined Patent Application Publication No. 2002-265541. Specifically, the compounds represented by Formulae (12-1) to (12-9) below are preferable.

[Chem. 144]
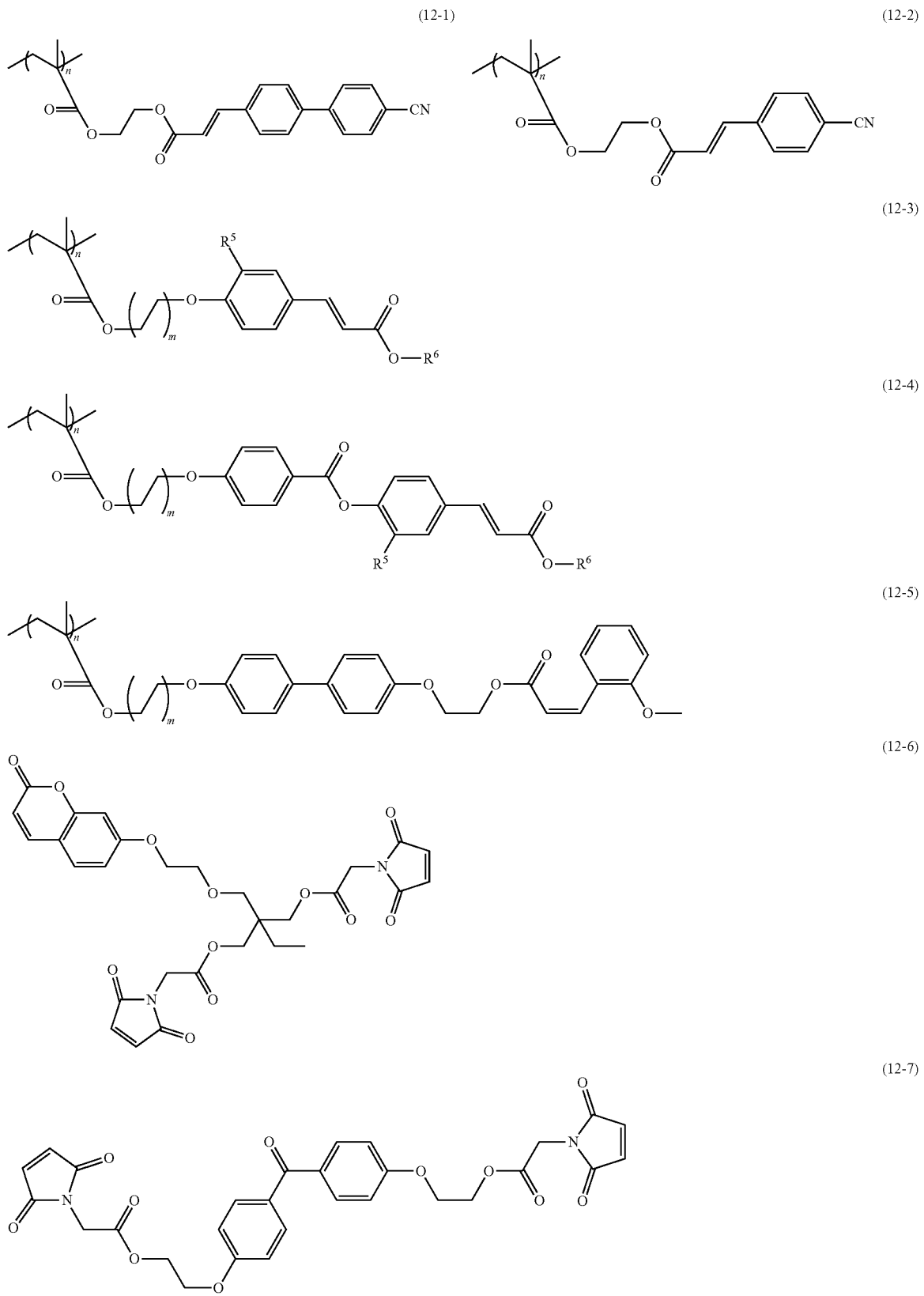

[Chem. 145]

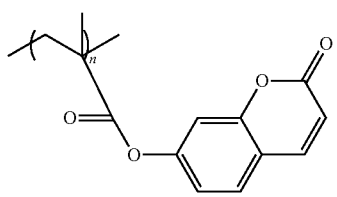

(12-8)

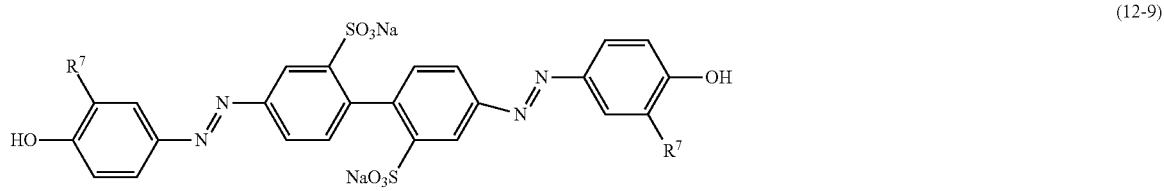

(12-9)

In Formulae (12-1) to (12-9) above, $R^5$ represents a hydrogen atom, a halogen atom, an alkyl group having 1 to 3 carbon atoms, an alkoxy group, or a nitro group; $R^6$ represents a hydrogen atom or an alkyl group having 1 to 10 carbon atoms, the alkyl group may be linear or branched, in the alkyl groups, a hydrogen atom may be replaced with a fluorine atom, and, in the alkyl groups, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and the terminal $CH_3$ groups may be replaced with a $CF_3$ group, a $CCl_3$ group, a cyano group, a nitro group, an isocyano group, or a thioisocyano group; n represents 4 to 100000, and m represents an integer of 1 to 10; and $R^7$ represents a hydrogen atom, a halogen atom, a halogenated alkyl group, an allyloxy group, a cyano group, a nitro group, an alkyl group, a hydroxyalkyl group, an alkoxy group, a carboxyl group or an alkali metal salt of a carboxyl group, an alkoxycarbonyl group, a halogenated methoxy group, a hydroxyl group, a sulfonyloxy group or an alkali metal salt of a sulfonyloxy group, an amino group, a carbamoyl group, a sulfamoyl group, or a polymerizable functional group selected from the group consisting of a (meth)acryloyl group, a (meth)acryloyloxy group, a (meth)acryloylamino group, a vinyl group, a vinyloxy group, and a maleimide group.

(Polymer)

The polymer according to the present invention is produced by polymerizing the polymerizable composition according to the present invention when the polymerizable composition includes the initiator. The polymer according to the present invention may be used for producing an optically anisotropic body, a phase retardation film, a lens, a coloring agent, a printed item, and the like.

(Method for Producing Optically Anisotropic Body)
(Optically Anisotropic Body)

The optically anisotropic body according to the present invention is produced by applying the polymerizable composition according to the present invention to a substrate or a substrate having an alignment function, aligning the liquid crystal molecules included in the polymerizable liquid crystal composition according to the present invention uniformly while maintaining the polymerizable composition to be in a nematic or smectic phase, and performing polymerization.

The optically anisotropic body according to the present invention is also produced by applying the polymerizable composition according to the present invention which includes a material having a photoalignment function, such as an azo derivative, a chalcone derivative, a coumarin derivative, a cinnamate derivative, or a cycloalkane derivative, to a substrate, aligning molecules of the liquid crystalline compound included in the polymerizable composition uniformly while maintaining the polymerizable composition to be in a nematic or smectic phase, and performing polymerization.

(Substrate)

The substrate used for producing the optically anisotropic body according to the present invention is not limited and may be any substrate that is commonly used for producing display elements, such as a liquid crystal display element and an organic light-emitting display element, optical components, coloring agents, markers, printed items, and optical films and composed of a heat-resistant material capable of withstanding heating performed when drying is performed subsequent to the application of the polymerizable composition according to the present invention. Examples of such substrates include a glass substrate, a metal substrate, a ceramic substrate, and an organic material, such as a plastic substrate or a paper sheet. In particular, in the case where the substrate is an organic material, examples thereof include a cellulose derivative, a polyolefin, a polyester, a polyolefin, a polycarbonate, a polyacrylate, a polyarylate, a polyethersulfone, a polyimide, a polyphenylene sulfide, a polyphenylene ether, a nylon, and a polystyrene. Among these, plastic substrates, such as a polyester, a polystyrene, a polyolefin, a cellulose derivative, a polyarylate, and a polycarbonate, are preferable. The shape of the substrate may be a flat sheet-like shape or a shape including a curved surface. The above substrates may include an electrode layer or have an antireflection function or a reflection function as needed.

The above substrates may be subjected to a surface treatment in order to increase ease of application of the polymerizable composition according to the present invention and adhesion to the polymer. Examples of the surface treatment include an ozone treatment, a plasma treatment, a corona treatment, and a silane coupling treatment. In order to adjust the transmittance and reflectance of the substrate, an organic thin-film, an inorganic oxide thin-film, a metal thin-film, or the like may be formed on the surface of the substrate by vapor deposition or the like. In order to add optical value to the substrate, the substrate may be a pickup lens, a rod lens, an optical disc, a phase retardation film, a light diffusion film, a color filter, or the like. Among these, a pickup lens, a phase retardation film, a light diffusion film, and a color filter, which provide the substrate with more added value, are preferable.

(Alignment Treatment)

The substrate is normally subjected to an alignment treatment or may be provided with an alignment film in order to enable the polymerizable composition according to the present invention to be aligned when a solution of the polymerizable composition is applied to the substrate and then dried. Examples of the alignment treatment include a stretching treatment, a rubbing treatment, a polarized ultraviolet-visible light radiation treatment, an ion-beam treatment, and oblique deposition of $SiO_2$ on the substrate. In the case where an alignment film is used, publicly known and commonly used alignment films may be used. Examples of the materials for such alignment films include polyimides, polysiloxanes, polyamides, polyvinyl alcohols, polycarbonates, polystyrenes, polyphenylene ethers, polyarylates, polyethylene terephthalates, polyethersulfones, epoxy resins, epoxy acrylate resins, acrylic resins, azo compounds, coumarin compounds, chalcone compounds, cinnamate compounds, fulgide compounds, anthraquinone compounds, azo compounds, and arylethene compounds; and polymers and copolymers of the above compounds. Compounds that become aligned by rubbing are preferably materials the crystallization of which can be facilitated by performing the alignment treatment or conducting a heating step subsequent to the alignment treatment. Among compounds that become aligned by a method other than rubbing, photoalignment materials are preferably used.

In general, when a liquid crystal composition is brought into contact with a substrate having an alignment function, the liquid crystal molecules become aligned in the vicinity of the substrate in the direction in which the substrate is aligned. The method used for aligning the substrate greatly affects whether the liquid crystal molecules are aligned in a direction horizontal to the substrate, in a direction inclined with respect to the substrate, or in a direction vertical to the substrate. For example, a polymerizable liquid crystal layer that is aligned substantially horizontally can be produced by forming an alignment film having a significantly small pretilt angle, which is used in-plane switching (IPS) liquid crystal display elements and the like, on the substrate.

A polymerizable liquid crystal layer having slightly inclined alignment can be produced by forming an alignment film similar to that included in TN liquid crystal display elements on the substrate. A polymerizable liquid crystal layer having greatly inclined alignment can be produced by using an alignment film similar to that included in STN liquid crystal display elements.

(Coating)

For producing the optically anisotropic body according to the present invention, for example, the following publicly known and commonly used coating methods may be used: a method in which applicator is used, bar coating, spin coating, roller coating, direct gravure coating, reverse gravure coating, flexo coating, an ink jet method, die coating, cap coating, dip coating, slit coating, and spray coating. Subsequent to the application of the polymerizable composition, drying is performed.

It is preferable to, subsequent to the application of the polymerizable composition, align the liquid crystal molecules included in the polymerizable composition according to the present invention uniformly while maintaining the polymerizable compound to be in a smectic or nematic phase. An example of the methods is a heat treatment method. Specifically, after the polymerizable composition according to the present invention has been applied to the substrate, the temperature is increased to a temperature equal to or higher than the N (nematic phase)-I (isotropic liquid phase) transition temperature (hereinafter, abbreviated as "N-I transition temperature") of the liquid crystal composition in order to bring the liquid crystal composition into an isotropic-phase liquid state. Subsequently, the temperature is gradually reduced as needed to form a nematic phase. In this process, it is desirable to maintain the temperature to be a temperature at which a liquid crystal phase is exhibited such that a liquid crystal phase domain grows to a sufficient degree to form a monodomain. Alternatively, after the polymerizable composition according to the present invention has been applied to the substrate, a heating treatment may be performed such that the temperature is maintained, for a certain period of time, to be within a temperature range in which the polymerizable composition according to the present invention exhibits a nematic phase.

If the heating temperature is excessively high, the polymerizable liquid crystal compounds may undergo an unfavorable polymerization reaction and become degraded. Excessive cooling may cause phase separation of the polymerizable composition, which results in precipitation of crystals and formation of high-order liquid crystal phases, such as a smectic phase. As a result, it may become impossible to perform an alignment treatment.

Performing the above heat treatment enables production of homogeneous optically anisotropic bodies in which the likelihood of alignment defects is small compared with a coating method in which only the application of the polymerizable composition is performed.

An optically anisotropic body having a further high alignment order and excellent transparency can be produced by, subsequent to the uniform alignment treatment described above, reducing the temperature to the minimum temperature at which the phase separation of a liquid crystal phase does not occur, that is, to the supercooling state, and performing polymerization at the temperature while the liquid crystal phase is aligned.

(Polymerization Step)

The polymerization treatment of the dried polymerizable composition is commonly performed by irradiating the polymerizable compound with light, such as visible-ultraviolet radiation, or heating the polymerizable compound while the polymerizable composition is aligned uniformly. In the case where the polymerization is performed by light radiation, specifically, it is preferable to irradiate the polymerizable composition with visible ultraviolet light of 420 nm or less and is most preferable to irradiate the polymerizable composition with ultraviolet light of 250 to 370 nm. Note that, in the case where the polymerizable composition becomes, for example, decomposed when irradiated with visible ultraviolet light of 420 nm or less, it may be preferable to perform the polymerization treatment using visible ultraviolet light of 420 nm or more.

(Polymerization Method)

For polymerizing the polymerizable composition according to the present invention, for example, a method in which the polymerizable composition is irradiated with an active energy ray and a thermal polymerization method may be used. The method in which the polymerizable composition is irradiated with an active energy ray is preferable because this method does not require heating and the reaction can be conducted at room temperature. It is particularly preferable to use a method in which the polymerizable composition is irradiated with light, such as ultraviolet radiation, in order to simplify the operation. The temperature at which the irradiation is performed is set to the temperature at which the polymerizable composition according to the present invention maintains to be in a liquid crystal phase and is preferably set to possibly 30° C. or less in order to prevent the induction of thermal polymerization of the polymerizable composition. In the temperature-rise process, the polymerizable liquid crystal composition normally exhibits a liquid crystal phase in the range of the C(solid phase)-N(nematic) transition temperature (hereinafter, abbreviated as "C-N transition temperature") and the N-I transition temperature. On the other hand, in the temperature-fall process, the polymerizable liquid crystal composition maintains to be in a thermodynamically non-equilibrium state and may maintain to be in a liquid crystal state without solidifying even at the C-N transition temperature or less. This state is referred to as "supercooling state". In the present invention, a liquid crystal composition that is in the supercooling state is also considered to be in the state in which a liquid crystal phase is maintained. Specifically, it is preferable to irradiate the polymerizable composition with ultraviolet light of 390 nm or less and is most preferable to irradiate the polymerizable composition with light having a wavelength of 250 to 370 nm. Note that, in the case where the polymerizable composition undergoes, for example, decomposition when irradiated with ultraviolet light of 390 nm or less, it may be preferable to perform the polymerization treatment using ultraviolet light of 390 nm or more. This light is preferably diffused unpolarized light. The intensity of the ultraviolet radiation is preferably 0.05 mW/cm$^2$ to 10 W/cm$^2$ and is particularly preferably 0.2 mW/cm$^2$ to 2 W/cm$^2$. In the case where the intensity of the ultraviolet radiation is less than 0.05 mW/cm$^2$ it may take an excessively large amount of time to complete the polymerization. On the other hand, if the intensity of the ultraviolet radiation is more than 2 W/cm$^2$, the liquid crystal molecules included in the polymerizable composition may undergo photodecomposition. Furthermore, a large amount of heat of polymerization may be generated and the temperature may be increased during polymerization. In such a case, the order parameter of the polymerizable liquid crystal may change and, consequently, the retardation of the film produced by the polymerization may become deviated.

The amount of ultraviolet radiation is preferably 10 mJ/cm$^2$ to 20 J/cm$^2$, is further preferably 50 mJ/cm$^2$ to 10 J/cm$^2$, and is particularly preferably 100 mJ/cm$^2$ to 5 J/cm$^2$.

It is also possible to produce an optically anisotropic body that includes a plurality of regions having different alignment orientations by irradiating only a particular portion with ultraviolet radiation using a mask to polymerize the portion, changing the alignment of the other portion, which has not been polymerized, by application of an electric field, a magnetic field, heat, or the like, and subsequently polymerizing the nonpolymerized portion.

The optically anisotropic body that includes a plurality of regions having different alignment orientations may also be produced by, before a particular portion is irradiated with ultraviolet radiation using a mask to polymerize the portion, controlling the alignment of the polymerizable liquid crystal composition, which has not been polymerized, by application of an electric field, a magnetic field, heat, or the like, and subsequently, while the alignment is maintained, irradiating the polymerizable liquid crystal composition with light using the mask to perform polymerization.

The optically anisotropic body produced by polymerizing the polymerizable liquid crystal composition according to the present invention may be used alone after being detached from the substrate or may be directly used as an optically anisotropic body without being detached from the substrate. Since contamination of the other components is not likely occur, it is particularly suitably used as a substrate for multilayer bodies or by being bonded to another substrate.

In order to enhance solvent resistance and consistencies in heat resistance of the optically anisotropic body, the optically anisotropic body may be subjected to thermal aging. In such a case, it is preferable to perform heating at a temperature equal to or higher than the glass transition point of the polymerized film. Normally, the above heating temperature is preferably 50° C. to 300° C., is further preferably 60° C. to 200° C., and is particularly preferably 80° C. to 150° C.

(Phase Retardation Film)

The phase retardation film according to the present invention includes the optically anisotropic body. The liquid crystalline compound is uniformly and continuously aligned with respect to the substrate. The phase retardation film has biaxiality in the in-plane direction, the out-of-plane direction, both in-plane direction and out-of-plane direction, or the in-plane direction with respect to the substrate. The phase retardation film may be provided with an adhesive or an adhesive layer, a pressure-sensitive adhesive or a pressure-sensitive adhesive layer, a protecting film, a polarizing film, or the like disposed thereon.

Examples of the alignment mode of the above phase retardation film include the following: a positive A-plate in which a rod-like liquid crystalline compound is aligned substantially horizontally with respect to the substrate; a negative A-plate in which a disc-like liquid crystalline compound is uniaxially aligned vertically with respect to the substrate; a positive C-plate in which a rod-like liquid crystalline compound is aligned substantially vertically with respect to the substrate; a negative C-plate in which a rod-like liquid crystalline compound is aligned in a cholesteric manner with respect to the substrate or a disc-like liquid crystalline compound is uniaxially aligned horizontally; a biaxial plate; a positive O-plate in which a rod-like liquid crystalline compound is aligned in a hybrid manner with respect to the substrate; and a negative O-plate in which a disc-like liquid crystalline compound is aligned in a hybrid manner with respect to the substrate. In the case where the phase retardation film is used as an optical compensation film for a liquid crystal display element, the alignment mode of the phase retardation film is not limited and any alignment mode with which the viewing angle dependence can be improved may be used.

Examples of such an alignment mode include a positive A-plate, a negative A-plate, a positive C-plate, a negative C-plate, a biaxial plate, a positive O-plate, and a negative O-plate. Among these, a positive A-plate and a negative C-plate are preferably used. It is more preferable to stack the positive A-plate and the negative C-plate on top of each other.

A liquid crystal cell that includes the phase retardation film preferably includes a positive A-plate that serve as a first phase retardation layer in order to compensate for the viewing angle dependence of the orthogonality of the polarization axis and increase the viewing angle. The positive A-plate satisfies the relationship: "nx>ny=nz", where nx is the refractive index of the film in the in-plane slow axis direction, ny is the refractive index of the film in the in-plane fast axis direction, and nz is the refractive index of the film in the thickness direction. A positive A-plate having an in-plane phase retardation of 30 to 500 nm at a wavelength of 550 nm is preferable. The phase retardation of the film in the thickness direction is not limited. The coefficient Nz is preferably 0.5 to 1.5.

In order to cancel the birefringence of liquid crystal molecules, it is preferable to use, as a second phase retardation layer, a phase retardation layer having a negative refractive index anisotropy, that is, a "negative C-plate". The negative C-plate may be disposed on the positive A-plate.

The negative C-plate is a phase retardation layer that satisfies the relationship: "nx=ny>nz", where nx is the refractive index of the phase retardation layer in the in-plane slow axis direction, ny is the refractive index of the phase retardation layer in the in-plane fast axis direction, and nz is the refractive index of the phase retardation layer in the thickness direction. The phase retardation of the negative C-plate in the thickness direction is preferably 20 to 400 nm.

The refractive index anisotropy of the film in the thickness direction is represented by the thickness-direction phase retardation Rth defined by Formula (2) below. The thickness-direction phase retardation Rth is determined by calculating nx, ny, and nz from the in-plane phase retardation $R_0$, the phase retardation $R_{50}$, which is measured at an inclination angle of 50° with respect to an inclination axis that is the slow axis, the film thickness d, and the average refractive index $n_0$ of the film, using the Formulae (1) and (4) to (7) below and substituting nx, ny, and nz into Formula (2). The coefficient Nz= is calculated using Formula (3). The same applies hereinafter.

$$R_0 = (nx-ny) \times d \tag{1}$$

$$Rth = [(nx+ny)/2 - nz] \times d \tag{2}$$

$$\text{Coefficient } Nz = (nx-nz)/(nx-ny) \tag{3}$$

$$R_{50} = (nx-ny') \times d/\cos(\phi) \tag{4}$$

$$(nx+ny+nz)/3 = n0 \tag{5}$$

where, $$\phi = \sin^{-1}[\sin(50°)/n_0] \tag{6}$$

$$ny' = ny \times nz/[ny^2 \times \sin^2(\phi) + nz^2 \times \cos^2(\phi)]^{1/2} \tag{7}$$

Most of the commercial phase retardation measuring apparatuses automatically perform the above mathematical calculations inside the apparatuses and display the in-plane phase retardation $R_0$, the thickness-direction phase retardation Rth, etc. An example of such measuring apparatuses is RETS-100 (produced by Otsuka Chemical Co., Ltd.).

In the case where the liquid crystal medium of a liquid crystal display element is an in-plane switching (IPS) mode or a fringe-field switching (FFS) mode, a positive A-plate, a positive C-plate, and/or a biaxial plate are preferably used. It is more preferable to use a positive A-plate and/or a positive C-plate. It is particularly preferable to use a positive A-plate and a positive C-plate that are stacked on top of one another.

A liquid crystal cell preferably includes, as a first phase retardation layer, a positive A-plate. The positive A-plate satisfies the relationship: "nx>ny=nz", where nx is the refractive index of the film in the in-plane slow axis direction, ny is the refractive index of the film in the in-plane fast axis direction, and nz is the refractive index of the film in the thickness direction. A positive A-plate having an in-plane phase retardation of 10 to 300 nm at a wavelength of 550 nm is preferable. The phase retardation of the film in the thickness direction is not limited. The coefficient Nz is preferably 0.9 to 1.1.

It is preferable to use, as a second phase retardation layer, a phase retardation layer having a positive refractive index anisotropy, that is, a "positive C-plate". The positive C-plate may be stacked on the positive A-plate.

The positive C-plate is a phase retardation layer that satisfies the relationship: "nx=ny<nz", where nx is the refractive index of the film in the in-plane slow axis direction, ny is the refractive index of the film in the in-plane fast axis direction, and nz is the refractive index of the phase retardation layer in the thickness direction. The phase retardation of the positive C-plate in the thickness direction is preferably 10 to 300 nm.

The refractive index anisotropy of the film in the thickness direction is represented by the thickness-direction phase retardation Rth defined by Formula (2). The thickness-direction phase retardation Rth is determined by calculating nx, ny, and nz from the in-plane phase retardation $R_0$, the phase retardation $R_{50}$, which is measured at an inclination angle of 500 with respect to an inclination axis that is the slow axis, the film thickness d, and the average refractive index $n_0$ of the film using the Formulae (1) and (4) to (7) below and substituting nx, ny, and nz into Formula (2). The coefficient Nz=can be calculated using Formula (3). The same applies hereinafter.

$$R_0 = (nx-ny) \times d \tag{1}$$

$$Rth = [(nx+ny)/2 - nz] \times d \tag{2}$$

$$\text{Coefficient } Nz = (nx-nz)/(nx-ny) \tag{3}$$

$$R_{50} = (nx-ny') \times d/\cos(\phi) \tag{4}$$

$$(nx+ny+nz)/3 = n0 \tag{5}$$

where, $$\phi = \sin^{-1}[\sin(50°)/n_0] \tag{6}$$

$$ny' = ny \times nz/[ny^2 \times \sin^2(\phi) + nz^2 \times \cos^2(\phi)]^{1/2} \tag{7}$$

The phase retardation film according to the present invention may be used in combination with a linearly polarizing plate as a circularly polarizing plate. In the case where the phase retardation film according to the present invention is used as a circularly polarizing plate, the phase retardation film is preferably a positive A-plate in which the polymerizable liquid crystalline compound is aligned substantially horizontally with respect to the substrate and the polarizing axis of the linearly polarizing plate and the slow axis of the phase retardation film form an angle of substantially 45°.

The phase retardation film according to the present invention may be used as a waveplate. In the case where the phase retardation film according to the present invention is used as a waveplate, the phase retardation film is preferably a positive A-plate in which the polymerizable liquid crystalline compound is aligned substantially horizontally with respect to the substrate, the positive A-plate serving as a half-wave or quarter-wave plate.

The phase retardation film according to the present invention may be used as a polarized-light reflection film or an infrared reflection film. In such a case, the phase retardation film according to the present invention is preferably a phase retardation film in which a rod-like liquid crystalline compound is aligned substantially horizontally with respect to the substrate in a cholesteric manner and the pitch is in the visible region when the phase retardation film is a polarized-light reflection film and is in the infrared region when the phase retardation film is an infrared reflection film.
(Lens)

A polymer produced by applying the polymerizable composition according to the present invention to a substrate or a substrate having an alignment function or injecting the polymerizable composition into a lens-shaped metal mold, aligning the polymerizable composition uniformly while maintaining the polymerizable composition to be in a nematic phase or a smectic phase, and performing polymerization may be used as a component of the lens according to the present invention. Examples of the shape of the lens include a simple cell shape, a prism shape, and a lenticular shape.
(Liquid Crystal Display Element)

A polymer produced by applying the polymerizable composition according to the present invention to a substrate or a substrate having an alignment function, aligning the polymerizable composition uniformly while maintaining the polymerizable composition to be in a nematic phase or a smectic phase, and performing polymerization may be used as a component of the liquid crystal display element according to the present invention. The above polymer may be used as, for example, an optical compensation film, a patterned phase retardation film included in a stereoscopic liquid crystal display element, a phase retardation compensation layer included in a color filter, an overcoat layer, and an alignment film included in a liquid crystal medium. A liquid crystal display element includes, at least, two substrates and a liquid crystal medium layer, a TFT-driving circuit, a black-matrix layer, a color-filter layer, a spacer, and an electrode circuit appropriate for the liquid crystal medium layer that are sandwiched between the substrates. While an optical-compensation layer, a polarizing-plate layer, and a tough panel layer are commonly disposed outside the two substrates, an optical compensation layer, an overcoat layer, a polarizing plate layer, and an electrode layer for the touch panel may be sandwiched between the two substrates.

Examples of the alignment mode of a liquid crystal display element include a TN mode, a VA mode, an IPS mode, an FFS mode, and an OCB mode. In the case where the polymer is used as an optical compensation film or an optical compensation layer, a film having a phase retardation appropriate for the alignment mode can be produced. In the case where the polymer is used as a patterned phase retardation film, the liquid crystalline compound included in the polymerizable composition is required to be aligned substantially horizontally with respect to the substrate. In the case where the polymer is used as an overcoat layer, it is suitable to perform thermal polymerization of a liquid crystalline compound having a larger number of polymerizable groups per molecule. In the case where the polymer is used as an alignment film for liquid crystal media, it is preferable to use a polymerizable composition prepared by mixing an alignment material with a liquid crystalline compound having a polymerizable group. The substance can also be mixed with a liquid crystal medium. In such a case, various properties such as response speed and contrast may be enhanced depending on the ratio between the liquid crystal medium and the liquid crystalline compound.
(Organic Light-Emitting Display Element)

A polymer produced by applying the polymerizable composition according to the present invention to a substrate or a substrate having an alignment function, aligning the polymerizable composition uniformly while maintaining the polymerizable composition to be in a nematic phase or a smectic phase, and performing polymerization may be used as a component of the organic light-emitting display element according to the present invention. The phase retardation film produced as a result of the above polymerization can be used in combination with a polarizing plate as an antireflection film included in an organic light-emitting display element. In the case where the phase retardation film is used as an antireflection film, the angle formed by the polarizing axis of the polarizing plate and the slow axis of the phase retardation film is preferably about 45°. The polarizing plate and the phase retardation film may be bonded to each other with an adhesive, a pressure-sensitive adhesive, or the like. The phase retardation film may be directly stacked on the polarizing plate by a rubbing treatment, an alignment treatment in which a photoalignment film is stacked, or the like. The polarizing plate used in such a case may be any film having a polarizing function. Examples of such a polarizing plate include a film produced by adsorbing iodine or a dichroic dye on a polyvinyl alcohol film and stretching the film; a film produced by stretching a polyvinyl alcohol film and adsorbing iodine, a dichroic dye, or a dichroic dye on the stretched film; a film produced by applying an aqueous solution including a dichroic dye to a substrate to form a polarizing layer on the substrate; and a wire grid polarizer.

The polyvinyl alcohol resin may be a resin produced by saponifying a polyvinyl acetate resin. Examples of the polyvinyl acetate resin include polyvinyl acetate, which is a homopolymer of vinyl acetate; and copolymers of vinyl acetate with other monomers capable of copolymerizing with vinyl acetate. Examples of the other monomers capable of copolymerizing with vinyl acetate include unsaturated carboxylic acids, olefins, vinyl ethers, unsaturated sulfonic acids, and acrylamides including an ammonium group. The method for producing a film of a polyvinyl alcohol resin is not limited; publicly known methods may be used. The thickness of the polyvinyl alcohol film is not limited and is, for example, about 10 to 150 μm.

In the case where iodine is used as a dichroic dye, commonly, the polyvinyl alcohol resin film is colored by being immersed in an aqueous solution that includes iodine and potassium iodide. In the case where a dichroic dye is used as a dichroic dye, commonly, the polyvinyl alcohol resin film is colored by being immersed in an aqueous solution that includes a water-soluble dichroic dye.

In the case where the polarizing plate is a film formed by applying an aqueous solution that includes a dichroic dye to a substrate to form a polarizing layer on the substrate, examples of the dichroic dye include, but vary with the type of the substrate used, water-soluble dyes, such as a direct dye, an acid dye, salts thereof; and water-insoluble colorants, such as a disperse dye and a lipid-soluble pigment. Commonly, the above colorants are dissolved in water or an organic solvent and a surfactant may be added to the resulting solution as needed, before the solution is applied to the substrate that has been subjected to a rubbing treatment or a corona treatment. Common examples of the organic solvent include, but vary with the resistance of the substrate to solvents, alcohols, such as methanol, ethanol, isopropyl alcohol; cellosolves, such as methyl cellosolve and ethyl cellosolve; ketones, such as acetone and methyl ethyl ketone; amides, such as dimethylformamide and N-methylpyrrolidone; and aromatic organic solvents, such as benzene and toluene. The amount of the colorant deposited is commonly, but varies with the polarizing function of the colorant, 0.05 to 1.0 g/po and is preferably 0.1 to 0.8 g/rrf. Examples of the method for applying the color PfJ liquid to the substrate include the following coating methods: bar coater coating, spray coating, roller co π ating, and gravure coating.

In the case where the wire grid polarizer is used, it is preferable to use a wire grid polarizer composed of a conductive material, such as Al, Cu, Ag, Cu, Ni, Cr, or Si.
(Lighting Element)

A polymer produced by polymerizing the polymerizable composition according to the present invention while maintaining the polymerizable composition in a nematic phase or a smectic phase or while aligning the polymerizable composition on a substrate having an aligning function can be used as a heat-dissipating material included in a lighting element or, in particular, a light-emitting diode element. The type of the heat-dissipating material is preferably a prepreg, a polymer sheet, an adhesive, a sheet with metal foil, or the like.
(Optical Component)

A polymer produced by polymerizing the polymerizable composition according to the present invention while maintaining the polymerizable composition in a nematic phase or a smectic phase or while the polymerizable composition is deposited on an alignment material may be used as an optical component according to the present invention.
(Coloring Agent)

The polymerizable composition according to the present invention may be used as a coloring agent after a coloring agent, such as a dye or an organic pigment, has been added to the polymerizable composition.
(Polarizing Film)

The polymerizable composition according to the present invention may be used as a polarizing film in combination with a dichroic dye, a lyotropic liquid crystal, a chromonic liquid crystal, or the like or after a dichroic dye, a lyotropic liquid crystal, a chromonic liquid crystal, or the like has been added to the polymerizable composition.

EXAMPLES

The present invention is described below with reference to Examples and Comparative examples. The present invention is not limited by Examples and Comparative examples. Hereinafter, all "part" and "%" are on a mass basis unless otherwise specified.
(Preparation of Polymerizable Composition (1))

To 300 parts of toluene, 100 parts of the compound represented by Formula (1A-1-1) was added. The resulting mixture was heated to 60° C. and stirred to form a solution. After the dissolution of the compound had been confirmed, the temperature was reduced to room temperature. To the solution, 6 parts of Irgacure OXE01 (OXE01: produced by BASF SE Japan), 0.2 parts of FTX-218 (produced by NEOS COMPANY LIMITED), and 0.1 parts of p-methoxyphenol (MEHQ) were added. The resulting mixture was further stirred to form a solution. The solution was transparent and uniform. The solution was filtered through a 0.20-μm membrane filter. Hereby, a polymerizable composition (1) used in Example 1, etc. was prepared.
(Preparation of Polymerizable Compositions (2) to (39) and Comparative Polymerizable Composition (C1))

Polymerizable compositions (2) to (39) used in Examples 2 to 39, etc. and a polymerizable composition (C1) used in Comparative example 1 were prepared under the same conditions as in the preparation of the polymerizable composition (1) of Example 1, except that the proportions of the compounds described in Tables 1 to 5 below were changed as described in Tables 1 to 5 below. The solvents used were toluene, chloroform, and cyclopentanone (CPN).

Tables 1 to 5 summarize the specific compositions of the polymerizable compositions (1) to (39) according to the present invention and the comparative polymerizable composition (C1).

TABLE 1

| | Composition | | | | | | | |
|---|---|---|---|---|---|---|---|---|
| | (1) | (2) | (3) | (4) | (5) | (6) | (7) | (8) |
| (1A-1-1) | 100 | 50 | 50 | 40 | 50 | 50 | | 50 |
| (1A-1-2) | | 50 | | | | | 30 | |
| (1A-1-3) | | | 50 | | | | | |
| (1-1-1-1) | | | | | | | | 50 |
| (2-1-1-1) | | | | 60 | | 20 | 30 | |
| (2-1-1-2) | | | | | 50 | 30 | 40 | |
| OXE-01 | 6 | 6 | 6 | 6 | 6 | 6 | 6 | |
| FTX-218 | 0.2 | 0.2 | 0.2 | 0.2 | 0.2 | 0.2 | 0.2 | 0.2 |
| MEHQ | 0.1 | 0.1 | 0.1 | 0.1 | 0.1 | 0.1 | 0.1 | 0.1 |
| Toluene | 300 | 300 | 300 | 300 | 300 | 300 | 300 | 300 |

TABLE 2

| | Composition | | | | | | | |
|---|---|---|---|---|---|---|---|---|
| | (9) | (10) | (11) | (12) | (13) | (14) | (15) | (16) |
| (1A-1-1) | 50 | | 80 | 30 | 40 | 50 | 50 | 50 |
| (1A-1-2) | | | | 20 | 20 | | | |
| (1A-1-3) | | 50 | | | | | | |
| (1-1-1-1) | | | | 50 | | 25 | 25 | |
| (1-1-1-2) | 50 | 50 | | | 40 | | | 25 |
| (1-1-1-3) | | | 20 | | | | | |
| (2-1-1-1) | | | | | | | 25 | |
| (2-1-1-2) | | | | | | 25 | | 25 |
| OXE-01 | 6 | 6 | 6 | 6 | 6 | 6 | 6 | 6 |
| FTX-218 | 0.2 | 0.2 | 0.2 | 0.2 | 0.2 | 0.2 | 0.2 | 0.2 |
| MEHQ | 0.1 | 0.1 | 0.1 | 0.1 | 0.1 | 0.1 | 0.1 | 0.1 |
| Toluene | 300 | 300 | 300 | 300 | 300 | 300 | 300 | 300 |

TABLE 3

| | Composition | | | | | | | |
|---|---|---|---|---|---|---|---|---|
| | (17) | (18) | (19) | (20) | (21) | (22) | (23) | (24) |
| (1A-1-1) | 40 | | 49 | 49 | 47.5 | 45 | 47.5 | |
| (1A-1-2) | | 20 | | | | | | |
| (1A-1-3) | | | | | | | | 47.5 |
| (1-1-1-1) | 30 | 50 | | | | | | |
| (2-1-1-1) | 30 | 30 | | | | | | |
| (2-1-1-2) | | | 49 | 49 | 47.5 | 45 | 47.5 | 47.5 |
| (2-2-1-1) | | | 2 | 2 | 5 | 10 | 2.5 | 5 |
| (2-2-1-2) | | | | | | | 2.5 | |
| OXE-01 | 6 | 6 | 6 | | 6 | 6 | 6 | 6 |
| OXE-04 | | | | 6 | | | | |
| FTX-218 | 0.2 | 0.2 | 0.2 | 0.2 | 0.2 | 0.2 | 0.2 | 0.2 |
| MEHQ | 0.1 | 0.1 | 0.1 | 0.1 | 0.1 | 0.1 | 0.1 | 0.1 |
| Toluene | 300 | 300 | 300 | 300 | 300 | 300 | 300 | 300 |

TABLE 4

| | Composition | | | | | | | |
|---|---|---|---|---|---|---|---|---|
| | (25) | (26) | (27) | (28) | (29) | (30) | (31) | (32) |
| (1A-1-1) | 40 | 45 | 45 | | 40 | 40 | 40 | 40 |
| (1A-1-2) | | | | 15 | | | | |
| (1-1-1-1) | | | | 50 | | | | |
| (1-1-1-2) | | 50 | 25 | | | | | |
| (2-1-1-1) | 30 | | | | 30 | | | |

TABLE 4-continued
| | Composition | | | | | | | |
|---|---|---|---|---|---|---|---|---|
| | (25) | (26) | (27) | (28) | (29) | (30) | (31) | (32) |
| (2-1-1-2) | 25 | | 25 | | 40 | 40 | 40 | 40 |
| (2-1-1-3) | | | | | 20 | | | |
| (2-1-1-4) | | | | | | 20 | | |
| (2-1-1-5) | | | | | | | 20 | |
| (2-1-1-6) | | | | | | | | 20 |
| (2-2-1-1) | 5 | 5 | 5 | 5 | | | | |
| OXE-01 | 6 | 6 | 6 | 6 | 6 | 6 | 6 | |
| FTX-218 | 0.2 | 0.2 | 0.2 | 0.2 | 0.2 | 0.2 | 0.2 | 0.2 |
| MEHQ | 0.1 | 0.1 | 0.1 | 0.1 | 0.1 | 0.1 | 0.1 | 0.1 |
| Toluene | 300 | 300 | 300 | 300 | | 150 | 300 | 200 |
| Chloroform | | | | | 300 | | | |
| CPN | | | | | | 150 | | 100 |
TABLE 5
| | Composition | | | | | | | |
|---|---|---|---|---|---|---|---|---|
| | (33) | (34) | (35) | (36) | (37) | (38) | (39) | (C1) |
| (1A-1-1) | 50 | 50 | 30 | 40 | | 45 | | |
| (1A-1-2) | | | 20 | 20 | 20 | | 15 | |
| (1-1-1-1) | 50 | | 50 | | 50 | | 50 | |
| (1-1-1-2) | | 50 | | 40 | | 50 | | |
| (2-1-1-1) | | | | 30 | | | 30 | |
| (2-1-1-3) | | | | | | | | 100 |
| (2-2-1-1) | | | | | | 5 | 5 | |
| OXE-01 | 6 | 6 | 6 | 6 | 6 | 6 | 6 | |
| FTX-218 | 0.05 | 0.05 | 0.05 | 0.05 | 0.05 | 0.05 | 0.05 | |
| F-554 | | | | | | | | 0.15 |
| MEHQ | 0.1 | 0.1 | 0.1 | 0.1 | 0.1 | 0.1 | 0.1 | 0.1 |
| Toluene | 300 | 300 | 300 | 300 | 300 | 300 | 300 | |
| Chloroform | | | | | | | | 600 |
[Chem. 146]
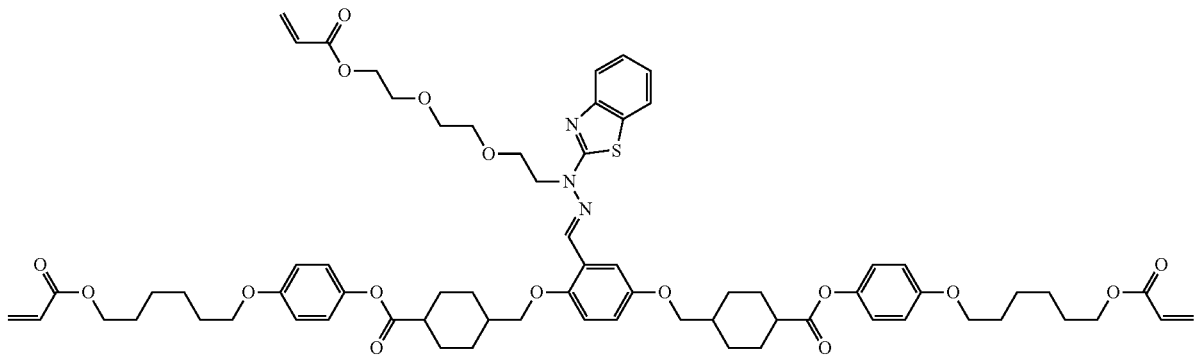
(IA-1-1)
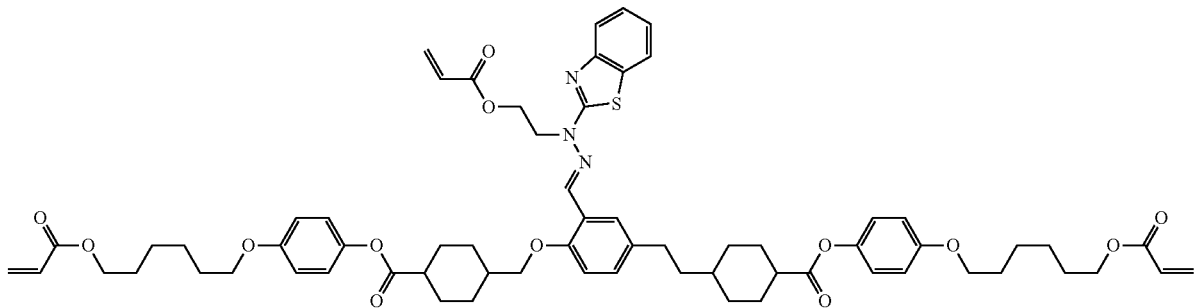
(IA-1-2)

(IA-1-3)
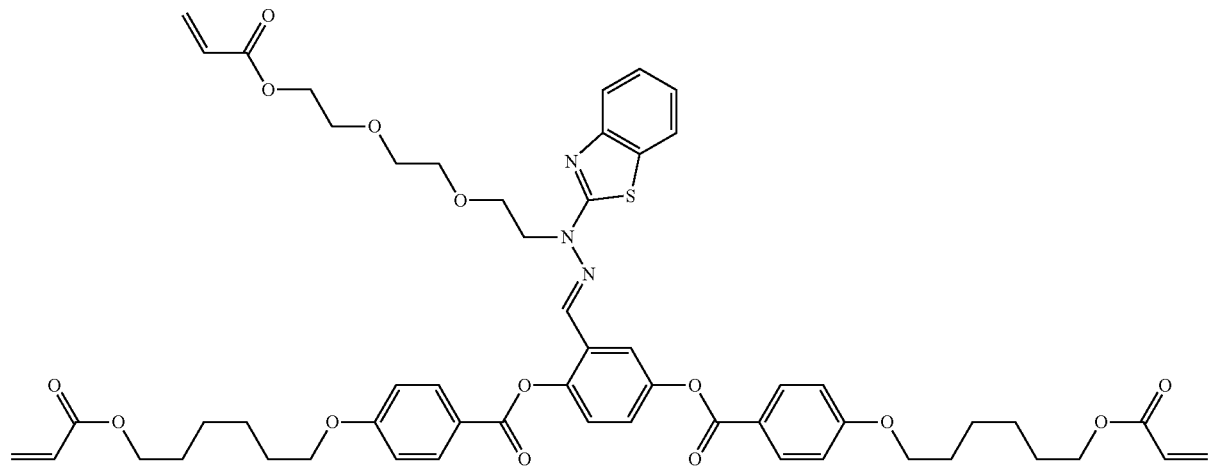
[Chem. 147]
(1-1-1-1)
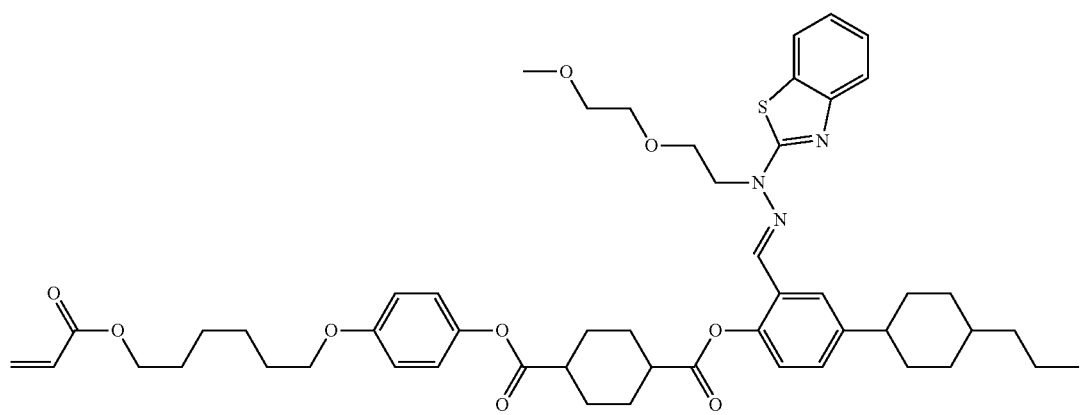
(1-1-1-2)
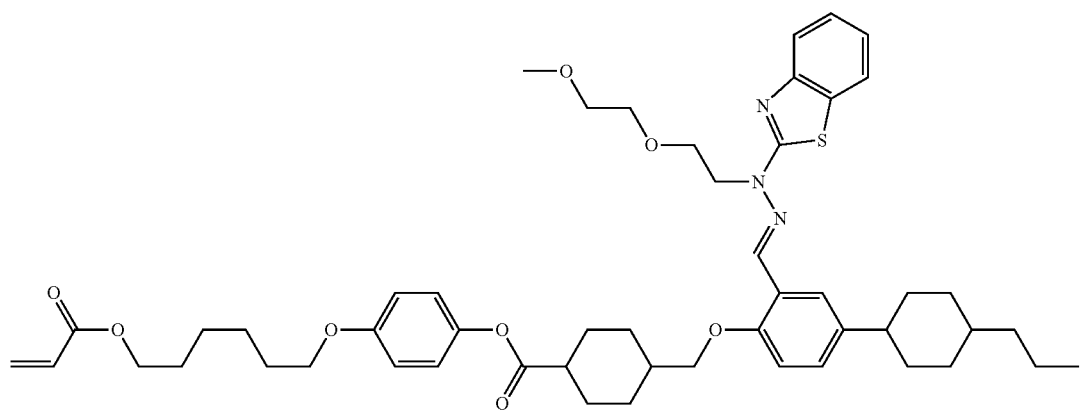

(1-1-1-3)
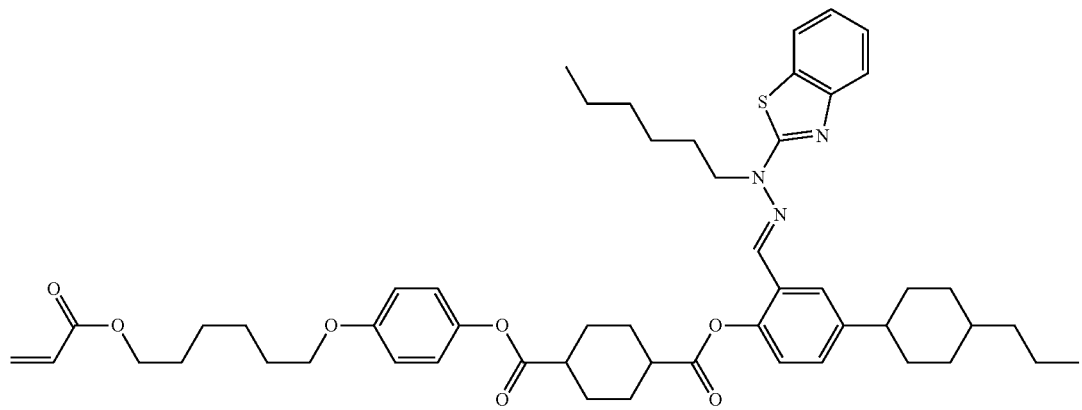
(2-1-1-1)
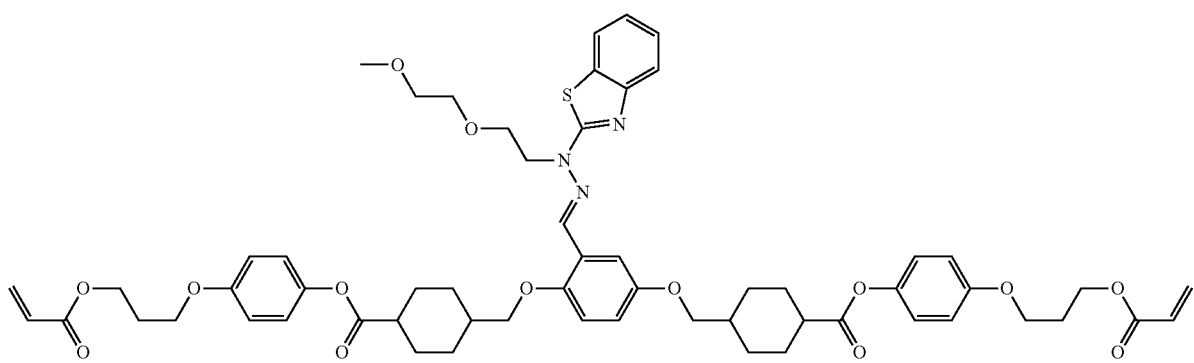
[Chem. 148]
(2-1-1-2)
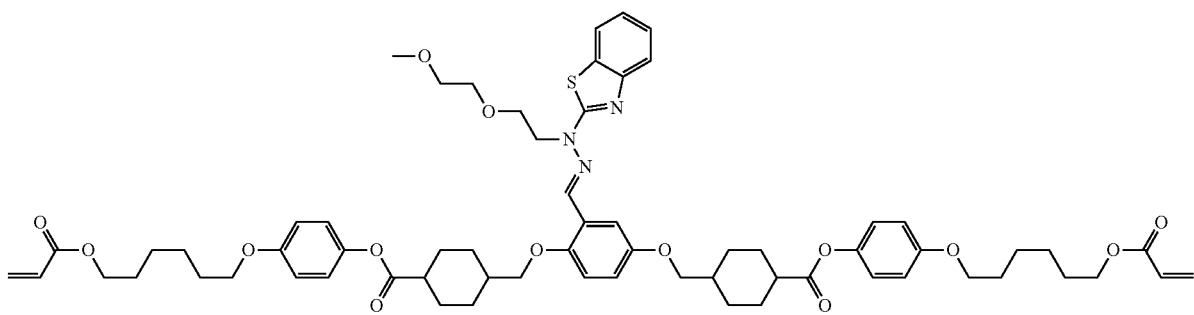
(2-1-1-3)
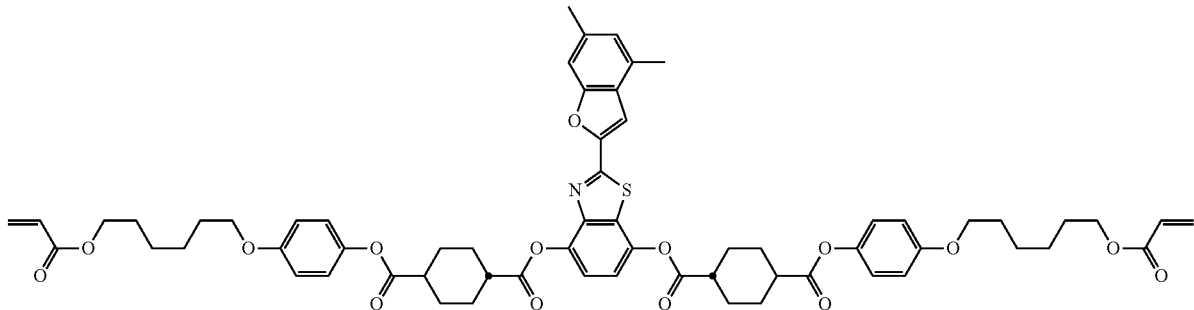

-continued

[Chem. 149]

(2-1-1-4)

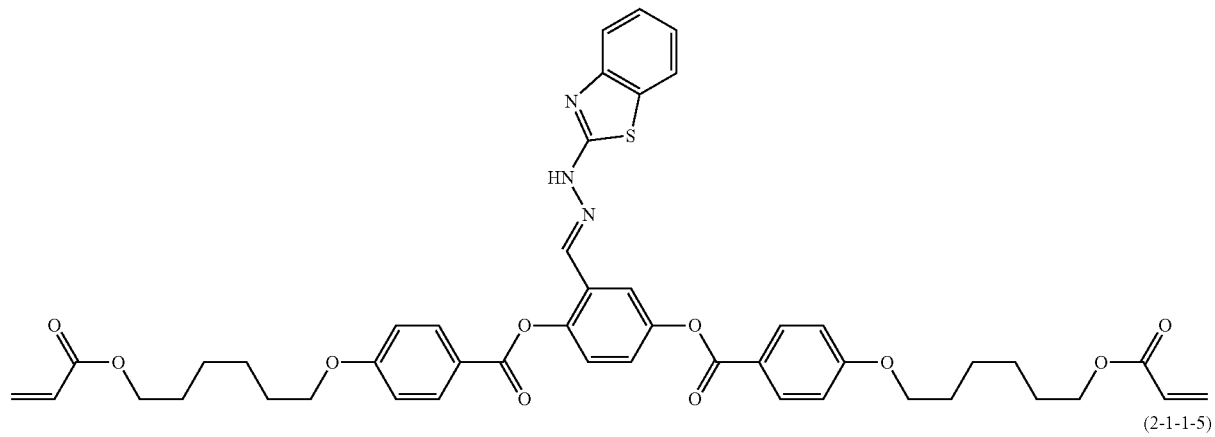

(2-1-1-5)

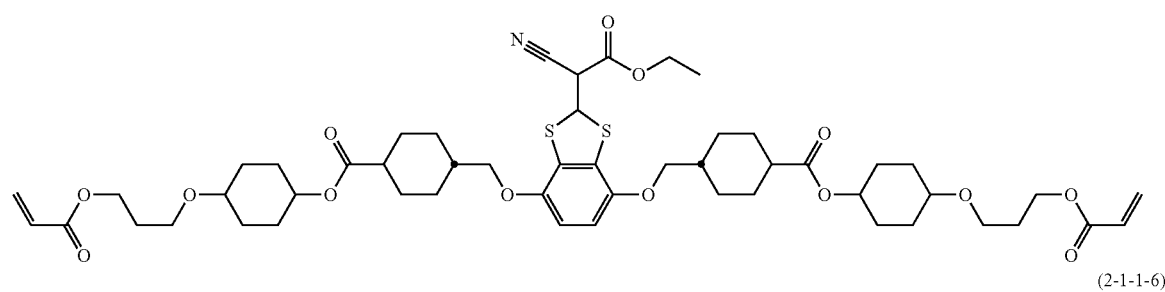

(2-1-1-6)

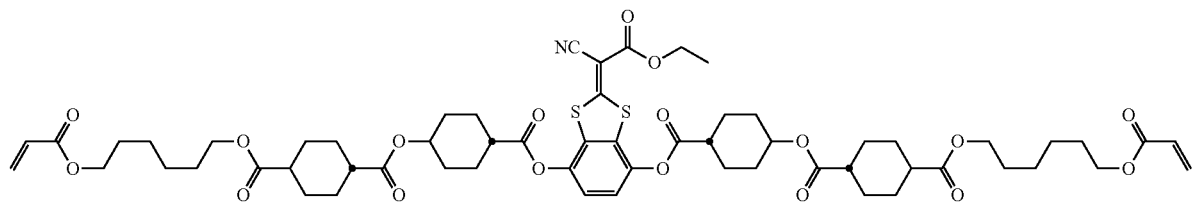

[Chem. 150]

(2-2-1-1)

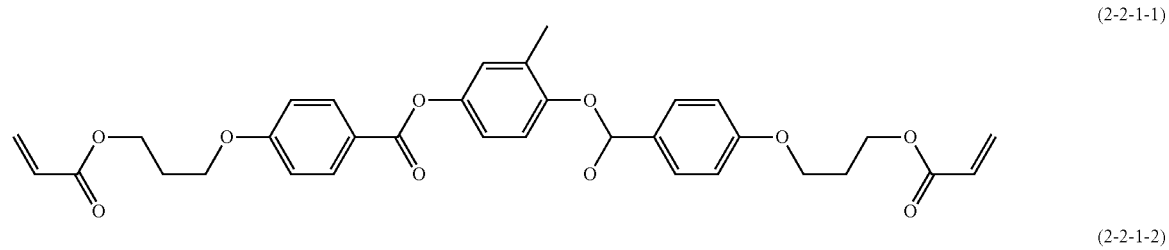

(2-2-1-2)

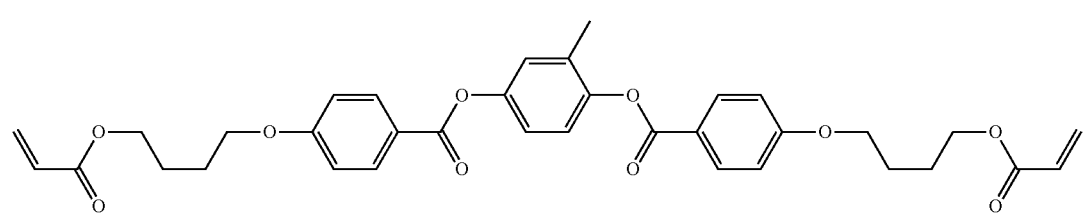

MEGAFACE F-554 (F-554; produced by DIC Corporation)

Example 1

A polyimide solution for alignment films was applied to a glass substrate having a thickness of 0.7 mm by spin coating. After drying had been performed at 100° C. for 10 minutes, firing was performed at 200° C. for 60 minutes. Hereby, a coating film was formed. The coating film was subjected to a rubbing treatment. The rubbing treatment was performed with a commercial rubbing apparatus.

To the substrate that had been subjected to the rubbing treatment, the polymerizable composition (1) according to the present invention was applied by spin coating. Subsequently, drying was performed at the phase transition temperature $T_{NI}$–20° C. for 2 minutes such that a nematic phase could be formed. After the resulting coating film had been cooled to room temperature, the coating film was irradiated with ultraviolet radiation emitted from a high-pressure mercury lamp at an intensity of 30 mW/cm² for 30 seconds. Hereby, an optically anisotropic body of Example 1 which was a positive A-plate was prepared. The alignment, phase retardation ratio, and hardness of the optically anisotropic body were evaluated in accordance with the following criteria.

(Alignment Evaluation)

☉: There was no visual defect, and no defect was observed with a polarizing microscope.

○: There was no visual defect, but some unaligned portions were observed with a polarizing microscope.

Δ: There was no visual defect, but unaligned portions were observed over the entirety with a polarizing microscope.

x: There were some visual defects, and unaligned portions were observed over the entirety with a polarizing microscope.

(Phase Retardation Ratio)

The retardation (phase retardation) of the optically anisotropic body, which was prepared as an evaluation sample, was measured using a retardation film and optical material evaluation system "RETS-100" (produced by Otsuka Electronics Co., Ltd.). The in-plane phase retardation of the optically anisotropic body at a wavelength of 550 nm (Re(550)) was 140 nm. The ratio of the in-plane phase retardation of the optically anisotropic body at a wavelength of 450 nm (Re(450)) to the Re(550) of the optically anisotropic body, that is, Re(450)/Re(550), was 0.864. This confirmed the formation of a uniform phase retardation film.

(Hardness Evaluation)

The optically anisotropic body prepared as an evaluation sample was placed under a crossed nichol condition. The surface of the film, that is, the optically anisotropic body, was scrubbed with a cotton swab impregnated with methyl isobutyl ketone. The number of times the film was scrubbed until the film detached from the substrate was visually determined.

☉: The film did not detach from the substrate even after being scrubbed 200 times or more.

○: The film detached from the substrate after being scrubbed 100 to 200 times.

Δ: The film detached from the substrate after being scrubbed 50 to 100 times.

x: The film detached from the substrate after being scrubbed less than 50 times.

(Durability)

The optically anisotropic body prepared as an evaluation sample was subjected to a heat resistance test at 85° C. for 500 hours. A change in the retardation (phase retardation) of the optically anisotropic body which occurred during the test was evaluated.

○: The change was less than 5%.

Δ: The change was 5% to 8%.

x: The change was 8% or more.

TABLE 6

| | Composition | Alignment | Phase retardation ratio | Hardness | Durability |
|---|---|---|---|---|---|
| Example 1 | Composition (1) | ☉ | 0.864 | ☉ | ○ |
| Example 2 | Composition (2) | ☉ | 0.890 | ☉ | ○ |
| Example 3 | Composition (3) | ☉ | 0.891 | ☉ | ○ |
| Example 4 | Composition (4) | ☉ | 0.828 | ☉ | ○ |
| Example 5 | Composition (5) | ☉ | 0.817 | ☉ | ○ |
| Example 6 | Composition (6) | ☉ | 0.824 | ☉ | ○ |
| Example 7 | Composition (7) | ☉ | 0.824 | ☉ | ○ |
| Example 8 | Composition (8) | ☉ | 0.839 | ○ | ○ |
| Example 9 | Composition (9) | ☉ | 0.829 | ○ | ○ |
| Example 10 | Composition (10) | ☉ | 0.856 | ○ | ○ |
| Example 11 | Composition (11) | ☉ | 0.778 | ○ | ○ |
| Example 12 | Composition (12) | ☉ | 0.849 | ○ | ○ |
| Example 13 | Composition (13) | ☉ | 0.847 | ○ | ○ |
| Example 14 | Composition (14) | ☉ | 0.828 | ○ | ○ |
| Example 15 | Composition (15) | ☉ | 0.836 | ○ | ○ |
| Example 16 | Composition (16) | ☉ | 0.823 | ○ | ○ |
| Example 17 | Composition (17) | ☉ | 0.831 | ○ | ○ |
| Example 18 | Composition (18) | ☉ | 0.831 | ○ | ○ |
| Example 19 | Composition (19) | ☉ | 0.823 | ☉ | ○ |
| Example 20 | Composition (20) | ☉ | 0.823 | ☉ | ○ |

TABLE 7

| | Composition | Alignment | Phase retardation ratio | Hardness | Durability |
|---|---|---|---|---|---|
| Example 21 | Composition (21) | ☉ | 0.832 | ☉ | ○ |
| Example 22 | Composition (22) | ☉ | 0.846 | ☉ | ○ |
| Example 23 | Composition (23) | ☉ | 0.831 | ☉ | ○ |
| Example 24 | Composition (24) | ☉ | 0.857 | ☉ | ○ |
| Example 25 | Composition (25) | ☉ | 0.834 | ☉ | ○ |
| Example 26 | Composition (26) | ☉ | 0.841 | ○ | ○ |
| Example 27 | Composition (27) | ☉ | 0.835 | ○ | ○ |
| Example 28 | Composition (28) | ☉ | 0.840 | ☉ | ○ |
| Example 29 | Composition (29) | ☉ | 0.831 | ☉ | ○ |
| Example 30 | Composition (30) | ○ | 0.831 | ☉ | ○ |
| Example 31 | Composition (31) | ○ | 0.803 | ☉ | ○ |
| Example 32 | Composition (32) | ○ | 0.822 | ☉ | ○ |
| Example 33 | Composition (33) | ☉ | 0.840 | ○ | ○ |
| Example 34 | Composition (34) | ☉ | 0.830 | ○ | ○ |
| Example 35 | Composition (35) | ☉ | 0.850 | ○ | ○ |
| Example 36 | Composition (36) | ☉ | 0.848 | ○ | ○ |
| Example 37 | Composition (37) | ☉ | 0.832 | ○ | ○ |
| Example 38 | Composition (38) | ☉ | 0.857 | ○ | ○ |
| Example 39 | Composition (39) | ☉ | 0.841 | ○ | ○ |
| Comparative example 1 | Composition (C1) | ○ | 0.934 | X | Δ |

Examples 2 to 39 and Comparative Example 1

The alignment, phase retardation ratio, hardness, and durability of the film prepared using a specific one of the polymerizable compositions (2) to (39) and the comparative polymerizable composition (C1) were measured under the same conditions as in Example 1. The films prepared using the polymerizable compositions (2) to (32) and the comparative polymerizable composition (C1) were optically anisotropic bodies that were positive A-plates. The films prepared using the polymerizable compositions (33) to (39) were optically anisotropic bodies that were positive C-plates. Tables 6 and 7 above summarize the results as Examples 2 to 39 and Comparative example 1.

(Preparation of Polymerizable Composition (40))

To 150 parts of methyl ethyl ketone and 150 parts of toluene, 40 parts of the compound represented by Formula (1A-1-1), 40 parts of the compound represented by Formula (2-1-1-2), 10 parts of the compound represented by Formula (2-2-1-1), 10 parts of the compound represented by Formula (2-2-1-2), and 6 parts of the compound represented by Formula (10-10) below were added. The resulting mixture was heated to 60° C. and stirred to form a solution. After the dissolution of the compounds had been confirmed, the temperature was reduced to room temperature. To the solution, 6 parts of Irgacure OXE01 (produced by BASF SE Japan), 0.05 parts of MEGAFACE F-554 (produced by DIC Corporation), 0.2 parts of polypropylene having a weight-average molecular weight of 1200, 0.1 parts of p-methoxyphenol, and 0.1 parts of IRGANOX 1076 (produced by BASF SE Japan) were added. The resulting mixture was further stirred to form a solution. The solution was transparent and uniform. The solution was filtered through a 0.20-μm membrane filter. Hereby, a polymerizable composition (40) according to the present invention was prepared. (Preparation of Polymerizable Compositions (41) and (42))

Polymerizable compositions (41) and (42) were prepared under the same conditions as in the preparation of the polymerizable composition (40), except that the proportions of the compounds described in Table 8 below were changed as described in Table 8 below.

Table 8 summarizes the specific compositions of the polymerizable compositions (40) to (42) according to the present invention.

TABLE 8

| Composition | (40) | (41) | (42) |
|---|---|---|---|
| (1A-1-1) | 40 | 40 | 40 |
| (2-1-1-2) | 40 | 40 | 40 |
| (2-2-1-1) | 10 | 10 | 10 |
| (2-2-1-2) | 10 | 10 | 10 |
| (10-10) | 6 | | |
| (10-33) | | 3 | |
| (10-38) | | | 8 |
| OXE-01 | 6 | 6 | 6 |
| F-554 | 0.05 | 0.05 | 0.05 |

TABLE 8-continued

| Composition | (40) | (41) | (42) |
|---|---|---|---|
| p-Methoxyphenol | 0.1 | 0.1 | 0.1 |
| IRGANOX 1076 | 0.1 | 0.1 | 0.1 |
| Polypropylene | 0.2 | 0.2 | 0.2 |
| Toluene | 150 | 150 | 150 |
| Methyl ethyl ketone | 150 | 150 | 150 |

[Chem. 151]

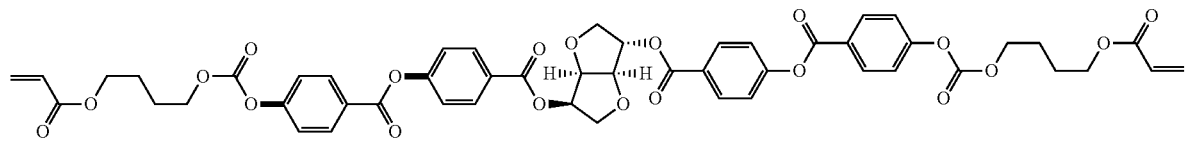

(10-10)

$m = n = 4$
$R = H$

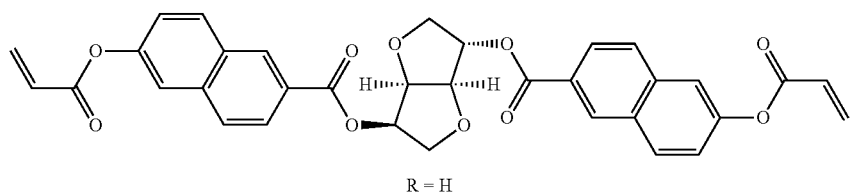

(10-34)

$R = H$

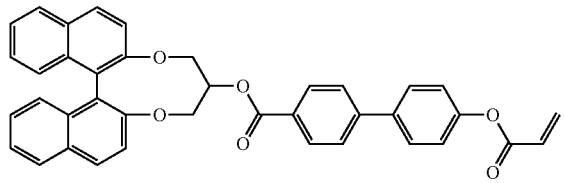

(10-38)

$R = H$

Polypropylene (weight-average molecular weight: 1200)

Example 40

A uniaxially stretched PET film having a thickness of 180 μm was subjected to a rubbing treatment with a commercial rubbing apparatus. To the PET film, the polymerizable composition (40) according to the present invention was applied by bar coating. Subsequently, drying was performed at 80° C. for 2 minutes. After the resulting coating film had been cooled to room temperature, the coating film was irradiated with ultraviolet radiation using an UV conveyor apparatus (produced by GS Yuasa Corporation) having a lamp power of 2 kW (80 W/cm) at a conveyor speed of 4 m/min. Hereby, an optically anisotropic body of Example 40 which was a negative C-plate was prepared. In the evaluation of the alignment of the optically anisotropic body, there was no visual defect and no defect was observed with a polarizing microscope. The optically anisotropic body appeared green. It was confirmed that the optically anisotropic body was a reflection film.

Example 41

An optically anisotropic body of Example 41 was prepared under the same conditions as in Example 40, except that the polymerizable composition used was changed to the polymerizable composition (41) according to the present invention. In the evaluation of the alignment of the optically anisotropic body, there was no visual defect and no defect was observed with a polarizing microscope. The optically anisotropic body was transparent. The results of the measurement of transmittance of the optically anisotropic body using a spectrophotometer (produced by Hitachi High-Tech Science Corporation) confirmed the presence of a part of the infrared region in which the transmittance of the optically anisotropic body decreased. Thus, it was confirmed that the optically anisotropic body served as an infrared reflection film. The phase retardation of the optically anisotropic body was measured with RETS-100 while the angle of incident light was changed from −50° to 500 in steps of 10°. The out-of-plane phase retardation (Rth) of the optically anisotropic body at a wavelength of 550 nm which was calculated on the basis of the phase retardation data was 130 nm. This confirmed that the optically anisotropic body was a negative C-plate.

Example 42

An optically anisotropic body of Example 42 was prepared under the same conditions as in Example 40, except that the polymerizable composition used was changed to the polymerizable composition (42) according to the present invention. In the evaluation of the alignment of the optically anisotropic body, there was no visual defect and no defect was observed with a polarizing microscope. The optically anisotropic body was transparent. The results of the measurement of transmittance of the optically anisotropic body using a spectrophotometer (produced by Hitachi High-Tech Science Corporation) confirmed the presence of a part of the ultraviolet region in which the transmittance of the optically anisotropic body decreased. Thus, it was confirmed that the optically anisotropic body was an ultraviolet reflection film. The phase retardation of the optically anisotropic body was measured with RETS-100 while the angle of incident light was changed from −50° to 50° in steps of 10°. The out-of-plane phase retardation (Rth) of the optically anisotropic body at a wavelength of 550 nm which was calculated on the basis of the phase retardation data was 132 nm. This confirmed that the optically anisotropic body was a negative C-plate.

(Preparation of Polymerizable Composition (43))

To 150 parts of methyl ethyl ketone and 150 parts of toluene, 45 parts of the compound represented by Formula (1A-1-1), 45 parts of the compound represented by Formula (2-1-1-2), 10 parts of the compound represented by Formula (2-2-1-1), and 1 part of the compound represented by Formula (12-9) below were added. The resulting mixture was heated to 60° C. and stirred to form a solution. After the dissolution of the compounds had been confirmed, the temperature was reduced to room temperature. To the solution, 6 parts of Irgacure OXE01 (produced by BASF SE Japan), 0.1 parts of MEGAFACE F-554 (produced by DIC Corporation), and 0.1 parts of p-methoxyphenol were added. The resulting mixture was further stirred to form a solution. The solution was transparent and uniform. The solution was filtered through a 0.20-μm membrane filter. Hereby, a polymerizable composition (43) according to the present invention was prepared.

(Preparation of Polymerizable Compositions (44) and (45))

Polymerizable compositions (44) and (45) were prepared under the same conditions as in the preparation of the polymerizable composition (43), except that the proportions of the compounds described in Table 9 below were changed as described in Table 9 below.

Table 9 summarizes the specific compositions of the polymerizable compositions (43) to (45) according to the present invention.

TABLE 9

| Composition | (43) | (44) | (45) |
|---|---|---|---|
| (1A-1-1) | 45 | 45 | 45 |
| (2-1-1-2) | 45 | 45 | 45 |
| (2-2-1-1) | 10 | 10 | 10 |
| (12-4) |  | 0.6 |  |
| (12-8) |  |  | 20 |
| (12-10) | 1 |  |  |
| OXE-01 | 6 | 6 | 6 |
| F-554 | 0.1 | 0.1 | 0.1 |
| p-Methoxyphenol | 0.1 | 0.1 | 0.1 |
| Toluene | 150 | 150 | 150 |
| Methyl ethyl ketone | 150 | 150 | 150 |

[Chem. 152]

(12-4)

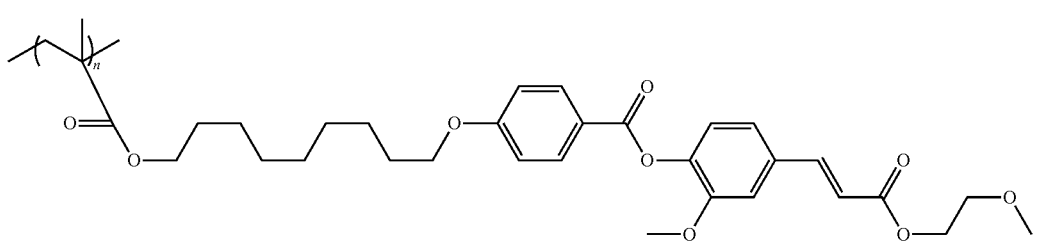

[Chem. 153]

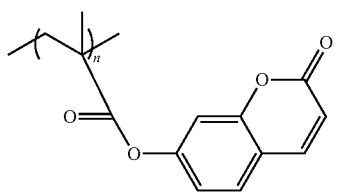

(12-8)

[Chem. 154]

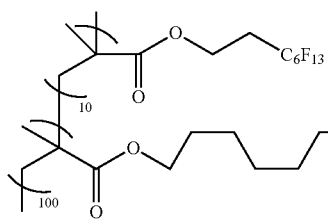

(12-10)

Example 43

The polymerizable composition (43) according to the present invention was applied to a glass substrate having a thickness of 0.7 mm by spin coating. The resulting coating film was dried for 2 minutes at 70° C. and for another 2 minutes at 100° C. Subsequently, the coating film was irradiated with linearly polarized light of 313 nm at an intensity of 10 mW/cm$^2$ for 30 seconds. After the coating film had been cooled to room temperature, the coating film was irradiated with ultraviolet radiation emitted from a high-pressure mercury lamp at an intensity of 30 mW/cm$^2$ for 30 seconds. Hereby, an optically anisotropic body of Example 43 which was a positive A-plate was prepared. In the evaluation of the alignment of the optically anisotropic body, there was no visual defect and no defect was observed with a polarizing microscope. The retardation of the optically anisotropic body was measured using RETS-100 (produced by Otsuka Electronics Co., Ltd.). The in-plane phase retardation of the optically anisotropic body at a wavelength of 550 nm (Re(550)) was 137 nm. This confirmed the formation of a uniform phase retardation film.

Example 44

The polymerizable composition (44) according to the present invention was applied to a glass substrate having a thickness of 0.7 mm by spin coating. The resulting coating film was dried for 2 minutes at 60° C. and for another 2 minutes at 110° C. After the temperature had been reduced to 60° C., the coating film was irradiated with linearly polarized light of 313 nm at an intensity of 10 mW/cm$^2$ for 50 seconds. After the coating film had been cooled to room temperature, the coating film was irradiated with ultraviolet radiation emitted from a high-pressure mercury lamp at an intensity of 30 mW/cm$^2$ for 30 seconds. Hereby, an optically anisotropic body of Example 44 which was a positive A-plate was prepared. In the evaluation of the alignment of the optically anisotropic body, there was no visual defect and no defect was observed with a polarizing microscope. The retardation of the optically anisotropic body was measured using RETS-100 (produced by Otsuka Electronics Co., Ltd.). The in-plane phase retardation of the optically anisotropic body at a wavelength of 550 nm (Re(550)) was 130 nm. This confirmed the formation of a uniform phase retardation film.

Example 45

The polymerizable composition (45) according to the present invention was applied to a glass substrate having a thickness of 0.7 mm by spin coating. The resulting coating film was dried for 2 minutes at 60° C. and for another 2 minutes at 110° C. After the temperature had been reduced to 60° C., the coating film was irradiated with linearly polarized light of 313 nm at an intensity of 10 mW/cm$^2$ for 100 seconds. After the coating film had been cooled to room temperature, the coating film was irradiated with ultraviolet radiation emitted from a high-pressure mercury lamp at an intensity of 30 mW/cm$^2$ for 30 seconds. Hereby, an optically anisotropic body of Example 45 was prepared. In the evaluation of the alignment of the optically anisotropic body, there was no visual defect and no defect was observed with a polarizing microscope. The retardation of the optically anisotropic body was measured using RETS-100 (produced by Otsuka Electronics Co., Ltd.). The in-plane phase retardation of the optically anisotropic body at a wavelength of 550 nm (Re(550)) was 108 nm. This confirmed the formation of a uniform phase retardation film.

(Preparation of Polymerizable Composition (46))

To 100 parts of toluene and 200 parts of cyclopentanone, 45 parts of the compound represented by Formula (1A-1-1), 45 parts of the compound represented by Formula (2-1-1-2), 10 parts of the compound represented by Formula (2-2-1-1), and 6 parts of the compound represented by Formula (d-7) were added. The resulting mixture was heated to 60° C. and stirred to form a dispersion solution. After the dispersion and dissolution of the compounds had been confirmed, the temperature was reduced to room temperature. To the solution, 6 parts of Irgacure OXE-01 (Irg.OXE-01; produced by BASF SE Japan), 0.20 parts of MEGAFACE F-554 (produced by DIC Corporation), 0.1 parts of p-methoxyphenol (MEHQ), 0.1 parts of IRGANOX 1076 (produced by BASF SE Japan), and 2 parts of trimethylolpropane tris(3-mercaptopropionate) TMMP (produced by SC Organic Chemical Co., Ltd.) were added. The resulting mixture was further stirred to form a solution. The solution was uniform. The solution was filtered through a 0.2-μm membrane filter. Hereby, a polymerizable composition (46) according to the present invention was prepared. The solution was transparent and uniform.

(Preparation of Polymerizable Composition (47))

A polymerizable composition (47) was prepared under the same conditions as in the preparation of the polymerizable composition (46), except that the proportions of the compounds described in Table 10 below were changed as described in Table 10 below.

Table 10 summarizes the specific compositions of the polymerizable compositions (46) and (47) according to the present invention.

TABLE 10

| Composition | (46) | (47) |
|---|---|---|
| (1A-1-1) | 45 | 45 |
| (2-1-1-2) | 45 | 45 |
| (2-2-1-1) | 10 | 10 |
| d-7 | 6 | |
| d-10 | | 6 |
| OXE-01 | 6 | 6 |
| F-554 | 0.2 | 0.2 |
| p-Methoxyphenol | 0.1 | 0.1 |
| IRGANOX 1076 | 0.1 | 0.1 |
| TMMP | 2 | 2 |
| Toluene | 100 | 100 |
| Cyclopentanone | 200 | 200 | ture over 2 minutes, the coating film was irradiated with ultraviolet radiation emitted from a high-pressure mercury lamp at an intensity of 30 mW/cm² for 30 seconds. Hereby, an optically anisotropic body of Example 46 which was a positive A-plate was prepared. Coating inconsistencies were not present in the optically anisotropic body. The degree of polarization, transmittance, and contrast of the optically anisotropic body measured with RETS-100 (produced by Otsuka Electronics Co., Ltd.) were 98.0%, 43.5%, and 92, respectively. This conformed that the optically anisotropic body was a polarizing film.

Example 47

An optically anisotropic body of Example 47 which was a positive A-plate was prepared under the same conditions as in Example 46, except that the polymerizable composition used was changed to the polymerizable composition (47) according to the present invention. Coating inconsistencies were not present in the optically anisotropic body. The degree of polarization, transmittance, and contrast of the optically anisotropic body measured with RETS-100 (produced by Otsuka Electronics Co., Ltd.) were 97.5%, 42.3%, and 90, respectively. This conformed that the optically anisotropic body was a polarizing film.

Example 48

A PET film having a thickness of 180 μm was subjected to a rubbing treatment in which a commercial rubbing

[Chem. 155]

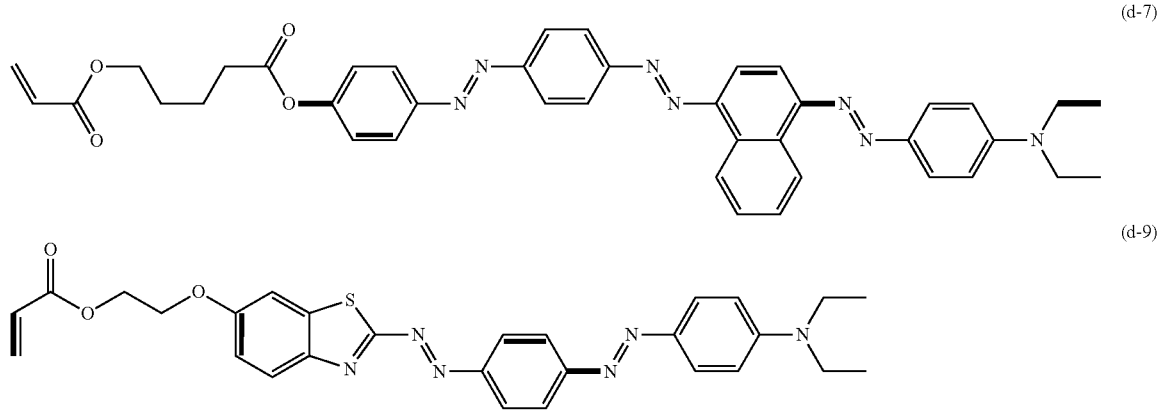

Trimethylolpropane tris (3-mercaptopropionate) (TMMP)

Example 46

A polyimide solution for alignment films was applied to a glass substrate having a thickness of 0.7 mm by spin coating. After drying had been performed at 100° C. for 10 minutes, firing was performed at 200° C. for 60 minutes. Hereby, a coating film was formed. The coating film was subjected to a rubbing treatment. The rubbing treatment was performed with a commercial rubbing apparatus.

To the substrate that had been subjected to the rubbing treatment, the polymerizable composition (46) according to the present invention was applied by spin coating. Subsequently, drying was performed at 90° C. for 2 minutes. After the resulting coating film had been cooled to room temperaapparatus is used. To the PET film, the polymerizable composition (19) according to the present invention was applied by bar coating. The resulting coating film was dried at 80° C. for 2 minutes. After the coating film had been cooled to room temperature, the coating film was irradiated with ultraviolet radiation using an UV conveyor apparatus (produced by GS Yuasa Corporation) having a lamp power of 2 kW at a conveyor speed of 5 m/min. Hereby, an optically anisotropic body which was a positive A-plate was prepared. The alignment, phase retardation ratio, hardness, and heat resistance of the optically anisotropic body were evaluated as in Example 1. The optically anisotropic body had no visual defect, and no defect was observed with a polarizing microscope. That is, the optically anisotropic body had suitable alignment. The phase retardation Re(550) of the optically anisotropic body was 137 nm. The ratio of the in-plane phase retardation of the optically anisotropic body at a wavelength of 450 nm (Re(450)) to the Re(550) of the optically anisotropic body, that is, Re(450)/Re(550), was 0.833. This confirmed the formation of a uniform phase retardation film. In the evaluation of the hardness of the optically anisotropic body, the film did not detach from the substrate even after being scrubbed 200 times or more. The change in the retardation (phase retardation) of the optically anisotropic body which occurred during a heat resistance test in which the optically anisotropic body was subjected to 85° C. for 500 hours was less than 5%.

A polyvinyl alcohol film having an average degree of polymerization of about 2400, a degree of saponification of 99.9 mol % or more, and a thickness of 75 µm was uniaxially stretched about 5.5 times in a dry process. While the film was maintained under tension, the film was immersed in pure water at 60° C. for 60 seconds and subsequently immersed in an aqueous solution including iodine, potassium iodide, and water at a ratio of 0.05/5/100 by weight at 28° C. for 20 seconds. Then, the film was immersed in an aqueous solution including potassium iodide, boric acid, and water at a ratio of 8.5/8.5/100 by weight at 72° C. for 300 seconds. Subsequently, the film was cleaned with pure water at 26° C. for 20 seconds and dried at 65° C. Hereby, a polarizing film including a polyvinyl alcohol resin and iodine adsorbed on the polyvinyl alcohol resin and aligned was prepared.

Saponified triacetyl cellulose films [KC8UX2MW produced by Konica Minolta Opto Products Co., Ltd.] were attached to the respective surfaces of the resulting polarizer with a polyvinyl alcohol adhesive prepared using 3 parts of carboxyl-modified polyvinyl alcohol [KURARAY POVAL KL318 produced by Kuraray Co., Ltd.] and 1.5 parts of a water-soluble polyamide epoxy resin [Sumirez Resin 650 (aqueous solution having a solid component concentration of 30%) produced by Sumika Chemtex Company, Limited] in order to protect the surfaces. Hereby, a polarizing film was prepared.

The polarizing film and the phase retardation film were bonded to each other with an adhesive such that the polarizing axis of the polarizing film and the slow axis of the phase retardation film formed an angle of 45°. Hereby, an antireflection film according to the present invention was prepared. The antireflection film was bonded to an aluminum plate, which was used as an alternative to an organic light-emitting element, with an adhesive. The visibility of reflection from the aluminum plate was visually confirmed from the front and from an angle of 45°. The reflection from the aluminum plate was not observed.

As described in Examples above, the polymerizable composition according to the present invention, which includes the polymerizable compound represented by General Formula (IA) which has a specific structure including a plurality of polymerizable groups, is considered excellent in terms of productivity since the optically anisotropic bodies according to the present invention (Examples 1 to 48) formed using the polymerizable compositions (1) to (47) were evaluated as good in terms of alignment, phase retardation ratio, hardness, and durability. In particular, in the case where the polymerizable composition included, as a polymerizable compound represented by General Formula (IA) which has a specific structure including a plurality of polymerizable groups, a polymerizable compound having a specific structure including three polymerizable groups, markedly good results were obtained in the evaluations of alignment, phase retardation ratio, hardness, and durability. In contrast, the results obtained in Comparative example 1 confirm that, in the case where the polymerizable composition did not include the polymerizable compound according to the present invention, which satisfies General Formula (IA), poor results were obtained in the evaluation of hardness and such a polymerizable composition was inferior to the polymerizable composition according to the present invention.

The invention claimed is:

1. A polymerizable composition comprising a compound represented by Formula (IA) below:

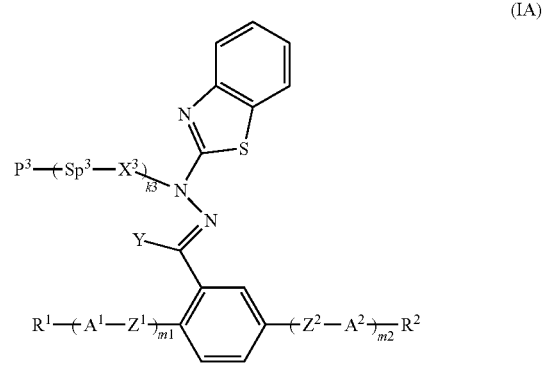

(IA)

in Formula (IA), $P^3$ represents a polymerizable group selected from Formulae (P-1) to (P-3) below:

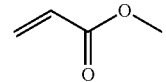

(P-1)

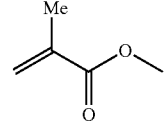

(P-2)

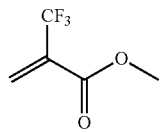

(P-3)

$Sp^3$ represents a spacer group and, when a plurality of $Sp^3$ groups are present, they may be identical to or different from one another, wherein $Sp^3$ represents an alkylene group having 1 to 20 carbon atoms in which one —CH$_2$— group or two or more —CH$_2$— groups that are not adjacent to one another may be each independently replaced with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—;

$X^3$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^3$ groups are present, they may be identical to or different from one another, $P^3$-(Sp$^3$-X$^3$)$_{k3}$— does not include an —O—O— linkage;

k3 represents an integer of 1 to 10;

$A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and the above groups may be optionally substituted with one or more L substituents;

L represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom, and, when a plurality of L substituents are present in the compound, they may be identical to or different from one another;

$Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, when a plurality of $Z^1$ groups are present, they may be identical to or different from one another, and, when a plurality of $Z^2$ groups are present, they may be identical to or different from one another; m1 and m2 each independently represent an integer of 0 to 6, and m1+m2 is an integer of 0 to 6;

Y represents a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, or where a hydrogen atom included in the alkyl group may be replaced with a fluorine atom;

$R^1$ represents a group represented by $P^1$-(Sp$^1$-X$^1$)$_{k1}$— wherein, $P^1$ represents a polymerizable group; Sp$^1$ represents a spacer group and, when a plurality of Sp$^1$ groups are present, they may be identical to or different from one another; $X^1$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^1$ groups are present, they may be identical to or different from one another, $P^1$-(Sp$^1$-X$^1$)$_{k1}$— does not include an —O—O— linkage; and k1 represents an integer of 0 to 10; and $R^2$ represents a group represented by $P^2$-(Sp$^2$-X$^2$)$_{k2}$— wherein, $P^2$ represents a polymerizable group; Sp$^2$ represents a spacer group and, when a plurality of Sp$^2$ groups are present, they may be identical to or different from one another; $X^2$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^2$ groups are present, they may be identical to or different from one another, $P^2$-(Sp$^2$-X$^2$)$_{k2}$— does not include an —O—O— linkage; and k2 represents an integer of 0 to 10, the polymerizable composition further comprising a polymerizable compound represented by Formula (1-1) below which includes one polymerizable group and/or a polymerizable compound represented by Formula (2-1) below which includes two polymerizable groups:

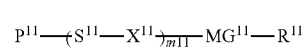 (1-1)

in Formula (1-1), $P^{11}$ represents a polymerizable group;

$S^{11}$ represents a spacer group or a single bond and, when a plurality of $S^{11}$ groups are present, they may be identical to or different from one another;

$X^{11}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^{11}$ groups are present, they may be identical to or different from one another, $P^{11}$—($S^{11}$—$X^{11}$)$_{m11}$— does not include an —O—O—; m11 represents an integer of 0 to 8;

$MG^{11}$ represents Formula (1-a) below:

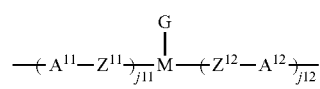 (1-a)

in Formula (1-a), $A^{11}$ and $A^{12}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^1$ substituents; and, when a plurality of $A^{11}$ groups and/or a plurality of $A^{12}$ groups are present, they may be identical to or different from one another;

$Z^{11}$ and $Z^{12}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, and, when a plurality of $Z^{11}$ groups and/or a plurality of $Z^{12}$ groups are present, they may be identical to or different from one another;

M represents a group selected from Formulae (M-1) to (M-11) below:

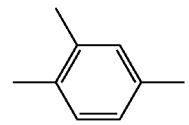 (M-1)

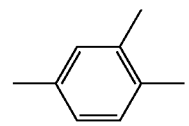 (M-2)

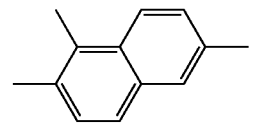 (M-3)

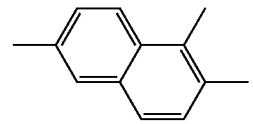 (M-4)

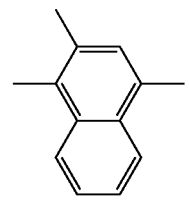 (M-5)

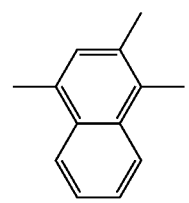 (M-6)

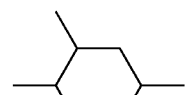 (M-7)

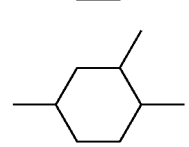 (M-8)

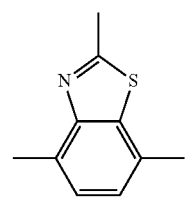 (M-9)

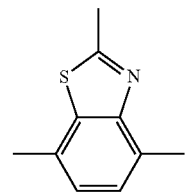 (M-10)

-continued (M-11)
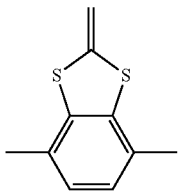

the above groups may be optionally substituted with one or more $L^1$ substituents;

G is selected from Formulae (G-1) to (G-6) below:

(G-1)
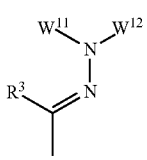

(G-2)
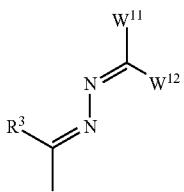

(G-3)
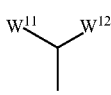

(G-4)
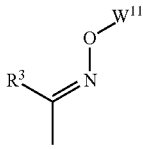

(G-5)
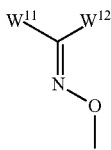

(G-6)
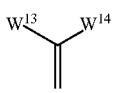

in Formulae (G-1) to (G-6), $R^3$ represents a hydrogen atom or an alkyl group having 1 to 20 carbon atoms, the alkyl group may be linear or branched, a hydrogen atom included in the alkyl group may be replaced with a fluorine atom, and, in the alkyl group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

$W^{11}$ represents a group having 5 to 30 carbon atoms, the group including at least one aromatic group, and the group may be optionally substituted with one or more $L^1$ substituents;

$W^{12}$ represents a hydrogen atom or an alkyl group having 1 to 20 carbon atoms, the alkyl group may be linear or branched, a hydrogen atom included in the alkyl group may be replaced with a fluorine atom and/or an —OH group, in the alkyl group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, or $W^{12}$ may represent the same thing as $W^{11}$, and $W^{11}$ and $W^{12}$ may be bonded to each other to form a ring structure;

$W^{13}$ and $W^{14}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms and, in the alkyl group, the cycloalkyl group, the alkenyl group, the cycloalkenyl group, the alkoxy group, the acyloxy group, and the alkylcarbonyloxy group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

when M is selected from Formulae (M-1) to (M-10), G is selected from Formulae (G-1) to (G-5) and, when M is Formula (M-11), G represents Formula (G-6);

$L^1$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms, the alkyl group may be linear or branched, a hydrogen atom may be replaced with a fluorine atom, in the alkyl group, one —CH$_2$— group or two or more —CH$_2$— groups that are not adjacent to one another may be each independently replaced with a group selected from —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—, and, when a plurality of $L^1$ substituents are present in the compound, they may be identical to or different from one another; and j11 represents an integer of 0 to 5, j 12 represents an integer of 1 to 5, and j11+j 12 is an integer of 1 to 5; and $R^{11}$ represents a hydrogen atom, a fluorine atom, a chlorine atom, a bromine atom, an iodine atom, a pentafluorosulfanyl group, a cyano group, a nitro group, an isocyano group, a thioisocyano group, or an alkyl group having 1 to 20 carbon atoms, the alkyl group may be linear or branched, a hydrogen atom included in the alkyl group may be replaced with a fluorine atom, and, in the alkyl group, one —CH$_2$— group or two or more —CH₂— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—,

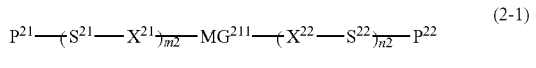
(2-1)

in Formula (2-1), $P^{21}$ and $P^{22}$ represent a polymerizable group;

$S^{21}$ and $S^{22}$ represent a spacer group or a single bond and, when a plurality of $S^{21}$ groups and/or a plurality of $S^{22}$ groups are present, they may be identical to or different from one another;

$X^{21}$ and $X^{22}$ represent —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH═CH—COO—, —CH═CH—OCO—, —COO—CH═CH—, —OCO—CH═CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH═CH—, —N═N—, —CH═N—N═CH—, —CF═CF—, —C≡C—, or a single bond and, when a plurality of $X^{21}$ groups and/or a plurality of $X^{22}$ groups are present, they may be identical to or different from one another the $P^{21}$—$(S^{21}$—$X^{21})_{m2}$— linkage and the $P^{22}$—$(S^{22}$—$X^{22})_{n2}$— linkage do not include —O—O—; MG211 is a group represented by Formula (8-a) below:

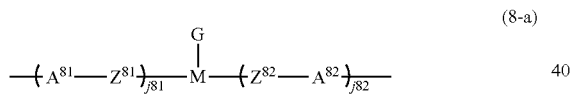
(8-a)

in Formula (8-a), $A^{81}$ and $A^{82}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^2$ substituents, and, when a plurality of $A^{81}$ groups and/or a plurality of $A^{82}$ groups are present, they may be identical to or different from one another;

$Z^{81}$ and $Z^{82}$ each independently represent —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH═CH—COO—, —CH═CH—OCO—, —COO—CH═CH—, —OCO—CH═CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH═CH—, —N═N—, —CH═N—N═CH—, —N═CH—, —CH═N—N═CH—, —CF═CF—, —C≡C—, or a single bond, and when a plurality of $Z^{81}$ groups and/or a plurality of $Z^{82}$ groups are present, they may be identical to or different from one another;

M represents a group selected from Formulae (M-81) to (M-813) below;

(M-81)

(M-82)

(M-83)

(M-84)

(M-85)

(M-86)

(M-87)

(M-88)

(M-89)

-continued (M-810)
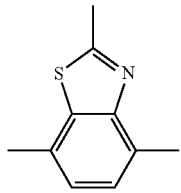

(M-811)
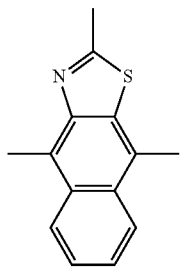

(M-812)
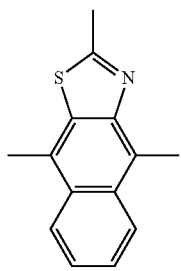

(M-813)
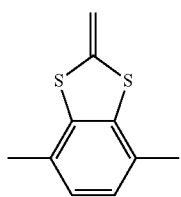

the above groups may be optionally substituted with one or more $L^2$ substituents;

G is selected from Formulae (G-81) to (G-86) below:

(G-81)
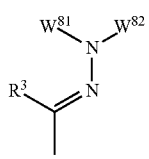

(G-82)
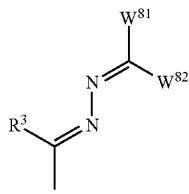

(G-83)
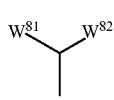

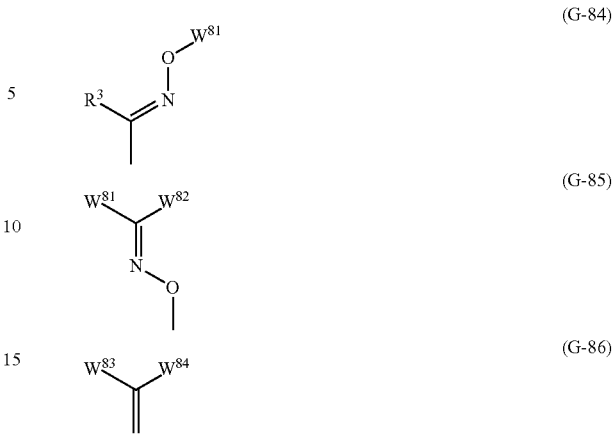

in Formulae (G-81) to (G-86), $R^3$ represents a hydrogen atom or an alkyl group having 1 to 20 carbon atoms, the alkyl group may be linear or branched, a hydrogen atom included in the alkyl group may be replaced with a fluorine atom, and, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

$W^{81}$ represents a group having 5 to 30 carbon atoms, the group including at least one aromatic group, and the group may be optionally substituted with one or more $L^2$ substituents;

$W^{82}$ represents a hydrogen atom or an alkyl group having 1 to 20 carbon atoms, the alkyl group may be linear or branched, a hydrogen atom included in the alkyl group may be replaced with a fluorine atom and/or an —OH group, in the alkyl group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, or $W^{82}$ may represent the same thing as $W^{81}$, and $W^{81}$ and $W^{82}$ may be bonded to each other to form a ring structure;

$W^{83}$ and $W^{84}$ each independently represent a halogen atom, a cyano group, a hydroxyl group, a nitro group, a carboxyl group, a carbamoyloxy group, an amino group, a sulfamoyl group, a group having 5 to 30 carbon atoms, the group including at least one aromatic group, an alkyl group having 1 to 20 carbon atoms, a cycloalkyl group having 3 to 20 carbon atoms, an alkenyl group having 2 to 20 carbon atoms, a cycloalkenyl group having 3 to 20 carbon atoms, an alkoxy group having 1 to 20 carbon atoms, an acyloxy group having 2 to 20 carbon atoms, or an alkylcarbonyloxy group having 2 to 20 carbon atoms and, in the alkyl group, the cycloalkyl group, the alkenyl group, the cycloalkenyl group, the alkoxy group, the acyloxy group, and the alkylcarbonyloxy group, one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—;

when M is selected from Formulae (M-81) to (M-812), G is selected from Formulae (G-81) to (G-85) and, when M is Formula (M-813), G represents Formula (G-86); $L^2$ represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms, the alkyl group may be linear or branched, a hydrogen atom may be replaced with a fluorine atom, in the alkyl group, one —CH$_2$— group or two or more —CH$_2$— groups that are not adjacent to one another may be each independently replaced with a group selected from —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—; and, when a plurality of $L^2$ substituents are present in the compound, they may be identical to or different from one another; and j81 and j82 each independently represent an integer of 0 to 5, and j81+j82 is an integer of 1 to 5; and m2 and n2 each independently represent an integer of 0 to 5.

2. The polymerizable composition according to claim 1, further comprising a polymerizable compound represented by Formula (2-2) below which includes two polymerizable groups:

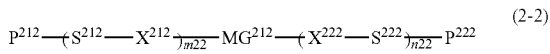

(2-2)

in Formula (2-2), $P^{212}$ and $P^{222}$ represent a polymerizable group;

$S^{212}$ and $S^{222}$ represent a spacer group or a single bond and, when a plurality of $S^{212}$ groups and/or a plurality of $S^{222}$ groups are present, they may be identical to or different from one another;

$X^{212}$ and $X^{222}$ represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^{212}$ groups and/or a plurality of $X^{222}$ groups are present, they may be identical to or different from one another, the $P^{212}$—(S$^{212}$—X$^{212}$)$_{m22}$— linkage and the $P^{222}$—(S$^{222}$—X$^{222}$)$_{n22}$— linkage do not include —O—O—;

MG212 represents a group represented by Formula (8-b) below:

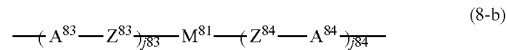

(8-b)

in Formula (8-b), $A^{83}$ and $A^{84}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more $L^2$ substituents, and, when a plurality of $A^{83}$ groups and/or a plurality of $A^{84}$ groups are present, they may be identical to or different from one another;

$Z^{83}$ and $Z^{84}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, and, when a plurality of $Z^{83}$ groups and/or a plurality of $Z^{84}$ groups are present, they may be identical to or different from one another;

$M^{81}$ represents a group selected from a 1,4-phenylene group, a 1,4-cyclohexylene group, a 1,4-cyclohexenyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a thiophene-2,5-diyl group-, a 1,2,3,4-tetrahydronaphthalene-2,6-diyl group, a naphthylene-1,4-diyl group, a naphthylene-1,5-diyl group, a naphthylene-1,6-diyl group, a naphthylene-2,6-diyl group, a phenanthrene-2,7-diyl group, a 9,10-dihydrophenanthrene-2,7-diyl group, a 1,2,3,4,4a,9,10a-octahydrophenanthrene-2,7-diyl group, a benzo[1,2-b:4,5-b']dithiophene-2,6-diyl group, a benzo[1,2-b:4,5-b]diselenophene-2,6-diyl group, a [1]benzothieno[3,2-b]thiophene-2,7-diyl group, a [1]benzoselenopheno[3,2-b]selenophene-2,7-diyl group, and a fluorene-2,7-diyl group, and the above groups may be optionally substituted with one or more $L^2$ substituents;

and j83 and j84 each independently represent an integer of 0 to 5, and j83+j84 is an integer of 1 to 5; and m22 and n22 each independently represent an integer of 0 to 5.

3. A polymer produced using the polymerizable composition according to claim 1.

4. An optically anisotropic body produced using the polymerizable composition according to claim 1.

5. A phase retardation film produced using the polymerizable composition according to claim 1.

6. A display element comprising the optically anisotropic body according to claim 4.

7. A light-emitting element comprising the optically anisotropic body according to claim 4.

8. A light-emitting diode lighting apparatus comprising the polymer according to claim 3.

9. A reflection film comprising the phase retardation film according to claim 6.

10. A lens sheet comprising the polymer according to claim 3.

11. A polymerizable composition comprising the polymerizable composition according to claim 1 and a dichroic dye.

12. A polarizing film produced using the polymerizable composition according to claim 11.

13. A polymerizable composition comprising the polymerizable composition according to claim 1 and one or more derivatives selected from an azo derivative, a chalcone derivative, a coumarin derivative, a cinnamate derivative, and a cycloalkane derivative.

14. An optically anisotropic body produced using the polymerizable composition according to claim 13.

15. A phase retardation film produced using the polymerizable composition according to claim 13.

16. A display element comprising the phase retardation film according to claim 6.

17. A light-emitting element comprising the phase retardation film according to claim 5.

18. The polymerizable composition according to claim 1, wherein $W^{82}$ represents an alkyl group having 1 to 20 carbon atoms, the alkyl group may be linear or branched, a hydrogen atom included in the alkyl group may be replaced with a fluorine atom and/or an —OH group, in the alkyl group, one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, $W^{82}$ may represent the same thing as $W^{81}$, and $W^{81}$ and $W^{82}$ may be bonded to each other to form a ring structure.

19. The polymerizable composition according to claim 2, wherein $Z^{83}$ and $Z^{84}$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—, —N═CH—, —CH═N—N═CH—, —CF═CF—, —C≡C—, or a single bond, and, when a plurality of $Z^{83}$ groups and/or a plurality of $Z^{84}$ groups are present, they may be identical to or different from one another.

* * * * *